(12) United States Patent
Vlahov et al.

(10) Patent No.: US 9,662,402 B2
(45) Date of Patent: May 30, 2017

(54) DRUG DELIVERY CONJUGATES CONTAINING UNNATURAL AMINO ACIDS AND METHODS FOR USING

(71) Applicant: ENDOCYTE, INC., West Lafayette, IN (US)

(72) Inventors: Iontcho Radoslavov Vlahov, West Lafayette, IN (US); Christopher Paul Leamon, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

(21) Appl. No.: 14/435,919

(22) PCT Filed: Oct. 15, 2013

(86) PCT No.: PCT/US2013/065079
§ 371 (c)(1),
(2) Date: Apr. 15, 2015

(87) PCT Pub. No.: WO2014/062697
PCT Pub. Date: Apr. 24, 2014

(65) Prior Publication Data
US 2015/0258203 A1   Sep. 17, 2015

Related U.S. Application Data

(60) Provisional application No. 61/714,565, filed on Oct. 16, 2012, provisional application No. 61/877,317, filed on Sep. 13, 2013, provisional application No. 61/865,382, filed on Aug. 13, 2013, provisional application No. 61/790,234, filed on Mar. 15, 2013.

(51) Int. Cl.
*A61K 38/08* (2006.01)
*A61K 47/48* (2006.01)
*C07K 7/06* (2006.01)

(52) U.S. Cl.
CPC .. *A61K 47/48092* (2013.01); *A61K 47/48107* (2013.01); *C07K 7/06* (2013.01)

(58) Field of Classification Search
CPC ........ A61K 47/48107; A61K 47/48092; C07K 7/06
See application file for complete search history.

(56) References Cited

U.S. PATENT DOCUMENTS

| | | | |
|---|---|---|---|
| 2,515,483 A | 7/1950 | Wolf et al. |
| 2,816,110 A | 12/1957 | Sletzinger et al. |
| 3,387,001 A | 6/1968 | Hargrove et al. |
| 3,392,173 A | 7/1968 | Hargrove et al. |
| 3,632,622 A | 1/1972 | Moore et al. |
| 3,641,109 A | 2/1972 | Emerson et al. |
| 4,166,810 A | 9/1979 | Cullinan et al. |
| 4,203,898 A | 5/1980 | Cullinan et al. |
| 4,316,885 A | 2/1982 | Rakhit |
| 4,337,339 A | 6/1982 | Farina et al. |
| 4,639,456 A | 1/1987 | Trouet et al. |
| 4,650,803 A | 3/1987 | Stella et al. |
| 4,691,024 A | 9/1987 | Shirahata |
| 4,713,249 A | 12/1987 | Schroder |
| 4,801,688 A | 1/1989 | Laguzza et al. |
| 4,866,180 A | 9/1989 | Vyas et al. |
| 4,870,162 A | 9/1989 | Trouet et al. |
| 5,006,652 A | 4/1991 | Cullinan et al. |
| 5,094,849 A | 3/1992 | Cullinan et al. |
| 5,100,883 A | 3/1992 | Schiehser |
| 5,108,921 A | 4/1992 | Low et al. |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,138,051 A | 8/1992 | Hughes et al. |
| 5,140,104 A | 8/1992 | Coughlin et al. |
| 5,151,413 A | 9/1992 | Caufield et al. |
| 5,169,851 A | 12/1992 | Hughes et al. |
| 5,194,447 A | 3/1993 | Kao |
| 5,221,670 A | 6/1993 | Caufield |
| 5,233,036 A | 8/1993 | Hughes |
| 5,258,389 A | 11/1993 | Goulet et al. |

(Continued)

FOREIGN PATENT DOCUMENTS

| | | |
|---|---|---|
| CA | 2372841 | 11/2000 |
| CA | 2376175 | 12/2000 |

(Continued)

OTHER PUBLICATIONS

Beil, Prevention, updated on Mar. 29, 2010, available via internet at: http://www.nbcnews.com/id/35874922/ns/health-diet_and_nutrition/t/your-breakfast-giving-you-cancer/#.V40lrflVj2l.*
Adessi et al., Current Medicinal Chemistry, 2002, 9, 963-978.*
Agoston E.S. et al., "Vitamin D Analogs as Anti-Carcinogenic Agents," *Anti-Cancer Agents in Medicinal Chemistry*, 2006; 6(1): 53-71.
Anderson et al., "Potocytosis: Sequestration and transport of small molecules by caveolae," *Science*, 1992; 255: 410-411.
Antony A.C., "Folate receptors," *Annu Rev Nutr*, 1996; 16: 501-21.
Antony A.C., "The biological chemistry of folate receptors," *Blood*, 1992; 79(11):2807-2820.
Antony A.C. et al., "Studies of the Role of a Particulate Folate-binding Protein in the Uptake of 5-Methyltetrahydrofolate by Cultured Human KB Cells," *J. Biological Chem.*, 1985; 260(28): 14911-7.

(Continued)

*Primary Examiner* — Hasan Ahmed
*Assistant Examiner* — Kaipeen Yang
(74) *Attorney, Agent, or Firm* — Barnes & Thornburg LLP

(57) ABSTRACT

Described herein are drug delivery conjugates for targeted therapy. In particular, described herein are drug delivery conjugates that include polyvalent linkers comprising one or more unnatural amino acids that are useful for treating cancers and inflammatory diseases. The invention described herein pertains to drug delivery conjugates for targeted therapy. In particular, the invention described herein pertains to drug delivery conjugates that include polyvalent linkers comprising one or more unnatural amino acids.

2 Claims, 22 Drawing Sheets

(56) References Cited

U.S. PATENT DOCUMENTS

| | | |
|---|---|---|
| 5,260,300 A | 11/1993 | Hu |
| 5,266,333 A | 11/1993 | Cady |
| 5,302,584 A | 4/1994 | Kao et al. |
| 5,362,718 A | 11/1994 | Skotnicki et al. |
| 5,378,696 A | 1/1995 | Caufield |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,416,016 A | 5/1995 | Low et al. |
| 5,417,982 A | 5/1995 | Modi |
| 5,463,048 A | 10/1995 | Skotnicki et al. |
| 5,491,231 A | 2/1996 | Nelson et al. |
| 5,547,668 A | 8/1996 | Kranz et al. |
| 5,552,545 A | 9/1996 | Pearce et al. |
| 5,562,907 A | 10/1996 | Arnon |
| 5,583,020 A | 12/1996 | Sullivan |
| 5,627,165 A | 5/1997 | Glazier |
| 5,635,382 A | 6/1997 | Low et al. |
| 5,672,486 A | 9/1997 | Soulillou |
| 5,688,488 A | 11/1997 | Low et al. |
| 5,998,603 A | 12/1999 | Cook |
| 6,004,555 A | 12/1999 | Thorpe et al. |
| 6,030,941 A | 2/2000 | Summerton et al. |
| 6,056,973 A | 5/2000 | Allen |
| 6,077,499 A | 6/2000 | Griffiths |
| 6,093,382 A | 7/2000 | Wedeking et al. |
| 6,171,614 B1 | 1/2001 | Chaikof et al. |
| 6,171,859 B1 | 1/2001 | Herrnstadt et al. |
| 6,177,404 B1 | 1/2001 | DeFeo-Jones et al. |
| 6,184,042 B1 | 2/2001 | Neumann et al. |
| 6,207,157 B1 | 3/2001 | Gu et al. |
| 6,290,929 B1 | 9/2001 | Camden et al. |
| 6,291,673 B1 | 9/2001 | Fuchs et al. |
| 6,291,684 B1 | 9/2001 | Borzilleri et al. |
| 6,315,978 B1 | 11/2001 | Grissom et al. |
| 6,335,434 B1 | 1/2002 | Guzaev et al. |
| 6,340,701 B1 | 1/2002 | Chari et al. |
| 6,342,244 B1 | 1/2002 | Zalipsky et al. |
| 6,365,179 B1 | 4/2002 | Zalipsky et al. |
| 6,399,625 B1 | 6/2002 | Zhu |
| 6,399,626 B1 | 6/2002 | Zhu et al. |
| 6,399,638 B1 | 6/2002 | Vite et al. |
| 6,432,973 B1 | 8/2002 | Zhu et al. |
| 6,440,991 B1 | 8/2002 | Zhu et al. |
| 6,511,986 B2 | 1/2003 | Zhang et al. |
| 6,541,612 B2 | 4/2003 | Molnar-Kimber et al. |
| 6,548,505 B1 | 4/2003 | Martin et al. |
| 6,596,757 B1 | 7/2003 | Chari et al. |
| 6,617,333 B2 | 9/2003 | Rabindran et al. |
| 6,670,355 B2 | 12/2003 | Azrulan et al. |
| 6,677,357 B2 | 1/2004 | Zhu et al. |
| 6,680,330 B2 | 1/2004 | Zhu et al. |
| 6,713,607 B2 | 3/2004 | Caggiano et al. |
| 6,800,653 B2 | 10/2004 | Regueiro-Ren et al. |
| 6,821,731 B2 | 11/2004 | Gillis et al. |
| 6,915,855 B2 | 7/2005 | Steele et al. |
| 6,958,153 B1 | 10/2005 | Ormerod et al. |
| 7,019,014 B2 | 3/2006 | Bernan et al. |
| 7,029,674 B2 | 4/2006 | Carreno et al. |
| 7,033,594 B2 | 4/2006 | Low et al. |
| 7,060,709 B2 | 6/2006 | Cooperstone et al. |
| 7,060,797 B2 | 6/2006 | O'Toole et al. |
| 7,067,111 B1 | 6/2006 | Yang et al. |
| 7,074,804 B2 | 7/2006 | Zhu et al. |
| 7,105,328 B2 | 9/2006 | Wood et al. |
| 7,122,361 B2 | 10/2006 | Liu et al. |
| 7,128,893 B2 | 10/2006 | Leamon et al. |
| 7,153,957 B2 | 12/2006 | Chew et al. |
| 7,238,368 B2 | 7/2007 | Zalipsky et al. |
| 7,279,562 B2 | 10/2007 | Molnar-Kimber et al. |
| 7,582,744 B2 | 9/2009 | Manoharan et al. |
| 7,601,332 B2 | 10/2009 | Vlahov et al. |
| 7,754,885 B2 | 7/2010 | Hoefle et al. |
| 7,776,814 B2 | 8/2010 | Dömling et al. |
| 7,816,377 B2 | 10/2010 | Dömling et al. |
| 7,910,594 B2 | 3/2011 | Vlahov et al. |
| 8,349,901 B2 | 1/2013 | Satyam |
| 8,383,122 B2 | 2/2013 | Dai et al. |
| 8,394,922 B2 | 3/2013 | Cheng et al. |
| 8,470,822 B2 | 6/2013 | Green et al. |
| 8,476,451 B2 | 7/2013 | Ellman et al. |
| 8,497,365 B2 | 7/2013 | Davis et al. |
| 8,546,425 B2 | 10/2013 | Leamon et al. |
| 8,580,820 B2 | 11/2013 | Zanda et al. |
| 8,765,096 B2 | 7/2014 | Leamon |
| 8,802,632 B2 | 8/2014 | Cheng et al. |
| 9,090,563 B2 | 7/2015 | Vlahov et al. |
| 9,138,484 B2 | 9/2015 | Leamon |
| 9,192,682 B2 | 11/2015 | Vlahov |
| 2001/0031252 A1 | 10/2001 | Low et al. |
| 2002/0151088 A1 | 10/2002 | Molnar-Kimber et al. |
| 2003/0086900 A1 | 5/2003 | Low et al. |
| 2003/0162234 A1 | 8/2003 | Jallad |
| 2003/0194409 A1 | 10/2003 | Rothman et al. |
| 2004/0018203 A1 | 1/2004 | Pastan et al. |
| 2004/0033195 A1 | 2/2004 | Leamon et al. |
| 2004/0047917 A1 | 3/2004 | Wilson et al. |
| 2004/0242582 A1 | 12/2004 | Green et al. |
| 2005/0002942 A1 | 1/2005 | Vlahov et al. |
| 2005/0004010 A1 | 1/2005 | Collins et al. |
| 2005/0026068 A1 | 2/2005 | Gogolides et al. |
| 2005/0107325 A1 | 5/2005 | Manoharan et al. |
| 2005/0165227 A1 | 7/2005 | Vlahov et al. |
| 2005/0227985 A9 | 10/2005 | Green et al. |
| 2005/0239713 A1 | 10/2005 | Domling et al. |
| 2005/0239739 A1 | 10/2005 | Matulic-Adamic et al. |
| 2005/0249740 A1 | 11/2005 | Domling |
| 2006/0019911 A1 | 1/2006 | Papisov |
| 2006/0058266 A1 | 3/2006 | Manoharan et al. |
| 2006/0105975 A1 | 5/2006 | Pendergrast et al. |
| 2006/0128754 A1 | 6/2006 | Hoefle et al. |
| 2006/0217360 A1 | 9/2006 | Hoefle et al. |
| 2006/0222653 A1 | 10/2006 | Abel et al. |
| 2007/0009434 A1 | 1/2007 | Low et al. |
| 2007/0134332 A1 | 6/2007 | Turnell et al. |
| 2007/0275904 A1 | 11/2007 | Vite et al. |
| 2008/0096893 A1 | 4/2008 | Zebala |
| 2008/0207625 A1 | 8/2008 | Xu et al. |
| 2008/0248052 A1 | 10/2008 | Vlahov et al. |
| 2008/0280937 A1 | 11/2008 | Leamon et al. |
| 2009/0203889 A1 | 8/2009 | Vlahov et al. |
| 2009/0247614 A1 | 10/2009 | Manoharan et al. |
| 2010/0004276 A1 | 1/2010 | Vlahov et al. |
| 2010/0040669 A1 | 2/2010 | Higuchi |
| 2010/0074863 A1 | 3/2010 | Or et al. |
| 2010/0104626 A1 | 4/2010 | Leamon et al. |
| 2010/0129314 A1 | 5/2010 | Singh et al. |
| 2010/0144647 A1 | 6/2010 | Kratz et al. |
| 2011/0027274 A1 | 2/2011 | Cheng et al. |
| 2011/0166319 A1 | 7/2011 | Dai et al. |
| 2011/0172254 A1 | 7/2011 | Leamon et al. |
| 2011/0245295 A1 | 10/2011 | Chai et al. |
| 2012/0065149 A1 | 3/2012 | Vlahov et al. |
| 2012/0129779 A1 | 5/2012 | Richter |
| 2012/0252738 A1 | 10/2012 | Richter |
| 2012/0252739 A1 | 10/2012 | Richter |
| 2012/0258905 A1 | 10/2012 | Leamon et al. |
| 2012/0259100 A1 | 10/2012 | Jin |
| 2012/0322741 A1 | 12/2012 | Low et al. |
| 2013/0029900 A1 | 1/2013 | Widdison |
| 2013/0116195 A1 | 5/2013 | Leamon et al. |
| 2013/0137139 A1 | 5/2013 | Vlahov et al. |
| 2013/0184435 A1 | 7/2013 | Vlahov et al. |
| 2013/0203680 A1 | 8/2013 | Leamon et al. |
| 2013/0217638 A1 | 8/2013 | Wessjohann et al. |
| 2013/0224228 A1 | 8/2013 | Jackson et al. |
| 2013/0281678 A1 | 10/2013 | Dai et al. |
| 2014/0058063 A1 | 2/2014 | Vlahov et al. |
| 2014/0058064 A1 | 2/2014 | Vlahov et al. |
| 2014/0066594 A1 | 3/2014 | Vlahov et al. |
| 2014/0073763 A1 | 3/2014 | Low et al. |
| 2014/0080175 A1 | 3/2014 | Vlahov et al. |

(56) References Cited

U.S. PATENT DOCUMENTS

| | | |
|---|---|---|
| 2014/0107316 A1 | 4/2014 | Vlahov et al. |
| 2014/0154702 A1 | 6/2014 | Parker et al. |
| 2014/0193437 A1 | 7/2014 | Lin et al. |
| 2014/0213760 A1 | 7/2014 | Leamon et al. |
| 2014/0227295 A1 | 8/2014 | Cong et al. |
| 2014/0227298 A1 | 8/2014 | Cong et al. |
| 2014/0249315 A1 | 9/2014 | Vlahov et al. |
| 2014/0309406 A1 | 10/2014 | Li et al. |
| 2014/0323690 A1 | 10/2014 | Cheng et al. |
| 2015/0258203 A1 | 9/2015 | Vlahov et al. |
| 2015/0314015 A1 | 11/2015 | Leamon et al. |
| 2016/0002167 A1 | 1/2016 | Vlahov et al. |
| 2016/0108085 A1 | 4/2016 | Vlahov et al. |
| 2016/0168183 A1 | 6/2016 | Leamon et al. |
| 2016/0220694 A1 | 8/2016 | Vlahov et al. |

FOREIGN PATENT DOCUMENTS

| | | |
|---|---|---|
| EP | 0 116 208 A1 | 8/1984 |
| EP | 0 163 550 A2 | 12/1985 |
| EP | 0 247 792 | 12/1987 |
| EP | 0 280 741 A1 | 9/1988 |
| EP | 0 354 728 | 2/1990 |
| JP | 59-175493 | 10/1984 |
| JP | 60-255789 | 12/1985 |
| WO | WO/85/05554 | 12/1985 |
| WO | WO 88/01622 | 3/1988 |
| WO | WO 90/12096 | 10/1990 |
| WO | WO 91/07418 | 5/1991 |
| WO | WO96/36367 | 11/1996 |
| WO | WO 98/08382 A1 | 3/1998 |
| WO | WO 98/08859 | 3/1998 |
| WO | WO 98/10651 A1 | 3/1998 |
| WO | WO 99/20626 A1 | 4/1999 |
| WO | WO95/15335 | 6/1999 |
| WO | WO 99/61055 | 12/1999 |
| WO | WO 00/35422 | 6/2000 |
| WO | WO 00/66091 | 11/2000 |
| WO | WO 00/74721 | 12/2000 |
| WO | WO01/13957 | 3/2001 |
| WO | WO 01/28592 | 4/2001 |
| WO | WO 01/74382 | 10/2001 |
| WO | WO02/059272 | 8/2002 |
| WO | WO 02/085908 | 10/2002 |
| WO | WO 02/087424 | 11/2002 |
| WO | WO 02/098868 | 12/2002 |
| WO | WO03/050295 | 6/2003 |
| WO | WO03/092742 | 11/2003 |
| WO | WO 03/097647 | 11/2003 |
| WO | WO 2004/005326 | 1/2004 |
| WO | WO 2004/005327 | 1/2004 |
| WO | WO 2004/012735 | 2/2004 |
| WO | WO/2004/022099 | 3/2004 |
| WO | WO/2004/037210 | 5/2004 |
| WO | WO 2004/046170 | 6/2004 |
| WO | WO 2004/054622 | 7/2004 |
| WO | WO 2004/069159 | 8/2004 |
| WO | WO2004/100983 | 11/2004 |
| WO | WO 2005/074901 | 8/2005 |
| WO | WO 2005/112919 | 12/2005 |
| WO | WO2005/115912 | 12/2005 |
| WO | WO 2006/012527 | 2/2006 |
| WO | WO 2006/042146 | 4/2006 |
| WO | WO/2006/089007 | 8/2006 |
| WO | WO 2006/101845 | 9/2006 |
| WO | WO2006/105141 | 10/2006 |
| WO | WO2007/002222 | 1/2007 |
| WO | WO 2007/022493 | 2/2007 |
| WO | WO 2007/022494 | 2/2007 |
| WO | WO2007/022512 | 2/2007 |
| WO | WO2007/140298 | 12/2007 |
| WO | WO2008/057437 | 5/2008 |
| WO | WO 2008/101231 | 8/2008 |
| WO | WO 2008/112873 | 9/2008 |
| WO | WO 2009/002993 | 12/2008 |
| WO | WO 2009/055562 | 4/2009 |
| WO | WO 2010/045598 | 4/2010 |
| WO | WO 2010/033733 | 5/2010 |
| WO | WO 2011/069116 | 6/2011 |
| WO | WO2011/106639 | 9/2011 |
| WO | WO2012/019123 | 2/2012 |
| WO | WO 2012/047525 | 4/2012 |
| WO | WO 2012/090104 A1 | 7/2012 |
| WO | WO 2013/126797 | 8/2013 |
| WO | WO 2013/130776 | 9/2013 |
| WO | WO2013/149185 | 10/2013 |
| WO | WO 2013/170272 | 11/2013 |
| WO | WO 2013/173392 | 11/2013 |
| WO | WO 2013/173393 | 11/2013 |
| WO | WO 2014/009774 | 1/2014 |
| WO | WO 2014/040752 | 3/2014 |
| WO | WO2014/078484 | 5/2014 |
| WO | WO 2014/080251 | 5/2014 |

OTHER PUBLICATIONS

Archer M.C. et al., "Separation of Folic Acid Derivatives and Pterins by High-Performance Liquid Chromatography," *Methods in Enzymology*, 1980; 66: pp. 452-459.

Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.

Ayers W.A., "Effect of Vitamin B12 and Analogs on the Respiration of a Marine Bacterium," *Archives of Biochemistry and Biophysics*, 1962, vol. 96, pp. 210-215.

Water, from http://www.biology-ionline.org/dictionary/Water, pp. 103, accessed Apr. 24, 2014.

Barnett C.J. et al., "Structure-Activity Relationships of Dimeric Catharanthus Alkaloids. 1. Deacetylvinblastine Amide (Vindesine) Sulfate," *J. Med. Chem.* 21: 88-96 (1978).

Bavetsias, V. et al., "Design and synthesis of Cyclopenta[g]quinazoline-based antifolates as inhibitors of thymidylate synthase and potential antitumor agents," J Med Chem, 2000; 43(10): 1910-1926.

Bavetsias, V., et al., "The design and synthesis of water-soluble analogues of CB30865, a quinazolin-4-one-based antitumor agent," J Med Chem, 2002; 45(17): 3692-3702.

Birinberg E. M. et al., "Synthesis and antimetabolic activity of pyrimidine analogs of folic and pteroic acids," *Pharmaceutical Chemistry Journal*, 1969; 3(6): pp. 331-333.

Bock et al., "Sulfonamide structure-activity relationships in a cell-free system. 2. Proof for the formation of a sulfonamide-containing folate analog," *Journal of Medical Chemistry*, 17: 23-28 (1974).

Boger, D.L. et al., "An improved synthesis of 1,2,9,9a-tetrahydrocyclopropa[c]benz[e]indol-4-one (CBI): a simplified analog of the CC-1065 alkylation subunit," *J. Org. Chem.*, 1992; 57: 2873-2876.

Campbell et al., "Folate-binding protein is a marker for ovarian cancer," *Cancer Res.*, 1991; 51: 5329-5338.

Cho et al., "Single-chain Fv/folate conjugates mediate efficient lysis of folate-receptor-positive tumor cells," *Bioconjug. Chem.* 8(3): 338-346 (1997).

Niosh List of antineoplastic and Other Hazardous Drugs in Healthcare settings 2010, pp. 1-16, published Sep. 20, 2010.

Christensen et al., "Membrane receptors for endocytosis in the renal proximal tubule," *Int. Rev. Cytol.*, 1998; 180: 237-284.

Churlaud C. et al., "Novel 4-(Trimethylsilyl)aminoalkanes and 4-(Trimethylsilyl)aminoalk-2-enes, via a 1,5-Hydride Shift, in the Reaction of α-Unsaturated Silanes with Aminomethylbenzotriazoles," *Organomettalics*, 1999; 18(21): 4270-4274.

Citro G. et al., "Inhibition of leukemia cell proliferation by folic acid—polylysine-mediated introduction of c-myb antisense oligodeoxynucelotides into HL-60 cells," *Br. J. Cancer*, 1994; 69: 463-467.

Cope A.C. et al., "Thermal Rearrangement of Allyl-type Sulfoxides, Sulfones and Sulfinates," *J. Am. Chem. Soc.*, 1950; 72; 59-67.

(56) References Cited

OTHER PUBLICATIONS

Cosulich D.B. et al., "Analogs of Pteroylglutamic Acid. I. N10-Alkylpteroic Acid and Derivatives," *JACS*, 1948, 70 (5), pp. 1922-1926.
Douglas J.T. et al., "Targeted Gene Delivery by Tropism-Modified Adenoviral Vectors," *Nat. Biotechnol.*, 1996, vol. 14, pp. 1574-1578.
Eichman, J.D. et al., "The Use of PAMAM Dendrimers in the Efficient Transfer of Genetic Material Into Cells", Jul. 2000, *PSTT*, vol. 3, No. 7, pp. 232-245.
Foong, L.Y. et al., "Development of a Novel Thiol Reagent for Probing Ion Channel Structure: Studies in a Model System," Biochemistry, 1997, vol. 36, pp. 1343-1348.
Chae et al, Recombinant Expression, Isotope labeling and purification of the Vitamin D Receptor Binding Peptide, Bull. Korean Chem Soc. 2011, 32, pp. 4337-4340.
Frankel AE., "Immunotoxin therapy of cancer," *Oncology*, 1993; 7(5): 69-78.
Shealy Y.F., "Synthesis and Evaluation of Some New Retinoids for Cancer Chemoprevention," *Preventive Medicine*, 1989, vol. 18, pp. 624-645.
Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," *J Med Chem.*, 2008; 51(15):4589-4600.
Garin-Chesa et al., "Trophoblast and ovarian cancer antigen LK26. Sensitivity and specificity in immunopathology and molecular identification as a folate-binding protein," *Am. J. Pathol.* 142(2): 557-562 (1993).
GE Healthcare, Instructions 71-7104-00 AD.
Gibbs, DD et al., "BGC 945, a novel tumor-selective thymidylate synthase inhibitor targeted to alpha-folate receptor-overexpressing tumors," Cancer Res, 2005; 65(24): 11721-11728.
Gottschalk S. et al., "Folate receptor mediated DNA delivery into tumor cells: potosomal disruption results in enhanced gene expression," *Gene Therapy*, 1994; 1(3): 185-191.
Greene T.E. et al., "Protective Groups in Organic Synthesis," 2d edition, John Wiley & Sons, Inc. New York (1991).
Rudinger, peptide Hormones, JA Parsons, Ed., 1976, pp. 1-7.
Hanck A.B. et al., "Dexpanthenol (Ro 01-4709) in the treatment of constipation," *Acta Vitaminol Enzymol*, 1982; vol. 4 (1-2), pp. 87-97 (abstract only).
Harvison, P.J. et al., "Synthesis and Biological Activity of Novel Folic Acid Analogues: Pteroyl-S-alkylhomocysteine Sulfoximines," *Journal of Medicinal Chemistry*, 1992, vol. 35, pp. 1227-1233.
Henderson, E.A. et al., Targeting the alpha-folate receptor with cyclopenta[g]quinazoline-based inhibitors of thymidylate synthase, Bioorg Med Chem, 2006; 14(14): 5020-5042.
Ho R. I. et al., "A simple radioassay for dihydrofolate synthetase activity in *Escherichia coli* and its application to an inhibition study of new pteroate analogs," *Anal. Biochem.*, 1976, 73(2), pp. 493-500.
Hofland et al., "Folate-targeted gene transfer in vivo," *Mol Ther* 5(6): 739-744 (2002).
Holladay et al., "Riboflavin-mediated delivery of a macromolecule into cultured human cells," *Biochim Biophys Acta*, 1426(1): 195-204 (1999).
Holm, J. et al., "Folate receptors in malignant and benign tissues of human female genital tract," *BioSci. Rep.*, 17(4): 415-427 (1997).
Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).
SIGMA, 2004, pp. 1-2.
U.S. Appl. No. 60/946,092, filed Jun. 25, 2007, Vlahov et al.
U.S. Appl. No. 60/982,595, filed Nov. 25, 2007, Vlahov et al.
U.S. Appl. No. 61/036,176, filed Mar. 13, 2008, Vlahov et al.
U.S. Appl. No. 61/036,186, filed Mar. 13, 2008, Vlahov et al.
Hosomi A. et al., "Affinity for a-tocopherol transfer protein as a determinant of the biological activities of vitamin E analogs," *Federation of European Biochemical Societies Letters*, 1997, vol. 409, pp. 105-108.
Houlihan, C. M. et al., "Preparation and Purification of Pteroic Acid from Folic Acid," *Analytical Biochemistry*, 1972, vol. 46, pp. 1-6.
Hynes et al., "Quinazolines as inhibitors of dihydrofolate reductase. 4. Classical analogues of folic and isofolic acids", *Journal of Medical Chemistry*, 1977; 20: 588-591.
Jackman, A. L. et al., "Antifolates targeted specifically to the folate receptor," Adv Drug Deliv Rev, 2004; 56(8): 1111-1125.
Jones T.R. et al., "A potent antitumour quinazoline inhibitor of thymidylate synthetase: synthesis, biological properties and therapeutic results in mice," *Eur J Cancer*, 1981; 17(1):11-9.
Jones T.R. et al., "Quinazoline antifolates inhibiting thymidylate synthase: variation of the amino acid," *J Med Chem*, 1986; 29(6):1114-8.
Jung K.H. et al., "Intramolecular o-glycoside bond formation," *Chem. Rev.*, 2000, 100, 4423-42.
Kagechika H et al., "Synthetic Retinoids: Recent Developments Concerning Structure and Clinical Utility," *Journal of Medicinal Chemistry*, 2005; vol. 48, No. 19, pp. 5875-5883.
Berendsen, A Glimpse of the Holy Grail?, Science, 1998, 282, pp. 642-643.
Kamen et al., "Delivery of folates to the cytoplasm fo MA104 cells is mediated by a surface receptor that recycles," *J. Biol. Chem.*, 263: 13602-13609 (1988).
Kamen et al., "The folate receptor works in tandem with a probenecid-sensitive carrier in MA104 cells in vitro," *J. Clin. Invest.*, 87(4): 1442-1449 (1991).
Kamen, B. A. et al., "Receptor-mediated folate accumulation is regulated by the cellular folate content," *Proc. Natl. Acad. Sci. USA*, 83: 5983-5987 (1986).
Kandiko C.T. et al., "Inhibition of Rat Brain Pyruvate Dehydrogenase by Thiamine Analogs," *Biochemical Pharmacology*, 1988; vol. 37, No. 22, pp. 4375-4380.
Kane et al., "The influence of extracellular folate concentration on methotrexate uptake by human KB cells. Partial characterization of a membrane-associated methotrexate binding protein," *J. Biol. Chem.*, 261: 44-49 (1986).
Kim et al., "Synthesis and biological activity of 10-thia-10-deaza analogs of folic acid, pteroic acid, and related compounds", *Journal of Medical Chemistry*, 18: 776-780 (1975).
Kranz et al., "Conjugates of folate and anti-T-cell-receptor antibodies specifically target folate-receptor-positive tumor cells for lysis," *Proc. Natl. Acad. Sci. USA*, 1995; 92(20), pp. 9057-9061.
Kumar H.P. et al., "Folate transport in Lactobacillus salivarius. Characterization of the transport mechanism and purification and properties of the binding component," *J. Biol. Chem..* 1987; 262(15):7171-7179.
Ladino et al., "Folate-maytansinoids: target-selective drugs of low molecular weight," *Int. J. Cancer*, 73(6): 859 864 (1997).
Lambooy J. P., "Riboflavin Analogs Utilized for Metabolism by a Lactobacillus Casei Mutant," *Int. J. Biochem.*, vol. 16, No. 2, 1984, pp. 231-234.
Landuer W. et al., "The Interaction in Teratogenic Activity of the Two Niacin Analogs 3-acetylpyridine and 6-aminonicotinamide," *J Exp Zool*, 151(3):253-258 (1962).
Langone, J.J., et al., "Radioimmunoassays for the Vinca Alkaloids, Vinblastine and Vincristine", 1979, *Analytical Biochemistry*, No. 95, pp. 214-221.
Larock R.C., "Comprehensive Organic Transformations, a guide to functional group preparations," VCH Publishers, Inc. New York (1989).
Leamon CP et al, "Cytotoxicity of folate-Pseudomonas exotoxin conjugates toward tumor cells. Contribution of translocation domain," *J. Biol. Chem.* 268(33): 24847-24854 (1993).
Leamon CP et al., "Comparative Preclinical Activity of the Folate-targeted Vinca Alkaloid Conjugates EC140 and EC145," *Int J Cancer*, 2007; 121(7):1585-92.
Leamon CP et al., "Cytotoxicity of momordin-folate conjugates in cultured human cells," *J. Biol. Chem.*, 1992; 267(35): 24966-24971.

(56) References Cited

OTHER PUBLICATIONS

Leamon CP et al., "Delivery of macromolecules into living cells: a method that exploits folate receptor endocytosis," *Proc. Natl. Acad. Sci. USA* 88(13): 5572-5573 (1991).
Leamon CP et al., "Folate-mediated targeting: from diagnostics to drug and gene delivery," *Drug Discovery Today* 6: 36-43 (2001).
Leamon CP et al., "Folate-targeted chemotherapy," *Adv Drug Deliv Rev*, 2004;56(8): 1127-41.
Leamon CP et al., "Membrane folate-binding proteins are responsible for folate-protein conjugate endocytosis into cultured cells," *Biochem. J.* 291: 855-860 (1993).
Leamon CP et al., "Selective targeting of malignant cells with cytotoxin-folate conjugates," *J. Drug Target*. 2(2): 101-112 (1994).
Leamon CP et al., "Synthesis and biological evaluation of EC140: A novel folate-targeted vinca alkaloid conjugate," *Bioconjug Chem*, 2006;17(5):1226-32.
Leamon CP et al., "Synthesis and Biological Evaluation of EC20: A New Folate-Derived, (99m)Tc-Based Radiopharmaceutical," *Bioconjug. Chem.* 13(6): 1200-1210 (2002).
Leamon CP et al., "Synthesis and biological evaluation of EC72: a new folate-targeted chemotherapeutic," *Bioconjug Chem.*, 2005;16(4):803-11.
Leamon et al., "Folate-mediated drug delivery: effect of alternative conjugation chemistry," *J. Drug Target* 7(3): 157-169 (1999).
Lee et al, "Measurement of Endosome pH Following Folate Receptor-Mediated Endocytosis," *Biochim. Biophys. Acta* 1312(3): 237-242 (1996).
Voet et al, Biochemistry, John Wiley & Sons Inc., 1995, pp. 235-241.
U.S. Appl. No. 60/590,580, filed Jul. 23, 2004, Vlahov et al.
Lee W.W. et al., "Folic acid antagonists. Methotrexate analogs containing spurious amino acids. Dichlorohomofolic acid," *Journal of Medical Chemistry*, 17: 326-330 (1974).
Lee et al., "Synthesis and evaluation of taxol-folic acid conjugates as targeted antineoplastics," *Bioorg Med Chem.* 10(7): 2397-2414, (2002).
Lee, R. J. and Huang, L., "Folate-Targeted, Anionic Liposome-Entrapped Polylysine-Condensed Dna for Tumor Cell-Specific Gene Transfer," *J. Biol. Chem.* 271(14): 8481-8487 (1996).
Lee, R. J. and Low, P. S, "Delivery of liposomes into cultured KB cells via folate receptor-mediated endocytosis," *J. Biol. Chem.* 269(5): 3198-3204 (1994).
Lee, R. J. and Low, P. S., "Folate-mediated tumor cell targeting of liposome-entrapped doxorubicin in vitro," *Biochim. Biophys. Acta* 1233: 134-144 (1995).
Lemon, Julia, et al., "Conversion of Pterolyglutamic Acid to Pteroic Acid by Bacterial Degradation," *Archives of Biochemistry*, 1948; vol. 19, pp: 311-316.
Levy, Carl C., et al. "The Enzymatic Hydrolysis of Methotrexate and Folic Acid", 1967, *The Journal of Biological Chemistry*, vol. 242, No. 12, pp. 2933-2938.
Lewis et al., "Receptor-mediated folate uptake is positively regulated by disruption of actin cytoskeleton," *Cancer Res.* 58(14): 2952-2956 (1998).
Ngo et al, Computational Complexity, Protein Structure protection, and the Levinthal Paradox, 1994, pp. 491-497.
Li et al, "Targeted delivery of antisense oligodeoxynucleotides by LPDII," *J. Liposome Res.* 7(1): 63 (1997).
Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," *J. Org. Chem.* 66: 5655-5663 (2001).
Lonsdale D, "A Review of the Biochemistry, Metabolism and Clinical Benefits of Thiamin(e) and Its Derivatives," publication, Advance Access Publication, vol. 3, Feb. 2006, pp. 49-59.
Lopes et al., "Acyloxymethyl as a drug protecting group. Part 5.1 Kinetics and mechanism of the hydrolysis of tertiary N-acyloxymethylsulfonamides," *J. Chem. Soc.*, Perkin Trans. 2, pp. 431-439 (1999).

Low P.S. et al., "Folate Receptor-Targeted Drugs for Cancer and Inflammatory Diseases," *Adv Drug Deliv Rev*, 2004;56(8):1055-238.
Lu et al., "Folate-targeted enzyme prodrug cancer therapy utilizing penicillin-V amidase and a doxorubicin prodrug," *J. Drug Target*, 7(1): 43-53 (1999).
Lu, J. Y. and Low, P. S., "Folate targeting of haptens to cancer cell surfaces mediates immunotherapy of syngeneic murine tumors," *Cancer Immunol Immunother*, 51: 153-162 (2002).
Lu, J. Y. and Low, P. S., "Folate-mediated delivery of macromolecular anticancer therapeutic agents," *Adv. Drug Del Rev*, 2002; 54(5): 675-693.
Bradley et al, Limits of Cooperativity in a Structurally Modular Protein: Response of the Notch Ankyrin Domain to Analogous Alanine Substitutions in Each Repeat, J. Mol. Biol, 2002, 324, pp. 373-386.
Luo et al., "Efficient syntheses of pyrofolic acid and pteroyl azide, reagents for the production of carboxyl-differentiated derivatives of folic acid," *J. Am. Chem. Soc.*, 119: 10004-10013 (1997).
Mack D.O. et al., "The Carboxylation Activity of Vitamin K Analogs with Substitutions at Position 2, 3, or 5," *Journal of Biological Chemistry*, 1979; vol. 254, pp. 2656-2664.
Mancuso A.J. et al., "Activated Dimethyl Sulfoxide: Useful Reagents for Synthesis," *Synthesis*, 1981, pp. 165-184.
March, Advanced Organic Chemistry, 1992, John Wiley & Sons, 4th Ed., pp. 362-363, 816, 885, 896.
Mathais et al., "Receptor-mediated targeting of 67Ga-deferoxamine-folate to folate-receptor-positive human KB tumor xenografts," *Nucl Med Biol*, 26(1): 23-25 (1999).
Mathias et al., "Indium-111-DTPA-Folate as a potential folate-receptor-targeted radiopharmaceutical," *J. Nucl. Med.*, 39(9): 1579-1585 (1998).
Mathias et al., "Tumor-Selective Radiopharmaceutical Targeting Via Receptor-Mediated Endocytosis of Gallium-67-Deferoxamine-Folate," *J. Nucl. Med*, 37(6): 1003-1008 (1996).
Definition of moiety, from http://dictionary.reference.com/browse/moiety, pp. 1-3, accessed Aug. 26, 2010.
Mathias, C. J., "A kit formulation for preparation of [(111)In]In-DTPA-folate, a folate-receptor-targeted radiopharmaceutical," *Nucl. Med. Biol.*, 25(6): 585-587 (1998).
Matsui et al., "Studies on mitomycins. III. The synthesis and properties of mitomycin derivatives," *J Antibiot*, 21: 189-198 (1968).
Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.
McAlinden TP et al., "Synthesis and Biological Evaluation of a Fluorescent Analogue of Folic Acid," *Biochemistry*, 1991; 30: 5674-81.
McHugh M et al., "Demonstration of a High Affinity Folate Binder in Human Cell Membranes and Its Characterization in Cultured Human KB Cells," *J Biol Chem*, 1979; 254(22):11312-8.
Melani et al., "Targeting of interleukin 2 to human ovarian carcinoma by fusion with a single-chain Fv of antifolate receptor antibody," *Cancer Res.* 58(18): 4146-4154 (1998).
Mislick et al., "Transfection of folate-polylysine DNA complexes: evidence for lysosomal delivery," *Bioconjug. Chem.*, 6(5): 512-515 (1995).
Mock D.M. et al., "Urinary Biotin Analogs Increase in Humans During Chronic Supplementation: the Analogs are Biotin Metabolites," *Am J Physiol Endocrinol Metab*, 1997; 272: E83-E85.
Muller, Prodrug approaches for Enhancing the Bioavailability of Drugs with Low Solubility, Chemistry & Biodiversity, 2009, 6, pp. 2071-2083.
U.S. Appl. No. 60/808,367, filed May 25, 2006, Vite et al.
Morshed et al., "Folate transport proteins mediate the bidirectional transport of 5-methyltetrahydrofolate in cultured human proximal tubule cells," *J. Nutr.*, 127(6): 1137-1147 (1997).
Nair et al., "Folate analogs altered in the C9-N10 bridge region. 14. 11-Oxahomofolic acid, a potential antitumor agent", *Journal of Medical Chemistry*, 23: 59-65 (1980).

(56) References Cited

OTHER PUBLICATIONS

Nair et al., "Folate analogs altered in the C9-N10 bridge region. 18. Synthesis and antitumor evaluation of 11-oxahomoaminopterin and related compounds," *Journal of Medical Chemistry*, 24: 1068-1073 (1981).

Nair et al., "Folate analogs altered in the C9-N10 bridge region: N10-tosylisohomofolic acid and N10-tosylisohomoaminopterin," *Journal of Medical Chemistry*, 21: 673-677 (1978).

Nair et al., "Folate analogs altered in the C9-N10 bridge region: 11-thiohomofolic acid," *Journal of Medical Chemistry*, 22: 850-855 (1979).

Nair et al., "Folate analogs. 20. Synthesis and antifolate activity of 1',2',3',4',5',6'—hexahydrohomofolic acid," *Journal of Medical Chemistry*, 26: 135-140 (1983).

Nair et al., "Folate analogs. 21. Synthesis and antifolate and antitumor activities of N10-(cyanomethyl)-5,8-dideazafolic acid," *Journal of Medical Chemistry*, 26: 605-607 (1983).

Nair et al., "Folate analogs. 22. Synthesis and biological evaluation of two analogs of dihydrofolic acid possessing a 7,8-dihydro-8-oxapterin ring system," *Journal of Medical Chemistry*, 26: 1164-1168 (1983).

Beaumont et al, Design of ester prodrugs to enhance oral absorption of poorly permeable compounds: Challenges to the Discovery Scientist, Current Drug Metbolism, 2003, 4, 461-485.

Nair et al., "Folate analogues altered in the C9-N10 bridge region. 10-Oxafolic acid and 10-oxaaminopterin," *Journal of Medical Chemistry*, 19: 825-829 (1976).

Neuss, N. et al., "Vinca Alkaloids. XXX (1). Chemistry of the Deoxyvinblastines (Deoxy-VLB), Leurosine (VLR), and Pleurosine, Dimeric Alkaloids From Vinca," *Tetrahedron Letters*, No. 7, pp. 783-787 (1968).

Neuzil J. et al., "Vitamin E Analogs: A New Class of Multiple Action Agents with Anti-Neoplastic and Anti-Atherogenic Activity," *Apoptosis*, 2002; vol. 7, pp. 179-187.

Nielsen P. et al., "Phosphates of Riboflavin and Riboflavin Analogs: A Reinvestigation by High-Performance Liquid Chromatography," *Analytical Biochemistry*, vol. 130, 1983, pp. 359-368.

Nimmo-Smirth R.H. et al., "Some Effects of 2-deaminopteroylglutamic Acid upon Bacterial Growth," *J. Gen. Microbial.*, 1953; 9: 536-544.

Nishikawa, Yuji et al., "Growth Inhibition of Hepatoma Cells Induced by Vitamin K and Its Analogs," *Journal of Biological Chemistry*, 1995; vol. 270, No. 47, pp. 28304-28310.

Nomura, Makoto et al., "Development of an Efficient Intermediate a-[2-(Trimethylsilyl)ethoxy]-2-N-[2-(trimethylsilyl)ethoxycarbonyl]folic Acid, for the Synthesis of Folate (y)-Conjugates, and Its Application to the Synthesis of Folate-Nucleoside Congugates," *Journal of Organic Chemistry*, 2000, vol. 65, pp. 5016-5021.

Nosaka K.et al., "Separate Determination of Anticoccidial Thiamine Analogs by High-performance Liquid Chromatography," *ActaA Vitaminol. Et Enzymol*, 1984, vol. 6 (2), pp. 137-142.

Hyo-Kyung Han, Targeted prodrug design to optimize drug delivery, AAPS Pharmsci 2000, 2(10), article 6, p. 1-11.

Oatis et al., "Synthesis of quinazoline analogues of folic acid modified at position 10," *Journal of Medical Chemistry*, 20: 1393-1396 (1977).

Patrick et al., "Folate Receptors As Potential Therapeutic Targets in Choroid Plexus Tumors of Sv40 Transgenic Mice," *J. Neurooncol,*. 32(2): 111-123 (1997).

Patrick et al., "Intracerebral bispecific ligand-antibody conjugate increases survival of animals bearing endogenously arising brain tumors," *Int. J. Cancer*, 78(4): 470-79 (1998).

Pizzorno G., et al., "Intracellular metabolism of 5,10-dideazatetrahydrofolic acid in human leukemia cell lines," *Molecular Pharmacology*, 1991, 39 (1), pp. 85-89.

Plante et al., "Polyglutamyl and polylysyl derivatives of the lysine analogues of folic acid and homofolic acid," *Journal of Medical Chemistry*, 19: 1295-1299 (1976).

Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.

Prabhu V. et al., "Arabidopsis dihydropteroate synthase: general properties and inhibition by reaction product and sulfonamides," *Phytochem.*, 1997; 45(1): 23-27.

Prasad et al., "Functional coupling between a bafilomycin A1-sensitive proton pump and a probenecid-sensitive folate transporter in human placental choriocarcinoma cells," *Biochim. Biophys. Acta*, 1994; 1222(2): 309.

Yashveer Singh et al, Recent trends in targeted anticancer prodrug and conjugate design, Curr Med Chem, 2008, 15(18): 1802-1826.

Pratt, A.G. et al. "The Hydrolysis of Mono-, Di, and Triglutamate Derivatives of Folic Acid With Bacterial Enzymes," *The Journal of Biological Chemistry*, 1968, vol. 243, No. 24, pp. 6367-6372.

Punj, V. et al., "Effect of Vitamin D Analog (1 α Hydroxy D5) Immunoconjugated to Her-2 Antibody on Breast Cancer," *Int. J. Cancer*, 2004; 108: 922-929.

Ranasinghe, M. G. et al.; "A Facile Synthesis of Unsymmetrical Thiolsulfonates via Sulfonylation of Mercaptans," *Synthetic Communications*, 1988; 18(3), pp. 227-232.

Reddy et al., "Optimization of folate-conjugated liposomal vectors for folate receptor-mediated gene therapy," *J. Pharm. Sci*, 88(11): 1112-1118 (1999).

Reddy et al., "Preclinical evaluation of EC145, a folate-vinca alkaloid conjugate," *Cancer Res.*, 2007; 67:4434-42.

Reddy et al., "Retargeting of viral vectors to the folate receptor endocytic pathway," *J Control Release*, 74(1-3): 77-82 (2001).

Reddy, J. A., Low, P. S., "Folate-Mediated Targeting of Therapeutic and Imaging Agents to Cancers," *Crit. Rev. Ther. Drug Carrier Syst.*, vol. 15, No. 6, 1998, pp. 587-627.

Remington: The Science & Practice of Pharmacy, 21th Edition (Lippincott Williams & Wilkins, 2005).

Testa B, Prodrug Research: Futile or Fertile?, Biochem Pharm, 2004, 68, pp. 2097-2106.

Renz P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52c, pp. 287-291.

Rijnboutt et al., "Endocytosis of GPI-linked membrane folate receptor-alpha," *J. Cell Biol.*, 132(1-2): 35-47 (1996).

Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).

Roberts et al., "Folic acid analogs. Modifications in the benzene-ring region. 2. Thiazole analogs," *Journal of Medical Chemistry*, 15: 1310-1312 (1972).

Roberts et al., "Folic acid analogs. Modifications in the benzene-ring region. 1. 2'- and 3'-Azafolic acids," *Journal of Medical Chemistry*, 14: 125-130 (1971).

Roberts et al., "Folic acid analogs. Modifications in the benzene-ring region. 4. 3'-Ethyl- and 3'-isopropylfolic acids," *Journal of Medical Chemistry*, 17: 219-222 (1974).

Ross et al., "Differential regulation of folate receptor isoforms in normal and malignant tissues in vivo and in established cell lines. Physiologic and clinical implications," *Cancer*, 73(9): 2432-2443, (1994).

Rothberg et al, "Cholesterol controls the clustering of the glycophospholipid-anchored membrane receptor for 5-methyltetrahydrofolate," *J. Cell Biol.*, 111(6): 2931-2938 (1990).

Ettmayer et al, Lessons learned from marketed and investigational prodrugs, J. Med Chem, 2004, 47(10), pp. 2393-2404.

Rothberg et al., "The glycophospholipid-linked folate receptor internalizes folate without entering the clathrin-coated pit endocytic pathway," *J. Cell Biol.*, 110(3): 637-649 (1990).

Roy et al., "Targeting T cells against brain tumors with a bispecific ligand-antibody conjugate," *Int. J. Cancer* 76(5): 761-66 (1998).

Sadasivan et al., "The complete amino acid sequence of a human folate binding protein from KB cells determined from the cDNA," *J. Biol. Chem.*, 1989; 264: 5806-5811.

(56) References Cited

OTHER PUBLICATIONS

Sargent D.R. et al., "Antimetabolites of Pantothenic Acid, Ureido- and Carbamoyl-Derivatives," *Texas Reports on Biology and Medicine*, 1975, vol. 33, No. 3, pp. 433-443.
Scott J.M, "Preparation and Purification of Pteroic Acid from Pteroylglutamic Acid (Folic Acid)," *Methods in Enzymology*, 1980, vol. 66, pp. 657-660.
Search Report for Taiwan Patent Application No. 093101735, dated Jul. 14, 2007, 1 page.
Semb J. et al., "Pteroic Acid Derivatives. V. Pteroyl-α-glutamyl-α-glutamylglutamic Acid, Pteroyl-γ-glutamyl-α-glutamylglutamic Acid, Pteroyl-α-glutamyl-γ-glutamylglutamic Acid," *JACS*, 1949; 71 (7): 2310-2315.
Senter et al., "Development of a Drug-Release Strategy Based on the Reductive Fragmentation of Benzyl Carbamate Disulfides," *J. Org. Chem.*, 55: 2975-2978 (1990).
Machine Translation of WO 2004/005326, Jan. 15, 2004, pp. 1-5.
Shimizu M. et al., "Synthesis and biological activities of new 1alpha, 25-dihydroxy-19-norvitamin D3 analogs with modifications in both the A-ring and the side chain," *Bioorganic & Medicinal Chemistry*, 2006; 14(12): 4277-94.
Shoup T.M. et al., "Synthesis of Fluorine-18-Labeled Biotin Derivatives: Biodistribution and Infection Localization," *J. Nucl. Med.*, 1994; 35: 1685-1690.
Skinner W.A. et al., "Structure-Activity Relations in the Vitamin E Series. II. Derivatives of α-Tocopherol Substituted at the 5-Methyl Group," *J. Med. Chem.*, 1969; 12 (1): 64-66.
Smart et al., "Clustered folate receptors deliver 5-methyltetrahydrofolate to cytoplasm of MA104 cells," *J. Cell Biol.*, 134(5): 1169-1177 (1996).
Smart et al., "Protein kinase C activators inhibit receptor-mediated potocytosis by preventing internalization of caveolae," *J. Cell Biol.*, 124(3): 307-313 (1994).
Spry C. et al., "A Class of Pantothenic Acid Analogs Inhibits Plasmodium Falciparum Pantothenate Kinase and Represses the Proliferation of Malaria Parasites," *Antimicrobial Agents and Chemotherapy*, 2005; 49(11): 4649-4657.
Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).
Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.
Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.
Takeda, K. et al., "A Synthesis of a New Type of Alkoxycarbonylating Reagents from 1,1-Bis[6-(trifluoromethyl)benzotriazolyl] Carbonate (BTBC) and Their Reactions," *Sythesis*, 1987; 6: 557-560.
Temple et al., "Synthesis of pseudo cofactor analogs as potential inhibitors of the folate enzymes," *Journal of Medical Chemistry*, 25: 161-166 (1982).
Theti, D. S. et al., "Selective delivery of CB300638, a cyclopenta[g]quinazoline-based thymidylate synthase inhibitor into human tumor cell lines overexpressing the alpha-isoform of the folate receptor," Cancer Res. 2003; 63(13): 3612-3618.
Toffoli et al., "Overexpression of folate binding protein in ovarian cancers," *Int. J. Cancer* 74(2): 193-198 (1997).
Toraya T. et al , "Immobilized Derivatives of Vitamin B12 Coenzyme and Its Analogs," *Methods in Enzymology*, vol. 67, pp. 57-66.
Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.
DeVita, Jr., Vincent et al (eds); *Biologic Therapy of Cancer*; 2nd ed., J.B. Lippincott Company; 1995.
Trachewsky D., "Antihypertensive Effect of Riboflavin Analogs in Rats with Mineralocorticoid-Induced Hypertension," *Hypertension*, 1981; vol. 3, No. 1, pp. 75-80.

Truneh A. et al., "Temperature-sensitive differential affinity of Trail for its receptors. DR5 is the highest affinity receptor," *J Biol Chem*, 2000; 275(30):23319-25.
Turek et al., "Endocytosis of folate-protein conjugates: ultrastructural localization in KB cells," *J. Cell Sci.* 106: 423-430 (1993).
Turk et al., "Characterization of a novel pH-sensitive peptide that enhances drug release from folate-targeted liposomes at endosomal pHs," *Biochim Biophys Acta*, 1559(1): 56-68 (2002).
Ueda M. et al., "Effect of Vitamin B12 Derivatives on Urinary Excretion of Methylmalonic Acid in Liver Diseases," *Acta Med. Okayama*, 1970; vol. 24, pp. 365-372.
Varma, R. et al., "GPI-anchored proteins are organized in submicron domains at the surface," *Nature*, 394(6695): 798-801 (1998).
Verwey, J., "Mitomycin C-Induced Renal Toxicity, a Dose-Dependent Side Effect?," *Eur J Cancer Clin Onco*, 1987; vol. 23, No. 2, pp. 195-199.
Vesely D.L. et al., "Biotin Analogs Activate Guanylate Cyclase," *Molecular and Cellular Biochemistry*, 1984; vol. 60, pp. 109-114.
Domling A. et al., "Myxobacterial Epothilones and Tubulysins as Promising Anticancer Agents," *Molecular Diversity*, 2005; 9: 141-147.
Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.
Vogel et al., "Peptide-Mediated Release of Folate-Targeted Liposome Contents From Endosomal Compartments," *J. Am. Chem. Soc.*, 1996; 118(7): 1581-1586.
Vyas D. et al., "A practical synthesis of mitomycin A and its analogs," *J Org Chem*, 1986; 31:4307-4309.
Wang et al., "Delivery of antisense oligodeoxyribonucleotides against the human epidermal growth factor receptor into cultured KB cells with liposomes conjugated to folate via polyethylene glycol," *Proc. Natl. Acad. Sci. USA*, 92(8): 3318-3322 (1995).
Wang et al., "Design and synthesis of [111In]DTPA-folate for use as a tumor-targeted radiopharmaceutical," *Bioconjug Chem.*, 8(5): 673-679 (1997).
Wang et al., "Synthesis, purification, and tumor cell uptake of 67Ga-deferoxamine—folate, a potential radiopharmaceutical for tumor imaging," *Bioconj. Chem.*, 1996; 7(1): 56-62.
Wang S. et al., "Folate-mediated targeting of antineoplastic drugs, imaging agents, and nucleic acids to cancer cells," *J. Control Rel*, 1998; 53(1-3): 39-48.
Wang, Xiu-Fang et al., "Vitamin E Analogs Trigger Apoptosis in HER2/erbB2-Overexpressing Breast Cancer Cells by Signaling Via the Mitochondrial Pathway," *Biochemical and Biophysical Research Communication*, 2005; vol. 326, pp. 282-289.
Hofle, G. et al., "Semisynthesis and Degradation of the Tubulin Inhibitors Epothilone and Tubulysin", 2003, *Pure Appl. Chem.*, vol. 75, Nos. 2-3, pp. 167-178.
Weinstock et al., "Folic acid analogs. II. p-{[(2,6-Diamino-8-purinyl)methyl]amino}-benzoyl-L-glutamic acid and related compounds," *Journal of Medical Chemistry*, 13: 995-997 (1970).
Weitman et al., "Cellular localization of the folate receptor: potential role in drug toxicity and folate homeostasis," *Cancer Res.*, 1992; 52(23): 6708-6711.
Weitman et al., "Distribution of the folate receptor GP38 in normal and malignant cell lines and tissues," *Cancer Res.*, 1992; 52(12): 3396-3401.
Westerhof GR et al., "A photoaffinity analogue of folic acid as a probe for the identification and function of a membrane folate binding protein (mFBP) in human CCRF-CEM leukemia cells," *Proccedings of the American Association for Cancer Research*, 1991; 32:328.
Wiener et al., "Targeting dendrimer-chelates to tumors and tumor cells expressing the high-affinity folate receptor," *Invest. Radiol.* 32(12): 748-54 (1997).
Wu M. et al., "Clustering of GPI-anchored folate receptor independent of both cross-linking and association with caveolin," *J. Membr. Biol.* 159(2): 137-147 (1997).

(56) References Cited

OTHER PUBLICATIONS

Zimmer H. et al., "Potential anticancer agents V., Synthesis of folic acid and pteroic acid analogs derived of caffeine and theophylline," *Arzneimittelforschung*, 1966, 16(4), pp. 541-545.

Zimmerman, J., "Folic acid transport in organ-cultured mucosa of human intestine. Evidence for distinct carriers," *Gastroenterol.* 99(4): 964-972 (1990).

Lee, Francis Y. F., et al., "BMS-247550: A Novel Epothilone Analog With a Mode of Action Similar to Paclitaxel But Possessing Superior Antitumor Efficacy," *Clin Cancer Res*, 2001, No. 7, pp. 1429-1437.

Angier, R. B., et al., "Pteroic Acid Analogs Containing Arsenic," J. American Chem. Soc., vol. 76, 1954, pp. 902-904.

Boothe, J. H., et al., "Pteroic Acid Derivatives. II. Pteroyl-γ-glutamylglutamic Acid and Pteroyl-γ-glutamyl-γ-glutamylglutamic Acid," J. American Chem. Soc., vol. 70, 1948, pp. 1099-1102.

Bartels R. et al., "Determination of pteroic acid by high-performance thin-layer chromatography: Contribution to the investigation of 7,8-dihydropteroate synthase," *Journal of Chromatography A*, 1994; vol. 659(1): 185-189 (abstract only).

Wikipedia, Derivative (Chemistry), http://en.wikipedia.org/wiki/Derivative_(chemistry), downloaded Dec. 16, 2009.

Wikipedia, Analog (Chemistry), http://en.wikipedia.org/wiki/Analog_(chemistry), downloaded Dec. 16, 2009.

Wikipedia, Solution, http://en.wikipedia.org/wiki/Solution, downloaded Dec. 17, 2009.

Wikipedia, List of Purification Methods in Chemistry, http://en.wikipedia.org/wiki/List_of_purification_methods_in_chemistry, downloaded Dec. 16, 2009.

Melby, E.L. et al, "Entry of Protein Toxins in Polarized Epithelial Cells"; *Cancer Research*, 1993; 53: 1755-1760.

Olsnes S. et al., "Immunotoxins-entry into cells and mechanisms of action," *Immunology Today*, 1989; vol. 10, No. 9, pp. 291-295.

Principles of Ion Exchange Chromatography, http://www.separations.us.tosohbioscience.com/ServiceSupport/TechSupport/ResourceCenter/PrinciplesofChromatography/IonExchange, downloaded Dec. 23, 2009.

Wikipedia, Conjugate, http://en.wikipedia.org/wiki/Conjugate, downloaded Dec. 17, 2009.

Wikipedia, Complex (Chemistry), http://en.wikipedia.org/wiki/Complex_(chemistry), downloaded Dec. 23, 2009.

Leamon Christopher P., "Aspects of Folate-Mediated Drug Delivery . . . Beyond Purdue" PowerPoint Presentation presented at Purdue University on May 4, 1999, (22 pages).

Achilefu et al. "A New Method for the Synthesis of Tri-tert-butyl Diethylenetriaminepentaacetic Acid Its Derivatives" *J. Org. Chem.* 2000;65:1562-1565.

Carl et al. "A novel connector linkage applicable in prodrug design" J. Med. Chem. 1981;24(5):479-480.

Coney et al. "Cloning of a tumor-associated antigent: MOv18 and MOv19 antibodies recognize a folate-binding protein" Cancer Res. 1991;51(22):6125-32.

Crapatureanu et al. "Molecular necklaces. Cross-linking hemoglobin with reagents containing covalently attached ligands" Bioconjugate Chemistry, 1999;10(6):1058-67.

Peltier, Hillary M., et al., "The Total Synthesis of Tubulysin D," 2006, *J. Am. Chem. Soc.*, No. 128, pp. 16018-16019.

Darnell, Ed. Molecular Cell Biology W. H. Freeman, San Francisco 1990;326-333.

DeNardo, Gerald. "When is Too Much Too Much and Yet Not Enough? Alas, a Plethora of Opportunities but Where's the Beef?" J. of Nuclear Medicine 2000; 41(3):470-3.

Dorwald, F. Z., "Side Reactions in Organic Synthesis: A Guide to Successful Synthesis Design," Wiley-VCH, Weinheim, 2005, p. ix of preface.

Forgac. "Structure and function of vacuolar class of ATP-driven pumps" Physiological Rev. 1989; 69(3): 765-795.

Garrett et al. "Synthesis and characterisation of polyamine-poly(ethylene glycol) constructs for DNA binding and gene delivery" Bioorganic & Medicinal Chemistry, 2000; 8(7):1779-1797.

Henderson et al. "Mediated uptake of folate by a high-affinity binding protein in sublines of L1210 cells adapted to nanomolar concentrations of folate" J. Membrane Biol., 1988;101:247-258.

Huang et al. "Design, syntheses and sequence selective DNA cleavage of functional models of bleomycin-II. 1,2-trans-di substituted cyclopropane units as novel linkers" Bioorganic & Medicinal Chemistry, 1995;3(6):647-57.

Jansen et al., "Identification of a Membrane-Associated Folate-Binding Protein in Human Leukemic CCRF-CEM Cells with Transport-Related Methotrexate Resistance"In Cancer Res., 1989, 49, 2455-2459.

Raghavan B et al., "Cytotoxic Simplified Tubulysin Analogues," *J. Med. Chem.*, 2008; 51(6), pp. 1530-1533.

Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.

Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.

Kamen et al., 1986, "Receptor-mediated folate accumulation is regulated by cellular folate content" Proc. Natl. Acad. Sci., U.S.A. 83, 5983-5987.

Ke et al. "Targeting the Tumor-Associated Folate Receptor with a I" IN-DTPA Conjugate of Pteroic Acid" Abstract No. 427. 48'h Annual Meeting of the Society of Nuclear Medicine Toronto, Canada, Jun. 26, 2001, available May 4, 2001; 1 pg.

Kemp et al. "New Protective Groups for Peptide Synthesis-I the Bic Group Base and Solvent Lability of the 5-B enzi soxazolymethyl eneoxycarbonyl amino function" Tet. Lett. 1975;52:4625-4628.

Kutsky RJ. Handbook of Vitamins, Minerals, and Hormones, 2" Edition. New York: Van Nostrand Reinhold: 1981;263-277.

Lee et al. "Prolonged circulating lives of single-chain Fv proteins conjugated with polyethylene glycol: a comparison of conjugation chemistries and compounds" Bioconjugate Chemistry, 1999;10(6):973-81.

Li et al. "Local concentration of folate binding protein GP38 in sections of human ovarian carcinoma by concentration of in vitro quantitative autoradiography." J. Nucl. Med. 1996; 37:665-672.

Rose W.C., "Taxol-Based Combination Chemotherapy and Other In Vivo Preclinical Antitumor Studies," *J Natl Cancer Inst Monogr*, 1993, No. 15, pp. 47-53.

Linder et al., In vitro & in vivo studies with a- and y-isomers of 99'Tc-oxa folate show uptake of both isomers in folate receipt (+) KB Cell Lines J. Nuclear Med. 2000;41(5):470 Suppl.

Mehvar R "Dextrans for targeted and sustained delivery of therapeutic and imaging agents" [Review] Journal of Controlled Release, 2000;69(1):1-25.

Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.

Miotti et al., "Characterization of Human Ovarian Carcinoma-Associated Antigens Defined by Novel Monoclonal Antibodies with Tumor-Restricted Specificity" Int. J. Cancer, 1987;39:297-303.

Pastan et al, eds. "The Pathways of Endocytosis" Endocytosis, Plenum Press, New York 1985;1-40.

Peterson et al. "Enzymatic cleavage of peptide-linked radiolabels from immunoconjugates" Bioconjugate Chemistry, 1999;10(4):553-7.

Pizzorno et al. "5,10-Dideazatetrahydrofolic acid (DDATHF) transport in CCRFCEM and MA104 cell lines." J. Biol, Chem., 1993; 268(2):247-258.

Rothenberg et al. "Further observations on the folate-binding factor in some leukemic cells" J. Clin. Invest. 1971; 50(3):719-726.

Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53, No. 9, pp. 879-885.

Selhub et al. "The folate binding protein of rat kidney. Purification, properties, and cellular distribution" J. Biol. Chem. 1984;259(10):6601-6606.

(56) References Cited

OTHER PUBLICATIONS

Selhub et al. "Renal folate adsorption and the kidney folate binding protein I. Urinary Clearance studies" Am. J Physiol. 252:F750-F756.
Selhub et al. "Renal folate adsorption and the kidney folate binding protein II. Microinfusion studies" Am. J. Physiol. 252:F757-F760.
Sirotnak. "Obligate genetic expression in tumor cells of a fetal membrane property mediating "Folate" transport: biological significance and implications for improved therapy of human cancer" Cancer Res., 1985;45(9):3992-4000.
Stein et al. "Normal tissue reactivity of four anti-tumor monoclonal antibodies of clinical interest" Int. J. Cancer 1991;47(2):163-169.
Tanaka et al. "Preparation and characterization of a disulfide-linked bioconjugate of annexin V with the B-chain of urokinase: an improved fibrinolytic agent targeted to phospholipid-containing thrombi" Biochemistry, 1996;35(3):922-9.
Thaden et al. "Photoaffinity behavior of a conjugate of oligonucleoside methylphosphonate, rhodamine, and psoralen in the presence of complementary oligonucleotides" Bioconjugate Chemistry, 1993;4(5):386-94.
Toffoli et al. "Expression of folate binding protein as a prognostic factor for response to platinum-containing chemotherapy and survival in human ovarian cancer" Int. J. Cancer (Pred. Oncol) 1998; 79:121-126.
Steinmetz, H. et al., "Isolation, Crystal and Solution Structure Determination, and Biosynthesis of Tubulysins—Powerful Inhibitors of Tubulin Polymerization from Microbacteria", *Angew. Chem. Int. Ed.*, 2004, No. 43, pp. 4888-4892.
Weitman et al. "Distribution of the folate receptor GP38 in normal and malignant cell lines and tissues" Cancer Res. 1992;52(12):3396-3401.
Westerhof et al. "Membrane transport of natural folates and antifolate compounds in murine L1210 Leukemia cells: role of carrier-and receptor mediated transport systems" Cancer Res. 1991;51:5507-5513.
Williams et al. "Renal tubular transport of folic acid and methotrexate in the monkey" Am. J. Physiol 1982; 242(5):F484-490.
Weygand, et al., Chemishe. Berichte (1950) 83, 460-467.
Beevers, Christopher S., et al., "Curcumin Inhibits the Mammalian Target of Rapamycin-Mediated Signaling Pathways in Cancer Cells", 2006; *Int. Journal Cancer*; Vo. 119; pp. 757-764.
Brown, Nicole E., et al., "Delayed Cystogenesis and Increased Ciliogenesis Associated with th Re-Expression of Polaris in Tg737 Mutant Mice", 2003, *Kidney International*, vol. 63, pp. 1220-1229.
Bukanov Nikolay, O. et al., "Long-Lasting Arrest of Murine Polycystic Kidney Disease With CDK Inhibitor Roscovitine", Dec. 14, 2006; *Nature*; vol. 444; pp. 949-952.
Hay, Nissim, et al., "Upstream and Downstream of mTOR", 2004, *Genes & Development*, vol. 18, No. 16, pp. 1926-1945.
Westerhof G.R. et al., "Carrier- and Receptor-Mediated Transport of Folate Antagonists Targeting Folate-Dependent Enzymes: Correlates of Molecular-Structure and Biological Activity," *Molecular Pharmacology*, 1995, 48, pp. 459-471.
Kennedy, Michael D., et al., "Evaluation of Folate Conjugate Uptake and Transport by the Choroid Plexus o Mice", (May 2003), vol. 20, No. 5, pp. 714-719.
Leamon, Christopher P., et al., "Folate-Liposome-Mediated Antisense Oligodeoxynucleotide Targeting to Cancer Cells: Evaluation in Vitro and in Vivo", 2003, *Bioconjugate Chemistry*, vol. 14, No. 14, No. 4, pp. 738-747.
Nauta, Jeroen, et al., "Renal and Biliary Abnormalities in a New Murine Model of Autosomal Recessive Polycystic Kidney Disease", 1993, *Pediatr. Nephrol.* No. 7, pp. 163-172.
Piontek, Klaus B., et al. "A Functional Floxed Allele of Pkd1 that Can Be Conditionally Inactivated In Vivo", *J Am. Soc. Nephrol.* vol. 15, pp. 3035-3043.
Shillingford, Jonathan M., et al., "The mTOR Pathway is Regulated by Polycystin-1, and its Inhibition Reverses Renal Cystogenesis in Polycyctic Kidney Disease", Apr. 4, 2006, *PNAS.* vol. 103, No. 14, pp. 5466-5471.

Ke CY et al., "Folate-Receptor-Targeting of In-111 Using Pteroic Acid Conjugates of Benzyl-DTPA and Benzyl-DOTA," J. Nucl. Med., 2004; 45(5):457P.
Regueiro-Ren et al., "Synthesis and Biological Activity of Novel Epothilone Aziridines," Organic Letters, 2001; vol. 3, No. 17: 2693-96.
Kamen et al., "A review of folate receptor alpha cycling and 5-methyltetrahydrofolate accumulation with an emphasis on cell models in vitro," Advanced Drug Delivery Reviews, 2004; vol. 56:1085-97.
Atkinson SF et al., "Conjugation of folate via gelonin carbohydrate residues retains ribosomal-inactivatin properties of the toxin and permits targeting to folate receptor positive cells," Journal of Biological Chemistry 2001; 276(30):27930-27935.
Elnakat et al., "Distribution, functionality and gene regulation of folate receptor isoforms: implications in targeted therapy," Advanced Drug Delivery Reviews, 2004; vol. 56:1067-84.
Sabharanjak et al., "Folate receptor endocytosis and trafficking," Advanced Drug Delivery Reviews, 2004; vol. 56: 1099-1109.
Paulos et al., "Folate receptor-mediated targeting of therapeutic and imaging agents to activated macrophages in rheumatoid arthritis," Advanced Drug Delivery Reviews, 2004; vol. 56: 1205-17.
Antony, "Folate receptors: reflections on a personal odysssey and a perspective on unfolding truth," Advanced Drug Delivery Reviews, 2004; vol. 56: 1059-66.
Lu et al., "Folate receptor-targeted immunotherapy of cancer: mechanism and therapeutic potential," Advanced Drug Delivery Reviews, 2004; vol. 56: 1161-76.
Roy et al., "Folate-mediated targeting of T cells to tumors," Advanced Drug Delivery Reviews, 2004; vol. 56: 1219-31.
Ke et al., "Folate-receptor-targeted radionuclide imaging agents," Advanced Drug Delivery Reviews, 2004; vol. 56: 1143-60.
Gabizon et al., "Tumor cell targeting of liposome-entrapped drugs with phospholipid-anchored folic acid-PEG Conjugates," Advanced Drug Delivery Reviews, 2004; vol. 56: 1177-92.
Matulic-Adamic J et al., "An efficient synthesis of the ribozyme-folate conjugate," Tetrahedron Letters, 2002 43(25):4439-4441.
Zhao et al., "Tumor-selective targeted delivery of genes and antisense oligodeoxyribonucleotides via the folate receptor," Advanced Drug Delivery Reviews, 2004; vol. 56: 1193-1204.
Paulos CM et al., "Ligand Binding and Kinetics of Folate Receptor Recycling in Vivo: Impact on Receptor-Mediated Drug Delivery," Molecular Pharmacology, 2004; 66:1406-1414.
Griesser UJ, "The Importance of Solvents," in Polymorphism in the Pharmaceutical Industry, Hilfiker ed., 2006; p. 211-230.
Wikipedia, Structural analog, http://en.wikipedia.org/wiki/Structural_analog, downloaded Apr. 7, 2009.
Wikipedia, Folic acid, http://en.wikipedia.org/wiki/Folic_acid, downloaded Apr. 7, 2009.
Wikipedia, Functional analog, http://en.wikipedia.org/wiki/Functional_analog, downloaded Apr. 7, 2009.
Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.
Harrison JG et al., A convenient synthetic route to oligonucleotide conjugates,: Bioorganic & Medicinal Chemistry Letters, 1997; 7(8): 1041-1046.
Dyson G., May P. "The Chemistry of Synthetic Pharmaceutical Substances", translation from English M.:-"The World", 1964, pp. 12-19.
Mashkovskiy M.D. Drugs, Moscow, New wave, 2001, vol. I, p. 11.
Robert Laplanche, et al.,"Physiologically Based Pharmacokinetic (PBPK) Modeling of Everolimus (RAD001) in Rats Involving Non-Linear Tissue Uptake,"Journal of Pharmacokinetics and Pharmacodynamics, 2007, vol. 34, No. 3, 373-400.
Pathalk et al., Enzymic protecting group techniques in organic synthesis, Stereosel. Biocatal. 775-797 (2000).
Dube D et al., "Preparation and Tumor Cell Uptake of Poly(N-isopropylacrylamide) Folate Conjugates"; *Bioconjugate Chem*, 2002; 13: 685-692.
Evans et al., "Synthesis of biotin conjugates of the antifungal compound cymoxanil," *Pest Manag Sci*, 2002; 58: 392-396.

(56) References Cited

OTHER PUBLICATIONS

Rao et al., Journal of Medicinal Chemistry, 1985, 28:1079-1088.
Conrad et al, Journal of Medicinal Chemistry, 1979, 22(4): 391-400.
Wang et al., "Structure-activity and high-content imaging analyses for novel tubulysins," Chemical Biology & Drug Design, 2007; 70(2): 75-86.
Patterson et al., "Design, synthesis, and biological properties of highly potent tubulysin D analogues," Chemistry—A European Journal, 2007; 13(34): 9534-9541.
Golub, T.R., et al., "Molecular Classification of Cancer: Class Discovery and Class Prediction by Gene Expression Monitoring," Science, 1999, vol. 286, 531-537 (Oct. 15, 1999).
Speckamp, et al.; "New Developments in the Chemistry of N-Acyliminium Ions and Related Intermediates" Tetrahedron 2000 vol. 56(24) 3817-3856.
Angier et al., Science, 1946, 103: 667-669.
Wolf et al., Journal of the American Chemical Society, 1947, 69: 2753-2759.
Parker et al., "Folate receptor expression in carcinomas and normal tissues determined by a quantitative radioligand binding assay," Analytical Biochemistry, 2005; 335:284-293.
Remy et al., Proceedings of the National Academy of Sciences of the United States of America, 1999, vol. 96, No. 10, pp. 5394-5399.
Na, Wang, and Kohn, "7-N-(Mercaptoalkylmitomycins: Implications of Cyclization for Drug Function," J Am Chem Soc 124:4666-77 (2002.
Putnam et al., "Polymer conjugates with anticancer activity", Advances in Polymer Science 1995, 122, 55-123.
Umemoto et al., "Molecular design of methotrexate-antibody conjugates for targeted cancer treatment", Journal of Bioactive and Compatible Polymers, 1992, 7(2), 191-219.
Sanderson et al., "In vivo drug-linker stability of an anti-CD30 dipeptide-linked auristatin immunoconjugate," *Clinical Cancer Research*, 2005; 11:843-852.
Wu et al., "Enhancing the enantioselectivity of candida lipase catalyzed ester hydrolysis via noncovalent enzyme modification," *Journal of American Chemical Society*, 1990; 112:1990-1995.
Patterson et al., "Expedient synthesis of N-Methyl tubulysin analogues with high cytotoxicity," *Journal of Organic Chemistry*, 2008; 73:4365-4369.
Gabizon et al., Clin Cancer Res 9:6551-59 (2003).
Pouvreau, Isabelle et al.: "Effect of macrophage depletion by liposomes containing dichloromethylene-diphosphonate on endotoxin induce uveitis." J. Neuroimmun. (1998)86 p. 171-181.
Lindstedt, E.W. et al.; "Anti-tnf-alpha therapy for sight threatening uveitis." Br. J. Opthalmol. (2005) 89 p. 533-536.
Mangel, Andreas: GMP news, 2002, www.gmp-compliance.ord/eca_news_159.html, downloaded Mar. 19, 2014.
Kaneko, Takushi, "New Hydrazone Derivatives of Adiramycin and their Immunoconjugates-A Correlation between Acid Stability and Cytotoxicity", *Bioconj. Chem.*, vol. 2, No. 3, pp. 131-141 (May 1, 1991).
PCT International Search Report/Written Opinion for PCT/US2009/061049, completed Mar. 15, 2010.
Polyak et al., "Introduction of spacer peptides N-terminal to a cleavage recognition motif in recombinant fusion proteins can improve site-specific cleavage," Protein Eng., 1997; 10(6):615-9.
Univesity of Maryland Medical Center (UMMC), Vitamin B9 (folic acid), 2014, http://umm.edu/health/medical/altmed/supplement/vitamin-b9-folic-acid, pp. 1-8.
Cerner Multum, Inc., Drugs.com, Folic Acid, http://www.drugs.com/folic_acid.html?printable=1, 1996-2014, Version: 5.01, Revision Date Oct. 15, 2009, pp. 104.
PCT International Search Report and Written Opinion for PCT/US2008/056824, completed Jul. 24, 2009.
PCT International Search Report/Written Opinion prepared for PCT/US2010/061897, mailed Mar. 11, 2011.
European Search Report prepared for corresponding European Application Serial No. 08841521.1, mailed Jul. 18, 2011.
Paranjpe, et al., "Tumor-targeted bioconjugate based delivery of camptothecin: design, synthesis and in vitro evaluation," ScienceDirect Journal of Controlled Release 100 (2004) 275-292.
Yang, et al., "Characterization of the pH of Folate Receptor-Containing Endosomes and the Rate of Hydrolysis of Internalized Acid-Labile Folate-Drug Conjugates," JPET 321: 462-468, 2007.
Henne, et al., "Synthesis and activity of a folate peptide camptothecin prodrug," ScienceDirect, Bioorganic & Medical Chemistry Letters 16 (2006) 5350-5355.
PCT International Search Report/Written Opinion prepared for PCT/US2013/065079, mailed May 1, 2014.
Zaragoza, D., Side Reactions in Organic Synthesis, 2005, Wiley-VCH Verlag GmbH & Co. KGaA, Weinheim, Preface, p. 9.
Attur, M. et al., "Differential anti-inflammatory effects of immunosuppressive drugs: Cyclosporin, rapamycin and FK-506 on inducible nitric oxide synthase, nitric oxide, cyclooxygenase-2 and $PGE_2$ production," Inflamm. res., 2000, 49, 020-026.
Written Opinion prepared for Singapore Patent Application No. 11201502896X, dated Dec. 11, 2015.
Mathais et al., "Synthesis of [(99m)Tc]DTPA-folate and its evaluation as a folate-receptor-targeted radiopharmaceutical," *Bioconjug Chem*, 11(2): 253-257 (2000).
Shimizu, Kazui, et al., "Novel vitamin D3 antipsoriatic antedrugs: 16-En-22-oxa-la,25-(OH)2D3 analogs," *Bioorganic & Medicinal Chemistry*, 2006;14: 1838-1850.
Lorusso, P. M. et al., "Phase I Study of Folate Conjugate EC145 (Vintafolide) in Patients with Refractory Solid Tumors," J. Clinical Oncology, 2012, 30, No. 32, 4011-4016.
Christoper Leamon et al., "Folate Receptor specific anti-tumor activity of EC0305, a folate-tubulysin conjugate," AACR Annual Meeting, 2007, 67, 9, (abstract only).
Dong, H. et al., "Self-assembled, redox-sensitive, H-shaped pegylated methotrexate conjugates with high drug-carrying capability for intracellular drug delivery," Med. CHem. Commun., 2013, 5, 147-152.
Beil,L. "Is your breakfast giving you cancer," Prevention, updated Mar. 29, 2010, available via internet at http://www.nbcnews.com/id/35874922/ns/health-diet_and_nutrition/t/your-breakfast-giving-you-cancer/#.V40IrflVj21, 2 pages.
Adessi, C. et al., "Converting a Peptide into a Drug: Strategies to Improve Stability and Bioavailability," Current Medicinal Chemistry, 2002, 9, 963-978.

\* cited by examiner

DRUG DELIVERY CONJUGATES CONTAINING UNNATURAL AMINO ACIDS AND METHODS FOR USING

CROSS REFERENCE TO RELATED APPLICATIONS

This application is a U.S. national stage application under 35 U.S.C. §371(b) of International Application No. PCT/US2013/065079 filed Oct. 15, 2013, and claims priority under 35 U.S.C. §119(e) to U.S. Provisional Application Ser. No. 61/714,565 filed Oct. 16, 2012, U.S. Provisional Application Ser. No. 61/790,234 filed Mar. 15, 2013, U.S. Provisional Application Ser. No. 61/865,382 filed Aug. 13, 2013, and U.S. Provisional Application Ser. No. 61/877,317 filed Sep. 13, 2013. The disclosures of all the above referenced applications are incorporated herein by reference in their entirety.

TECHNICAL FIELD

The invention described herein pertains to drug delivery conjugates for targeted therapy. In particular, the invention described herein pertains to drug delivery conjugates that include polyvalent linkers comprising one or more unnatural amino acids.

BACKGROUND AND SUMMARY OF THE INVENTION

The mammalian immune system provides a means for the recognition and elimination of pathogenic cells, such as tumor cells, and other invading foreign pathogens. While the immune system normally provides a strong line of defense, there are many instances where pathogenic cells, such as cancer cells, and other infectious agents evade a host immune response and proliferate or persist with concomitant host pathogenicity. Chemotherapeutic agents and radiation therapies have been developed to eliminate, for example, replicating neoplasms. However, many of the currently available chemotherapeutic agents and radiation therapy regimens have adverse side effects because they lack sufficient selectivity to preferentially destroy pathogenic cells, and therefore, may also harm normal host cells, such as cells of the hematopoietic system, and other non-pathogenic cells. The adverse side effects of these anticancer drugs highlight the need for the development of new therapies selective for pathogenic cell populations and with reduced host toxicity.

It has been discovered herein that drug delivery conjugates that include polyvalent linkers formed from one or more unnatural amino acids are efficacious in treating pathogenic cell populations, and exhibit low host animal toxicity.

In one illustrative and non-limiting embodiment of the invention, described herein are compounds of the formula $$B\text{-}L\text{-}D_X$$

wherein each of B, L, D, and x are as defined in the various embodiments and aspects described herein.

In another embodiment, pharmaceutical compositions containing one or more of the compounds are also described herein. In one aspect, the compositions include a therapeutically effective amount of the one or more compounds for treating a patient with cancer, inflammation, and the like. It is to be understood that the compositions may include other components and/or ingredients, including, but not limited to, other therapeutically active compounds, and/or one or more carriers, diluents, excipients, and the like, and combinations thereof. In another embodiment, methods for using the compounds and pharmaceutical compositions for treating patients or host animals with cancer, inflammation, and the like are also described herein. In one aspect, the methods include the step of administering one or more of the compounds and/or compositions described herein to a patient with cancer, inflammation, and the like. In another aspect, the methods include administering a therapeutically effective amount of the one or more compounds and/or compositions described herein for treating patients with cancer, inflammation, and the like. In another embodiment, uses of the compounds and compositions in the manufacture of a medicament for treating patients with cancer, inflammation, and the like are also described herein. In one aspect, the medicaments include a therapeutically effective amount of the one or more compounds and/or compositions for treating a patient with cancer, inflammation, and the like.

BRIEF DESCRIPTION OF THE DRAWINGS

FIG. 4A shows 4/4 PRs in test animals.

DETAILED DESCRIPTION

Figure 1:
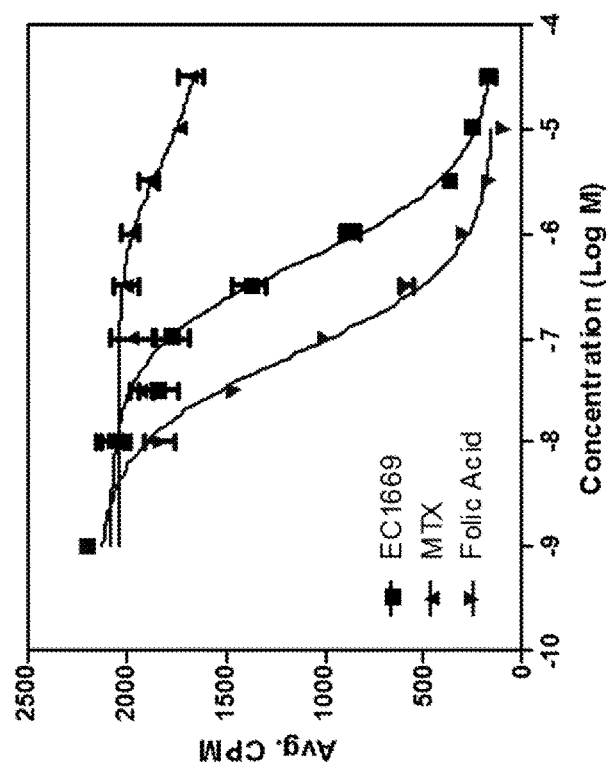
FIG. 1A shows the relative affinity of EC1669 in KB cells, 1 h at 37° C.
FIG. 1B shows the relative affinity of EC1669 in CHO-β cells, 1 h at 37° C.
Figure 1:
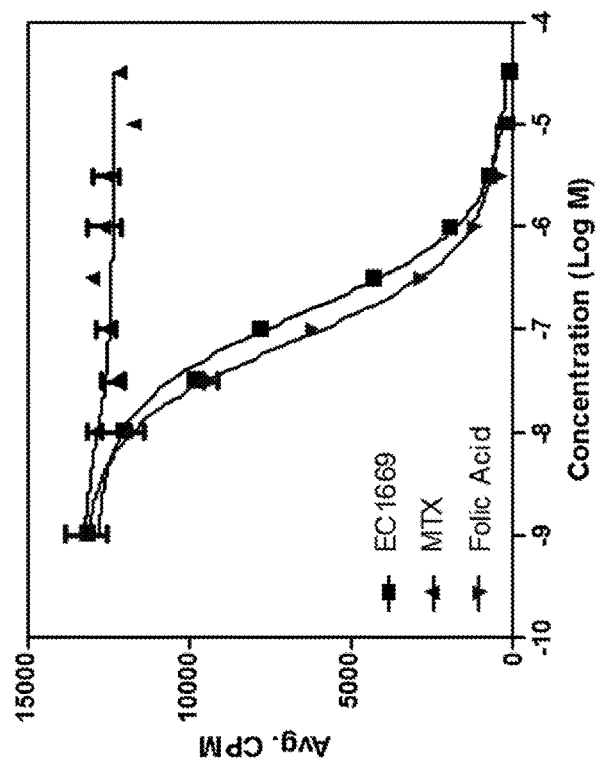

Several illustrative embodiments of the invention are described by the following clauses:

A compound of the formula B-L(D)$_x$, or a pharmaceutically acceptable salt thereof, wherein B is a radical of a cell surface receptor binding and/or targeting ligand, D is in each instance a radical of an independently selected drug, x is an integer selected from 1, 2, 3, 4 and 5; and L is a polyvalent releasable linker comprising one or more unnatural amino acids; and where B is covalently attached to L, and L is covalently attached to each D; and where the compound is not any one of or any subgroup or subset of the following formulae

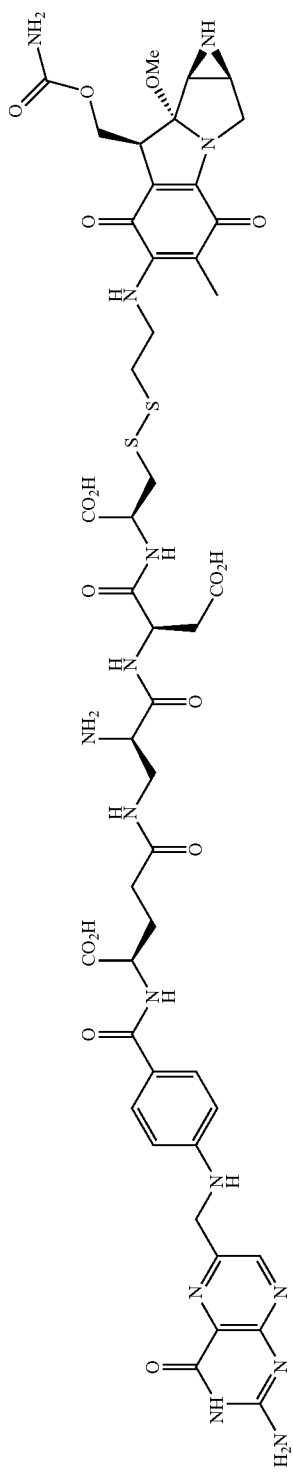
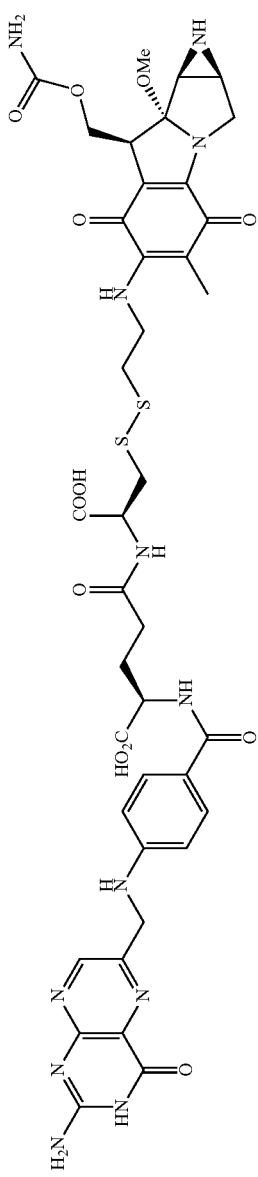

-continued
EC0056
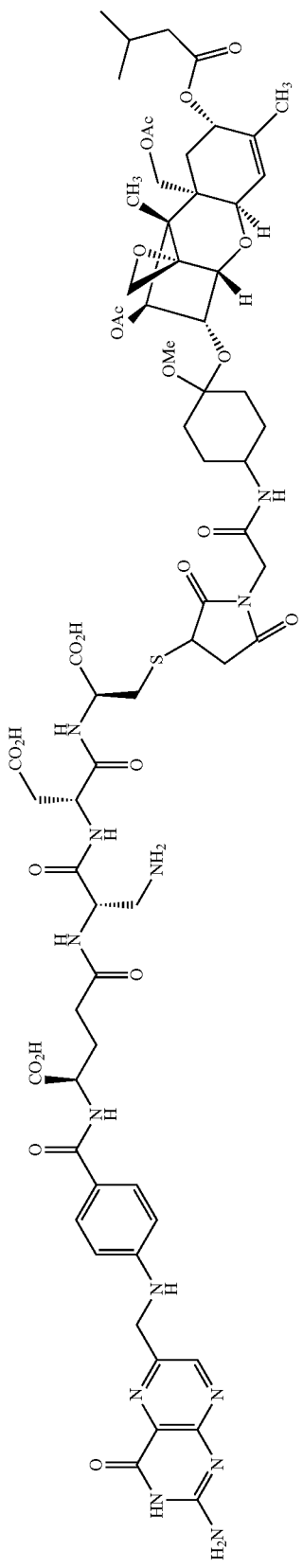
EC0074
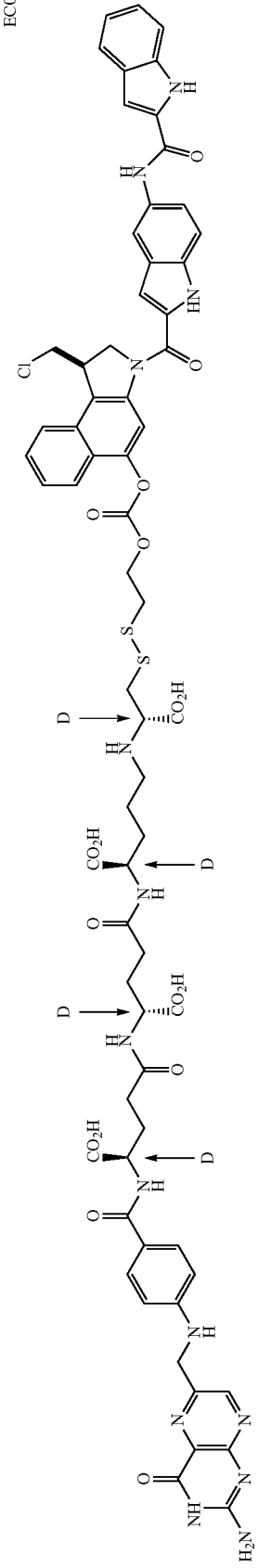

-continued
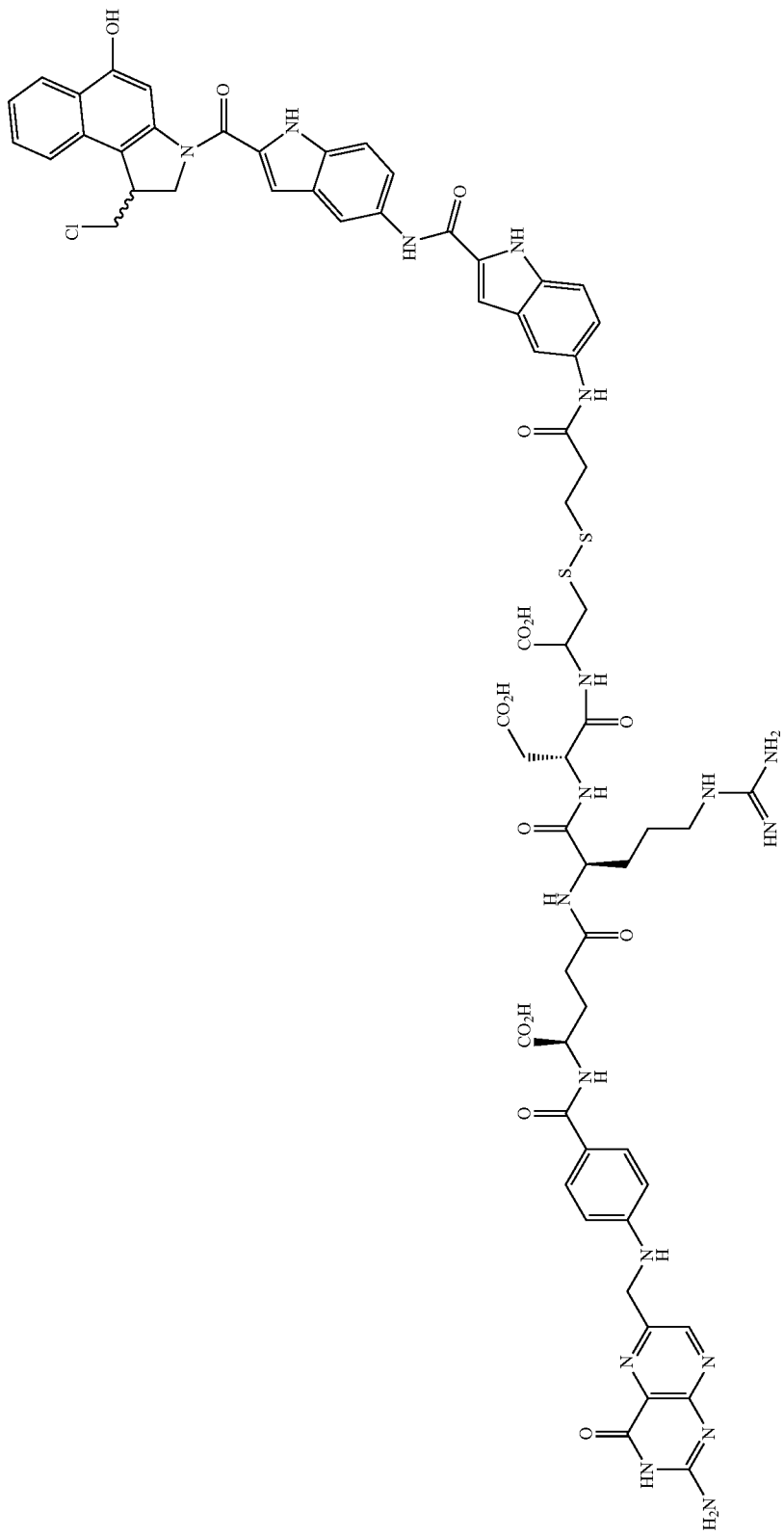

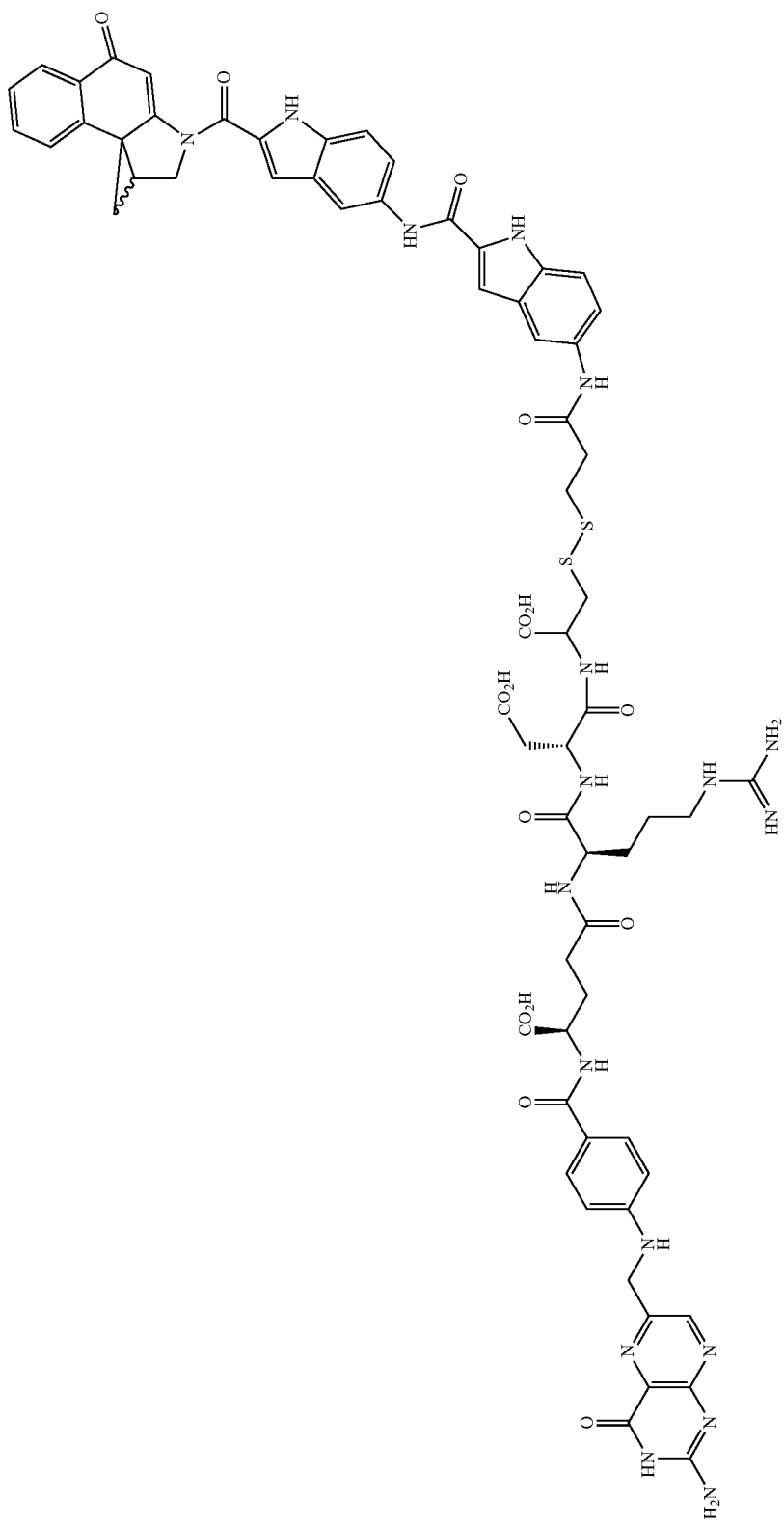

-continued
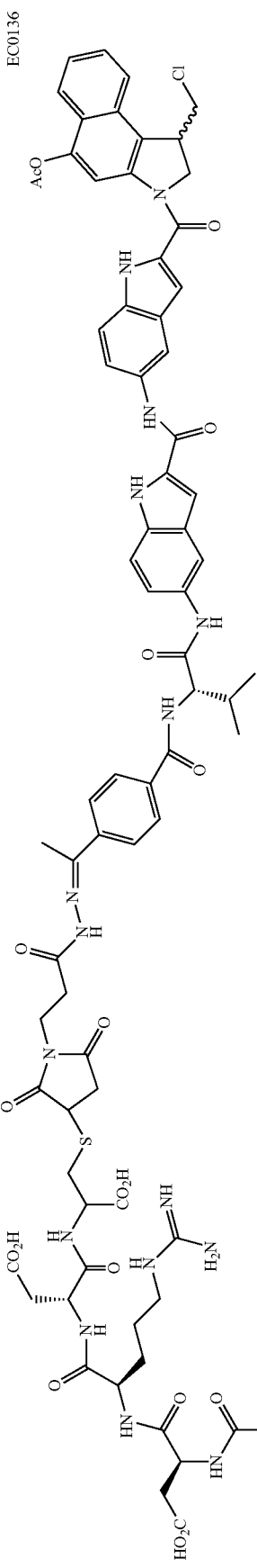
EC0136
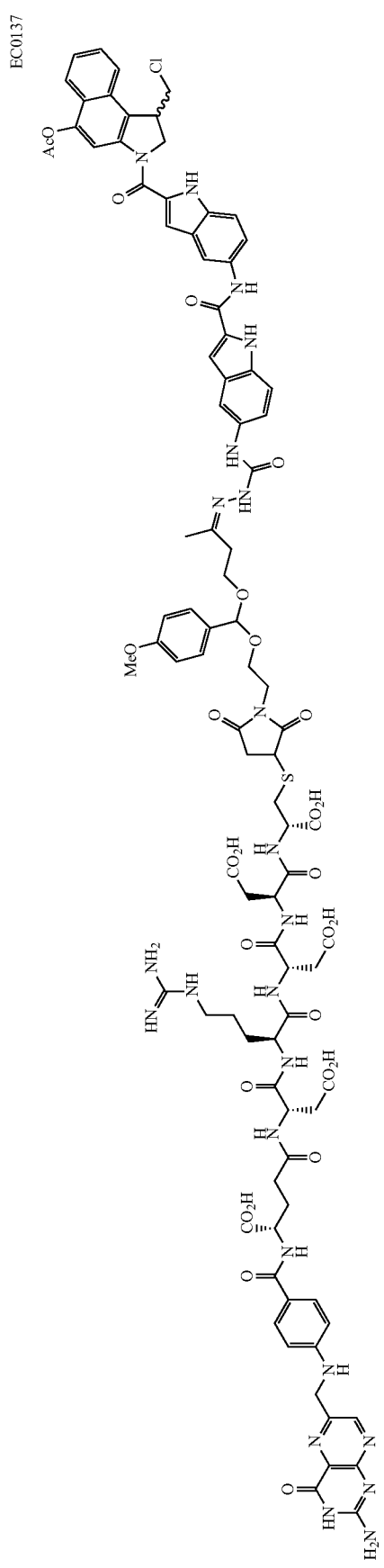
EC0137

-continued
EC0138
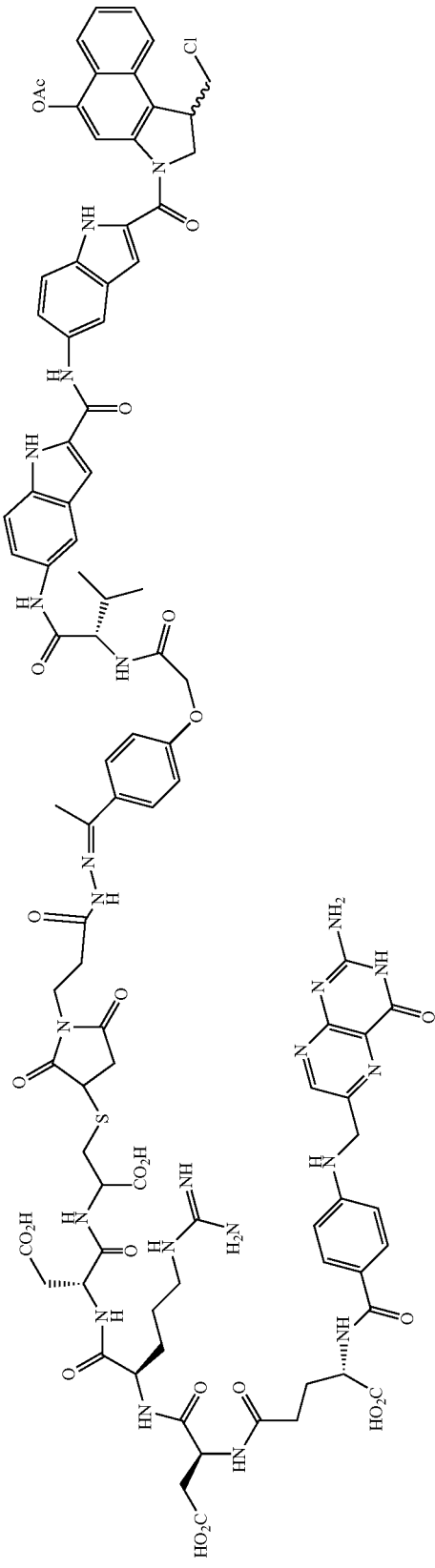
EC0260
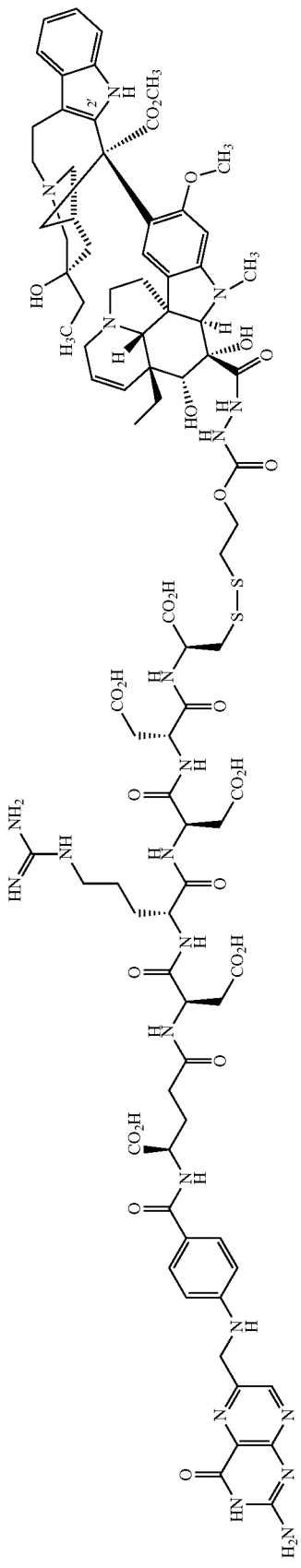

and/or where the compound is not of the following formula
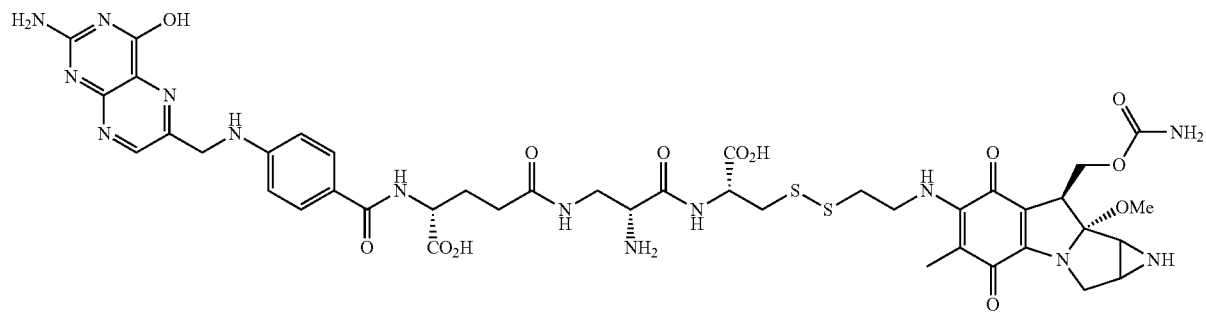
and/or where the compound is not any one of or any subgroup or subset of the following formulae

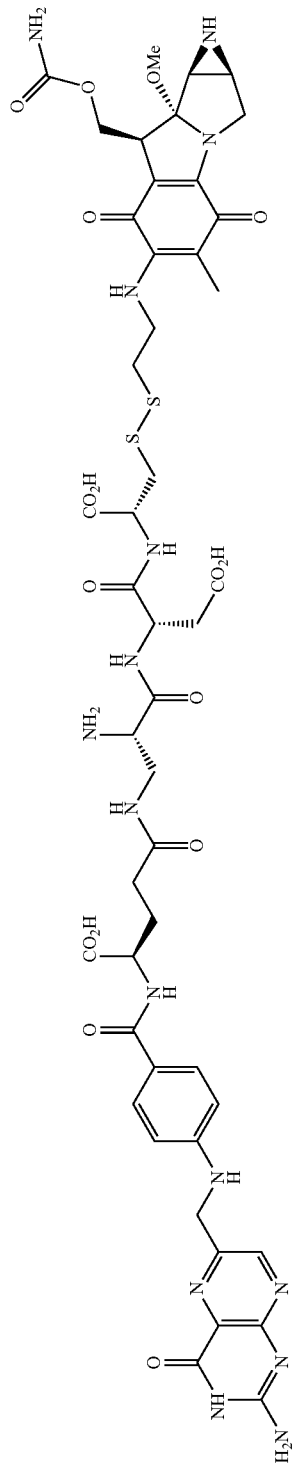
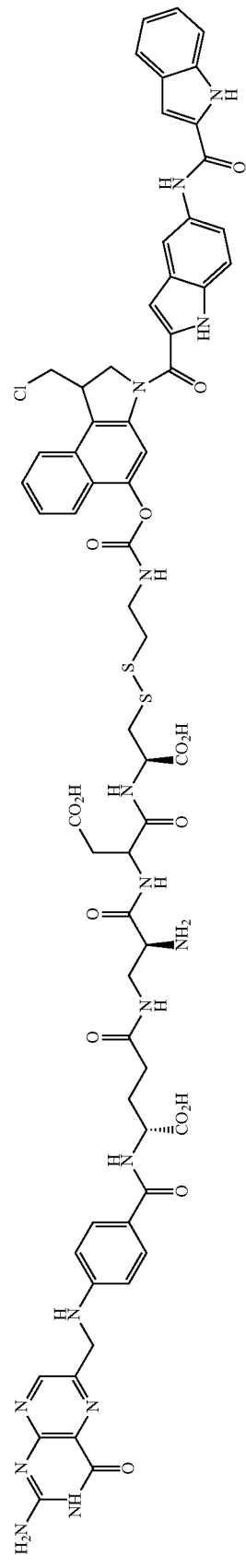

21
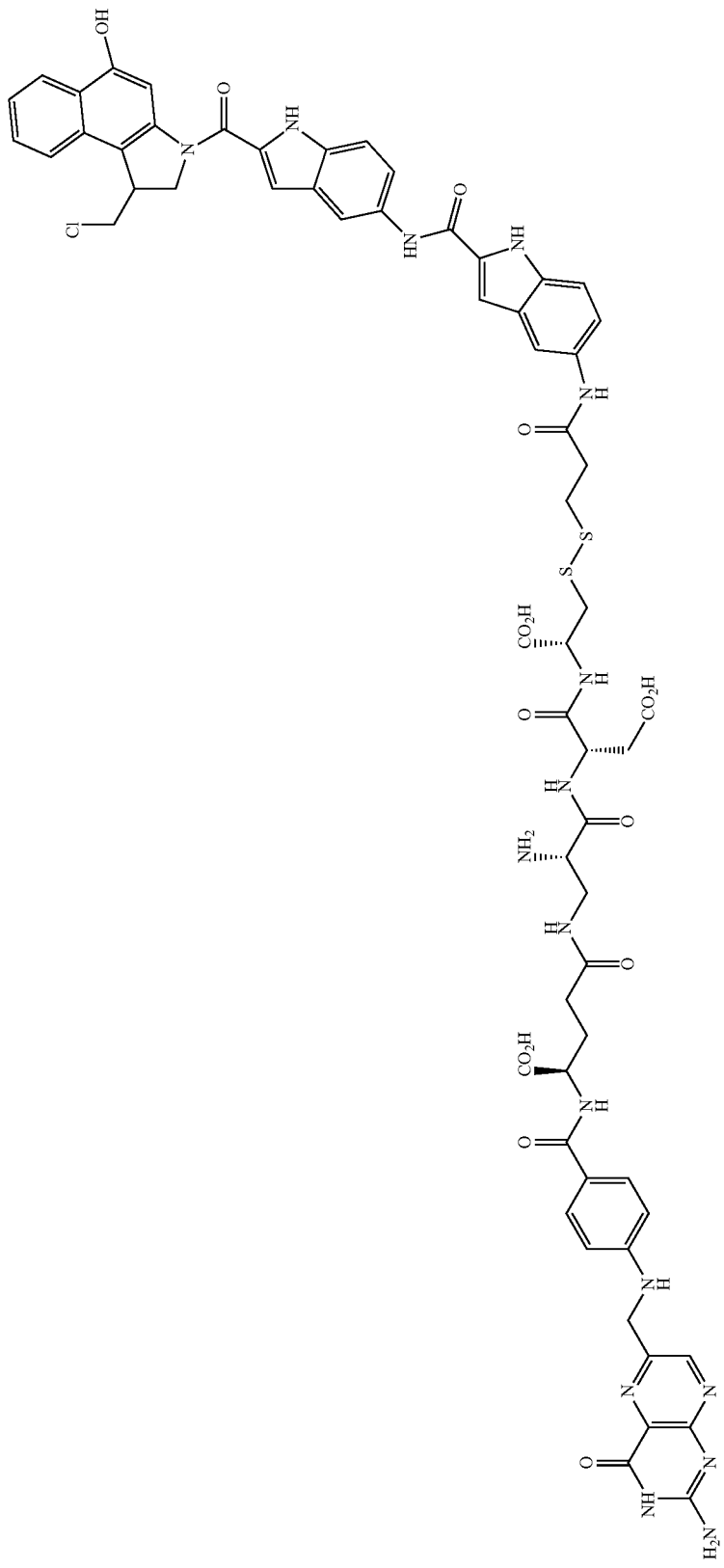
EC0070
22
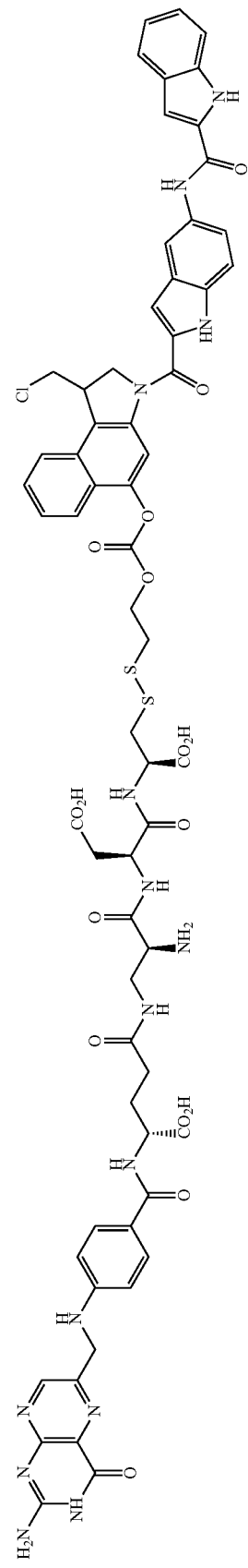
EC0071

-continued
EC0111
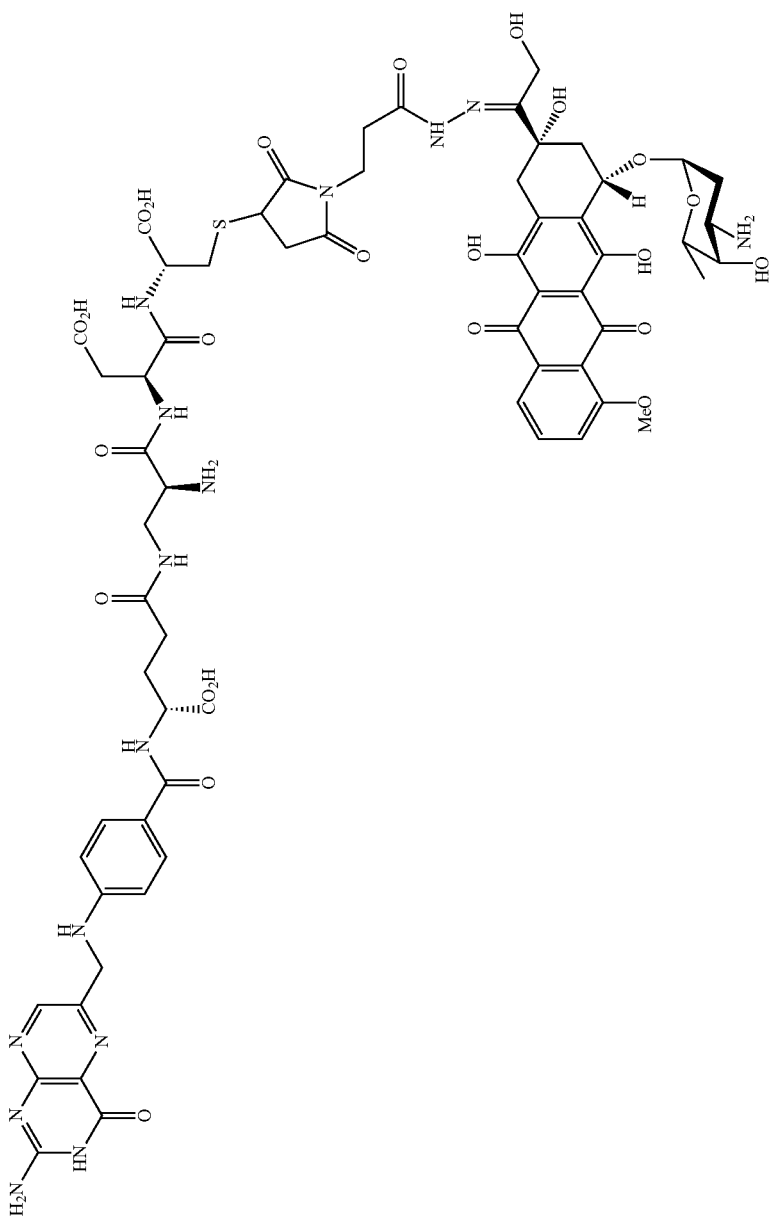

-continued
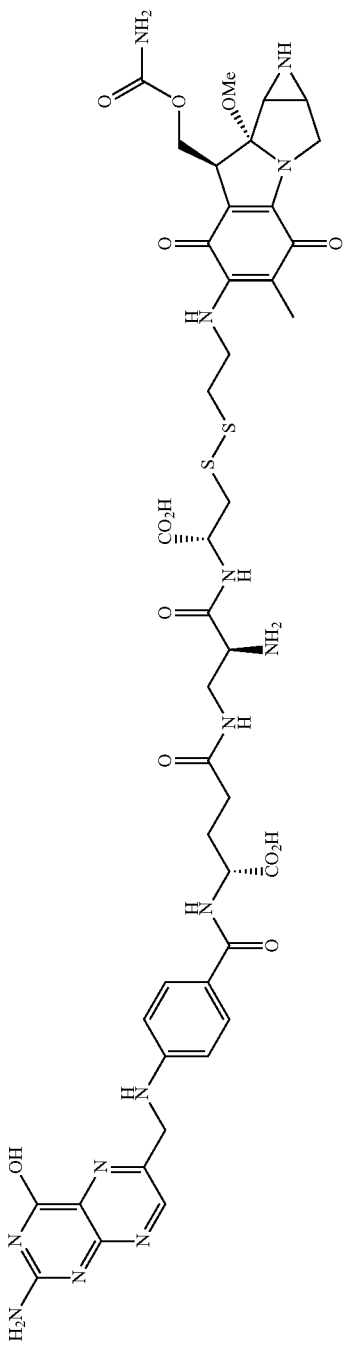
EC0155
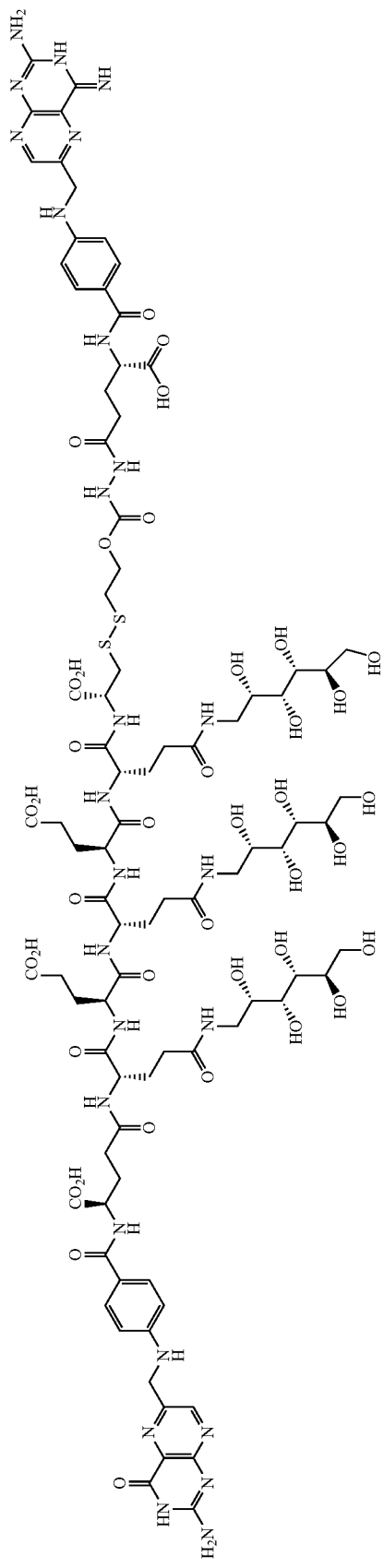
EC0894 and/or where the compound is not any one of or any subgroup or subset of the following formulae

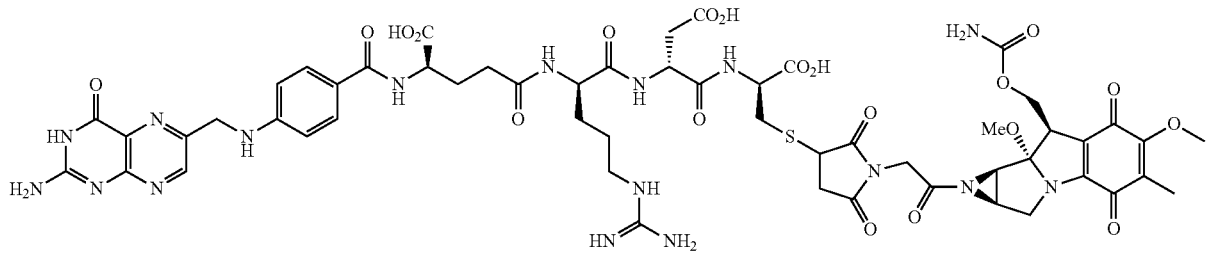

EC0082

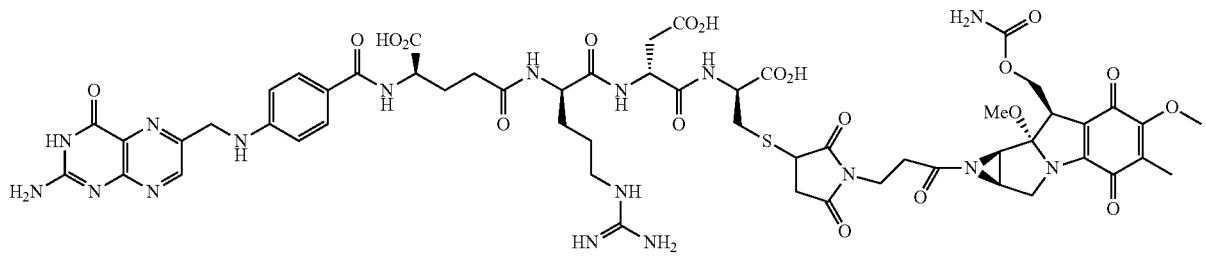

EC0083

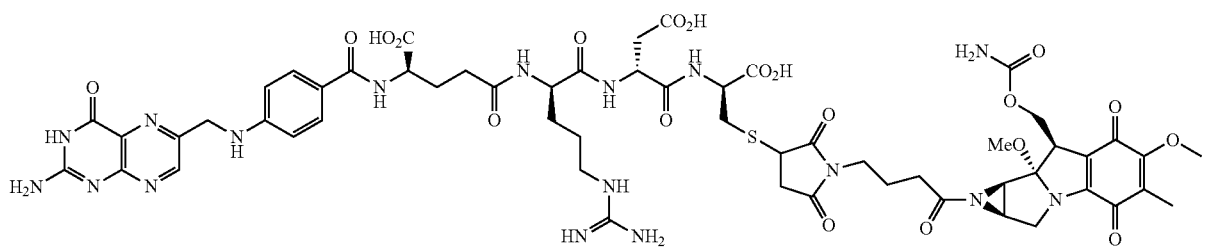

EC0084 and/or where the compound is not of the following formula

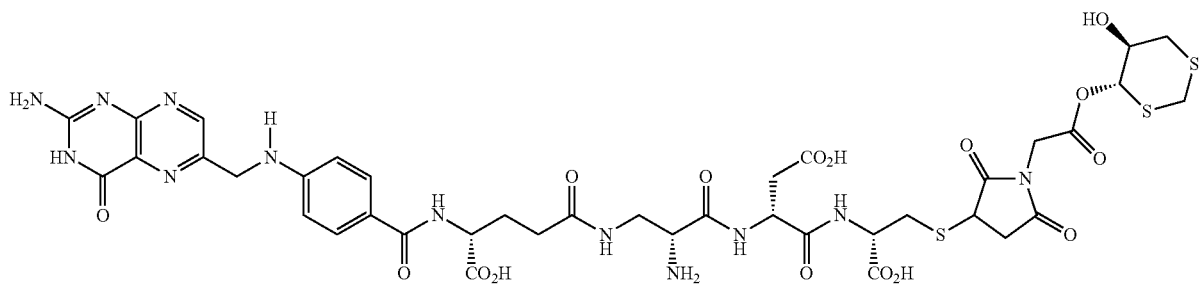

EC0060 and/or any combination of the foregoing;
or any pharmaceutically acceptable salt thereof.

The compound of the preceding clause wherein B-L(D)$_X$ is capable of binding to the cell surface receptor.

The compound of any one of the preceding clauses wherein the ligand is a vitamin receptor binding ligand.

The compound of any one of the preceding clauses wherein the ligand is a folate receptor binding ligand.

The compound of any one of the preceding clauses wherein the ligand is a folate.

The compound of any one of the preceding clauses wherein the ligand is a folate comprising D-glutamyl, also referred to herein as D-folate, or pteroyl-D-glutamic acid. It is to be understood herein that when B is a radical of D-folate, the included D-glutamyl portion of B is not part of the linker L.

The compound of any one of the preceding clauses wherein B is an unnatural folate radical of the formula

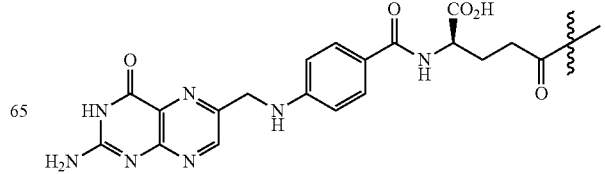

The compound of any one of the preceding clauses wherein the ligand is folic acid.

The compound of any one of the preceding clauses wherein B is a radical of the formula

The compound of any one of the preceding clauses wherein at least one unnatural amino acid has the D-configuration.

The compound of any one of the preceding clauses wherein at least one unnatural amino acid is selected from D-alanine, D-aspartic acid, D-asparagine, D-cysteine, D-glutamic acid, D-phenylalanine, D-histidine, D-isoleucine, D-lysine, D-leucine, D-methionine, D-proline, D-glutamine, D-arginine, D-serine, D-threonine, D-valine, D-tryptophan, D-tyrosine, and D-ornithine, and any amino acid derivatives thereof.

The compound of any one of the preceding clauses wherein at least one unnatural amino acid is selected from D-aspartic acid, D-asparagine, D-cysteine, D-glutamic acid, D-histidine, D-lysine, D-methionine, D-glutamine, D-arginine, D-serine, D-threonine, D-tryptophan, D-tyrosine, and D-ornithine, and any amino acid derivatives thereof.

The compound of any one of the preceding clauses wherein at least one unnatural amino acid is selected from D-aspartic acid, D-asparagine, D-cysteine, D-glutamic acid, D-histidine, D-lysine, D-glutamine, D-arginine, D-serine, D-threonine, D-tryptophan, and D-ornithine, and any amino acid derivatives thereof.

The compound of any one of the preceding clauses wherein at least one unnatural amino acid is selected from D-aspartic acid, D-cysteine, D-glutamic acid, D-lysine, D-arginine, D-serine, and D-ornithine, and any amino acid derivatives thereof.

The compound of any one of the preceding clauses wherein L comprises two or more unnatural amino acids.

The compound of any one of the preceding clauses wherein L comprises three or more unnatural amino acids.

The compound of any one of the preceding clauses wherein L comprises four or more unnatural amino acids.

The compound of any one of the preceding clauses wherein L further comprises one or more disulfides.

The compound of any one of the preceding clauses wherein at least one disulfide comprises L-cysteinyl.

The compound of any one of the preceding clauses wherein at least one disulfide comprises D-cysteinyl.

The compound of any one of the preceding clauses wherein L further comprises one or more divalent hydrophilic radicals.

The compound of any one of the preceding clauses wherein L further comprises two or more divalent hydrophilic radicals.

The compound of any one of the preceding clauses wherein L further comprises three or more divalent hydrophilic radicals.

The compound of any one of the preceding clauses wherein L further comprises four or more divalent hydrophilic radicals.

The compound of any one of the preceding clauses wherein L further comprises one or more divalent polyoxy radicals.

The compound of any one of the preceding clauses wherein L further comprises two or more divalent polyoxy radicals.

The compound of any one of the preceding clauses wherein L further comprises three or more divalent polyoxy radicals.

The compound of any one of the preceding clauses wherein L further comprises four or more divalent polyoxy radicals.

The compound of any one of the preceding clauses wherein L further comprises one or more divalent polyhydroxy radicals.

The compound of any one of the preceding clauses wherein L further comprises two or more divalent polyhydroxy radicals.

The compound of any one of the preceding clauses wherein L further comprises three or more divalent polyhydroxy radicals.

The compound of any one of the preceding clauses wherein L further comprises four or more divalent polyhydroxy radicals.

The compound of any one of the preceding clauses wherein at least one unnatural amino acid comprises a polyhydroxy radical.

The compound of any one of the preceding clauses wherein at least two unnatural amino acids comprise a polyhydroxy radical.

The compound of any one of the preceding clauses wherein at least three unnatural amino acids comprise a polyhydroxy radical.

The compound of any one of the preceding clauses wherein at least four unnatural amino acids comprise a polyhydroxy radical.

The compound of any one of the preceding clauses wherein at least one of the polyhydroxy radicals is of the formula

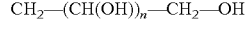

$CH_2-(CH(OH))_n-CH_2-OH$ where n is selected from 1, 2, 3, 4, 5, and 6.

The compound of any one of the preceding clauses wherein n is selected from 1, 2, 3, and 4.

The compound of any one of the preceding clauses wherein n is selected from 3 and 4.

The compound of any one of the preceding clauses wherein n is 3.

The compound of any one of the preceding clauses wherein L comprises a divalent polyglutamic acid radical, where at least one glutamic acid forms an amide with an aminopolyhydroxy radical.

The compound of any one of the preceding clauses wherein L comprises a divalent polyglutamic acid radical, where at least two glutamic acids form an amide with an aminopolyhydroxy radical.

The compound of any one of the preceding clauses wherein L comprises a divalent polyglutamic acid radical, where at least three glutamic acids form an amide with an aminopolyhydroxy radical.

The compound of any one of the preceding clauses wherein L comprises a divalent polyglutamic acid radical, where at least four glutamic acids form an amide with an aminopolyhydroxy radical.

The compound of any one of the preceding clauses wherein at least one of the glutamic acids is D-glutamic acid.

The compound of any one of the preceding clauses wherein at least two of the glutamic acids is D-glutamic acid.

The compound of any one of the preceding clauses wherein at least three of the glutamic acids is D-glutamic acid.

The compound of any one of the preceding clauses wherein at least four of the glutamic acids is D-glutamic acid.

The compound of any one of the preceding clauses wherein at least one of the glutamic acids is unsubstituted D-glutamic acid.

The compound of any one of the preceding clauses wherein at least two of the glutamic acids is unsubstituted D-glutamic acid.

The compound of any one of the preceding clauses wherein at least three of the glutamic acids is unsubstituted D-glutamic acid.

The compound of any one of the preceding clauses wherein at least four of the glutamic acids is unsubstituted D-glutamic acid.

The compound of any one of the preceding clauses wherein L comprises a divalent poly(D-glutamic acid) radical, where at least one glutamic acid forms an amide with an aminopolyhydroxy radical.

The compound of any one of the preceding clauses wherein L comprises a divalent poly(D-glutamic acid) radical, where at least two glutamic acids form an amide with an aminopolyhydroxy radical.

The compound of any one of the preceding clauses wherein L comprises a divalent poly(D-glutamic acid) radical, where at least three glutamic acids form an amide with an aminopolyhydroxy radical.

The compound of any one of the preceding clauses wherein L comprises a divalent poly(D-glutamic acid) radical, where at least four glutamic acids form an amide with an aminopolyhydroxy radical.

The compound of any one of the preceding clauses wherein L comprises a divalent radical of the formula $(K-L)_d$, where K is a divalent D-glutamic acid radical, L is a divalent L-glutamic acid radical that forms an amide with an aminopolyhydroxy radical, and d is 1, 2, 3, or 4.

The compound of the preceding clause wherein d is 2, 3, or 4.

The compound of the preceding clause wherein d is 3 or 4.

The compound of the preceding clause wherein d is 3.

The compound of any one of the preceding clauses wherein at least one of the aminopolyhydroxy radicals is of the formula

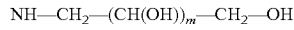
NH—CH$_2$—(CH(OH))$_m$—CH$_2$—OH where m is selected from 1, 2, 3, 4, 5, and 6.

The compound of any one of the preceding clauses wherein at least one of the aminopolyhydroxy radicals is of the formula

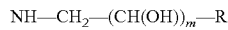
NH—CH$_2$—(CH(OH))$_m$—R where m is selected from 1, 2, 3, 4, 5, and 6; and R is H, alkyl, cycloalkyl, or arylalkyl.

The compound of any one of the preceding clauses wherein m is selected from 1, 2, 3, and 4.

The compound of any one of the preceding clauses wherein m is selected from 3 and 4.

The compound of any one of the preceding clauses wherein L comprises a divalent radical of the formula

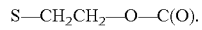
S—CH$_2$CH$_2$—O—C(O).

The compound of any one of the preceding clauses wherein L comprises a divalent radical of the formula

S—S—CH$_2$CH$_2$—O—C(O).

The compound of any one of the preceding clauses wherein L-D comprises a radical of the formula

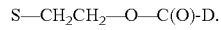
S—CH$_2$CH$_2$—O—C(O)-D.

The compound of any one of the preceding clauses wherein L-D comprises a radical of the formula

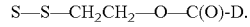
S—S—CH$_2$CH$_2$—O—C(O)-D.

The compound of any one of the preceding clauses wherein x is 3.

The compound of any one of the preceding clauses wherein x is 2.

The compound of any one of the preceding clauses wherein x is 1.

The compound of any one of the preceding clauses wherein at least one drug is a cytotoxic agent.

The compound of any one of the preceding clauses wherein at least one drug is a cancer treating agent.

The compound of any one of the preceding clauses wherein at least one drug is a vinca alkaloid.

The compound of any one of the preceding clauses wherein at least one drug is desacetylvinblastine monohydrazide.

The compound of any one of the preceding clauses wherein at least one drug is a tubulysin.

The compound of any one of the preceding clauses wherein at least one drug is tubulysin A.

The compound of any one of the preceding clauses wherein at least one drug is tubulysin B.

The compound of any one of the preceding clauses wherein at least one drug is tubulysin A hydrazide.

The compound of any one of the preceding clauses wherein at least one drug is tubulysin B hydrazide.

The compound of any one of the preceding clauses wherein at least one drug is a tubulysin where the Tuv residue includes an ether aminal.

The compound of any one of the preceding clauses wherein at least one drug is a tubulysin hydrazide where the Tuv residue includes an ether aminal.

The compound of any one of the preceding clauses wherein at least one drug is a inflammation-treating agent.

The compound of any one of the preceding clauses wherein at least one drug is an anti-inflammatory agent.

The compound of any one of the preceding clauses wherein at least one drug is a dihydrofolate reductase inhibitor.

The compound of any one of the preceding clauses wherein at least one drug is aminopterin or methotrexate.

The compound of any one of the preceding clauses wherein at least one drug is an aminopterin.

The compound of any one of the preceding clauses wherein at least one drug is an inhibitor of mammalian target of rapamycin (mTOR).

The compound of any one of the preceding clauses wherein at least one drug is sirolimus (rapamycin), temsirolimus, everolimus, or ridaforolimus.

The compound of any one of the preceding clauses wherein at least one drug is not T-2 mycotoxin.

The compound of any one of the preceding clauses wherein at least one drug is not a duocarmycin.

The compound of any one of the preceding clauses wherein at least one drug is not a mitomycin.

33

The compound of any one of the preceding clauses wherein at least one drug is not desacetylvinblastine monohydrazide.

34

The compound of any one of the preceding clauses wherein at least one D is a radical of the formula

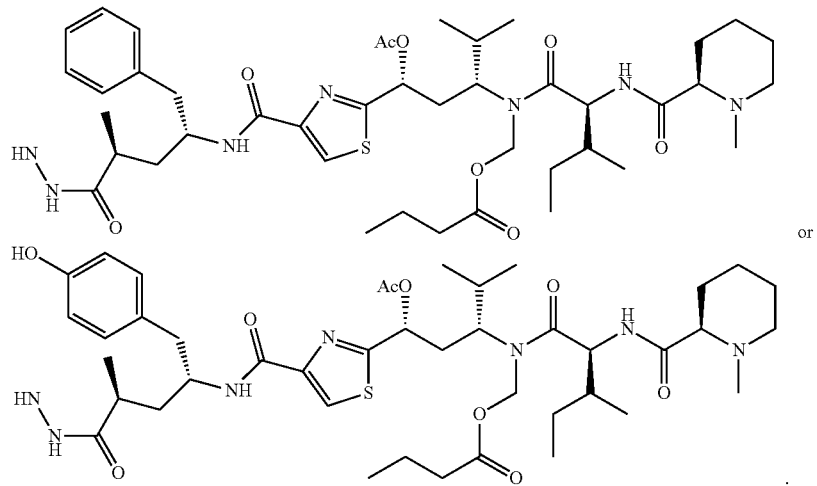

or

25

The compound of any one of the preceding clauses wherein at least one D is a radical of the formula

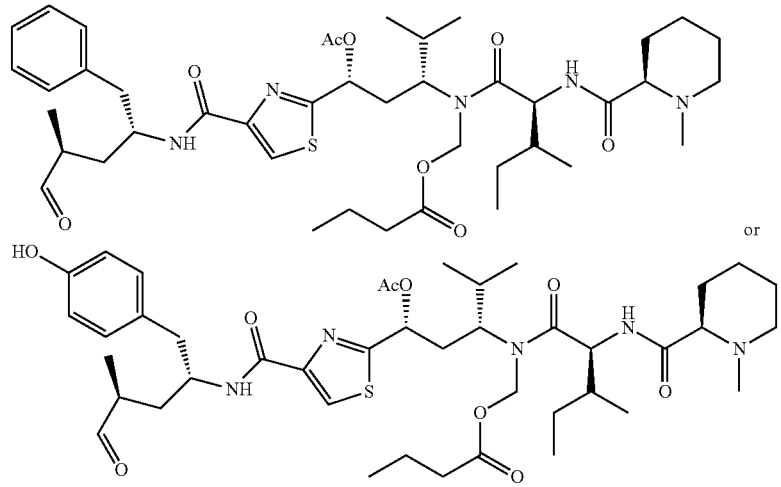

or

50

The compound of any one of the preceding clauses wherein at least one D is a radical of the formula

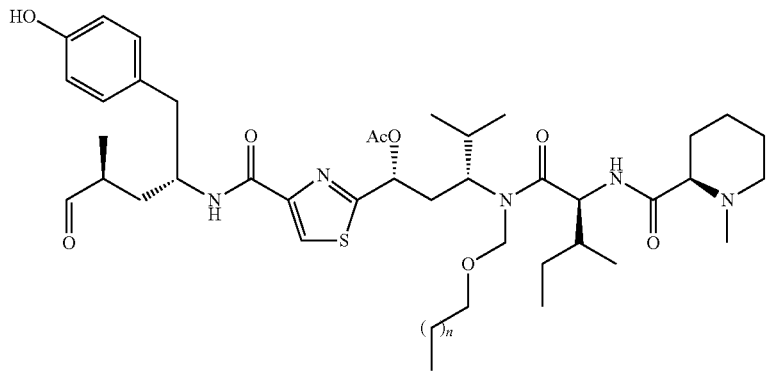

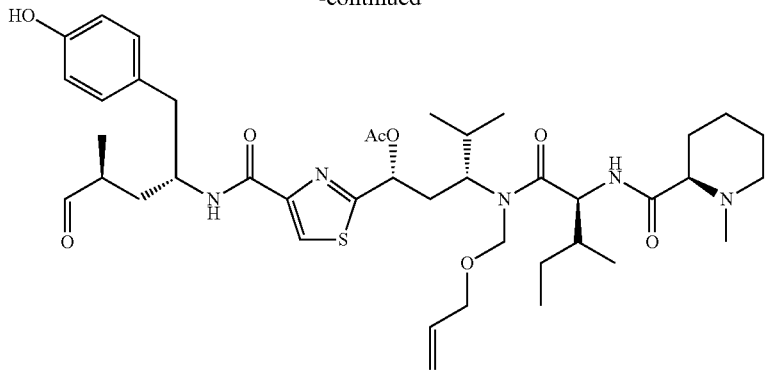
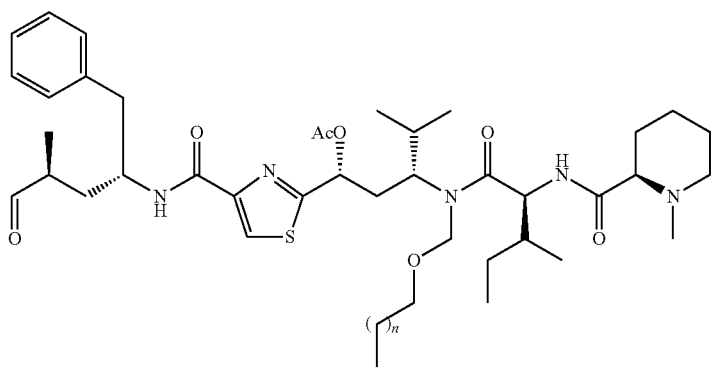
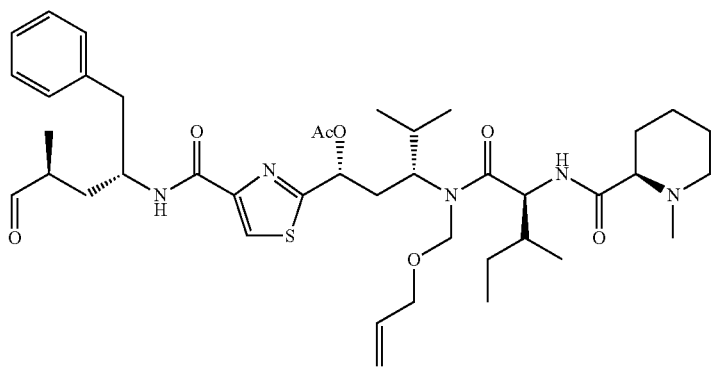
where n=1, 2, 3, 4, 5, or 6, or alternatively, n=1, 2, or 3, or alternatively, n=2 or 3.
The compound of any one of the preceding clauses wherein at least one D is a radical of the formula
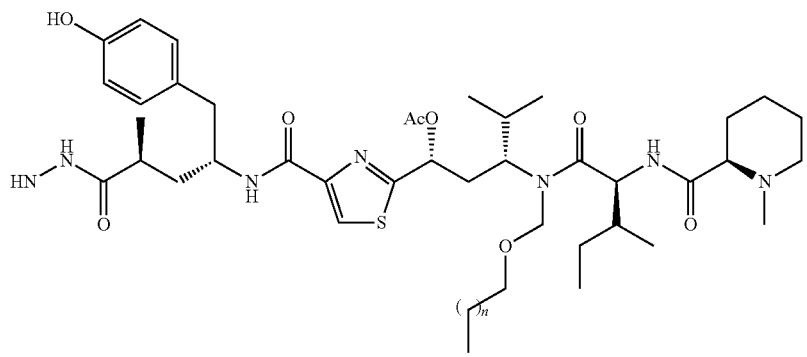

-continued
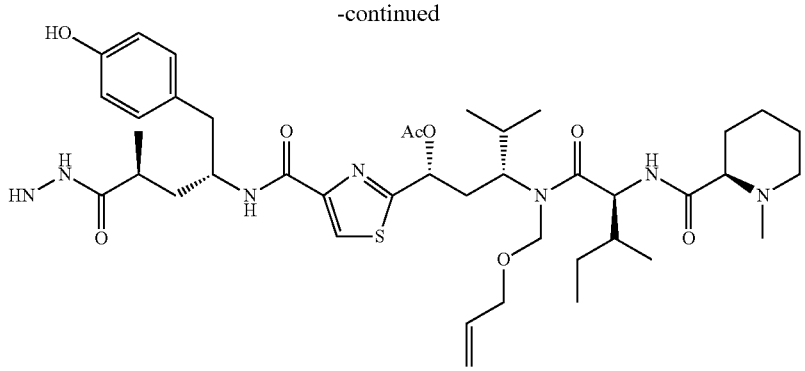
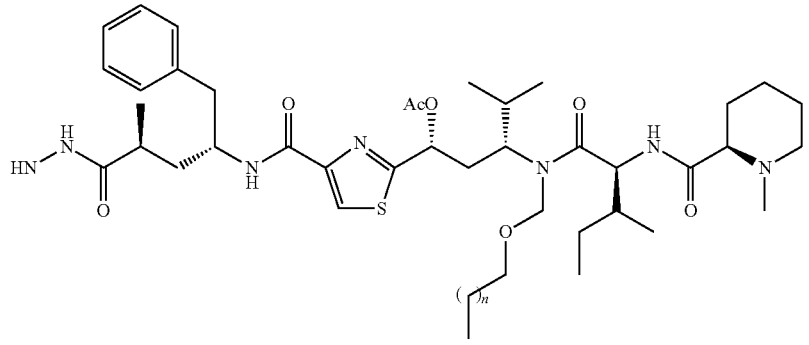
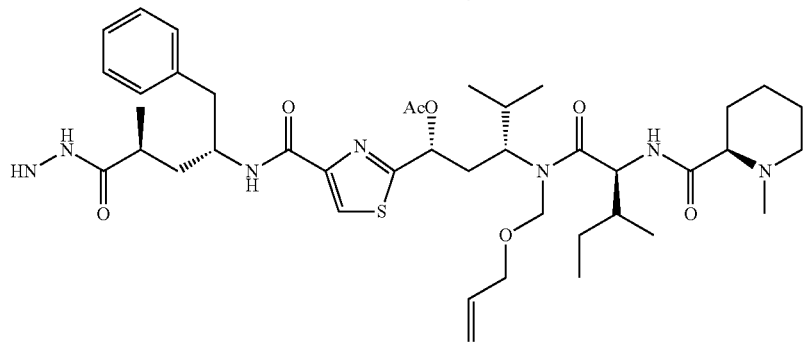
where n=1, 2, 3, 4, 5, or 6, or alternatively, n=1, 2, or 3, or alternatively, n=2 or 3.
The compound of any one of the preceding clauses wherein at least one drug is a compound capable of binding to or reacting with a nucleic acid or a DNA transcription factor, or a prodrug thereof.
The compound of any one of the preceding clauses wherein B-L is a radical of the formula
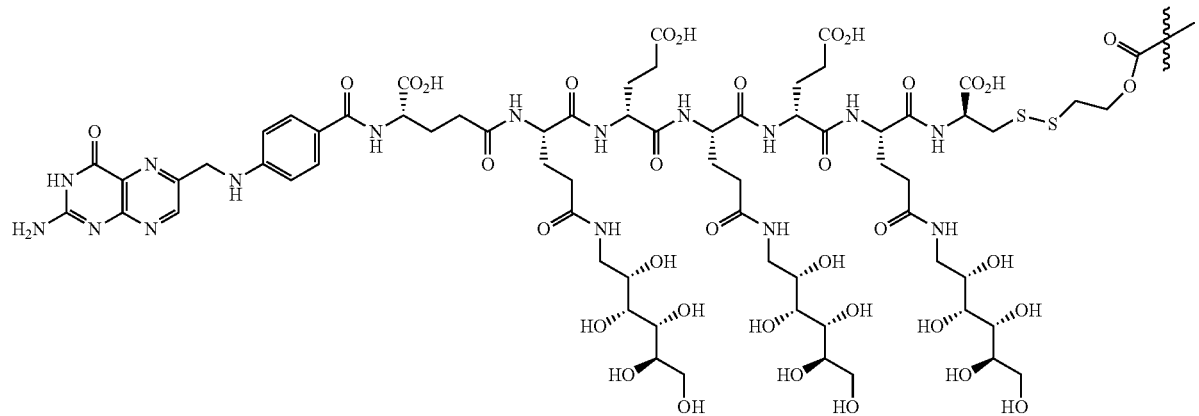

The compound of any one of the preceding clauses wherein B-L is a radical of the formula
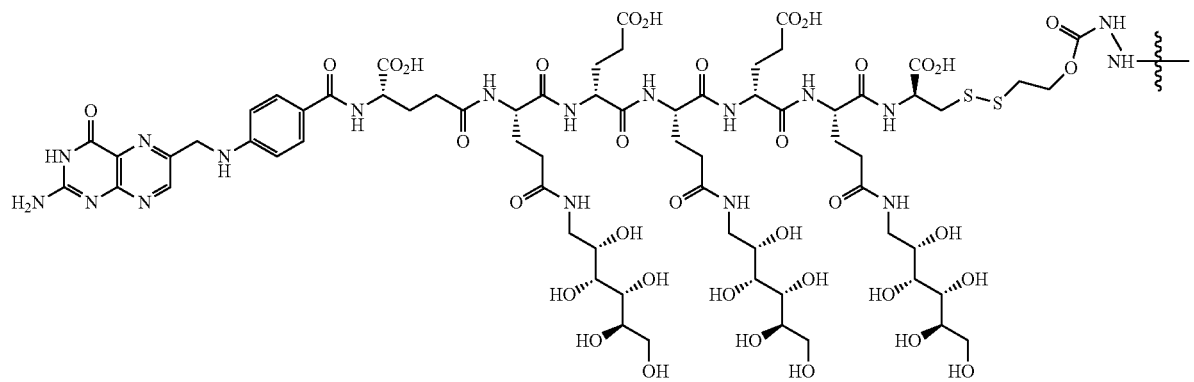
The compound of any one of the preceding clauses wherein B-L is a radical of the formula
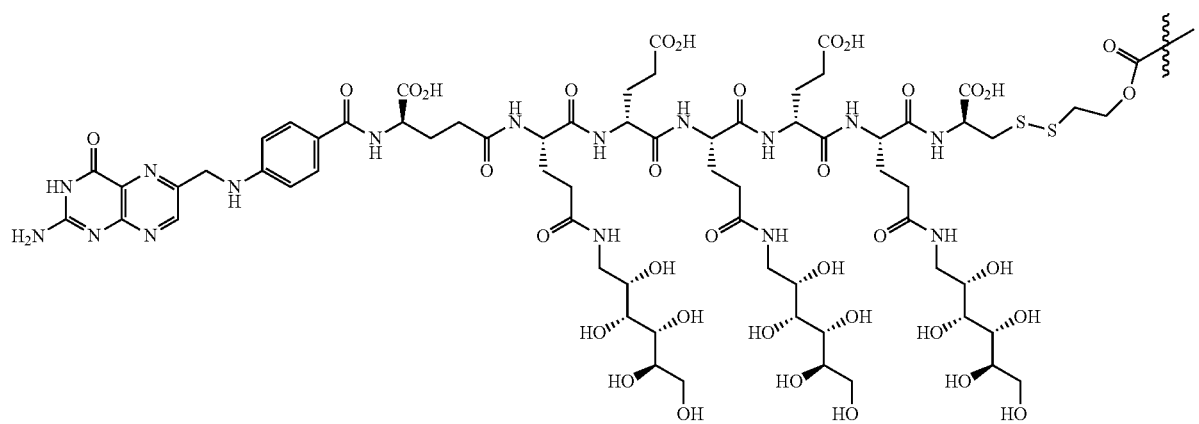
The compound of any one of the preceding clauses wherein B-L is a radical of the formula
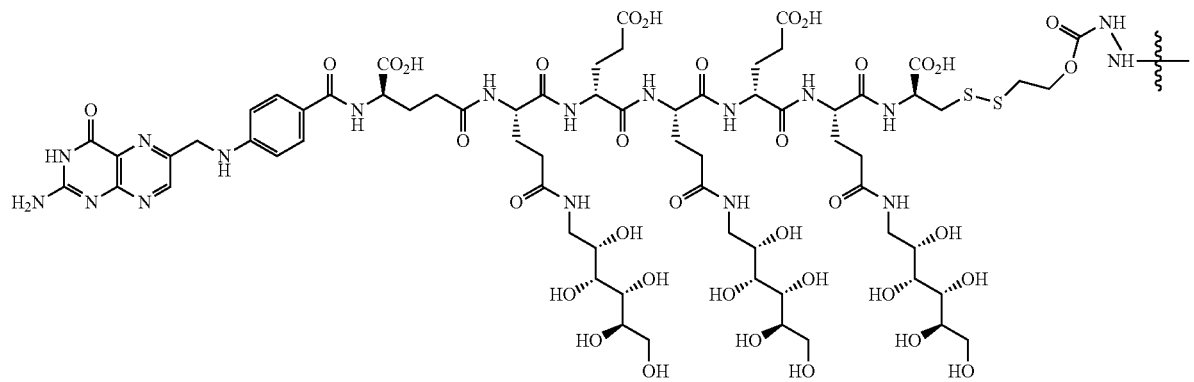

The compound of any one of the preceding clauses wherein the compound is of the formula EC1456

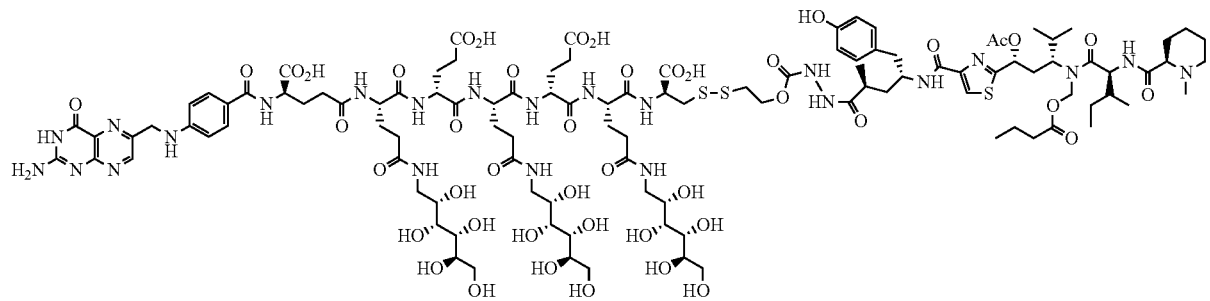 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)CC[C@@H](NC(=O)c2ccc(NCc3cnc4nc(N)[nH]c(=O)c4n3)cc2)C(=O)O)C(=O)O)cs1)C(C)C]

or a pharmaceutically acceptable salt thereof.

The compound of any one of the preceding clauses wherein the compound is not of the formula EC1456

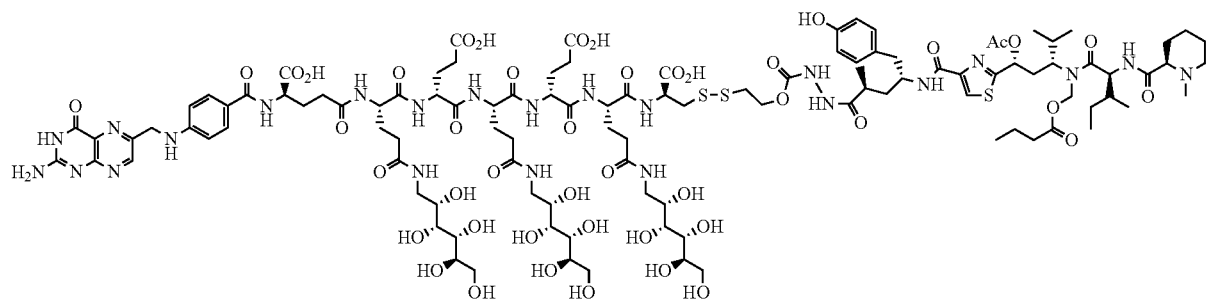 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)CC[C@@H](NC(=O)c2ccc(NCc3cnc4nc(N)[nH]c(=O)c4n3)cc2)C(=O)O)C(=O)O)cs1)C(C)C]

or a pharmaceutically acceptable salt thereof.

The compound of any one of the preceding clauses wherein the compound is of the formula EC1496

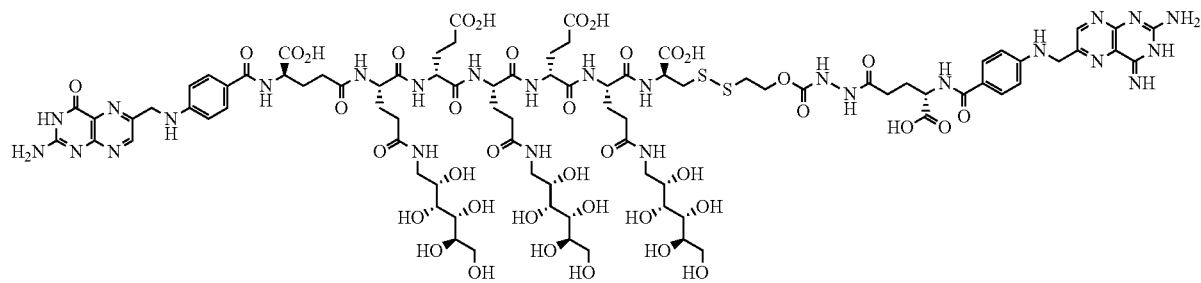 [SMILES: N=c1[nH]c(N)nc2ncc(CNc3ccc(C(=O)N[C@@H](CCC(=O)NNC(=O)OCCSSC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)CC[C@@H](NC(=O)c4ccc(NCc5cnc6nc(N)[nH]c(=O)c6n5)cc4)C(=O)O)C(=O)O)C(=O)O)cc3)nc12]

or a pharmaceutically acceptable salt thereof.

The compound of any one of the preceding clauses wherein the compound is not of the formula EC1496

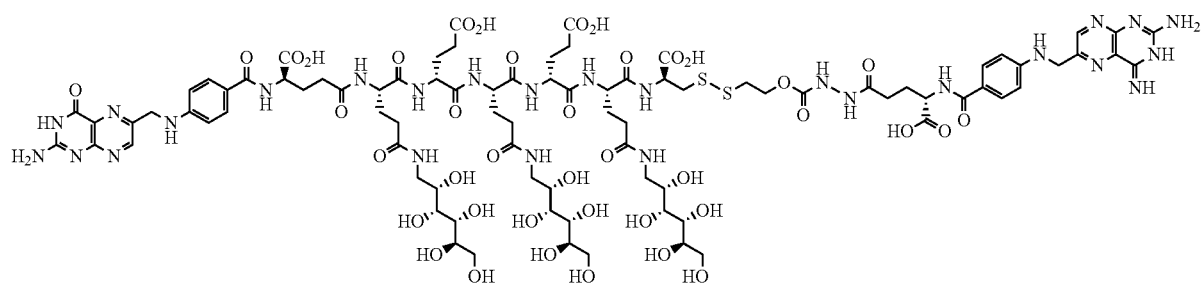 [SMILES: N=c1[nH]c(N)nc2ncc(CNc3ccc(C(=O)N[C@@H](CCC(=O)NNC(=O)OCCSSC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)CC[C@@H](NC(=O)c4ccc(NCc5cnc6nc(N)[nH]c(=O)c6n5)cc4)C(=O)O)C(=O)O)C(=O)O)cc3)nc12]

or a pharmaceutically acceptable salt thereof.

The compound of any one of the preceding clauses wherein the compound is of the formula EC1669

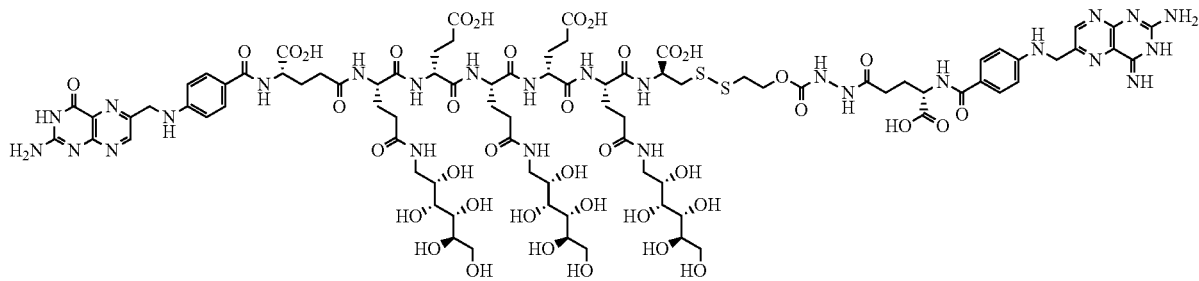 [SMILES: N=c1[nH]c(N)nc2ncc(CNc3ccc(C(=O)N[C@@H](CCC(=O)NNC(=O)OCCSSC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)CC[C@H](NC(=O)c4ccc(NCc5cnc6nc(N)[nH]c(=O)c6n5)cc4)C(=O)O)C(=O)O)C(=O)O)cc3)nc12]

or a pharmaceutically acceptable salt thereof.

The compound of any one of the preceding clauses wherein the compound is not of the formula EC1669

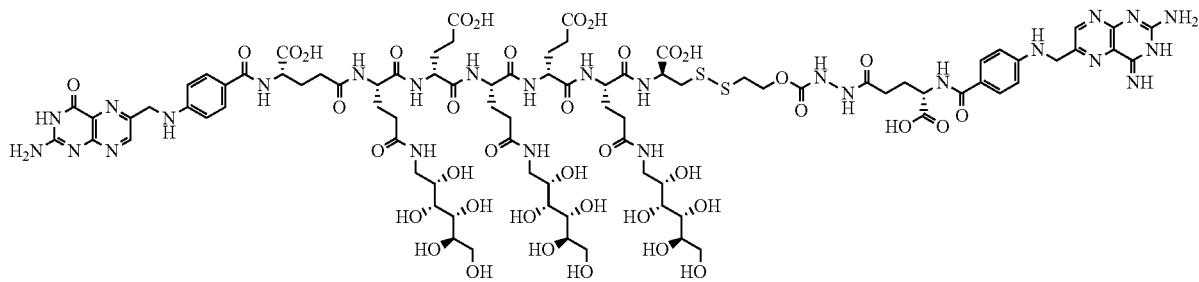 [SMILES: N=c1[nH]c(N)nc2ncc(CNc3ccc(C(=O)N[C@@H](CCC(=O)NNC(=O)OCCSSC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)CC[C@H](NC(=O)c4ccc(NCc5cnc6nc(N)[nH]c(=O)c6n5)cc4)C(=O)O)C(=O)O)C(=O)O)cc3)nc12]

or a pharmaceutically acceptable salt thereof.

A pharmaceutical composition comprising a compound of any one of the preceding clauses in combination with one or more carriers, diluents, or excipients, or a combination thereof.

A unit dose or unit dosage form composition comprising a therapeutically effective amount of one or more compounds of any one of the preceding clauses, optionally in combination with one or more carriers, diluents, or excipients, or a combination thereof.

A composition for treating cancer or inflammation in a host animal, the composition comprising a therapeutically effective amount of one or more compounds of any one of the preceding clauses; or a pharmaceutical composition comprising a therapeutically effective amount of one or more compounds of any one of the preceding clauses, optionally further comprising one or more carriers, diluents, or excipients, or a combination thereof.

A method for treating cancer or inflammation in a host animal, the method comprising the step of administering to the host animal a composition comprising a therapeutically effective amount of one or more compounds of any one of the preceding clauses; or a pharmaceutical composition comprising one or more compounds of any one of the preceding clauses, optionally further comprising one or more carriers, diluents, or excipients, or a combination thereof.

Use of one or more compounds of any one of the preceding clauses, optionally in combination with one or more carriers, diluents, or excipients, or a combination thereof, in the manufacture of a medicament for treating a cancer or inflammation in a host animal.

The method or composition or unit dose or use of any one of the preceding clauses wherein the cancer is drug resistant cancer.

The method or composition or unit dose or use of any one of the preceding clauses wherein the cancer is a platinum resistant cancer.

The method or composition or unit dose or use of any one of the preceding clauses wherein the cancer is a cisplatin resistant cancer.

The method or composition or unit dose or use of any one of the preceding clauses wherein the cancer is an ovarian cancer.

The method or composition or unit dose or use of any one of the preceding clauses wherein the cancer is a drug resistant ovarian cancer.

The method or composition or unit dose or use of any one of the preceding clauses wherein the cancer is a cisplatin resistant ovarian cancer.

The method or composition or unit dose or use of any one of the preceding clauses wherein the cancer is a platinum resistant ovarian cancer, such as NCI/ADR-RES or NCI/ADR-RES related ovarian cancer.

The method or composition or unit dose or use of any one of the preceding clauses wherein the cancer is a platinum resistant ovarian cancer, such as IGROVCDDP or IGROVCDDP related ovarian cancer.

The method or composition or unit dose or use of any one of the preceding clauses wherein the cancer is a breast cancer.

The method or composition or unit dose or use of any one of the preceding clauses wherein the cancer is a drug resistant breast cancer.

The method or composition or unit dose or use of any one of the preceding clauses wherein the cancer is a triple negative breast cancer, such as MDA-MB-231 or MDA-MB-231 related breast cancer.

The method or composition or unit dose or use of any one of the preceding clauses wherein the cancer is a non-small cell lung cancer.

The method or composition or unit dose or use of any one of the preceding clauses wherein the cancer is a hepatocellular carcinoma or cancer.

An intermediate for preparing a compound of any one of the preceding clauses of the formula

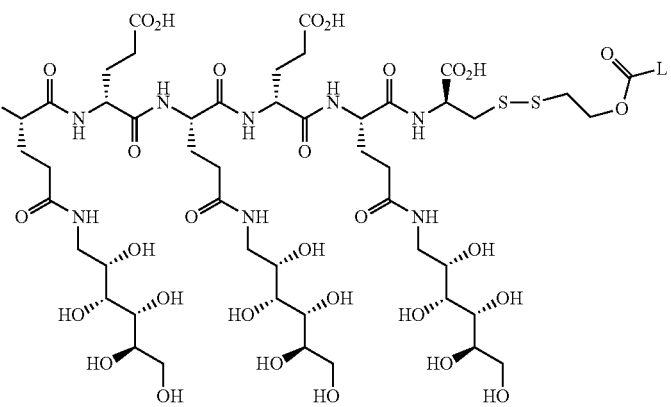

or a pharmaceutically acceptable salt thereof, wherein L is a leaving group.

An intermediate for preparing a compound of any one of the preceding clauses of the formula

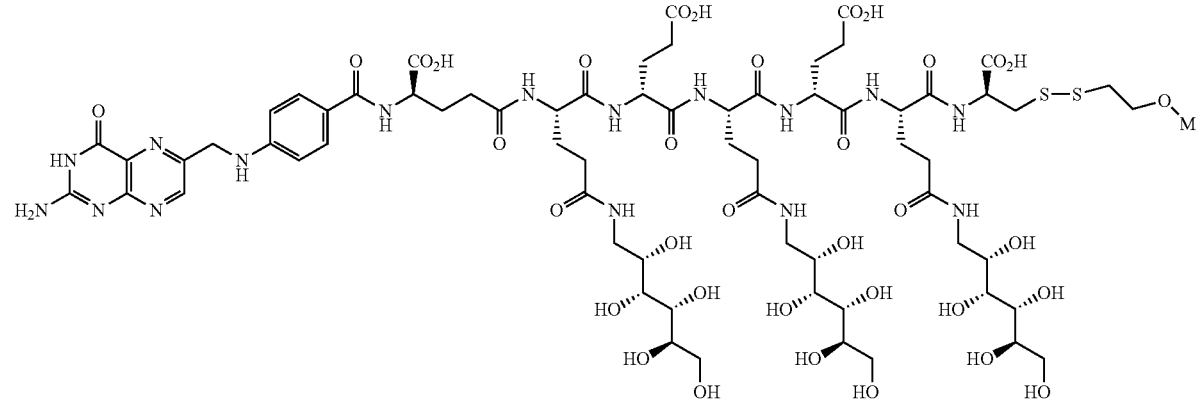

or a pharmaceutically acceptable salt thereof, wherein M is hydrogen or a cation.

An intermediate for preparing a compound of claim 1 of the formula

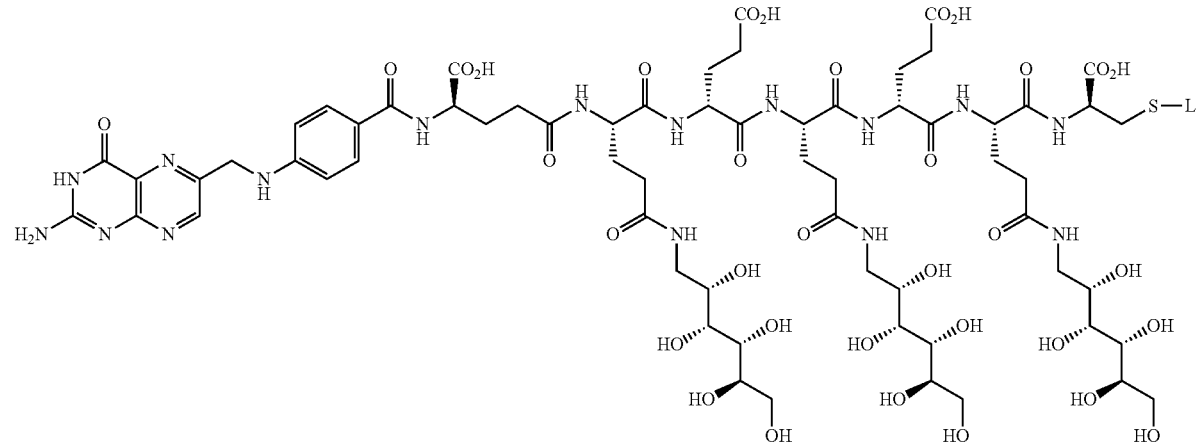

or a pharmaceutically acceptable salt thereof, wherein L is a leaving group.

In another embodiment, the compounds described herein can be internalized into the targeted pathogenic cells by binding to the corresponding cell surface receptor. In particular, vitamin receptors, such as folate receptors, selectively and/or specifically bind the vitamin, and internalization can occur, for example, through receptor-mediated endocytosis. Once internalized, the releasable linker included in the compounds described herein allows for the delivery of the drug cargo to the interior of the target cell, thus decreasing toxicity against non-target tissues because the releasable linker remains substantially or completely intact until the compounds described herein are delivered to the target cells. Accordingly, the compounds described herein act intracellularly by delivering the drug to an intracellular biochemical process, a decrease the amount of unconjugated drug exposure to the host animal's healthy cells and tissues.

In another embodiment, compounds described herein that include a folate receptor binding ligand exhibit greater specificity for the folate receptor compared to the corresponding compounds that do not include at least one unnatural amino acid. In another embodiment, compounds described herein that include a folate receptor binding ligand show high activity for folate receptor expressing cells. In another embodiment, compounds described herein exhibit potent in vitro and in vivo activity against pathogenic cells, such as KB cells, including cisplatin resistant KB cells, NCI/ADR-RES-Cl$_2$ cells, IGROV1 cells, and MDA-MB-231 cells. In another embodiment, compounds described herein that include a folate receptor binding ligand do not show significant binding to folate receptor negative cells. In another embodiment, compounds described herein that include a folate receptor binding ligand enter cells preferentially or exclusively via the high affinity folate receptors, such as folate receptor alpha ($\alpha$) and/or folate receptor beta ($\beta$). In another embodiment, compounds described herein generally do not substantially enter cells via passive transport, such as via the reduced folate carrier (RFC). In another embodiment, compounds described herein exhibit lower host animal toxicity compared to compounds that do not include at least one unnatural amino acid. In another embodiment, compounds described herein exhibit greater serum stability compared to compounds that do not include at least one unnatural amino acid. In another embodiment, compounds described herein are cleared rapidly compared to compounds that do not include at least one unnatural amino acid. In another embodiment, compounds described herein are cleared primarily via renal clearance compared to hepatic clearance.

The compounds described herein can be used for both human clinical medicine and veterinary applications. Thus, the host animal harboring the population of pathogenic cells and treated with the compounds described herein can be human or, in the case of veterinary applications, can be a laboratory, agricultural, domestic, or wild animal. The present invention can be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The invention is applicable to populations of pathogenic cells that cause a variety of pathologies in these host animals. In accordance with the invention "pathogenic cells" means cancer cells, infectious agents such as bacteria and viruses, bacteria- or virus-infected cells, activated macrophages capable of causing a disease state, other pathogenic cells causing inflammation, any other type of pathogenic cells that uniquely express, preferentially express, or overexpress vitamin receptors or receptors that bind vitamins and/or vitamin receptor binding ligands, and any other type of pathogenic cells that uniquely express, preferentially express, or overexpress high affinity folate receptors or receptors that bind folates and/or folate receptor binding ligands. Pathogenic cells can also include any cells causing a disease state for which treatment with the compounds described herein results in reduction of the symptoms of the disease. For example, the pathogenic cells can be host cells that are pathogenic under some circumstances such as cells of the immune system that are responsible for graft versus host disease, but not pathogenic under other circumstances.

Thus, the population of pathogenic cells can be a cancer cell population that is tumorigenic, including benign tumors and malignant tumors, or it can be non-tumorigenic. The cancer cell population can arise spontaneously or by such processes as mutations present in the germline of the host animal or somatic mutations, or it can be chemically-, virally-, or radiation-induced. The invention can be utilized to treat such cancers as carcinomas, sarcomas, lymphomas, Hodgekin's disease, melanomas, mesotheliomas, Burkitt's lymphoma, nasopharyngeal carcinomas, leukemias, and myelomas. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

In another embodiment, the method or pharmaceutical composition of any one of the preceding embodiments wherein the disease is selected from the group consisting of arthritis, including rheumatoid arthritis and osteoarthritis, glomerulonephritis, proliferative retinopathy, restenosis, ulcerative colitis, Crohn's disease, fibromyalgia, psoriasis and other inflammations of the skin, osteomyelitis, Sjögren's syndrome, multiple sclerosis, diabetes, atherosclerosis, pulmonary fibrosis, lupus erythematosus, sarcoidosis, systemic sclerosis, organ transplant rejection (GVHD) and chronic inflammations is described.

The drug can be any molecule capable of modulating or otherwise modifying cell function, including pharmaceutically active compounds. Illustrative drugs include, but are not limited to, peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; immunosuppressants, stimulants; decongestants; antiemetics; diuretics; antispasmodics; antiasthmatics; anti-Parkinson agents; expectorants; cough suppressants; mucolytics; and mineral and nutritional additives.

Further, the drug can be one that is cytotoxic, enhances tumor permeability, inhibits tumor cell proliferation, promotes apoptosis, decreases anti-apoptotic activity in target cells, is used to treat diseases caused by infectious agents, enhances an endogenous immune response directed to the pathogenic cells, or is useful for treating a disease state caused by any type of pathogenic cell. Additional illustrative drugs include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, rhizoxin, T2 toxin, plant alkaloids, prednisone, hydroxyurea, teniposide, mitomycins, discodermolides, microtubule inhibitors, epothilones, tubulysins, cyclopropyl benz[e]indolone, seco-cyclopropyl benz[e]indolone, O—Ac-seco-cyclopropyl benz[e]indolone, bleomycin and any other antibiotic, nitrogen mustards, nitrosureas, vinca alkaloids, such as vincristine, vinblastine, vindesine, vinorelbine and analogs and derivative thereof such as deacetylvinblastine monohydrazide (DAVLBH), colchicine, colchicine derivatives, allocolchicine, thiocolchicine, trityl cysteine, halicondrin B, dolastatins such as dolastatin 10, amanitins such as $\alpha$-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other drug or toxin. Other drugs that can be included in the conjugates described herein include rapamycins, such as sirolimus or everolimus, penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, and any other antimicrobial compound.

In another embodiment, the drug is selected from cryptophycins, bortezomib, thiobortezomib, tubulysins, aminopterin, rapamycins, paclitaxel, docetaxel, doxorubicin, daunorubicin, everolimus, $\alpha$-amanatin, verucarin, didemnin B, geldanamycin, purvalanol A, ispinesib, budesonide, dasatinib, epothilones, maytansines, and tyrosine kinase inhibitors, including analogs and derivatives of the foregoing.

In another embodiment, the compounds described herein include at least two drugs (D), which are illustratively selected from vinca alkaloids, cryptophycins, bortezomib, thiobortezomib, tubulysins, aminopterin, rapamycins, such as everolimus and sirolimus, paclitaxel, docetaxel, doxorubicin, daunorubicin, $\alpha$-amanatin, verucarin, didemnin B, geldanamycin, purvalanol A, ispinesib, budesonide, dasatinib, epothilones, maytansines, and tyrosine kinase inhibitors, including analogs and derivatives of the foregoing. In one variation, the drugs (D) are the same. In another variation, the drugs (D) are different.

The drug delivery conjugate compounds described herein can be administered in a combination therapy with any other known drug whether or not the additional drug is targeted. Illustrative additional drugs include, but are not limited to, peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins, antigens and antibodies thereto, haptens and antibodies thereto, hormones, lipids, phospholipids, liposomes, toxins, antibiotics, analgesics, bronchodilators, beta-blockers, antimicrobial agents, antihypertensive agents, cardiovascular agents including antiarrhythmics, cardiac glycosides, antianginals, vasodilators, central nervous system agents including stimulants, psychotropics, antimanics, and depressants, antiviral agents, antihistamines, cancer drugs including chemotherapeutic agents, tranquilizers, anti-depressants, H-2 antagonists, anticonvulsants, antinauseants, prostaglandins and prostaglandin analogs, muscle relaxants, anti-inflammatory substances, stimulants, decongestants, antiemetics, diuretics, antispasmodics, antiasthmatics, anti-Parkinson agents, expectorants, cough suppressants, mucolytics, and mineral and nutritional additives.

In another embodiment, at least one additional composition comprising a therapeutic factor can be administered to the host in combination or as an adjuvant to the above-detailed methodology, to enhance the drug delivery conjugate-mediated elimination of the population of pathogenic cells, or more than one additional therapeutic factor can be administered. The therapeutic factor can be selected from a compound capable of stimulating an endogenous immune response, a chemotherapeutic agent, or another therapeutic factor capable of complementing the efficacy of the administered drug delivery conjugate. The method of the invention can be performed by administering to the host, in addition to the above-described conjugates, compounds or compositions capable of stimulating an endogenous immune response (e.g. a cytokine) including, but not limited to, cytokines or immune cell growth factors such as interleukins 1-18, stem cell factor, basic FGF, EGF, G-CSF, GM-CSF, FLK-2 ligand, HILDA, MIP-1$\alpha$, TGF-$\alpha$, TGF-$\beta$, M-CSF, IFN-$\alpha$, IFN-$\beta$, IFN-$\gamma$, soluble CD23, LIF, and combinations thereof.

Therapeutically effective combinations of these factors can be used. In one embodiment, for example, therapeutically effective amounts of IL-2, for example, in amounts ranging from about 0.1 MIU/m$^2$/dose/day to about 15 MIU/m$^2$/dose/day in a multiple dose daily regimen, and IFN-$\alpha$, for example, in amounts ranging from about 0.1 MIU/m$^2$/dose/day to about 7.5 MIU/m$^2$/dose/day in a multiple dose daily regimen, can be used along with the drug delivery conjugates to eliminate, reduce, or neutralize pathogenic cells in a host animal harboring the pathogenic cells (MIU=million international units; m$^2$=approximate body surface area of an average human). In another embodiment IL-12 and IFN-$\alpha$ are used in the above-described therapeutically effective amounts for interleukins and interferons, and in yet another embodiment IL-15 and IFN-$\alpha$ are used in the above described therapeutically effective amounts for interleukins and interferons. In an alternate embodiment IL-2, IFN-$\alpha$ or IFN-$\gamma$, and GM-CSF are used in combination in the above described therapeutically effective amounts. The invention also contemplates the use of any other effective combination of cytokines including combinations of other interleukins and interferons and colony stimulating factors.

Chemotherapeutic agents, which are, for example, cytotoxic themselves or can work to enhance tumor permeability, are also suitable for use in the method of the invention in combination with the drug delivery conjugate compounds. Such chemotherapeutic agents include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O—Ac-seco-cyclopropyl benz[e]indolone, bleomycin and any other antibiotic, nitrogen mustards, nitrosureas, vincristine, vinblastine, and analogs and derivative thereof such as deacetylvinblastine monohydrazide, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used in accordance with the invention include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, maytansines and analogs and derivatives thereof, gemcitabine, and any other art-recognized antimicrobial compound.

As used herein, the term "linker" includes is a chain of atoms that connects two or more functional parts of a molecule to form a conjugate. Illustratively, the chain of atoms is selected from C, N, O, S, Si, and P, or C, N, O, S, and P, C, N, O, and S. The chain of atoms covalently connects different functional capabilities of the conjugate, such as binding ligands, drugs, diagnostic agents, imaging agents, and the like. The linker may have a wide variety of lengths, such as in the range from about 2 to about 100 atoms in the contiguous backbone. The atoms used in forming the linker may be combined in all chemically relevant ways, such as chains of carbon atoms forming alkylene, alkenylene, and alkynylene groups, and the like; chains of carbon and oxygen atoms forming ethers, polyoxyalkylene groups, or when combined with carbonyl groups forming esters and carbonates, and the like; chains of carbon and nitrogen atoms forming amines, imines, polyamines, hydrazines, hydrazones, or when combined with carbonyl groups forming amides, ureas, semicarbazides, carbazides, and the like; chains of carbon, nitrogen, and oxygen atoms forming alkoxyamines, alkoxylamines, or when combined with carbonyl groups forming urethanes, amino acids, acyloxylamines, hydroxamic acids, and the like; and many others. In addition, it is to be understood that the atoms forming the chain in each of the foregoing illustrative embodiments may be either saturated or unsaturated, thus forming single, double, or triple bonds, such that for example, alkanes, alkenes, alkynes, imines, and the like may be radicals that are included in the linker. In addition, it is to be understood that the atoms forming the linker may also be cyclized upon each other or be part of cyclic structure to form divalent cyclic structures that form the linker, including cyclo alkanes, cyclic ethers, cyclic amines, and other heterocycles, arylenes, heteroarylenes, and the like in the linker. In this latter arrangement, it is to be understood that the linker length may be defined by any pathway through the one or more cyclic structures. Illustratively, the linker length is defined by the shortest pathway through the each one of the cyclic structures. It is to be understood that the linkers may be optionally substituted at any one or more of the open valences along the chain of atoms, such as optional substituents on any of the carbon, nitrogen, silicon, or phosphorus atoms. It is also to be understood that the linker may connect the two or more functional parts of a molecule to form a conjugate at any open valence, and it is not necessary that any of the two or more functional parts of a molecule forming the conjugate are attached at any apparent end of the linker.

In another embodiment, a folate-linker radical is described having the following formula

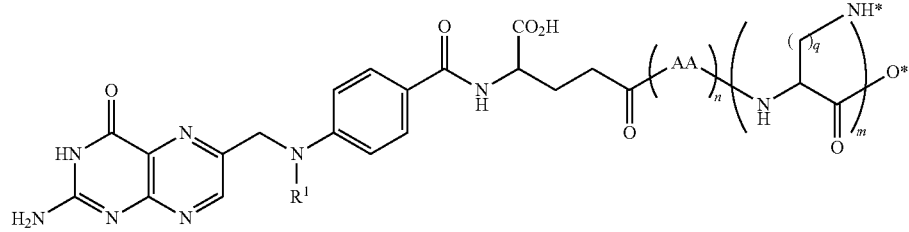

wherein m, n, and q are integers that are independently selected from the range of 0 to about 8; AA is an amino acid, $R^1$ is hydrogen, alkyl, or a nitrogen protecting group, and drugs are optionally attached at the (*) atoms. In one aspect, AA is a naturally occurring amino acid of either the natural or unnatural configuration. In another aspect, one or more of AA is a hydrophilic amino acid. In another aspect, one or more of AA is Asp and/or Arg. In another aspect, the integer n is 1 or greater. In another aspect, the integer n is 2 or greater. In another aspect, the integer n is 3 or greater. In another aspect, the integer n is 4 or greater. In another aspect, the integer n is 5 or greater. In another aspect, the integer q is 1 or greater. In another aspect, the integer q is 1. In another aspect, the integer m is 1 or greater. In another aspect, the integer m is 1. In another aspect, $R^1$ is hydrogen. The drugs and optionally additional linkers and additional receptor-binding ligands may be connected to the above formula at the free NH side chains of the 2,ω-diaminoalkanoic acid fragments, or at the terminal carboxylate as indicated by the free valences therein. It is to be understood that every combination of the foregoing aspects is described herein as further illustrative embodiments of the invention. For example, in another embodiment, n is 1 or greater, and m is one or greater; or n is 1 or greater, m is 1, and q is 1; and so forth.

In another embodiment, a folate-linker radical is described having the following formula

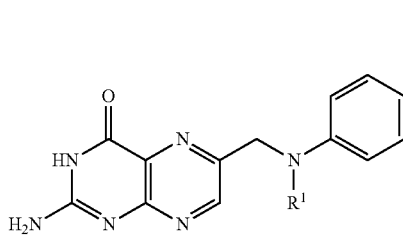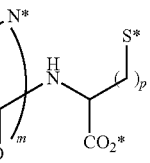

wherein m, n, q, and p are integers that are independently selected from the range of 0 to about 8; AA is an amino acid, $R^1$ is hydrogen, alkyl, or a nitrogen protecting group, and drugs are optionally attached at the (*) atoms. In one aspect, AA is as a naturally occurring amino acid of either the natural or unnatural configuration. In another aspect, one or more of AA is a hydrophilic amino acid. In another aspect, one or more of AA is Asp and/or Arg. In another aspect, the integer n is 1 or greater. In another aspect, the integer n is 2 or greater. In another aspect, the integer n is 3 or greater. In another aspect, the integer n is 4 or greater. In another aspect, the integer n is 5 or greater. In another aspect, the integers q and/or p are 1 or greater. In another aspect, the integer integers q and/or p are 1. In another aspect, the integer m is 1 or greater. In another aspect, the integer m is 1. In another aspect, $R^1$ is hydrogen. The drugs and optionally additional linkers and additional receptor-binding ligands may be connected to the above formula at the free NH side chains of the 2,ω-diaminoalkanoic acid fragments, at the cysteinyl thiol groups, or at the terminal carboxylate, as indicated by the free valences therein. It is to be understood that every combination of the foregoing aspects is described herein as further illustrative embodiments of the invention. For example, in another embodiment, n is 1 or greater, and m is one or greater; or n is 2 or greater, m is 1, and q is 1; or n is 2 or greater, m is 1, q is 1, and p is 1; and so forth.

In another embodiment, a folate-linker radical is described having the following formula

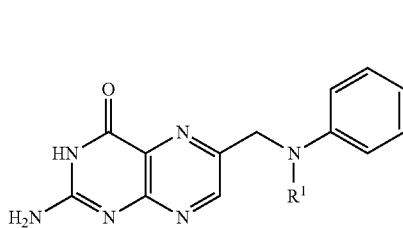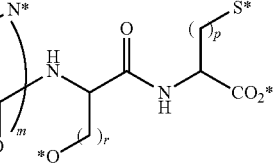

wherein m, n, q, p, and r are integers that are independently selected from the range of 0 to about 8; AA is an amino acid, $R^1$ is hydrogen, alkyl, or a nitrogen protecting group, and drugs are optionally attached at the (*) atoms. In one aspect, AA is as a naturally occurring amino acid of either the natural or unnatural configuration. In another aspect, one or more of AA is a hydrophilic amino acid. In another aspect, one or more of AA is Asp and/or Arg. In another aspect, the integer n is 1 or greater. In another aspect, the integer n is 2 or greater. In another aspect, the integer n is 3 or greater. In another aspect, the integer n is 4 or greater. In another aspect, the integer n is 5 or greater. In another aspect, the integers q and/or p and/or r are 1 or greater. In another aspect, the integers q and/or p and/or r are 1. In another aspect, the integer m is 1 or greater. In another aspect, the integer m is 1. In another aspect, $R^1$ is hydrogen. The drugs and optionally additional linkers and additional receptor-binding ligands may be connected to the above formula at the free NH side chains of the 2,ω-diaminoalkanoic acid fragments, at the cyteinyl thiol groups, at the serinyl hydroxy groups, or at the terminal carboxylate, as indicated by the free valences therein. It is to be understood that every combination of the foregoing aspects is described herein as further illustrative embodiments of the invention. For example, in another embodiment, n is 1 or greater, and m is one or greater; or n is 2 or greater, m is 1, and q is 1; or n is 2 or greater, m is 1, q is 1, and p is 1; or n is 2 or greater, m is 1, q is 1, and r is 1; or n is 2 or greater, m is 1, q is 1, p is 1, and r is 1; and so forth.

In another embodiment, the polyvalent linker includes one or more divalent hydrophilic radicals, as described herein, also called linkers or spacer linkers. It is appreciated that the arrangement and/or orientation of the various hydrophilic linkers may be in a linear or branched fashion, or both. For example, the hydrophilic linkers may form the backbone of the linker forming the conjugate between the ligand and the one or more drugs. Alternatively, the hydrophilic portion of the linker may be pendant to or attached to the backbone of the chain of atoms connecting the binding ligand B to the one or more drugs D. In this latter arrangement, the hydrophilic portion may be proximal or distal to the backbone chain of atoms.

In another embodiment, the linker is more or less linear, and the hydrophilic groups are arranged largely in a series to form a chain-like linker in the conjugate. Said another way, the hydrophilic groups form some or all of the backbone of the linker in this linear embodiment.

In another embodiment, the linker is branched with hydrophilic groups. In this branched embodiment, the hydrophilic groups may be proximal to the backbone or distal to the backbone. In each of these arrangements, the linker is more spherical or cylindrical in shape. In one variation, the linker is shaped like a bottle-brush. In one aspect, the backbone of the linker is formed by a linear series of amides, and the hydrophilic portion of the linker is formed by a parallel arrangement of branching side chains, such as by connecting monosaccharides, sulfonates, and the like, and derivatives and analogs thereof.

It is understood that the linker may be neutral or ionizable under certain conditions, such as physiological conditions encountered in vivo. For ionizable linkers, under the selected conditions, the linker may deprotonate to form a negative ion, or alternatively become protonated to form a positive ion. It is appreciated that more than one deprotonation or protonation event may occur. In addition, it is understood that the same linker may deprotonate and protonate to form inner salts or zwitterionic compounds.

In another embodiment, the hydrophilic spacer linkers are neutral, an in particular neutral under physiological conditions, the linkers do not significantly protonate nor deprotonate. In another embodiment, the hydrophilic spacer linkers may be protonated to carry one or more positive charges. It is understood that the protonation capability is condition dependent. In one aspect, the conditions are physiological conditions, and the linker is protonated in vivo. In another embodiment, the spacers include both regions that are neutral and regions that may be protonated to carry one or more positive charges. In another embodiment, the spacers include both regions that may be deprotonated to carry one or more negative charges and regions that may be protonated to carry one or more positive charges. It is understood that in this latter embodiment that zwitterions or inner salts may be formed.

In one aspect, the regions of the linkers that may be deprotonated to carry a negative charge include carboxylic acids, such as aspartic acid, glutamic acid, and longer chain carboxylic acid groups, and sulfuric acid esters, such as alkyl esters of sulfuric acid. In another aspect, the regions of the linkers that may be protonated to carry a positive charge include amino groups, such as polyaminoalkylenes including ethylene diamines, propylene diamines, butylene diamines and the like, and/or heterocycles including pyrolidines, piperidines, piperazines, and other amino groups, each of which is optionally substituted. In another embodiment, the regions of the linkers that are neutral include poly hydroxyl groups, such as sugars, carbohydrates, saccharides, inositols, and the like, and/or polyether groups, such as polyoxyalkylene groups including polyoxyethylene, polyoxypropylene, and the like.

In one embodiment, the hydrophilic spacer linkers described herein include are formed primarily from carbon, hydrogen, and oxygen, and have a carbon/oxygen ratio of about 3:1 or less, or of about 2:1 or less. In one aspect, the hydrophilic linkers described herein include a plurality of ether functional groups. In another aspect, the hydrophilic linkers described herein include a plurality of hydroxyl functional groups. Illustrative fragments and radicals that may be used to form such linkers include polyhydroxyl compounds such as carbohydrates, polyether compounds such as polyethylene glycol units, and acid groups such as carboxyl and alkyl sulfuric acids. In one variation, oligoamide spacers, and the like may also be included in the linker.

Illustrative divalent hydrophilic linkers include carbohydrates such as saccharopeptides as described herein that include both a peptide feature and sugar feature; glucuronides, which may be incorporated via [2+3] Huisgen cyclization, also known as click chemistry; β-alkyl glycosides, such as of 2-deoxyhexapyranoses (2-deoxyglucose, 2-deoxyglucuronide, and the like), and β-alkyl mannopyranosides. Illustrative PEG groups include those of a specific length range from about 4 to about 20 PEG groups. Illustrative alkyl sulfuric acid esters may also be introduced with click chemistry directly into the backbone. Illustrative oligoamide spacers include EDTA and DTPA spacers, β-amino acids, and the like.

In another embodiment, the polyvalent linker L comprises one or more polyethers, such as the linkers of the following formulae:

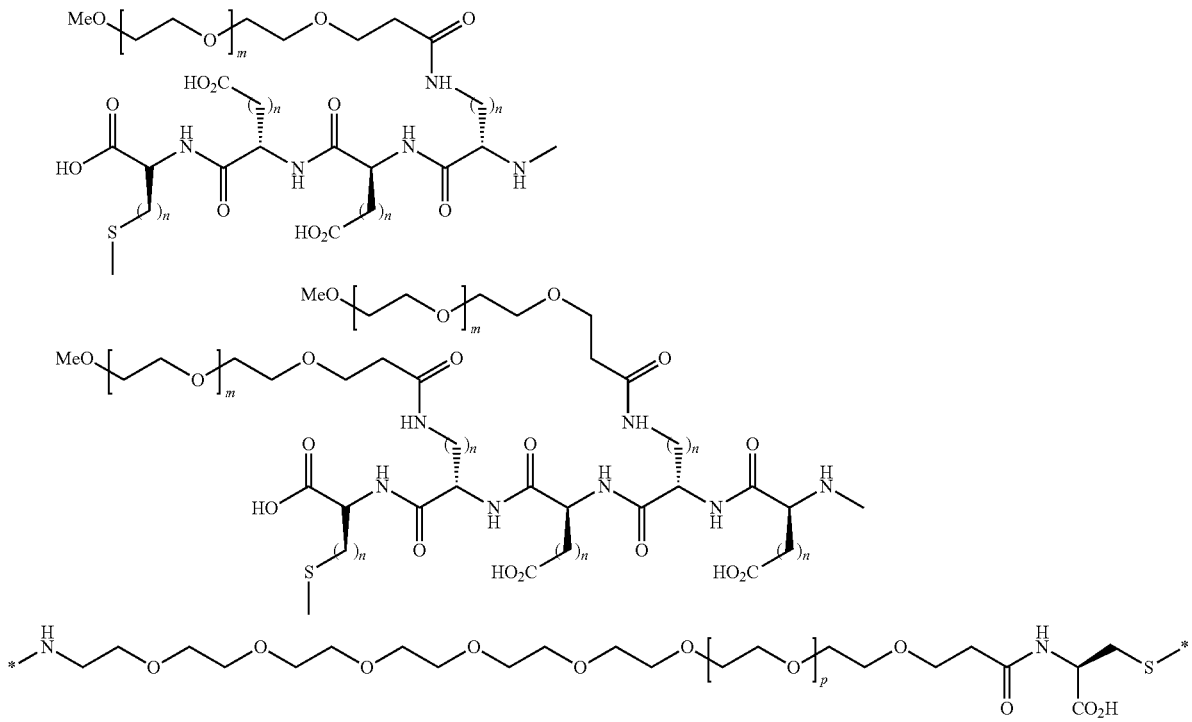

where m is an integer independently selected in each instance from 1 to about 8; p is an integer selected 1 to about 10; and n is an integer independently selected in each instance from 1 to about 3. In one aspect, m is independently in each instance 1 to about 3. In another aspect, n is 1 in each instance. In another aspect, p is independently in each instance about 4 to about 6. Illustratively, the corresponding polypropylene polyethers corresponding to the foregoing are contemplated herein and may be included in the conjugates as hydrophilic spacer linkers. In addition, it is appreciated that mixed polyethylene and polypropylene polyethers may be included in the conjugates as hydrophilic spacer linkers. Further, cyclic variations of the foregoing polyether compounds, such as those that include tetrahydrofuranyl, 1,3-dioxanes, 1,4-dioxanes, and the like are contemplated herein.

In another embodiment, the polyvalent linker L comprises a plurality of hydroxyl functional groups, such as linkers that incorporate monosaccharides, oligosaccharides, polysaccharides, and the like. It is to be understood that the polyhydroxyl containing spacer linkers comprises a plurality of —(CROH)— groups, where R is hydrogen or alkyl.

In another embodiment, the polyvalent linker L comprises one or more of the following fragments:

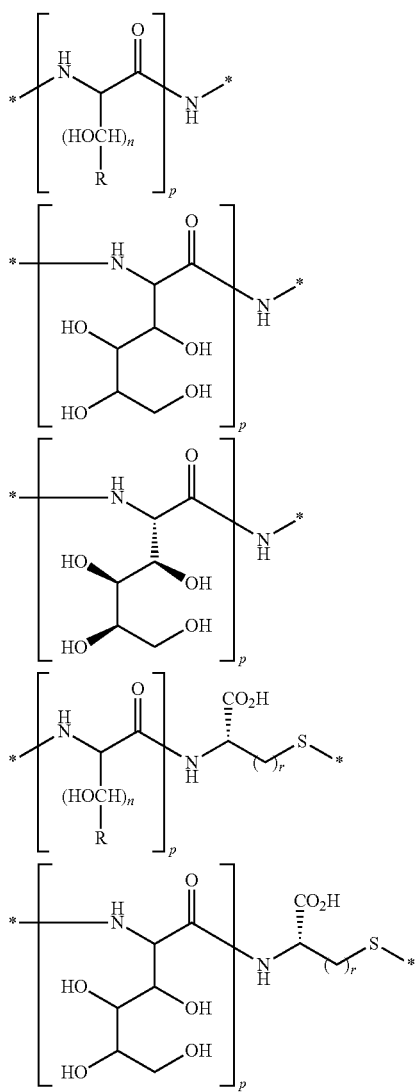

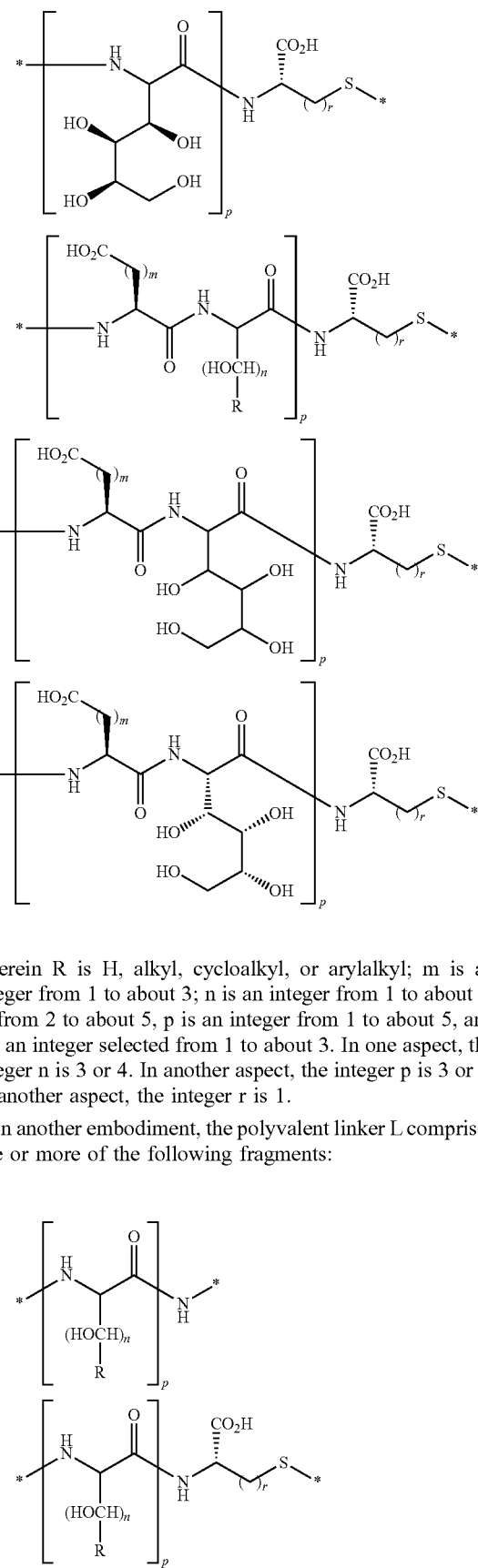

wherein R is H, alkyl, cycloalkyl, or arylalkyl; m is an integer from 1 to about 3; n is an integer from 1 to about 5, or from 2 to about 5, p is an integer from 1 to about 5, and r is an integer selected from 1 to about 3. In one aspect, the integer n is 3 or 4. In another aspect, the integer p is 3 or 4. In another aspect, the integer r is 1.

In another embodiment, the polyvalent linker L comprises one or more of the following fragments:

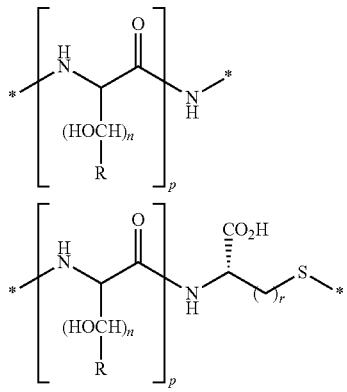

-continued

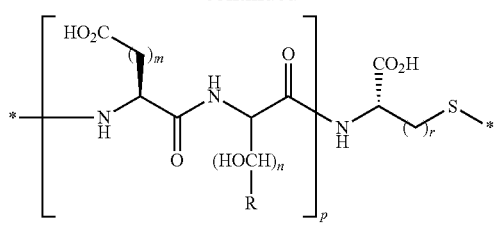

wherein R is H, alkyl, cycloalkyl, or arylalkyl; m is an integer from 1 to about 3; n is an integer from 1 to about 5, or from 2 to about 5, p is an integer from 1 to about 5, and r is an integer selected from 1 to about 3. In one aspect, the integer n is 3 or 4. In another aspect, the integer p is 3 or 4. In another aspect, the integer r is 1.

In another embodiment, the polyvalent linker L comprises one or more of the following cyclic polyhydroxyl groups:

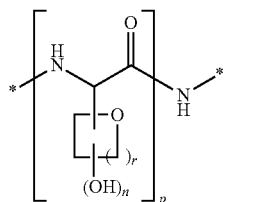

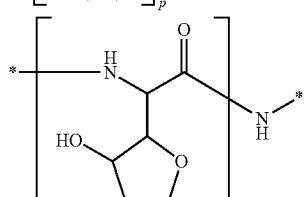

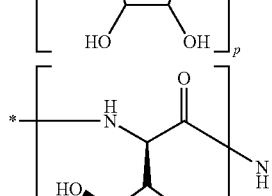

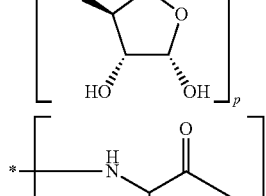

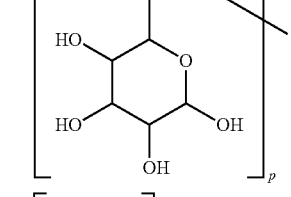

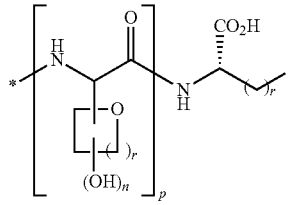

-continued

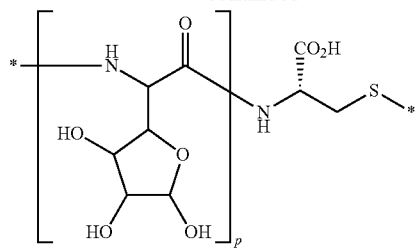

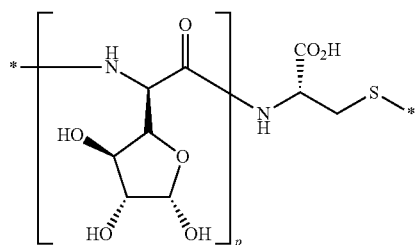

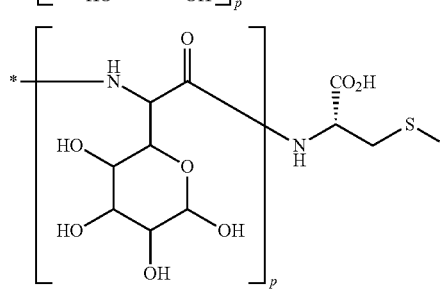

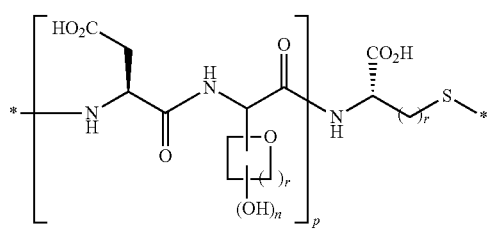

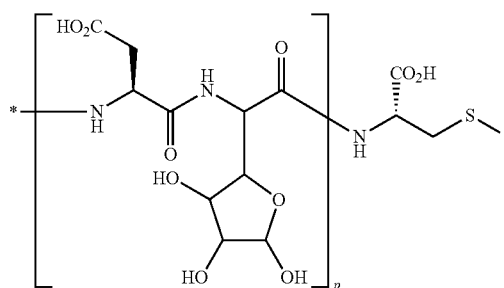

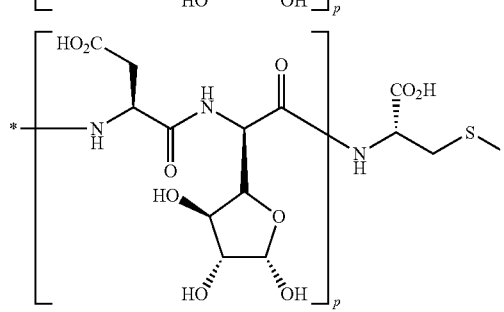

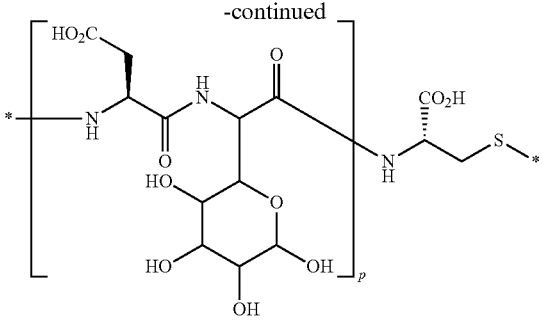

wherein n is an integer from 2 to about 5, p is an integer from 1 to about 5, and r is an integer from 1 to about 4. In one aspect, the integer n is 3 or 4. In another aspect, the integer p is 3 or 4. In another aspect, the integer r is 2 or 3. It is understood that all stereochemical forms of such sections of the linkers are contemplated herein. For example, in the above formula, the section may be derived from ribose, xylose, glucose, mannose, galactose, or other sugar and retain the stereochemical arrangements of pendant hydroxyl and alkyl groups present on those molecules. In addition, it is to be understood that in the foregoing formulae, various deoxy compounds are also contemplated. Illustratively, compounds of the following formulae are contemplated:

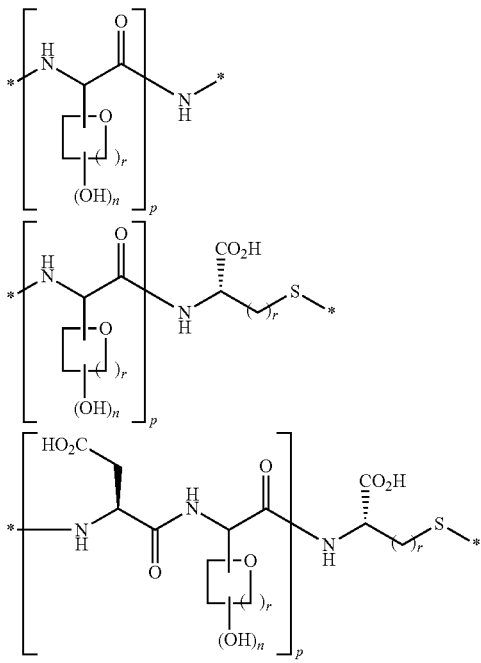

wherein n is equal to or less than r, such as when r is 2 or 3, n is 1 or 2, or 1, 2, or 3, respectively.

In another embodiment, the polyvalent linker L comprises one or more polyhydroxyl radicals of the following formula:

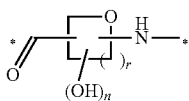

wherein n and r are each an integer selected from 1 to about 3. In one aspect, the linker includes one or more polyhydroxyl compounds of the following formulae:

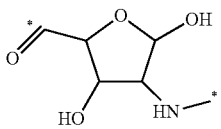 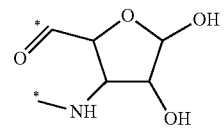

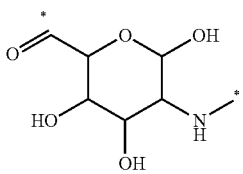 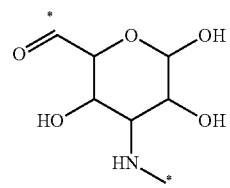

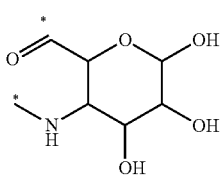

It is understood that all stereochemical forms of such sections of the linkers are contemplated herein. For example, in the above formula, the section may be derived from ribose, xylose, glucose, mannose, galactose, or other sugar and retain the stereochemical arrangements of pendant hydroxyl and alkyl groups present on those molecules.

In another embodiment, the polyvalent linker L comprises one or more polyhydroxyl groups that are spaced away from the backbone of the linker. In one embodiment, such carbohydrate groups or polyhydroxyl groups are connected to the back bone by a triazole group, forming triazole-linked hydrophilic spacer linkers. Illustratively, the linker includes fragments of the following formulae:

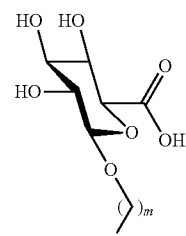

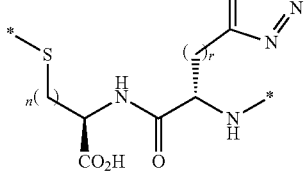

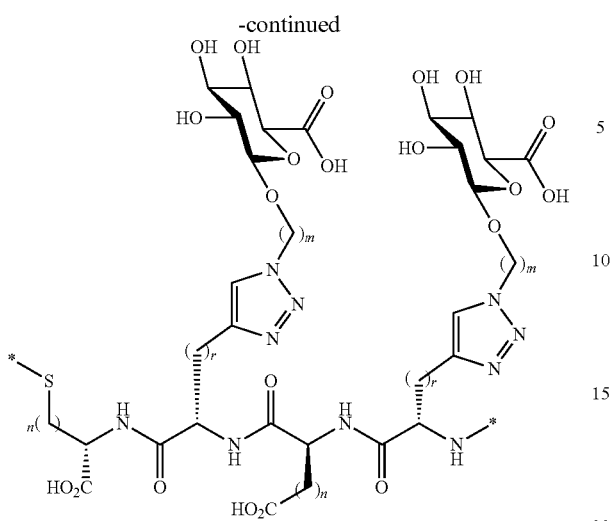

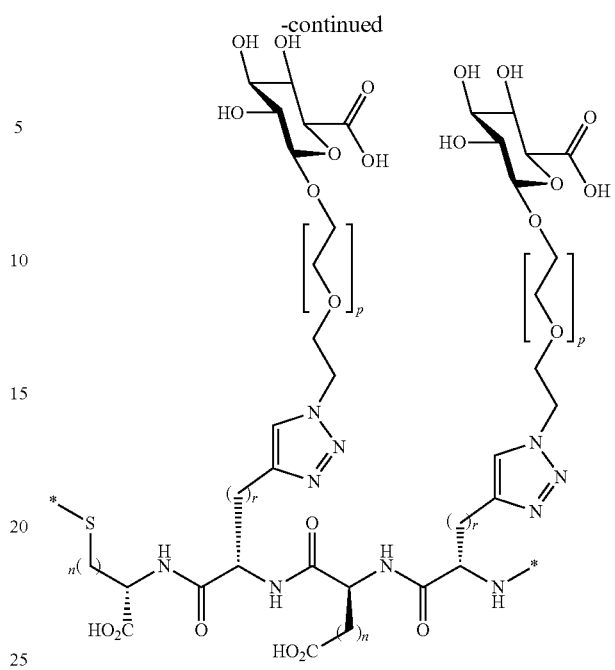

wherein n, m, and r are integers and are each independently selected in each instance from 1 to about 5. In one illustrative aspect, m is independently 2 or 3 in each instance. In another aspect, r is 1 in each instance. In another aspect, n is 1 in each instance. In one variation, the group connecting the polyhydroxyl group to the backbone of the linker is a different heteroaryl group, including but not limited to, pyrrole, pyrazole, 1,2,4-triazole, furan, oxazole, isoxazole, thienyl, thiazole, isothiazole, oxadiazole, and the like. Similarly, divalent 6-membered ring heteroaryl groups are contemplated. Other variations of the foregoing illustrative hydrophilic spacer linkers include oxyalkylene groups, such as the following formulae:

wherein n and r are integers and are each independently selected in each instance from 1 to about 5; and p is an integer selected from 1 to about 4.

In another embodiment, the polyvalent linker L comprises one or more carbohydrate groups or polyhydroxyl groups connected to the back bone by an amide group, forming amide-linked hydrophilic spacer linkers. Illustratively, such linkers include fragments of the following formulae:

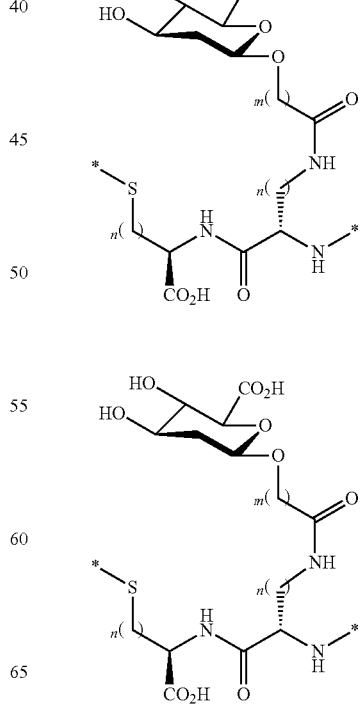

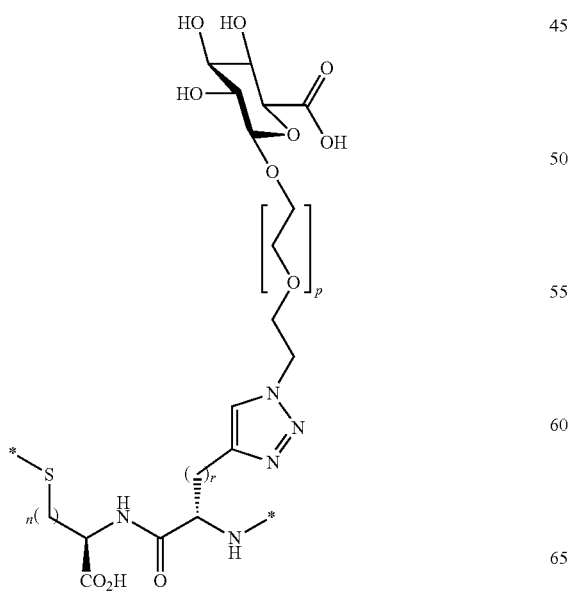

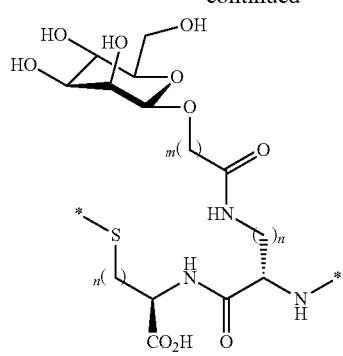

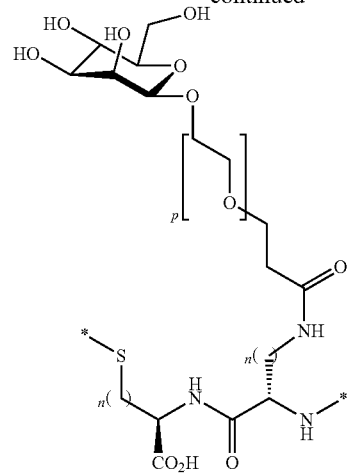

wherein n is an integer selected from 1 to about 3, and m is an integer selected from 1 to about 22. In one illustrative aspect, n is 1 or 2. In another illustrative aspect, m is selected from about 6 to about 10, illustratively 8. In one variation, the group connecting the polyhydroxyl group to the backbone of the linker is a different functional group, including but not limited to, esters, ureas, carbamates, acylhydrazones, and the like. Similarly, cyclic variations are contemplated. Other variations of the foregoing illustrative hydrophilic spacer linkers include oxyalkylene groups, such as the following formulae:

wherein n and r are integers and are each independently selected in each instance from 1 to about 5; and p is an integer selected from 1 to about 4.

In another embodiment, the polyvalent linker L comprises one or more of the following fragments:

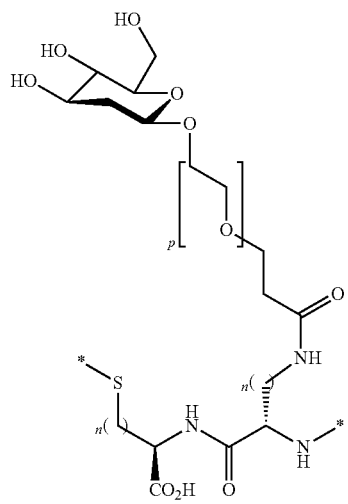

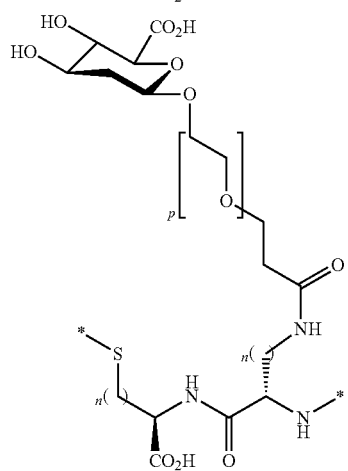

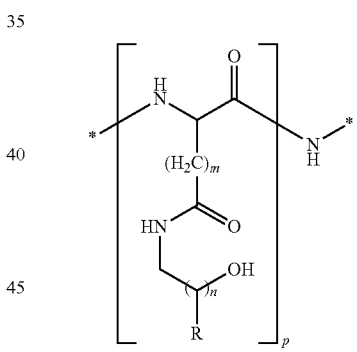

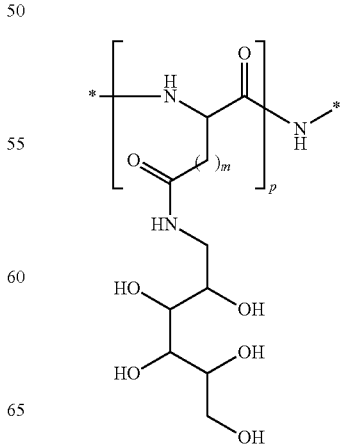

67
-continued
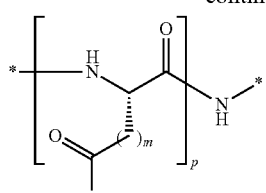
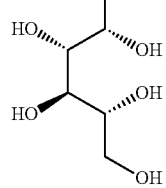
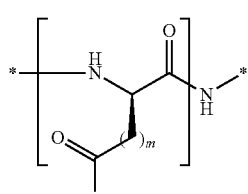
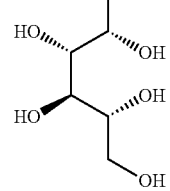
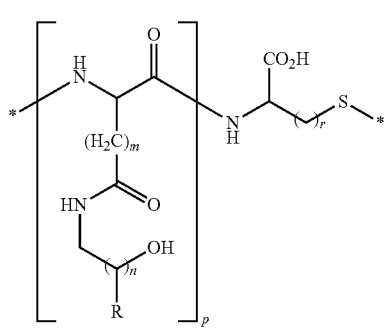
68
-continued
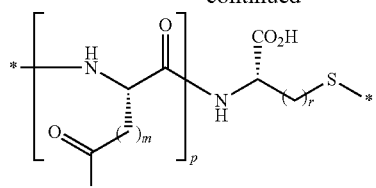
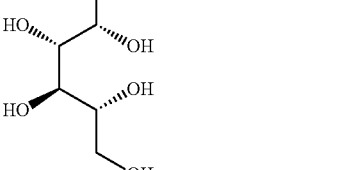
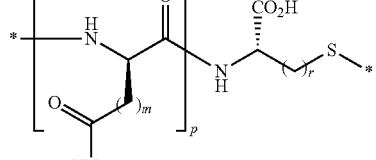
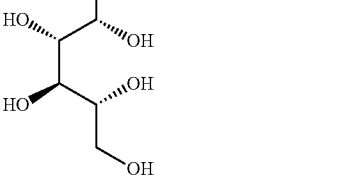
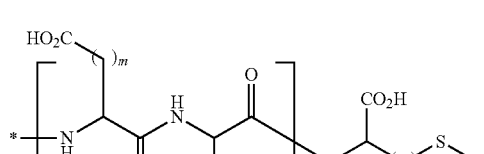
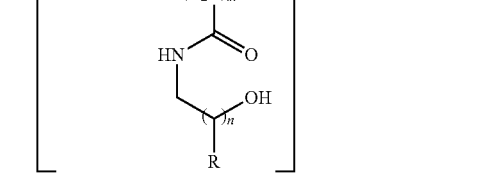
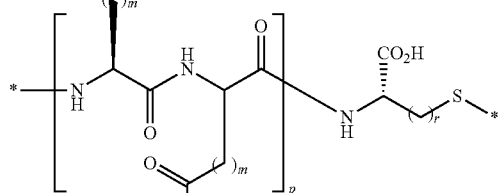
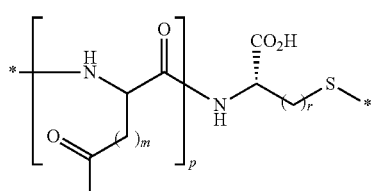
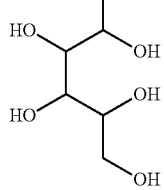
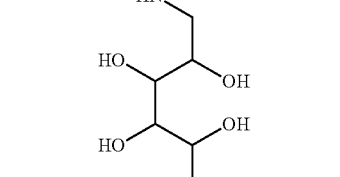

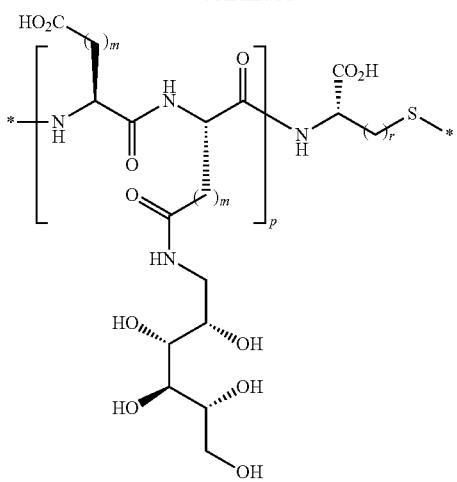

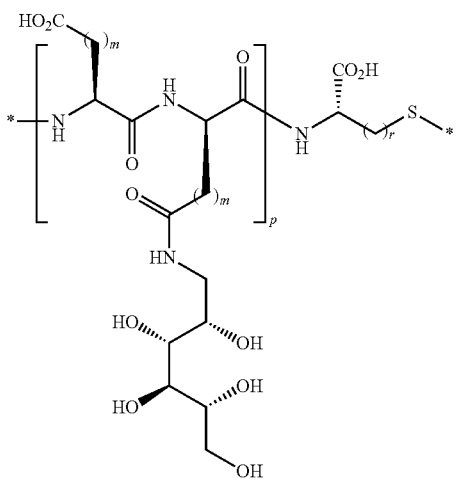

wherein R is H, alkyl, cycloalkyl, or arylalkyl; m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the polyvalent linker L comprises one or more of the following fragments:

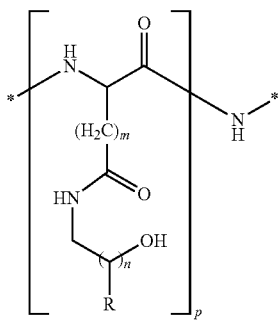

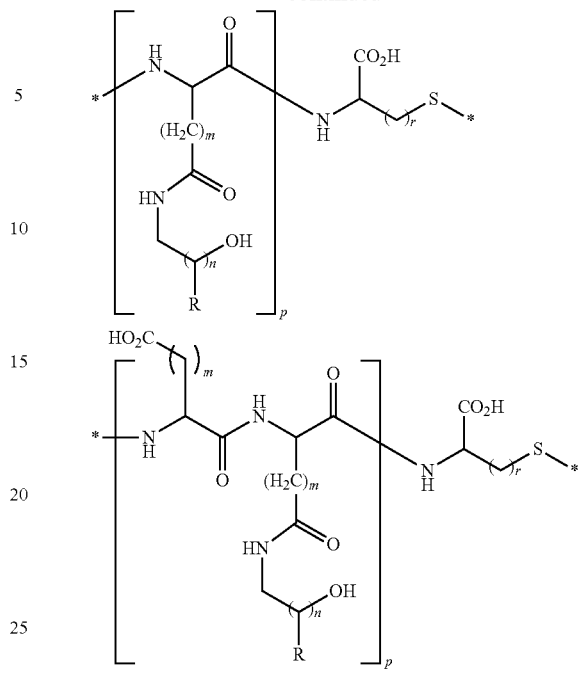

wherein R is H, alkyl, cycloalkyl, or arylalkyl; m is an independently selected integer from 1 to about 3; n is an integer from 2 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the polyvalent linker L comprises one or more of the following fragments:

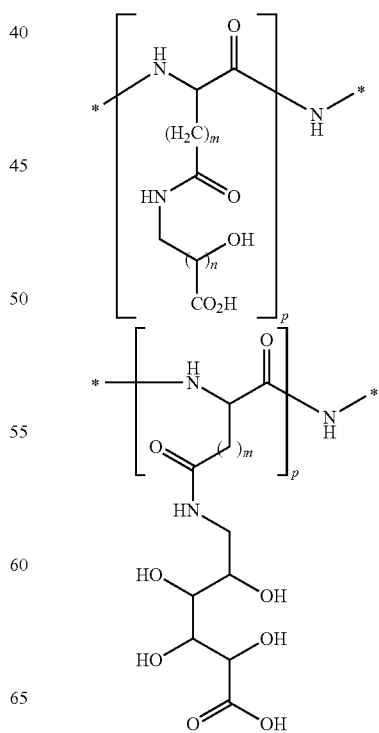

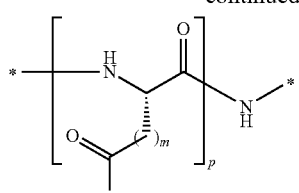
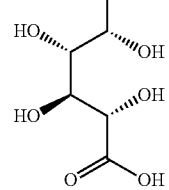
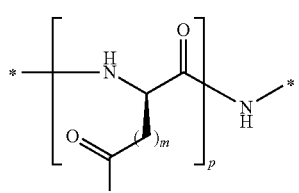
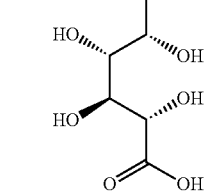
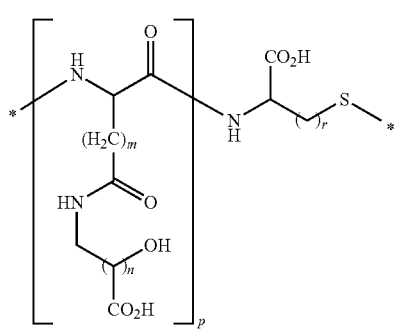
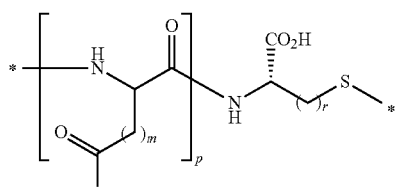
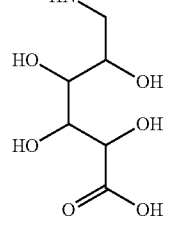
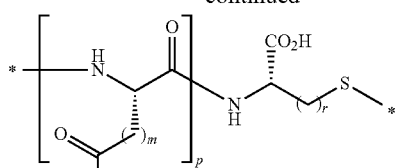
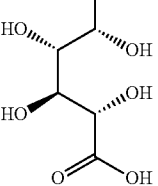
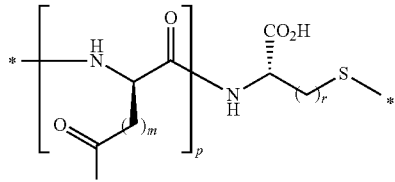
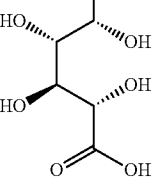
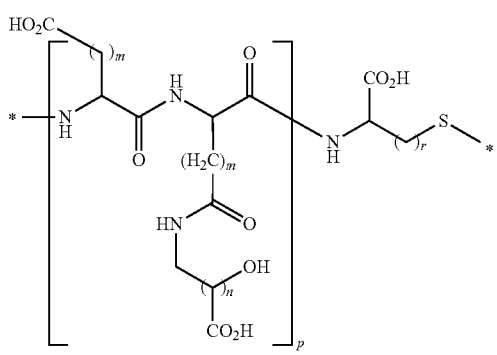
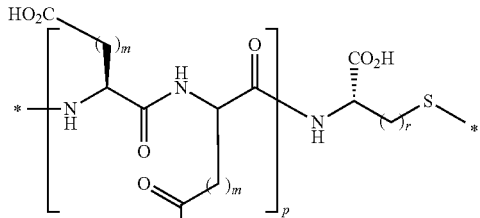
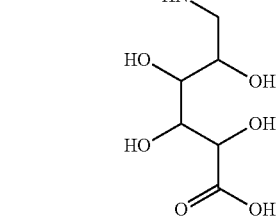

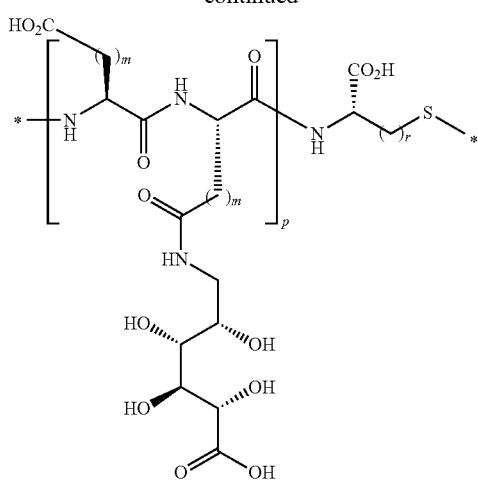

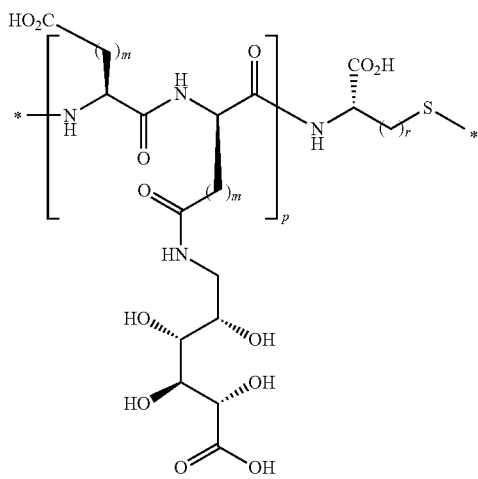

wherein m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the polyvalent linker L comprises one or more of the following fragments:

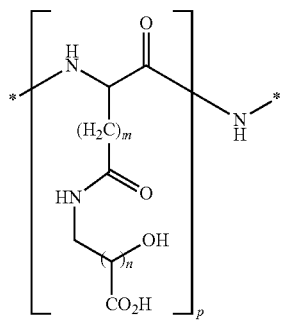

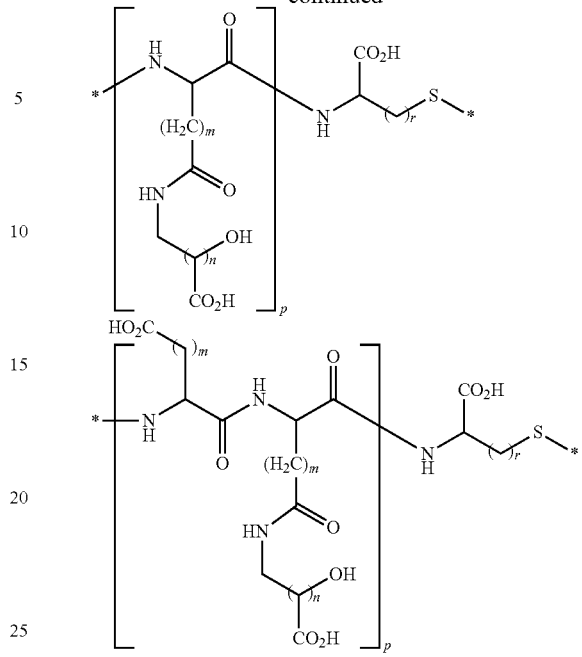

wherein m is an independently selected integer from 1 to about 3; n is an integer from 2 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the polyvalent linker L comprises one or more of the following fragments:

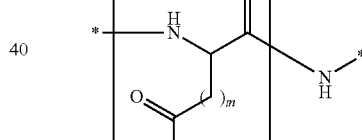

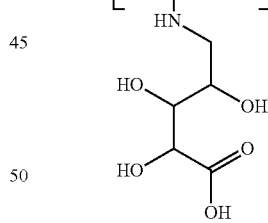

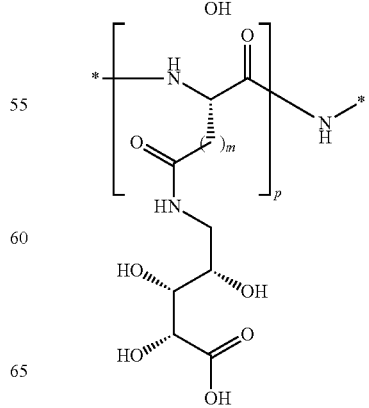

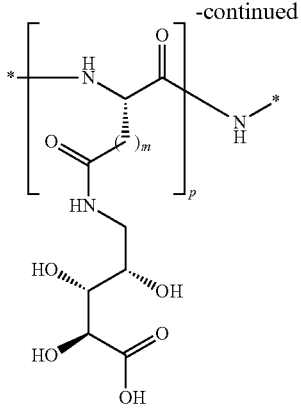

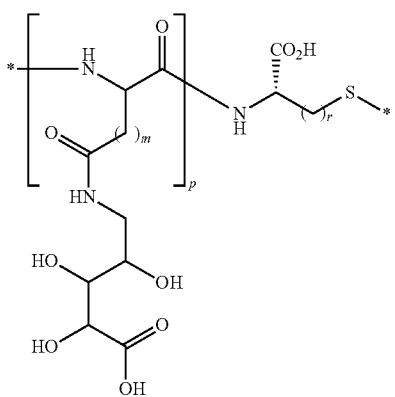

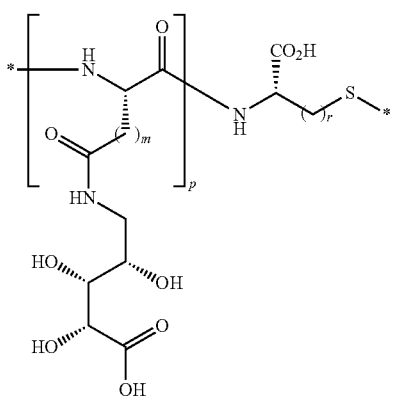

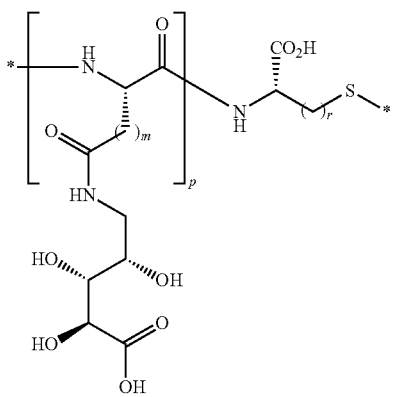

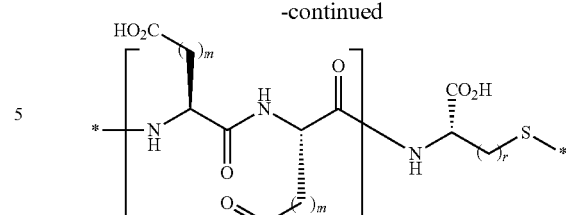

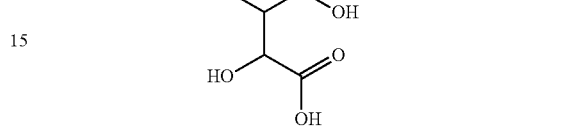

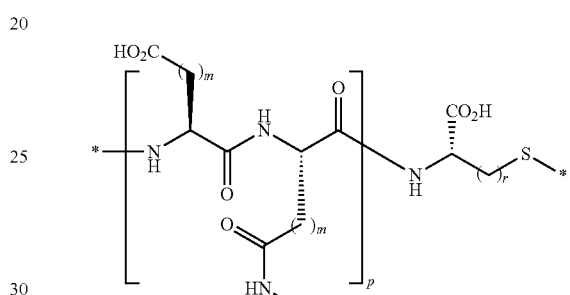

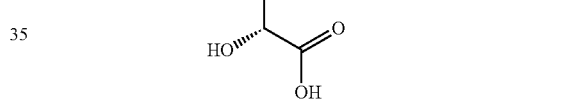

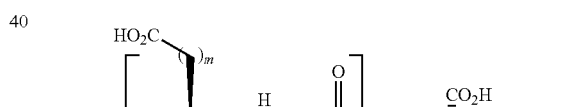

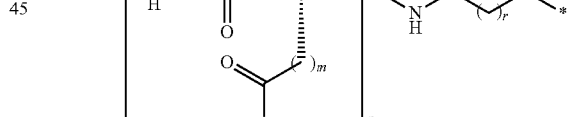

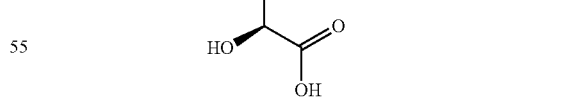

wherein m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the polyvalent linker L comprises a combination of backbone and branching side motifs such as is illustrated by the following formulae

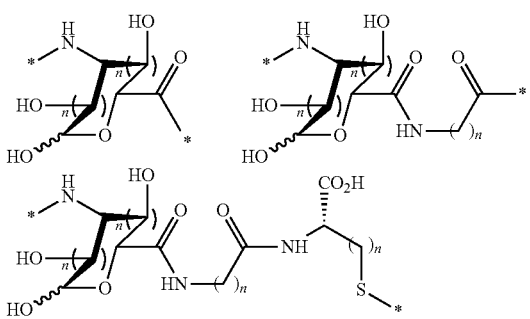

wherein n is an integer independently selected in each instance from 0 to about 3. The above formula are intended to represent 4, 5, 6, and even larger membered cyclic sugars. In addition, it is to be understood that the above formula may be modified to represent deoxy sugars, where one or more of the hydroxy groups present on the formulae are replaced by hydrogen, alkyl, or amino. In addition, it is to be understood that the corresponding carbonyl compounds are contemplated by the above formulae, where one or more of the hydroxyl groups is oxidized to the corresponding carbonyl.

In addition, in this illustrative embodiment, the pyranose includes both carboxyl and amino functional groups and (a) can be inserted into the backbone and (b) can provide synthetic handles for branching side chains in variations of this embodiment. Any of the pendant hydroxyl groups may be used to attach other chemical fragments, including additional sugars to prepare the corresponding oligosaccharides. Other variations of this embodiment are also contemplated, including inserting the pyranose or other sugar into the backbone at a single carbon, i.e. a spiro arrangement, at a geminal pair of carbons, and like arrangements. For example, one or two ends of the linker, or the drug D, or the binding ligand B may be connected to the sugar to be inserted into the backbone in a 1,1; 1,2; 1,3; 1,4; 2,3, or other arrangement.

In another embodiment, the hydrophilic spacer linkers described herein include are formed primarily from carbon, hydrogen, and nitrogen, and have a carbon/nitrogen ratio of about 3:1 or less, or of about 2:1 or less. In one aspect, the hydrophilic linkers described herein include a plurality of amino functional groups.

In another embodiment, the polyvalent linker L comprises one or more amino groups of the following formulae:

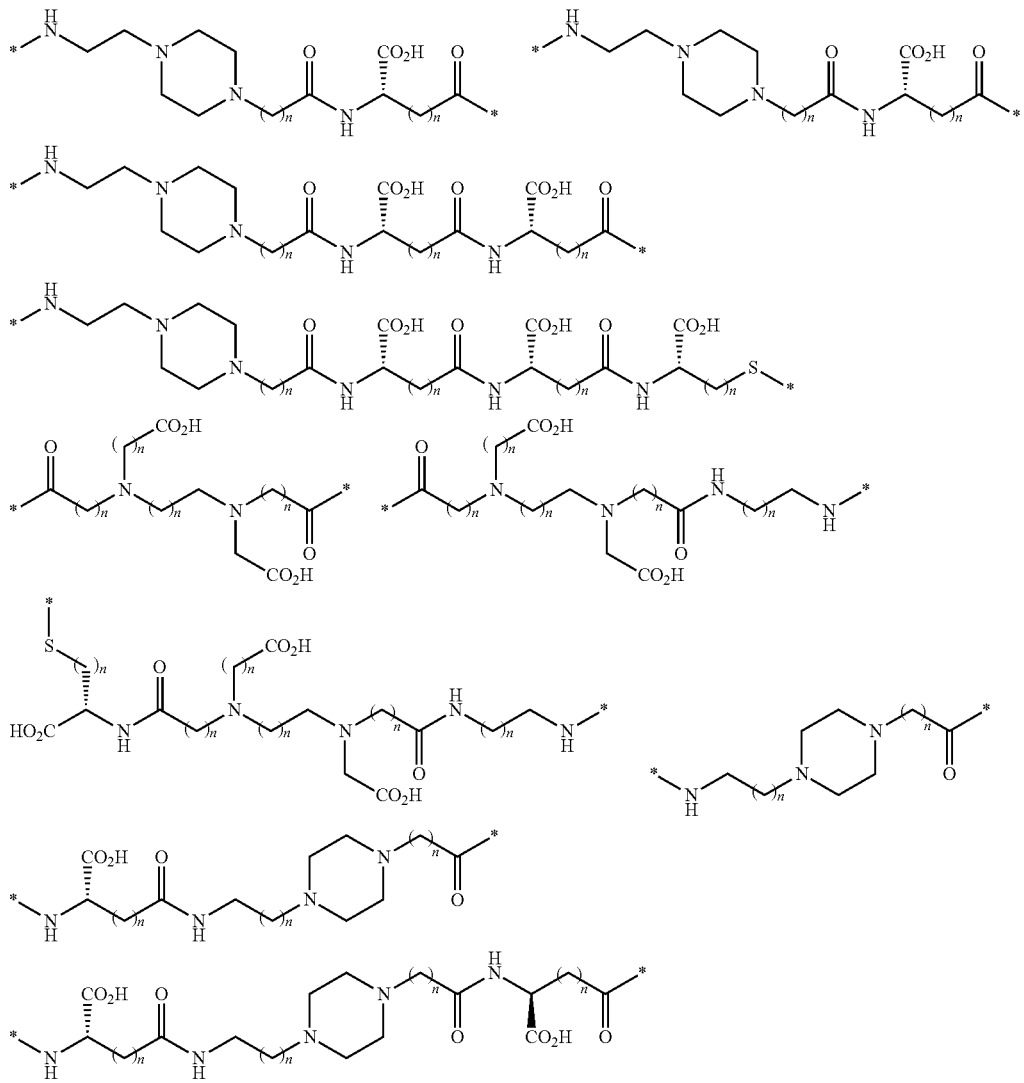

-continued

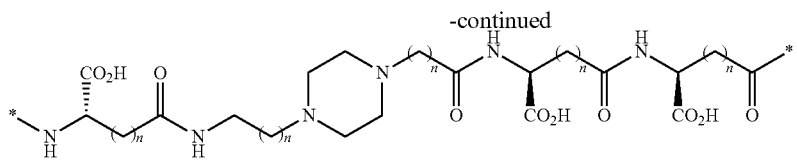

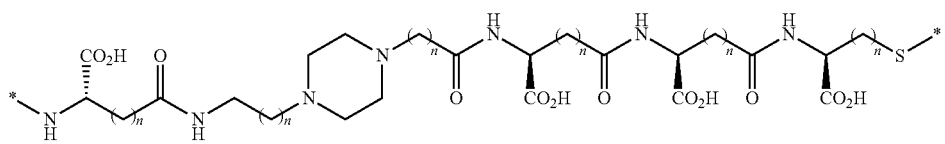

where n is an integer independently selected in each instance from 1 to about 3. In one aspect, the integer n is independently 1 or 2 in each instance. In another aspect, the integer n is 1 in each instance.

In another embodiment, the polyvalent linker L comprises one or more sulfuric acid esters, such as an alkyl ester of sulfuric acid. Illustratively, the linker includes the following formula(e):

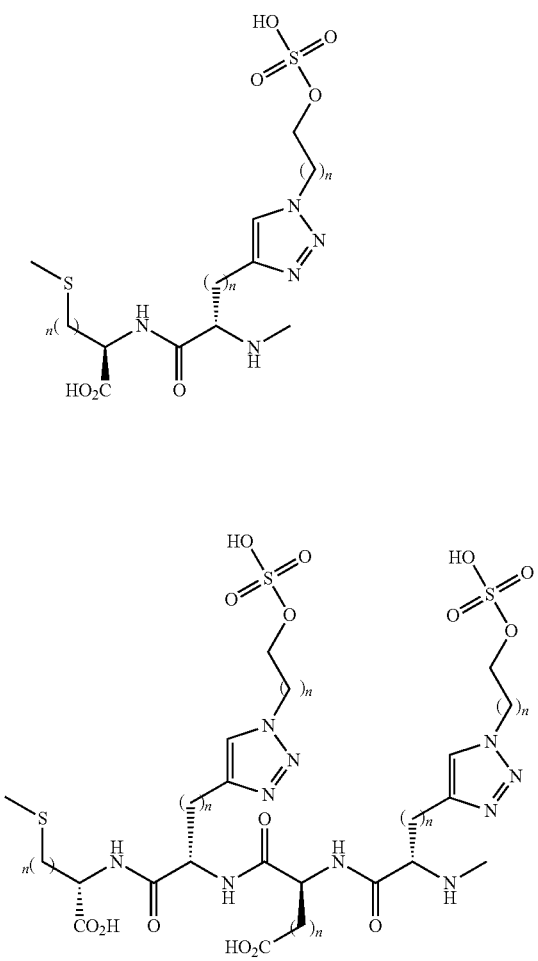

where n is an integer independently selected in each instance from 1 to about 3. Illustratively, n is independently 1 or 2 in each instance.

It is understood, that in such polyhydroxyl, polyamino, carboxylic acid, sulfuric acid, and like linkers that include free hydrogens bound to heteroatoms, one or more of those free hydrogen atoms may be protected with the appropriate hydroxyl, amino, or acid protecting group, respectively, or alternatively may be blocked as the corresponding pro-drugs, the latter of which are selected for the particular use, such as pro-drugs that release the parent drug under general or specific physiological conditions.

In another embodiment, the polyvalent linker comprises one or more of the following divalent radicals:

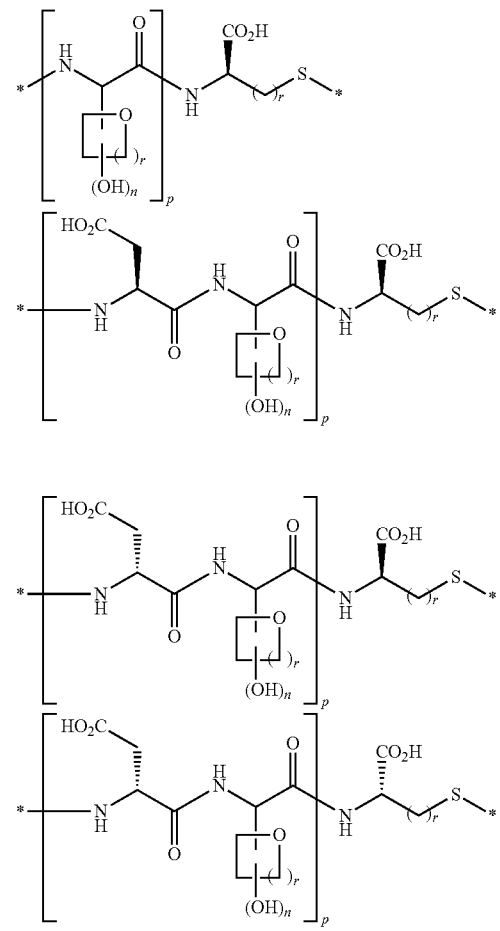

wherein n is an integer from 2 to about 5, p is an integer from 1 to about 5, and r is an integer from 1 to about 4, as described above.

It is to be further understood that in the foregoing embodiments, open positions, such as (*) atoms are locations for attachment of the binding ligand (B) or any drug (D) to be delivered. In addition, it is to be understood that such attachment of either or both of B and any D may be direct or through an intervening linker comprising one or more of the radicals described herein. In addition, (*) atoms may form releasable linkers with any drug D, or other portion of the linker L.

In another embodiment, the hydrophilic spacer linker comprises one or more carbohydrate containing or polyhydroxyl group containing linkers. In another embodiment, the hydrophilic spacer linker comprises at least three carbohydrate containing or polyhydroxyl group containing linkers. In another embodiment, the hydrophilic spacer linker comprises one or more carbohydrate containing or polyhydroxyl group containing linkers, and one or more aspartic acids. In another embodiment, the hydrophilic spacer linker comprises one or more carbohydrate containing or polyhydroxyl group containing linkers, and one or more glutamic acids. In another embodiment, the hydrophilic spacer linker comprises one or more carbohydrate containing or polyhydroxyl group containing linkers, one or more glutamic acids, one or more aspartic acids, and one or more beta amino alanines. In a series of variations, in each of the foregoing embodiments, the hydrophilic spacer linker also includes one or more cysteines. In another series of variations, in each of the foregoing embodiments, the hydrophilic spacer linker also includes at least one arginine.

In another embodiment, the polyvalent linker L includes a hydrophilic spacer linker comprising one or more divalent 1,4-piperazines that are included in the chain of atoms connecting at least one of the binding ligands (L) with at least one of the drugs (D). In one variation, the hydrophilic spacer linker includes one or more carbohydrate containing or polyhydroxyl group containing linkers. In another variation, the hydrophilic spacer linker includes one or more carbohydrate containing or polyhydroxyl group containing linkers and one or more aspartic acids. In another variation, the hydrophilic spacer linker includes one or more carbohydrate containing or polyhydroxyl group containing linkers and one or more glutamic acids. In a series of variations, in each of the foregoing embodiments, the hydrophilic spacer linker also includes one or more cysteines. In another series of variations, in each of the foregoing embodiments, the hydrophilic spacer linker also includes at least one arginine.

In another embodiment, the hydrophilic spacer linker comprises one or more oligoamide hydrophilic spacers, such as but not limited to aminoethylpiperazinylacetamide.

In another embodiment, the polyvalent linker L includes a hydrophilic spacer linker comprising one or more triazole linked carbohydrate containing or polyhydroxyl group containing linkers. In another embodiment, the hydrophilic spacer linker comprises one or more amide linked carbohydrate containing or polyhydroxyl group containing linkers. In another embodiment, the hydrophilic spacer linker comprises one or more PEG groups and one or more cysteines. In another embodiment, the hydrophilic spacer linker comprises one or more EDTE derivatives.

In another embodiment, the polyvalent linker L includes a divalent radical of the formula

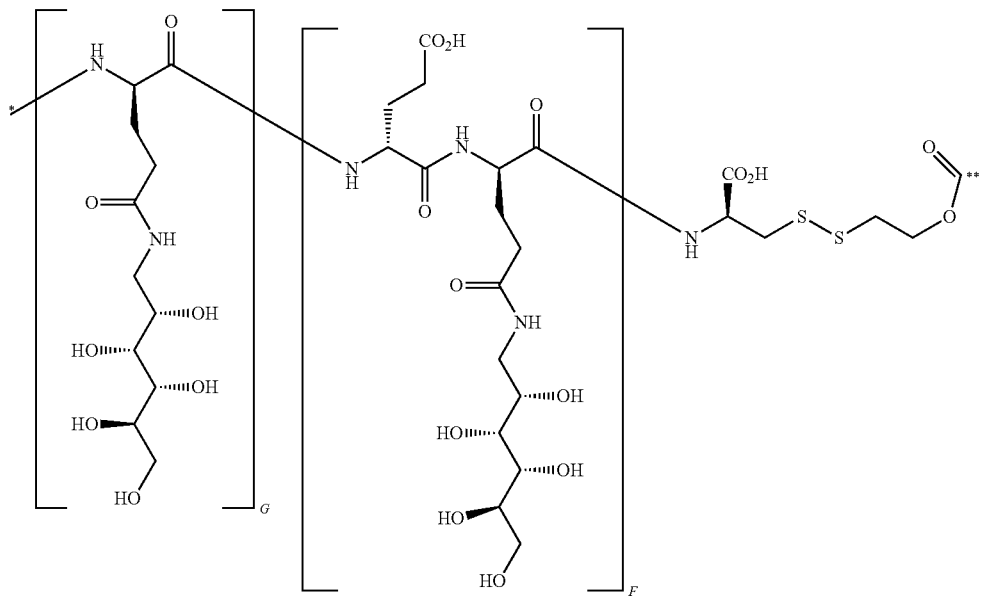

wherein * indicates the point of attachment to a folate and ** indicates the point of attachment to a drug; and F and G are each independently 1, 2, 3 or 4 are described.

In another embodiment, the polyvalent linker L includes a trivalent radical of the formula

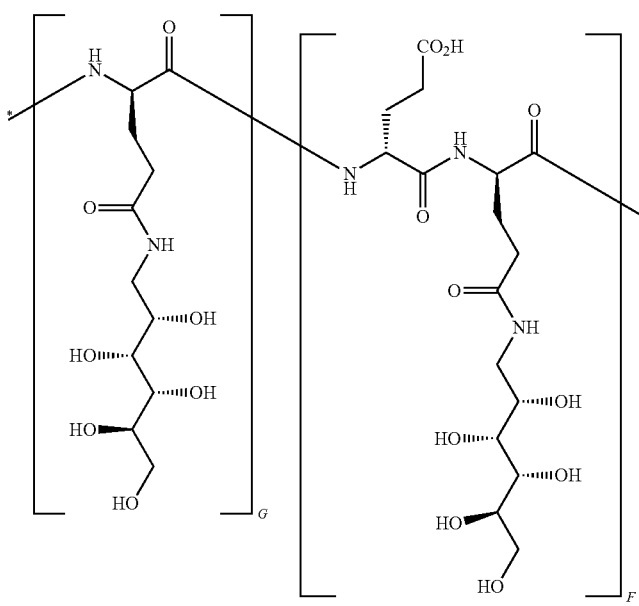

wherein *, , * each indicate points of attachment to the folate receptor binding moiety B, and the one or more drugs D. It is to be understood that when there are fewer drugs, *, , * are substituted with hydrogen or a heteroatom. F and G are each independently 1, 2, 3 or 4; and $W^1$ is NH or O is described. In another aspect, $m^1$ is 0 or 1.

In any of the embodiments described herein heteroatom linkers can also be included in the polyvalent linker L, such as —$NR^1R^2$—, oxygen, sulfur, and the formulae —($NHR^1NHR^2$)—, —SO—, —($SO_2$)—, and —$N(R^3)O$—, wherein $R^1$, $R^2$, and $R^3$ are each independently selected from hydrogen, alkyl, aryl, arylalkyl, substituted aryl, substituted arylalkyl, heteroaryl, substituted heteroaryl, and alkoxyalkyl. It is to be understood that the heteroatom linkers may be used to covalently attach any of the radicals described herein, including drug radicals D to the polyvalent linker, ligand radicals B to the polyvalent linker, or various di and polyvalent radicals that from the polyvalent linker L Illustrative additional bivalent radicals that can be used to form part of the linker are as follows.

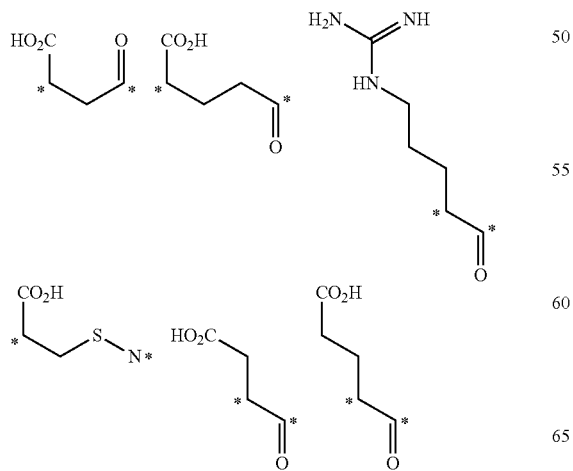

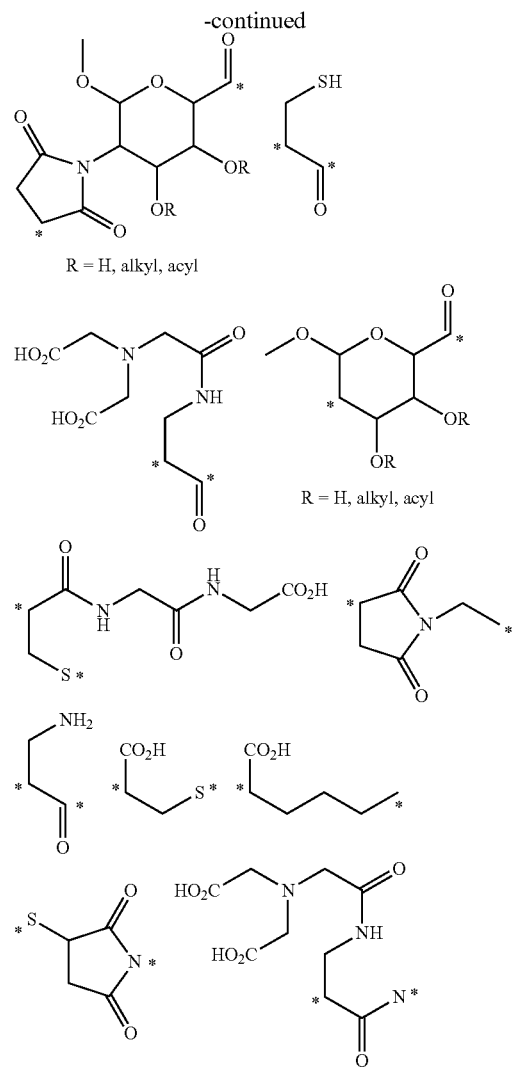

85
-continued
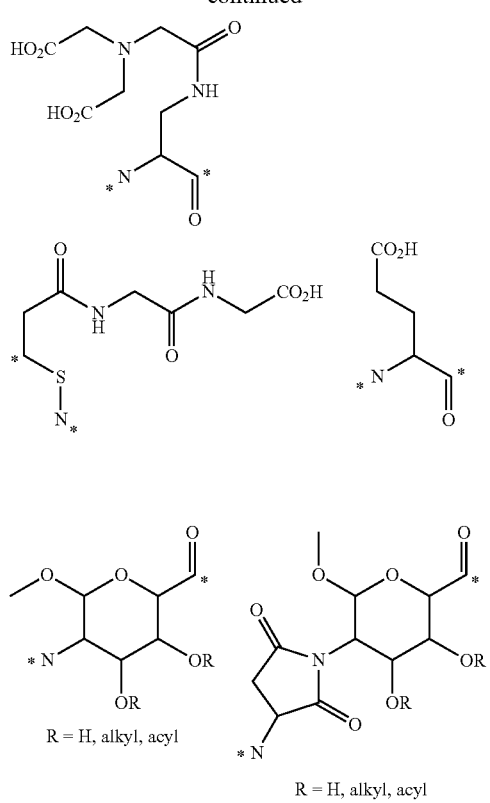
86
-continued
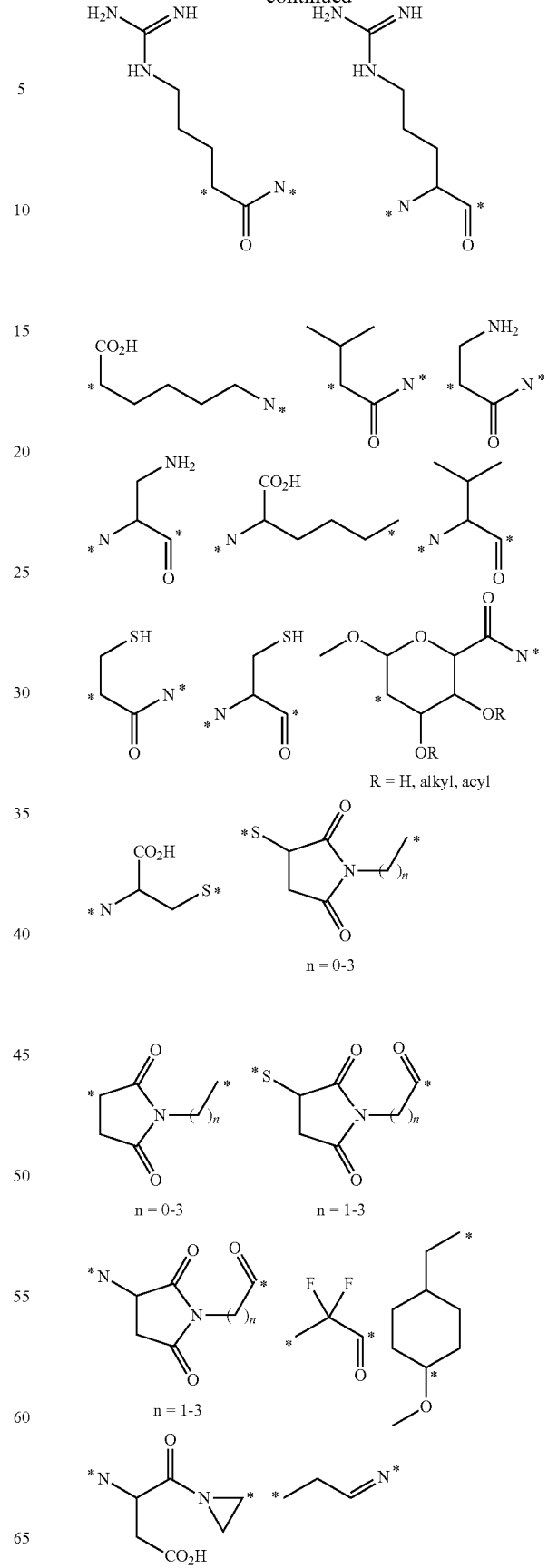

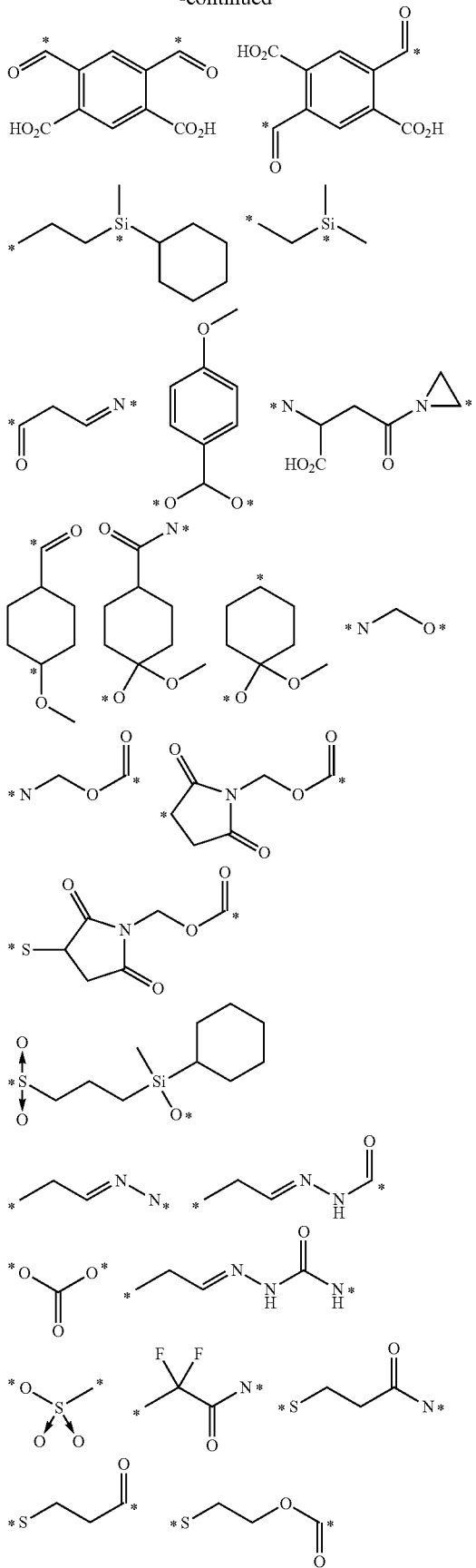
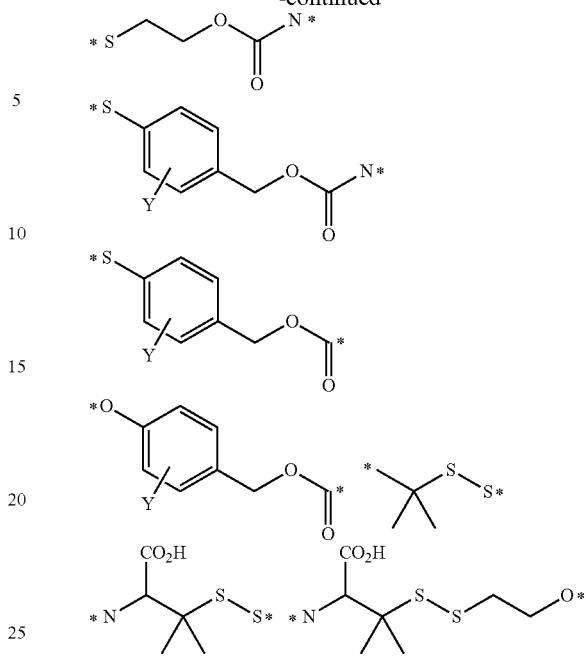

The polyvalent linker L is a releasable linker.

As used herein, the term "releasable linker" refers to a linker that includes at least one bond that can be broken under physiological conditions when the compounds described herein are delivered to or inside of the target cell. Accordingly, the term releasable linker does not generally refer simply to a bond that is labile in vivo, such as in serum, plasma, the gastrointestinal tract, or liver, unless those systems are the target for the cell surface receptor binding ligand. However, after delivery and/or selective targeting, releasable linkers may be cleaved by any process that includes at least one bond being broken in the linker or at the covalent attachment of the linker to B or any D under physiological conditions, such as by having one or more pH-labile, acid-labile, base-labile, oxidatively labile, metabolically labile, biochemically labile, and/or enzyme-labile bonds. It is appreciated that such physiological conditions resulting in bond breaking do not necessarily include a biological or metabolic process, and instead may include a standard chemical reaction, such as a hydrolysis reaction, for example, at physiological pH, or as a result of compartmentalization into a cellular organelle such as an endosome having a lower pH than cytosolic pH.

It is understood that a cleavable bond can connect two adjacent atoms within the releasable linker, and/or connect other linkers with B, and/or any D, as described herein, at any ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an additional heteroatom, a spacer linker, another releasable portion of the linker, any D, or B, following breakage of the bond, the releasable linker is separated from the other moiety.

Illustrative radicals that themselves include a cleavable bond, or form a cleavable bond with B and/or any D hemiacetals and sulfur variations thereof, acetals and sulfur variations thereof, hemiaminals, aminals, and the like, or which can be formed from methylene fragments substituted with at least one heteroatom, such as 1-alkoxyalkylene, 1-alkoxycycloalkylene, 1-alkoxyalkylenecarbonyl, 1-alkoxycycloalkylenecarbonyl, and the like. Illustrative releasable linkers described herein include polyvalent linkers that include carbonylarylcarbonyl, carbonyl(carboxyaryl)carbonyl, carbonyl(biscarboxyaryl)carbonyl, haloalkylenecarbonyl, and the like. Illustrative releasable linkers described herein include polyvalent linkers that include alkylene(dialkylsilyl), alkylene(alkylarylsilyl), alkylene(diarylsilyl), (dialkylsilyl)aryl, (alkylarylsilyl)aryl, (diarylsilyl)aryl, and the like. Illustrative releasable linkers described herein include oxycarbonyloxy, oxycarbonyloxyalkyl, sulfonyloxy, oxysulfonylalkyl, and the like. Illustrative releasable linkers described herein include polyvalent linkers that include iminoalkylidenyl, carbonylalkylideniminyl, iminocycloalkylidenyl, carbonylcycloalkylideniminyl, and the like. Illustrative releasable linkers described herein include polyvalent linkers that include alkylenethio, alkylenearylthio, and carbonylalkylthio, and the like. Each of the foregoing fragments is optionally substituted with a substituent $X^2$, as defined herein.

The substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the heteroatom linker can be nitrogen, and the substituent $X^2$ and the heteroatom linker can be taken together with the releasable linker to which they are bound to form an heterocycle.

The heterocycles can be pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

In any of the embodiments described herein, the releasable linker may include oxygen bonded to methylene, 1-alkoxyalkylene, 1-alkoxycycloalkylene, 1-alkoxyalkylenecarbonyl, and 1-alkoxycycloalkylenecarbonyl to form an acetal or ketal, wherein each of the fragments is optionally substituted with a substituent $X^2$, as defined herein. Alternatively, the methylene or alkylene is substituted with an optionally-substituted aryl.

In any of the embodiments described herein, the releasable linker may include oxygen bonded to sulfonylalkyl to form an alkylsulfonate.

In any of the embodiments described herein, the releasable linker may include nitrogen bonded to iminoalkylidenyl, carbonylalkylideniminyl, iminocycloalkylidenyl, and carbonylcycloalkylideniminyl to form an hydrazone, each of which is optionally substituted with a substituent $X^2$, as defined herein. In an alternate configuration, the hydrazone may be acylated with a carboxylic acid derivative, an orthoformate derivative, or a carbamoyl derivative to form releasable linkers containing various acylhydrazones.

In any of the embodiments described herein, the releasable linker may include oxygen bonded to alkylene(dialkylsilyl), alkylene(alkylarylsilyl), alkylene(diarylsilyl), (dialkylsilyl)aryl, (alkylarylsilyl)aryl, and (diarylsilyl)aryl to form a silanol, each of which is optionally substituted with a substituent $X^2$, as defined herein.

In any of the embodiments described herein, the releasable linker may include nitrogen bonded to carbonylarylcarbonyl, carbonyl(carboxyaryl)carbonyl, carbonyl(biscarboxyaryl)carbonyl to form an amide, or alternatively an amide with a drug nitrogen.

In any of the embodiments described herein, the releasable linker may include oxygen bonded to carbonylarylcarbonyl, carbonyl(carboxyaryl)carbonyl, carbonyl(biscarboxyaryl)carbonyl to form an ester, or alternatively an ester with drug oxygen.

It is to be understood that the bivalent spacer linkers may be combined in any chemically relevant way, either directly or via an intervening heteroatom to construct the releasable linkers described herein. It is further understood that the nature of the arrangement of spacer and heteroatom linkers defines where the releasable linker will cleave in vivo. For example, two spacer linkers that terminate in a sulfur atom when combined form a disulfide, which is the cleavable bond in the releasable linker formed thereby.

For example, in another embodiment, the polyvalent linker comprises a 3-thiosuccinimid-1-ylalkyloxymethyloxy moiety, where the methyl is optionally substituted with alkyl or substituted aryl.

In another embodiment, the polyvalent linker comprises a 3-thiosuccinimid-1-ylalkylcarbonyl, where the carbonyl forms an acylaziridine with the drug.

In another embodiment, the polyvalent linker comprises a 1-alkoxycycloalkylenoxy moiety.

In another embodiment, the polyvalent linker comprises an alkyleneaminocarbonyl(dicarboxylarylene)carboxylate.

In another embodiment, the polyvalent linker comprises a dithioalkylcarbonylhydrazide, where the hydrazide forms an hydrazone with the drug.

In another embodiment, the polyvalent linker comprises a 3-thiosuccinimid-1-ylalkylcarbonylhydrazide, where the hydrazide forms a hydrazone with the drug.

In another embodiment, the polyvalent linker comprises a 3-thioalkylsulfonylalkyl(disubstituted silyl)oxy, where the disubstituted silyl is substituted with alkyl or optionally substituted aryl.

In another embodiment, the polyvalent linker comprises a plurality of spacer linkers selected from the group consisting of the naturally occurring amino acids and stereoisomers thereof.

In another embodiment, the polyvalent linker comprises a 2-dithioalkyloxycarbonyl, where the carbonyl forms a carbonate with the drug.

In another embodiment, the polyvalent linker comprises a 2-dithioarylalkyloxycarbonyl, where the carbonyl forms a carbonate with the drug and the aryl is optionally substituted.

In another embodiment, the polyvalent linker comprises a 4-dithioarylalkyloxycarbonyl, where the carbonyl forms a carbonate with the drug, and the aryl is optionally substituted.

In another embodiment, the polyvalent linker comprises a 3-thiosuccinimid-1-ylalkyloxyalkyloxyalkylidene, where the alkylidene forms an hydrazone with the drug, each alkyl is independently selected, and the oxyalkyloxy is optionally substituted with alkyl or optionally substituted aryl.

In another embodiment, the polyvalent linker comprises a 2-dithioalkyloxycarbonylhydrazide.

In another embodiment, the polyvalent linker comprises a 2- or 3-dithioalkylamino, where the amino forms a vinylogous amide with the drug.

In another embodiment, the polyvalent linker comprises a 2-dithioalkylamino, where the amino forms a vinylogous amide with the drug, and the alkyl is ethyl.

In another embodiment, the polyvalent linker comprises a 2- or 3-dithioalkylaminocarbonyl, where the carbonyl forms a carbamate with the drug.

In another embodiment, the polyvalent linker comprises a 2-dithioalkylaminocarbonyl, where the carbonyl forms a carbamate with the drug. In another aspect, the alkyl is ethyl.

In another embodiment, the polyvalent linker comprises a 2-dithioalkyloxycarbonyl, where the carbonyl forms a carbamate with the drug. In another aspect, the alkyl is ethyl.

In another embodiment, the polyvalent linker comprises a 2-dithioarylalkyloxycarbonyl, where the carbonyl forms a carbamate or a carbamoylaziridine with the drug.

In another embodiment, the polyvalent linker comprises a 4-dithioarylalkyloxycarbonyl, where the carbonyl forms a carbamate or a carbamoylaziridine with the drug.

In another embodiment, the polyvalent linkers described herein comprise divalent radicals of formulae (II)

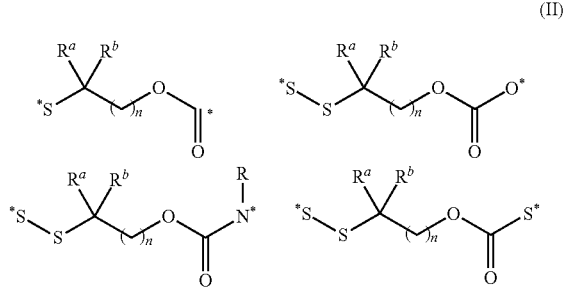

(II)

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates points of attachment for the drug, vitamin, imaging agent, diagnostic agent, other bivalent linkers, or other parts of the conjugate.

In another embodiment, the polyvalent linkers described herein comprise divalent radicals of formulae (III)

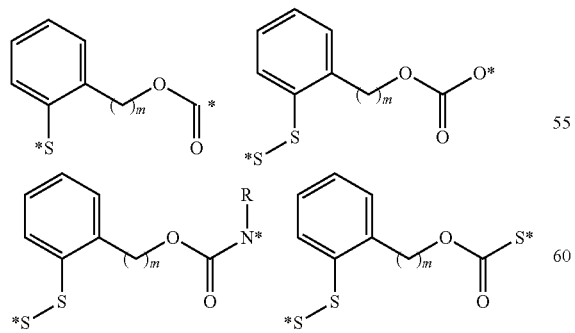

(III)

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other bivalent linkers, or other parts of the conjugate.

In another embodiment, the polyvalent linkers described herein comprise divalent radicals of formulae (IV)

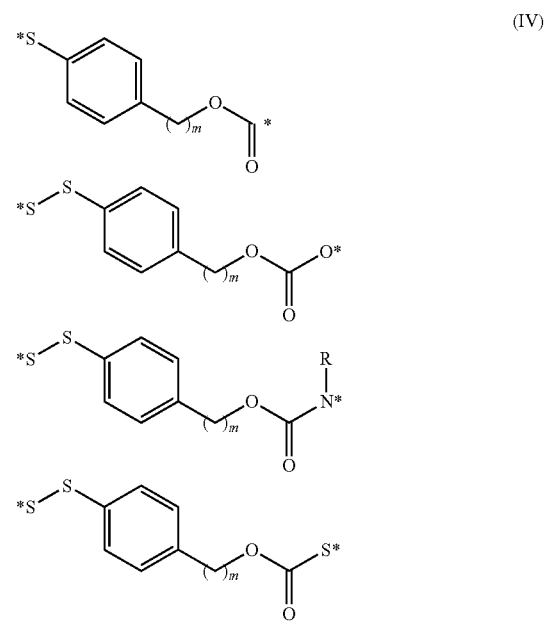

(IV)

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other bivalent linkers, or other parts of the conjugate.

In another embodiment, the compounds described herein comprise one or more radicals selected from the formulae:

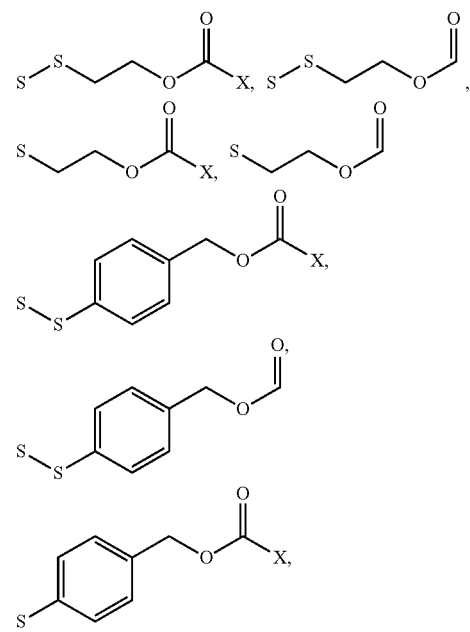

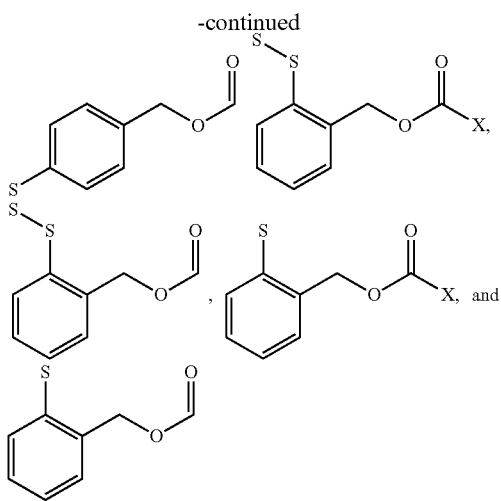

wherein X is NH, O, or S.

In another embodiment, the polyvalent linkers herein described comprise a radical having the formula:

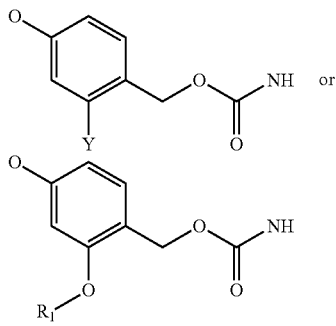

Another embodiment, the polyvalent linkers described herein comprise a radical of having the formula:

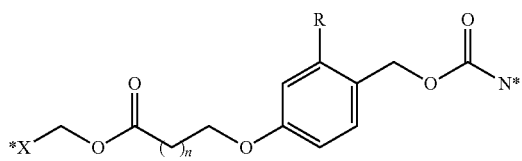

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and the symbol (*) indicates points of attachment. It is appreciated that other substituents may be present on the aryl ring, the benzyl carbon, the alkanoic acid, or the methylene bridge, including but not limited to hydroxy, alkyl, alkoxy, alkylthio, halo, and the like.

In another embodiment, the polyvalent linkers described herein comprise radicals selected from carbonyl, thionocarbonyl, alkylene, cycloalkylene, alkylenecycloalkyl, alkylenecarbonyl, cycloalkylenecarbonyl, carbonylalkylcarbonyl, 1 alkylenesuccinimid-3-yl, 1-(carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl) succinimid-3-yl, and 1-(carbonyltetrahydrofuranyl)succinimid-3-yl, wherein each of said spacer linkers is optionally substituted with one or more substituents $X^1$;

wherein each substituent $X^1$ is independently selected from the group consisting of alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from the group consisting of an amino acid, an amino acid derivative, and a peptide, and wherein $R^6$ and $R^7$ are each independently selected from the group consisting of an amino acid, an amino acid derivative, and a peptide.

The compounds described herein may contain one or more chiral centers, or may otherwise be capable of existing as multiple stereoisomers. It is to be understood that in one embodiment, the invention described herein is not limited to any particular stereochemical requirement, except where specifically indicated, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "cell surface receptor binding or targeting ligand" generally refers to compounds that bind to and/or target receptors that are found on cell surfaces, and in particular those that are found on, over-expressed by, and/or preferentially expressed on the surface of pathogenic cells. Illustrative ligands include, but are not limited to, vitamins and vitamin receptor binding compounds.

Illustrative vitamin moieties include carnitine, inositol, lipoic acid, pyridoxal, ascorbic acid, niacin, pantothenic acid, folic acid, riboflavin, thiamine, biotin, vitamin $B_{12}$, and the lipid soluble vitamins A, D, E and K. These vitamins, and their receptor-binding analogs and derivatives, constitute the targeting entity from which a radical can be formed for covalent attachment to the polyvalent linker L. Illustrative biotin analogs that bind to biotin receptors include, but are not limited to, biocytin, biotin sulfoxide, oxybiotin, and the like.

Illustrative folic acid analogs that bind to folate receptors include, but are not limited to, folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refer to the art-recognized analogs having a carbon atom substituted for one or two nitrogen atoms in the naturally occurring folic acid structure, or analog or derivative thereof. For example, the deaza analogs include the 1-deaza, 3-deaza, 5-deaza, 8-deaza, and 10-deaza analogs of folate, folinic acid, pteropolyglutamic acid, and folate receptor-binding pteridines such as tetrahydropterins, dihydrofolates, and tetrahydrofolates. The dideaza analogs include, for example, 1,5-dideaza, 5,10-dideaza, 8,10-dideaza, and 5,8-dideaza analogs of folate, folinic acid, pteropolyglutamic acid, and folate receptor-binding pteridines such as tetrahydropterins, dihydrofolates, and tetrahydrofolates. Other folates useful as complex forming ligands for this invention are the folate receptor-binding analogs aminopterin, amethopterin (also known as methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate). The foregoing folic acid analogs and/or derivatives are conventionally termed "folates," reflecting their ability to bind with folate-receptors, and such ligands when conjugated with exogenous molecules are effective to enhance transmembrane transport, such as via folate-mediated endocytosis as described herein.

Additional analogs of folic acid that bind to folic acid receptors are described in US Patent Application Publication Serial Nos. 2005/0227985 and 2004/0242582, the disclosures of which are incorporated herein by reference. Illustratively, such folate analogs have the general formula:

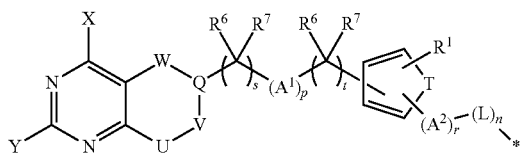

wherein X and Y are each—independently selected from the group consisting of halo, $R^2$, $OR^2$, $SR^3$, and $NR^4R^5$;

U, V, and W represent divalent moieties each independently selected from the group consisting of —$(R^{6a})C=$, —$N=$, —$(R^{6a})C(R^{7a})$—, and —$N(R^{4a})$—; Q is selected from the group consisting of C and CH; T is selected from the group consisting of S, O, N, and —$C=C$—;

$A^1$ and $A^2$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$)($R^{7b}$)—, —N(C=CH)—, —N(CH$_2$C=CH)—, $C_1$-$C_{12}$ alkylene, and $C_1$-$C_{12}$ alkyeneoxy, where Z is oxygen or sulfur;

$R^1$ is selected—from the group consisting of hydrogen, halo, $C_1$-$C_{12}$ alkyl, and $C_1$-$C_{12}$ alkoxy; $R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

L is a divalent linker as described herein; and n, p, r, s and t are each independently either 0 or 1.

As used herein, the term "amino acid" refers generally to beta, gamma, and longer amino acids, such as amino acids of the formula:

$$—N(R)—(CR'R'')_q—C(O)—$$

where R is hydrogen, alkyl, acyl, or a suitable nitrogen protecting group, R' and R'' are hydrogen or a substituent, each of which is independently selected in each occurrence, and q is an integer such as 1, 2, 3, 4, or 5. Illustratively, R' and/or R'' independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornitine, threonine, and the like.

As used herein, the term "amino acid derivative" generally refers to an amino acid as defined herein where either, or both, the amino group and/or the side chain is substituted. Illustrative amino acid derivatives include prodrugs and protecting groups of the amino group and/or the side chain, such as amine, amide, hydroxy, carboxylic acid, and thio prodrugs and protecting groups. Additional Illustrative amino acid derivatives include substituted variations of the amino acid as described herein, such as, but not limited to, ethers and esters of hydroxy groups, amides, carbamates, and ureas of amino groups, esters, amides, and cyano derivatives of carboxylic acid groups, and the like.

As used herein, the terms "tubulysin" and "tubulysins" refer generally to tetrapeptide compounds of the formula

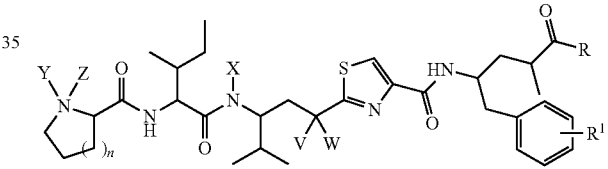

and pharmaceutical salts thereof, where n is 1-3;

V is H, $OR^2$, or halo, and W is H, $OR^2$, or alkyl, where $R^2$ is independently selected in each instance from H, alkyl, and $C(O)R^3$, where $R^3$ is alkyl, cycloalkyl, alkenyl, aryl, or arylalkyl, each of which is optionally substituted; providing that $R^2$ is not H when both V and W are $OR^2$; or V and W are taken together with the attached carbon to form a carbonyl;

X=H, $C_{1-4}$ alkyl, alkenyl, each of which is optionally substituted, or $CH_2QR^9$; where Q is —O—, or —S—; $R^9$=H, $C_{1-4}$ alkyl, alkenyl, aryl, or $C(O)R^{10}$; and $R^{10}$=$C_{1-6}$ alkyl alkenyl, aryl, or heteroaryl, each of which is optionally substituted;

Z is alkyl and Y is O; or Z is alkyl or $C(O)R^4$, and Y is absent, where $R^4$ is alkyl, $CF_3$, or aryl;

$R^1$ is H, or $R^1$ represents 1 to 3 substituents selected from halo, nitro, carboxylate or a derivative thereof, cyano, hydroxyl, alkyl, haloalkyl, alkoxy, haloalkoxy, and $OR^6$, where $R^6$ is hydrogen or optionally substituted aryl, a phenol protecting group, a prodrug moiety, alkyl, arylalkyl, C(O)$R^7$, P(O)(O$R^8$)$_2$, or SO$_3R^8$, where $R^7$ and $R^8$ are independently selected in each instance from H, alkyl, alkenyl, cycloalkyl, heterocyclyl, aryl, and arylalkyl, each of which is optionally substituted, or $R^8$ is a metal cation; and R is OH or a leaving group, or R forms a carboxylic acid derivative, such as an acylhydrazide.

Conjugates of each of the foregoing tubulysins are described herein. In one variation, Z is methyl. In another variation, $R^1$ is H. In another variation, $R^1$ is $OR^6$ at C(4), where $R^6$ is H, alkyl, or $COR^7$. In another variation, V and W is $OC(O)R^3$. In another variation, $X=CH_2QR^9$. In another variation, $X=CH_2OR^9$. In another variation, $R^9$ is alkyl or alkenyl. In another variation, $R^9$ is $C(O)R^{10}$. In another variation, $R^{10}$=optionally substituted $C_{1-6}$ alkyl. In another variation, $R^{10}=C_{1-6}$ alkyl. In another variation, R forms an acylhydrazide. It is to be understood that the foregoing description is an explicit description of each chemically possible combination of variations of the general tubulysin structure. For example, it is to be understood that the foregoing description is a description of the variation where Z is methyl, and $R^1$ is H; where $R^1$ is $OR^6$ at C(4), and $R^6$ is H; where Z is methyl, $R^1$ is $OR^6$ at C(4), $R^6$ is H, and $X=CH_2OR^9$; and the like.

Natural tubulysins are generally linear tetrapeptides consisting of N-methyl pipecolic acid (Mep), isoleucine (Ile), an unnatural aminoacid called tubuvaline (Tuv), and either an unnatural aminoacid called tubutyrosine (Tut, an analog of tyrosine) or an unnatural aminoacid called tubuphenylalanine (Tup, an analog of phenylalanine). In another embodiment, naturally occurring tubulysins, and analogs and derivatives thereof, of the following general formula are described

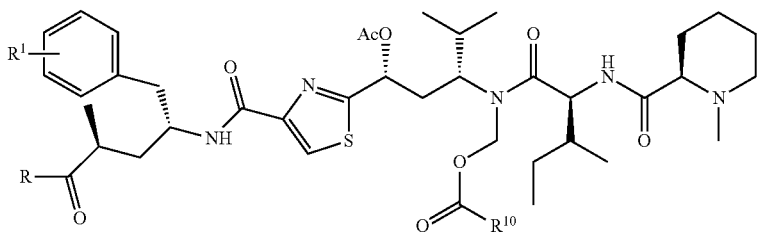

and pharmaceutical salts thereof, where R, $R^1$, and $R^{10}$ are as described in the various embodiments herein. Conjugates of each of the foregoing tubulysins are described herein.

In another embodiment, conjugates of naturally occurring tubulysins of the following general formula are described

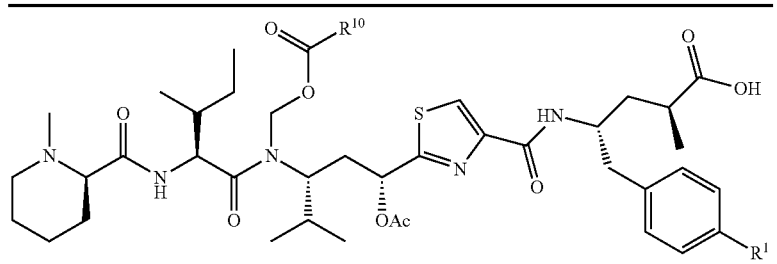

| Factor | $R^{10}$ | $R^1$ |
|---|---|---|
| A | $(CH_3)_2CHCH_2$ | OH |
| B | $CH_3(CH_2)_2$ | OH |
| C | $CH_3CH_2$ | OH |
| D | $(CH_3)_2CHCH_2$ | H |
| E | $CH_3(CH_2)_2$ | H |
| F | $CH_2CH_3$ | H |
| G | $(CH_3)_2C=CH$ | OH |
| H | $CH_3$ | H |
| I | $CH_3$ | OH | and pharmaceutical salts thereof.

In another embodiment, compounds are described herein where the conjugate is formed at the terminal carboxylic acid group or the terminal acylhydrazine group of each of the tybulysins described herein.

As used herein, the term "a rapamycin" is understood to include sirolimus (rapamycin), temsirolimus, everolimus, and ridaforolimus, and related compounds, and compounds of the formula

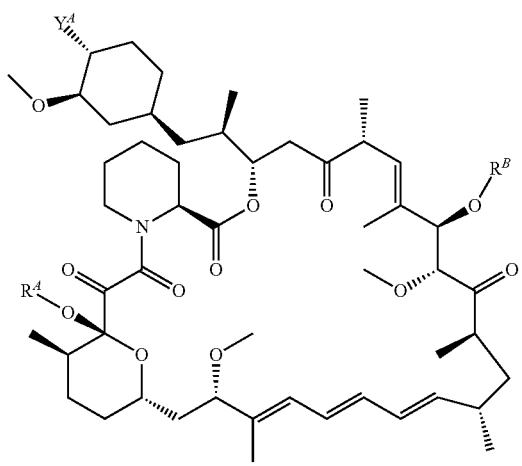

and pharmaceutically acceptable salts thereof, wherein
Y$^A$ is OR$^C$ or OCH$_2$CH$_2$OR$^C$;
one of R$^A$, R$^B$, or R$^C$ is a bond connected to L; and
the other two of R$^A$, R$^B$, and R$^C$ are independently selected in each case from the group consisting of hydrogen, optionally substituted heteroalkyl, prodrug forming group, and C(O)R$^D$, where R$^D$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted is described.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkyl groups, including $C_1$-$C_8$, $C_1$-$C_6$, and $C_1$-$C_4$ may be referred to as lower alkyl. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenyl and/or alkynyl groups, including $C_2$-$C_8$, $C_2$-$C_6$, and $C_2$-$C_4$ may be referred to as lower alkenyl and/or alkynyl. It is appreciated herein that shorter alkyl, alkenyl, and/or alkynyl groups may add less lipophilicity to the compound and accordingly will have different pharmacokinetic behavior. In embodiments of the invention described herein, it is to be understood, in each case, that the recitation of alkyl refers to alkyl as defined herein, and optionally lower alkyl. In embodiments of the invention described herein, it is to be understood, in each case, that the recitation of alkenyl refers to alkenyl as defined herein, and optionally lower alkenyl. In embodiments of the invention described herein, it is to be understood, in each case, that the recitation of alkynyl refers to alkynyl as defined herein, and optionally lower alkynyl. Illustrative alkyl, alkenyl, and alkynyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like, and the corresponding groups containing one or more double and/or triple bonds, or a combination thereof.

As used herein, the term "alkylene" includes a divalent chain of carbon atoms, which is optionally branched. As used herein, the term "alkenylene" and "alkynylene" includes a divalent chain of carbon atoms, which is optionally branched, and includes at least one double bond or triple bond, respectively. It is to be understood that alkynylene may also include one or more double bonds. It is to be further understood that in certain embodiments, alkylene is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkylene groups, including $C_1$-$C_8$, $C_1$-$C_6$, and $C_1$-$C_4$ may be referred to as lower alkylene. It is to be further understood that in certain embodiments alkenylene and/or alkynylene may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenylene and/or alkynylene groups, including $C_2$-$C_8$, $C_2$-$C_6$, and $C_2$-$C_4$ may be referred to as lower alkenylene and/or alkynylene. It is appreciated herein that shorter alkylene, alkenylene, and/or alkynylene groups may add less lipophilicity to the compound and accordingly will have different pharmacokinetic behavior. In embodiments of the invention described herein, it is to be understood, in each case, that the recitation of alkylene, alkenylene, and alkynylene refers to alkylene, alkenylene, and alkynylene as defined herein, and optionally lower alkylene, alkenylene, and alkynylene. Illustrative alkyl groups are, but not limited to, methylene, ethylene, n-propylene, isopropylene, n-butylene, isobutylene, sec-butylene, pentylene, 1,2-pentylene, 1,3-pentylene, hexylene, heptylene, octylene, and the like.

As used herein, the term "cycloalkyl" includes a chain of carbon atoms, which is optionally branched, where at least a portion of the chain is cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopenteleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylic acid and derivatives thereof" includes the group $CO_2H$ and salts thereof, and esters and amides thereof, and CN.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $-(CH_2)_x-Z^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from $-CO_2R^4$ and $-CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

As used herein the term "radical" with reference to, for example, the cell surface receptor binding and/or targeting ligand, and/or the independently selected drug, refers to a cell surface receptor binding and/or targeting ligand, and/or an independently selected drug, as described herein, where one or more atoms or groups, such as a hydrogen atom, or an alkyl group on a heteroatom, and the like, is removed to provide a radical for conjugation to the polyvalent linker L. Such ligand radicals and drug radicals may also be referred herein as ligand analogs and drug analogs, respectively.

As used herein, the term "leaving group" refers to a reactive functional group that generates an electrophilic site on the atom to which it is attached such that nucleophiles may be added to the electrophilic site on the atom. Illustrative leaving groups include, but are not limited to, halogens, optionally substituted phenols, acyloxy groups, sulfonoxy groups, and the like. It is to be understood that such leaving groups may be on alkyl, acyl, and the like. Such leaving groups may also be referred to herein as activating groups, such as when the leaving group is present on acyl. In addition, conventional peptide, amide, and ester coupling agents, such as but not limited to PyBop, BOP-Cl, BOP, pentafluorophenol, isobutylchloroformate, and the like, form various intermediates that include a leaving group, as defined herein, on a carbonyl group.

It is to be understood that in every instance disclosed herein, the recitation of a range of integers for any variable describes the recited range, every individual member in the range, and every possible subrange for that variable. For example, the recitation that n is an integer from 0 to 8, describes that range, the individual and selectable values of 0, 1, 2, 3, 4, 5, 6, 7, and 8, such as n is 0, or n is 1, or n is 2, etc. In addition, the recitation that n is an integer from 0 to 8 also describes each and every subrange, each of which may for the basis of a further embodiment, such as n is an integer from 1 to 8, from 1 to 7, from 1 to 6, from 2 to 8, from 2 to 7, from 1 to 3, from 2 to 4, etc.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is appreciated that certain functional groups, such as the hydroxy, amino, and like groups form complexes and/or coordination compounds with water and/or various solvents, in the various physical forms of the compounds. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. In addition, it is to be understood that the compositions may be prepared from various co-crystals of the compounds described herein.

Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustrative formats for oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration.

Depending upon the disease as described herein, the route of administration and/or whether the compounds and/or compositions are administered locally or systemically, a wide range of permissible dosages are contemplated herein, including doses falling in the range from about 1 µg/kg to about 1 g/kg. The dosages may be single or divided, and may administered according to a wide variety of protocols, including q.d., b.i.d., t.i.d., or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal.

775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl,β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl,β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, (C$_3$-C$_{20}$)alkanoyl; halo-(C$_3$-C$_{20}$)alkanoyl; (C$_3$-C$_{20}$)alkenoyl; (C$_4$-C$_7$)cycloalkanoyl; (C$_3$-C$_6$)-cycloalkyl(C$_2$-C$_{16}$)alkanoyl; optionally substituted aroyl, such as unsubstituted aroyl or aroyl substituted by 1 to 3 substituents selected from the group consisting of halogen, cyano, trifluoromethanesulphonyloxy, (C$_1$-C$_3$)alkyl and (C$_1$-C$_3$)alkoxy, each of which is optionally further substituted with one or more of 1 to 3 halogen atoms; optionally substituted aryl(C$_2$-C$_{16}$)alkanoyl and optionally substituted heteroaryl(C$_2$-C$_{16}$)alkanoyl, such as the aryl or heteroaryl radical being unsubstituted or substituted by 1 to 3 substituents selected from the group consisting of halogen, (C$_1$-C$_3$)alkyl and (C$_1$-C$_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, (C$_1$-C$_3$)alkyl, and (C$_1$-C$_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The compounds, linkers, intermediates, and conjugates described herein may be prepared using conventional processes, including those described in International Patent Publication Nos. WO 2009/002993, WO 2004/069159, WO 2007/022494, and WO 2006/012527, and U.S. patent application Ser. No. 13/837,539 (filed Mar. 15, 2013). The disclosures of each of the foregoing are herein incorporated by reference in their entirety.

Each publications cited herein is incorporated herein by reference.

The following examples further illustrate specific embodiments of the invention; however, the following illustrative examples should not be interpreted in any way to limit the invention.

EXAMPLES

Compound Examples

The compounds described herein may be prepared using the process and syntheses described herein, as well as using general organic synthetic methods. In particular, methods for preparing the compounds are described in U.S. patent application publication 2005/0002942, the disclosure of which is incorporated herein by reference.

Example

General formation of folate-peptides. The folate-containing peptidyl fragment Pte-Glu-(AA)$_n$-NH(CHR$_2$)CO$_2$H (3) is prepared by a polymer-supported sequential approach using standard methods, such as the Fmoc-strategy on an acid-sensitive Fmoc-AA-Wang resin (1), as shown in the following Scheme:

Scheme

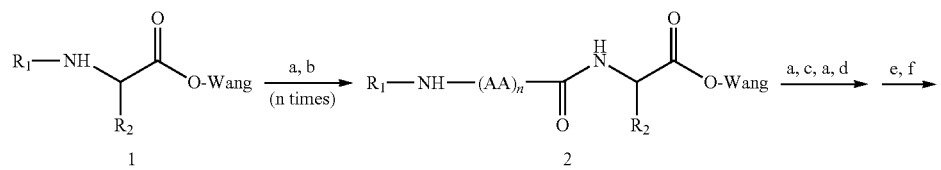

-continued

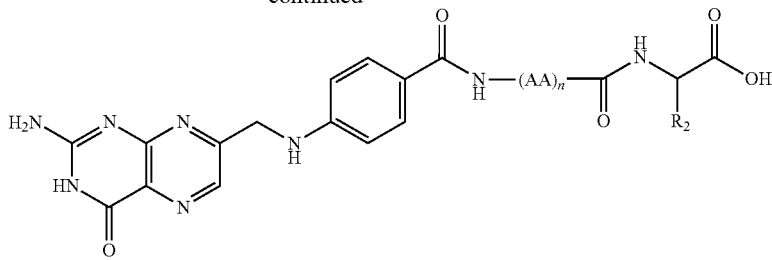

3

(a) 20% piperidine/DMF; (b) Fmoc—AA—OH, PyBop, DIPEA, DMF; (c) Fmoc-Glu(O—t-Bu)—OH, PyBop, DIPEA, DMF;
(d) 1. N[10](TFA)—Pte—OH; PyBop, DIPEA, DMSO; (e) TFAA, (CH$_2$SH)$_2$, i-Pr$_3$SiH; (f) NH$_4$OH, pH 10.3.

It is to be understood that unnatural amino acids may be included in the foregoing process using the appropriate starting materials.

In this illustrative embodiment of the processes described herein, $R_1$ is Fmoc, $R_2$ is the desired appropriately-protected amino acid side chain, and DIPEA is diisopropylethylamine. Standard coupling procedures, such as PyBOP and others described herein or known in the art are used, where the coupling agent is illustratively applied as the activating reagent to ensure efficient coupling. Fmoc protecting groups are removed after each coupling step under standard conditions, such as upon treatment with piperidine, tetrabutylammonium fluoride (TBAF), and the like. Appropriately protected amino acid building blocks, such as Fmoc-Glu-OtBu, Fmoc-D-Glu-OtBu, N[10]-TFA-Pte-OH, and the like, are used, as described in the Scheme, and represented in step (b) by Fmoc-AA-OH. Thus, AA refers to any amino acid starting material, that is appropriately protected. It is to be understood that the term amino acid as used herein is intended to refer to any reagent having both an amine and a carboxylic acid functional group separated by one or more carbons, and includes the naturally occurring alpha and beta amino acids, as well as amino acid derivatives and analogs of these amino acids. In particular, amino acids having side chains that are protected, such as protected serine, threonine, cysteine, aspartate, and the like may also be used in the folate-peptide synthesis described herein. Further, gamma, delta, or longer homologous amino acids may also be included as starting materials in the folate-peptide synthesis described herein. Further, amino acid analogs having homologous side chains, or alternate branching structures, such as norleucine, isovaline, β-methyl threonine, β-methyl cysteine, β,β-dimethyl cysteine, and the like, may also be included as starting materials in the folate-peptide synthesis described herein.

The coupling sequence (steps (a) & (b)) involving Fmoc-AA-OH is performed "n" times to prepare solid-support peptide (2), where n is an integer and may equal 0 to about 100. Following the last coupling step, the remaining Fmoc group is removed (step (a)), and the peptide is sequentially coupled to a glutamate derivative (step (c)), deprotected, and coupled to TFA-protected pteroic acid (step (d)). Subsequently, the peptide is cleaved from the polymeric support upon treatment with trifluoroacetic acid, ethanedithiol, and triisopropylsilane (step (e)). These reaction conditions result in the simultaneous removal of the t-Bu, t-Boc, and Trt protecting groups that may form part of the appropriately-protected amino acid side chain. The TFA protecting group is removed upon treatment with base (step (f)) to provide the folate-containing peptidyl fragment (3).

EC119

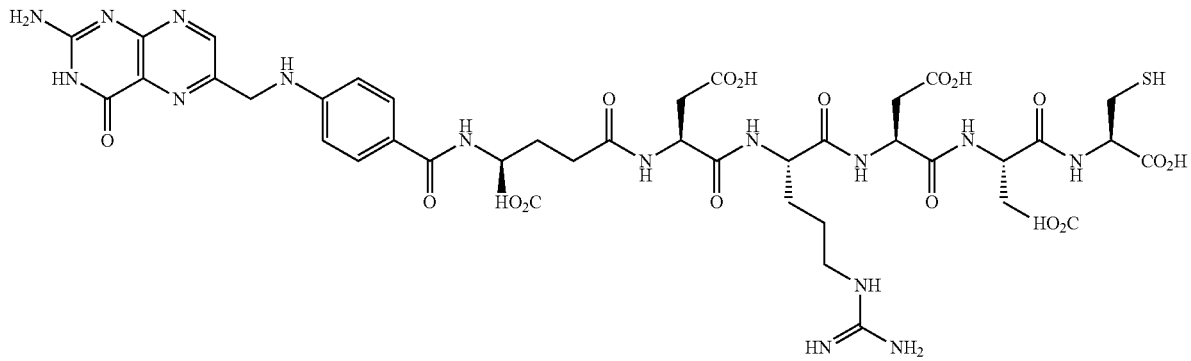

LCMS [ESI [M+H]$^+$: 1046; Partial $^1$H NMR (D$_2$O, 300 MHz): δ 8.68 (s, 1H, FA H-7), 7.57 (d, 2H, J=8.4 Hz, FA H-12 &16), 6.67 (d, 2H, J=9 Hz, FA H-13 &15), 4.40-4.75 (series of m, 5H), 4.35 (m, 2H), 4.16 (m, 1H), 3.02 (m, 2H), 2.55-2.95 (series of m, 8H), 2.42 (m, 2H), 2.00-2.30 (m, 2H), 1.55-1.90 (m, 2H), 1.48 (m, 2H) ppm.

Example
The corresponding compounds containing one or more D-amino acids may also be prepared, such as the following:
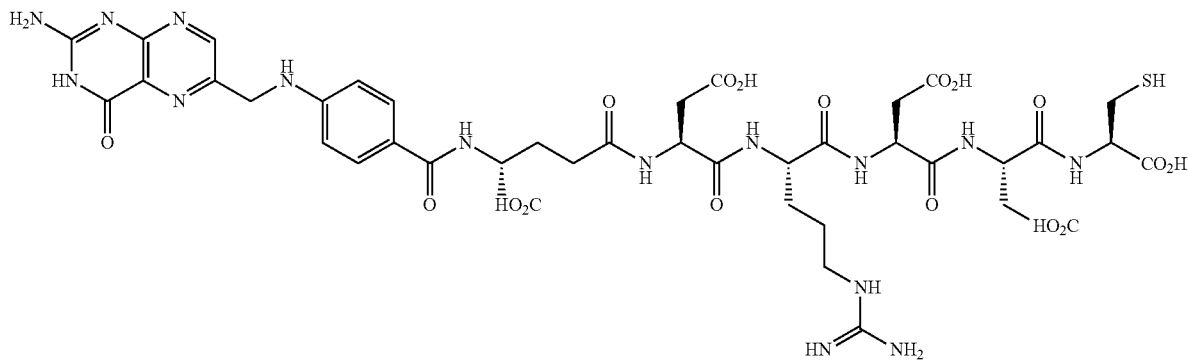
EC1213
LCMS [ESI, [M+H]$^{+1}$) 1046. Partial 1H-NMR (DMSO) δ (ppm): 8.6 (s), 7.5 (d), 6.6 (d), 3.8-4.6 (m), 2.8-3.2 (m), 2.2-2.8 (m), 1-2.2 (m)
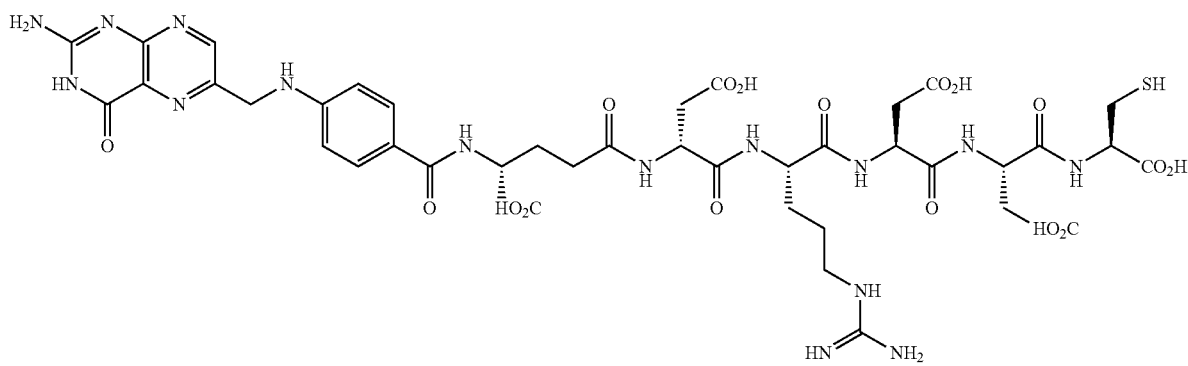
EC0835
MS (ESI, [M+H]$^{+1}$)=1046.5. Partial 1H-NMR (DMSO) δ (ppm): 8.6 (s), 7.5 (d), 6.6 (d), 3.8-4.6 (m), 2.8-3.2 (m), 2.2-2.8 (m), 1-2.2 (m)
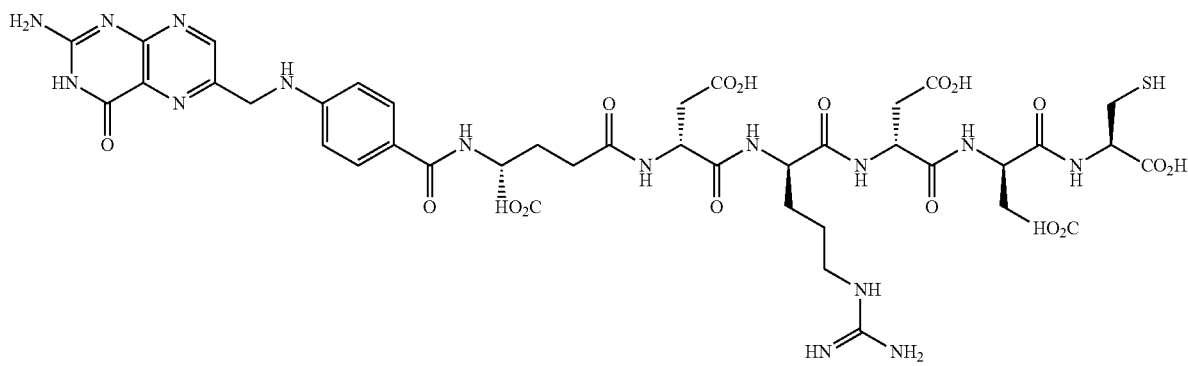
EC819
MS (ESI, [M+H]$^{+1}$)=1046.4. Partial 1H-NMR (DMSO) δ (ppm): 8.6 (s), 7.6 (d), 6.6 (d), 4-4.6 (m), 3.4-3.8 (m), 3-3.15 (m), 1-2.8 (m)

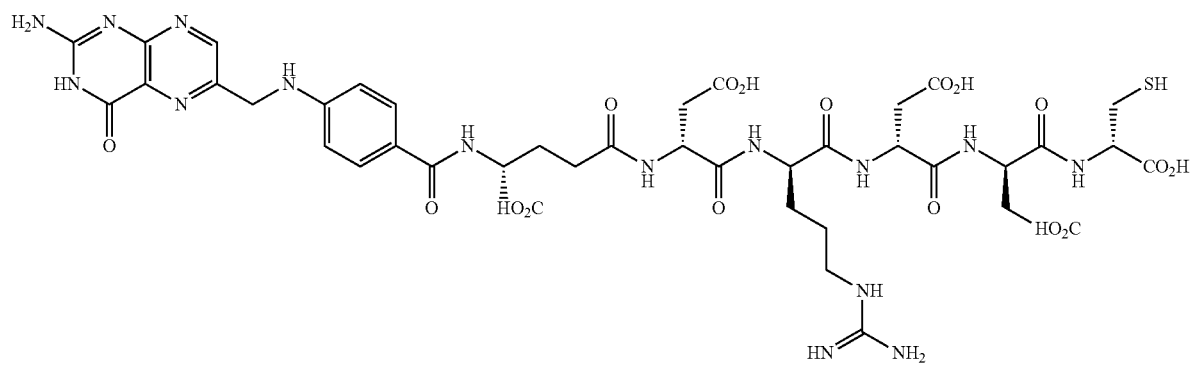
EC259
[M+H]⁺=1047.52. Partial 1H NMR (D2O): 8.6 (s, 1H), 7.5 (d, 2H), 6.65 (d, 2H), 4.4 (dd, 2H), 4.18 (m, 4H), 2.9 (t, 2H), 2.75 (t, 2H), 2.6-2.15 (m, 10H), 2.1-1.8 (m, 3H), 1.7-1.4 (m, 3H), 1.3 (m, 3H).
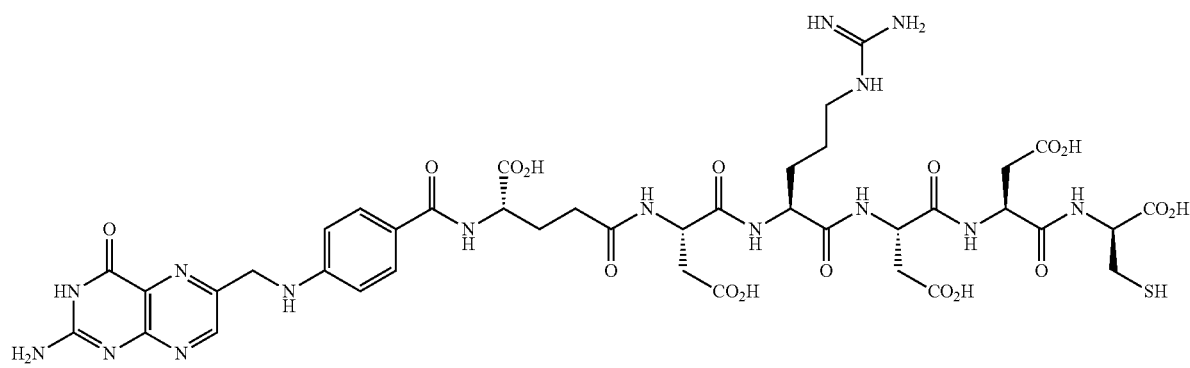
EC1544
MS (ESI [M+H]⁺): 1046. Partial $^1$H NMR data (D$_2$O, 300 MHz): δ (ppm) 8.68 (s, 1H, FA H-7), 7.57 (d, 2H, J=8.4 Hz, FA H-12 &16), 6.67 (d, 2H, J=9 Hz, FA H-13 &15).
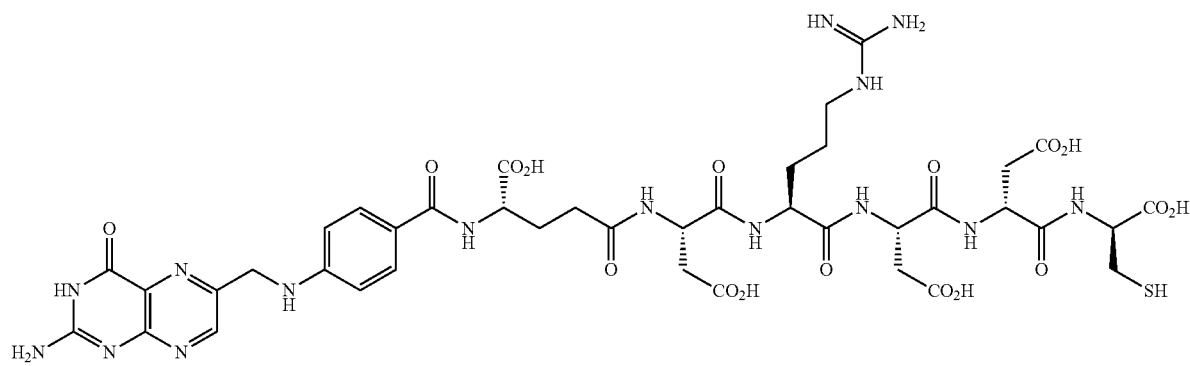
EC1547
MS (ESI, [M+H]⁺)=1046.7. Partial 1H-NMR (D$_2$O) δ(ppm): 8.6 (s), 7.5 (d), 6.6 (d), 4.4-4.8 (m), 4-4.2 (m) 2.2-3 (m), 1.8-2.2 (m), 1.3-1.7 (m)

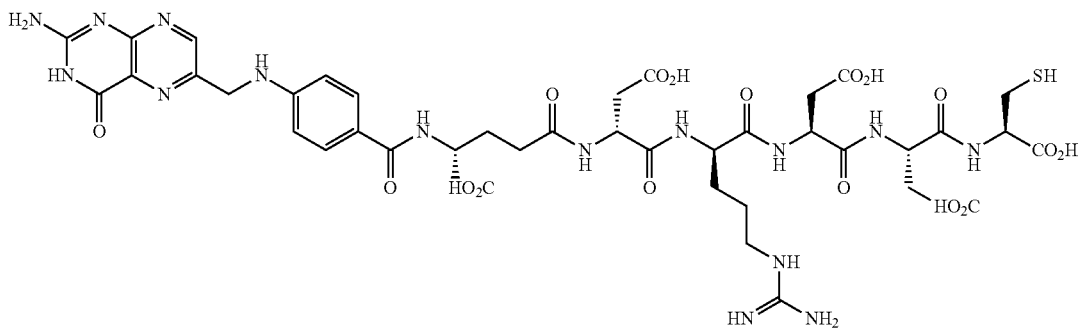

and

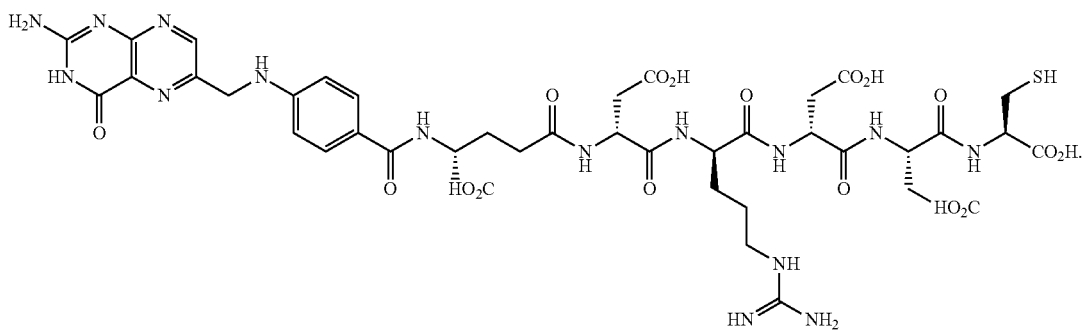

Example 30

Preparation of tubulysin hydrazides. Illustrated by preparing EC0347 (TubB-H).

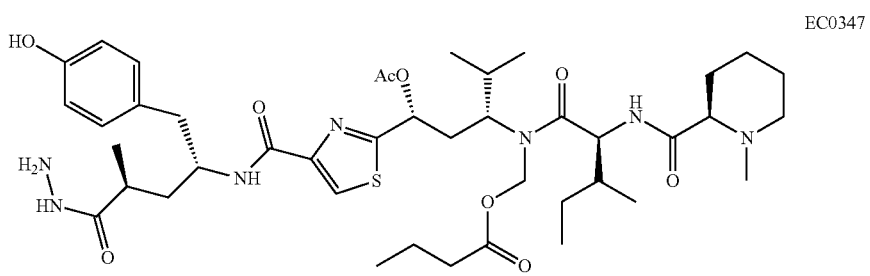 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NN)cs1)C(C)C]

N,N-Diisopropylethylamine (DIPEA, 6.1 μL) and isobutyl chloroformate (3.0 μL) were added with via syringe in tandem into a solution of tubulysin B (0.15 mg) in anhydrous EtOAc (2.0 mL) at −15° C. After stirring for 45 minutes at −15° C. under argon, the reaction mixture was cooled down to −20° C. and to which was added anhydrous hydrazine (5.0 μL). The reaction mixture was stirred under argon at −20° C. for 3 hours, quenched with 1.0 mM sodium phosphate buffer (pH 7.0, 1.0 mL), and injected into a preparative HPLC for purification. Column: Waters XTerra Prep MS $C_{18}$ 10 μm, 19×250 mm; Mobile phase A: 1.0 mM sodium phosphate buffer, pH 7.0; Mobile phase B: acetonitrile; Method: 10% B to 80% B over 20 minutes, flow rate=25 mL/min. Fractions from 15.14-15.54 minutes were collected and lyophilized to produce EC0347 as a white solid (2.7 mg). The foregoing method is equally applicable for preparing other tubulysin hydrazides by the appropriate selection of the tubulysin starting compound.

Example

Synthesis of Coupling Reagent EC0311

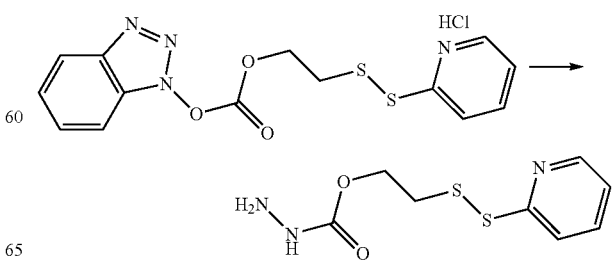

DIPEA (0.60 mL) was added to a suspension of HOBt-OCO₂—(CH₂)₂—SS-2-pyridine HCl (685 mg, 91%) in anhydrous DCM (5.0 mL) at 0° C., stirred under argon for 2 minutes, and to which was added anhydrous hydrazine (0.10 mL). The reaction mixture was stirred under argon at 0° C. for 10 minutes and room temperature for an additional 30 minutes, filtered, and the filtrate was purified by flash chromatography (silica gel, 2% MeOH in DCM) to afford EC0311 as a clear thick oil (371 mg), solidified upon standing.

Example

Preparation of Tubulysin Disulfides (Stepwise Process)

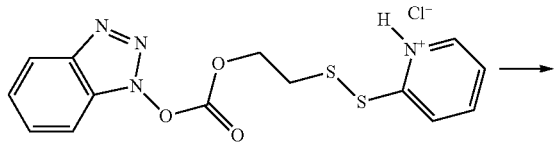

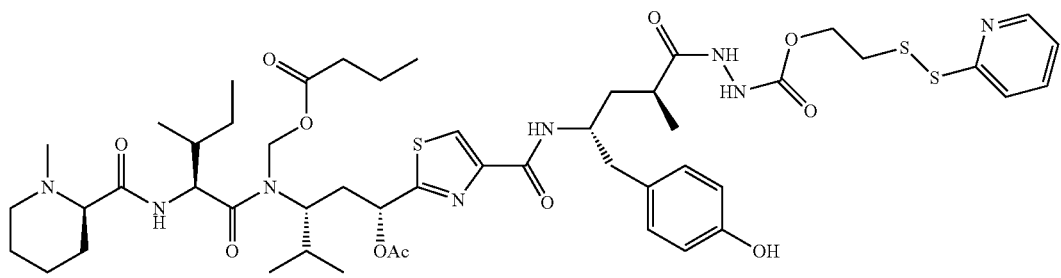 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSc2ccccn2)cs1)C(C)C]

Illustrated for EC0312. DIPEA (36 μL) and isobutyl chloroformate (13 μL) were added by syringe in tandem into a solution of tubulysin B (82 mg) in anhydrous EtOAc (2.0 mL) at −15° C. After stirring for 45 minutes at −15° C. under argon, to the reaction mixture was added a solution of EC0311 in anhydrous EtOAc (1.0 mL). The resulting solution was stirred under argon at −15° C. for 15 minutes and room temperature for an additional 45 minutes, concentrated, and the residue was purified by flash chromatography (silica gel, 2 to 8% MeOH in DCM) to give EC0312 as a white solid (98 mg). The foregoing method is equally applicable for preparing other tubulysin derivatives by the appropriate selection of the tubulysin starting compound.

Example

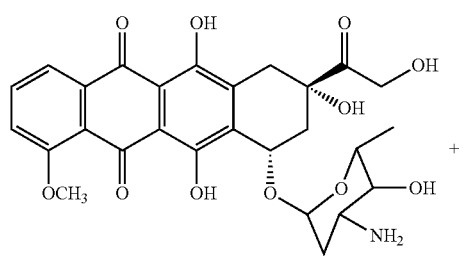

-continued

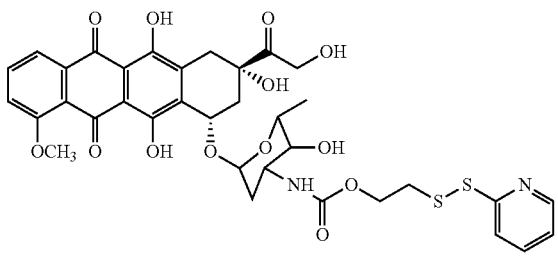

To a solution of doxorubicin (100 mg, 0.184 mmol) and 2-[benzotriazole-1-yl-(oxycarbonyloxy)-ethyldisulfanyl]-pyridine (77.8 mg, 0.184 mmol) in DCM (4 ml) was added DIPEA (0.064 ml, 0.368 mmol.). The reaction was allowed to stir for 2 hours. TLC (10% MeOH in DCM) indicated that the reaction was complete. DCM was removed under reduced pressure and purified on SiO₂ column (10% MeOH in DCM) to yield pure product (90 mg, 65%). LCMS (ESI): (M+H)⁺ Calculated for $C_{35}H_{36}N_2O_{13}S_2$, 757.17. found 757.30, ¹H NMR (300 MHz, CDCl₃/CD₃OD): δ 8.44 (br s, 1H), 8.00 (d, 1H), 7.65-7.82 (m, 3H), 7.38 (d, 1H), 7.18 (br s, 1H), 5.45 (s, 1H), 5.25 (s, 3H), 4.70 (m, 2H), 4.3 (m, 1H), 4.22-3.90 (m, 2H), 3.75 (s, 1H), 3.62 (s, 1H), 3.35-2.90 (m, 2H), 2.45-2.10 (m, 2H), 1.85 (m, 5H), 1.32 (d, 3H).

Example
Tubulysin B pyridyldisulfide.
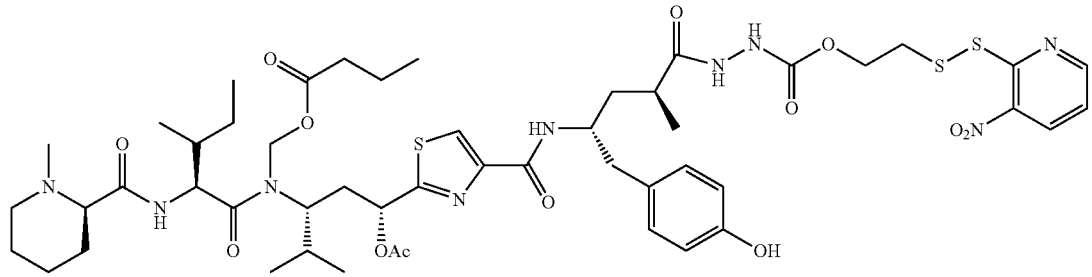 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSc2ncccc2[N+](=O)[O-])cs1)C(C)C]
Similarly, Tubulysin B pyridyldisulfide is prepared as described herein.
Example 20
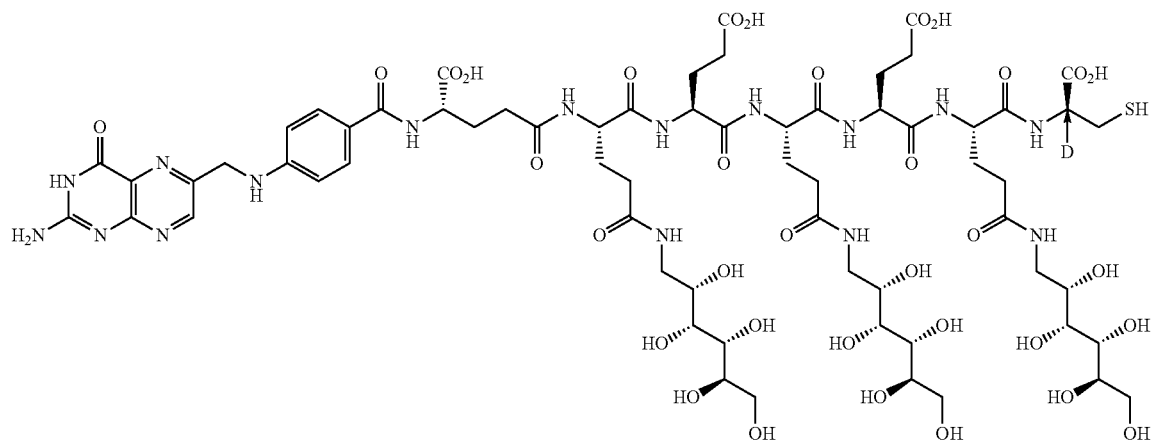
EC1577
MS (ESI, [M+H]$^+$)=1681. Partial $^1$H NMR (D$_2$O): 8.96 (s), 7.65 (d), 6.81 (d), 4.66 (s), 4.40-4.15 (m), 3.90-3.54 (m), 3.50-3.18 (m), 2.97-2.90 (m), 2.51-1.80 (m).
Example
General Synthesis of Disulfide Containing Tubulysin Conjugates.
B—L—SH +
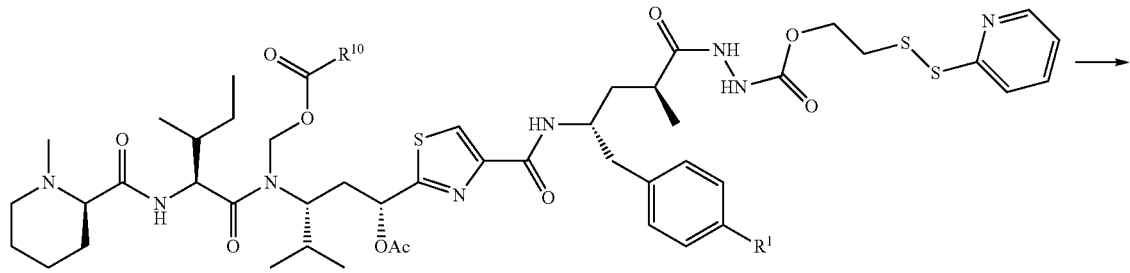

-continued

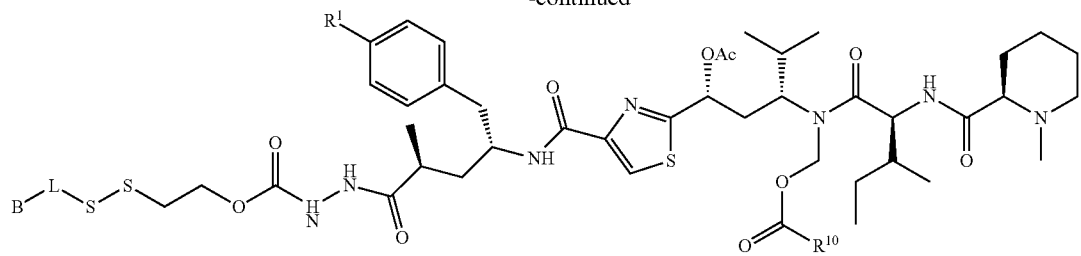

Illustrated with pyridinyl disulfide derivatives of certain naturally occurring tubulysins, where $R^1$ is H or OH, and $R^{10}$, is alkyl or alkenyl. A binding ligand-linker intermediate containing a thiol group is taken in deionized water (ca. 20 mg/mL, bubbled with argon for 10 minutes prior to use) and the pH of the suspension was adjusted by saturated $NaHCO_3$ (bubbled with argon for 10 minutes prior to use) to about 6.9 (the suspension may become a solution when the pH increased). Additional deionized water is added (ca. 20-25%) to the solution as needed, and to the aqueous solution is added immediately a solution of EC0312 in THF (ca. 20 mg/mL). The reaction mixture becomes homogenous quickly. After stirring under argon, e.g. for 45 minutes, the reaction mixture is diluted with 2.0 mM sodium phosphate buffer (pH 7.0, ca 150 volume percent) and the THF is removed by evacuation. The resulting suspension is filtered and the filtrate may be purified by preparative HPLC (as described herein). Fraction are lyophilized to isolate the conjugates. The foregoing method is equally applicable for preparing other tubulysin conjugates by the appropriate selection of the tubulysin starting compound.

Example

EC1663 and EC1664 The following additional compounds are preparable using the methods and processed described herein:

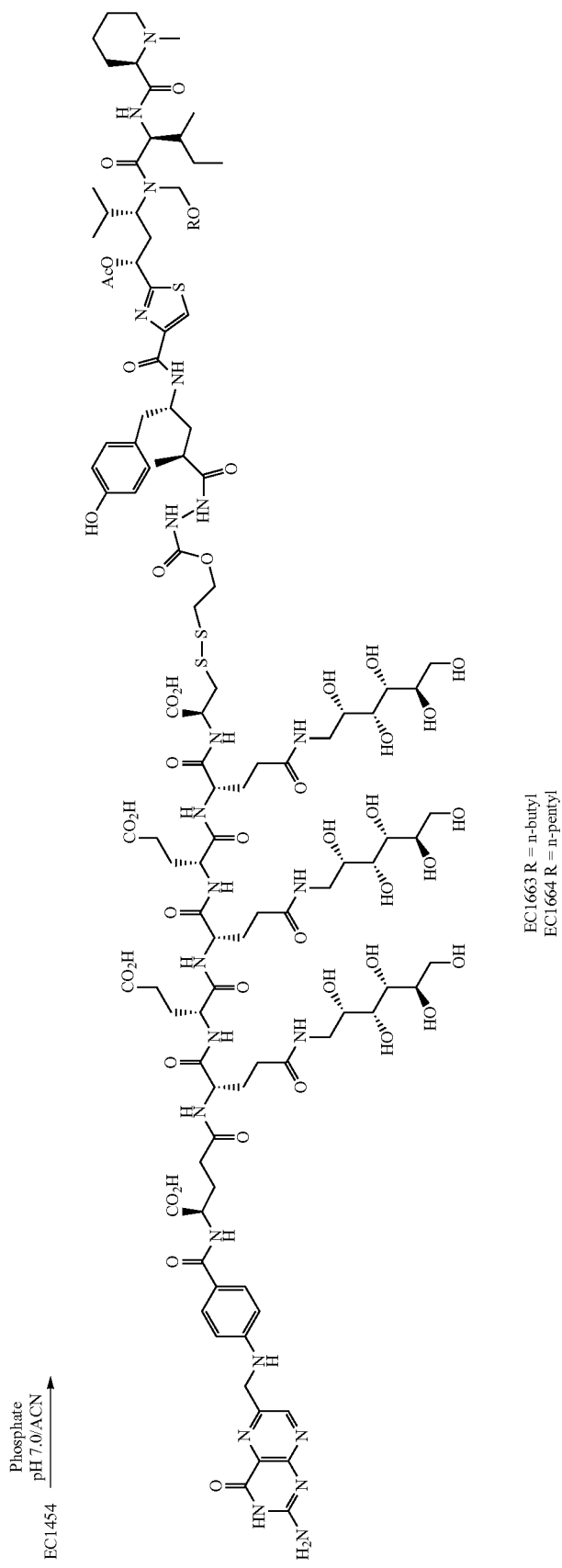

123
Example
EC1426 is prepared according to the following process.
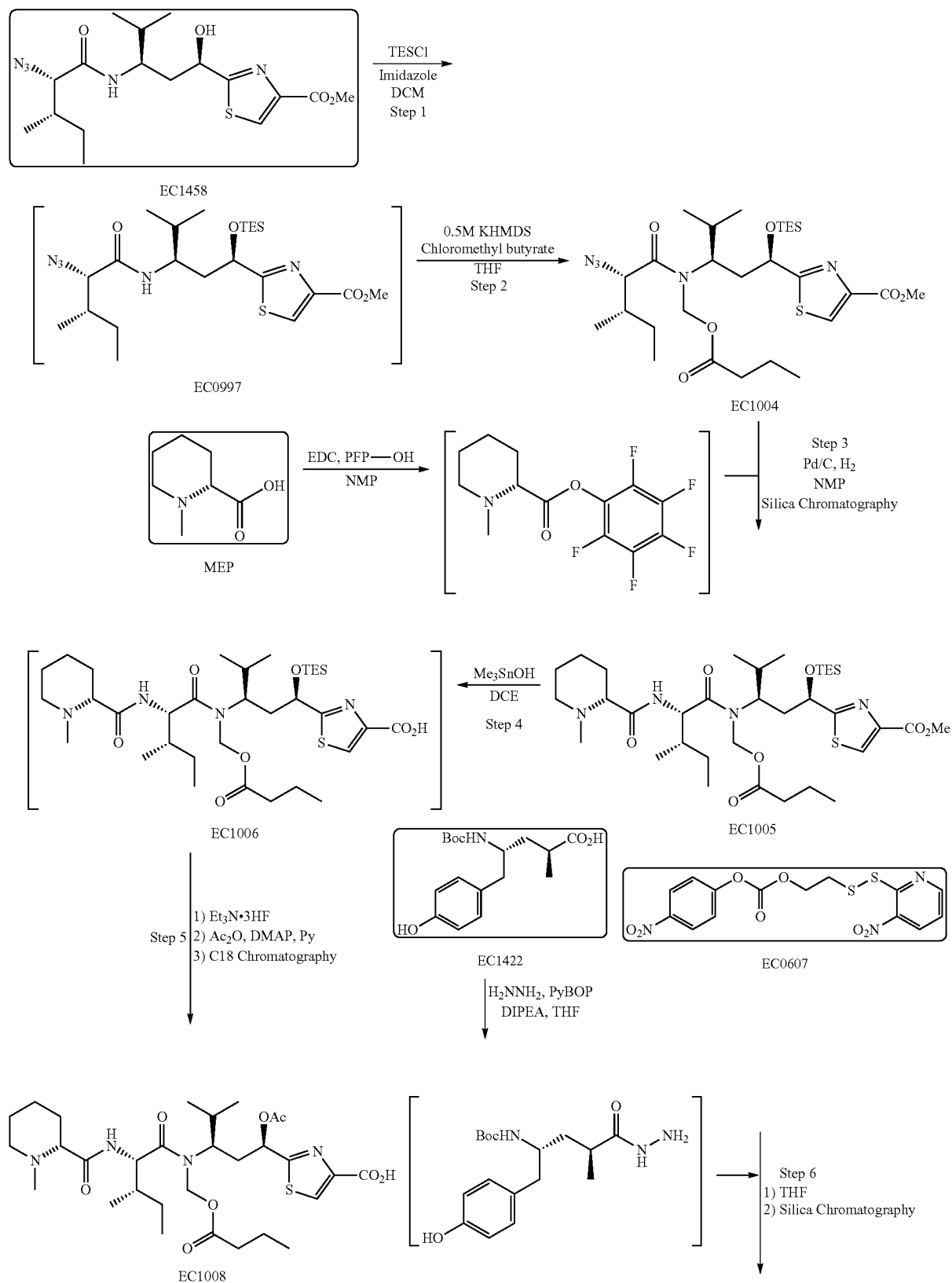

-continued
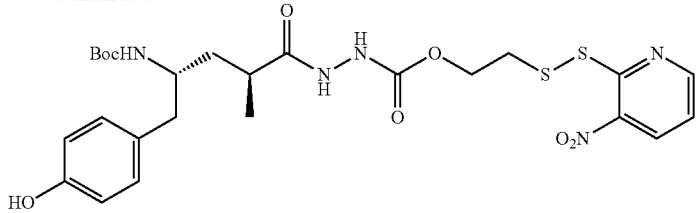
EC1426
Example
EC1456 is prepared according to the following process.

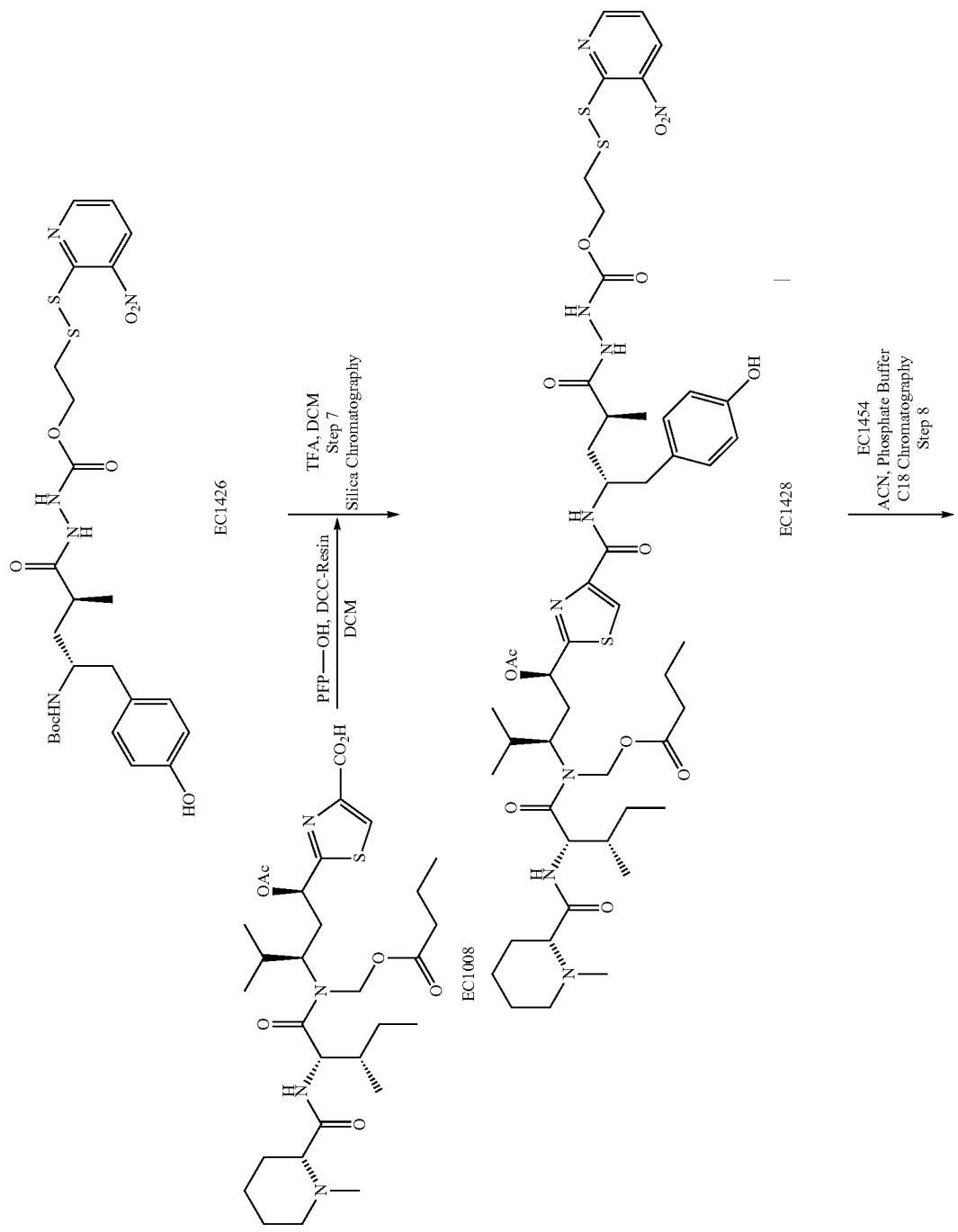

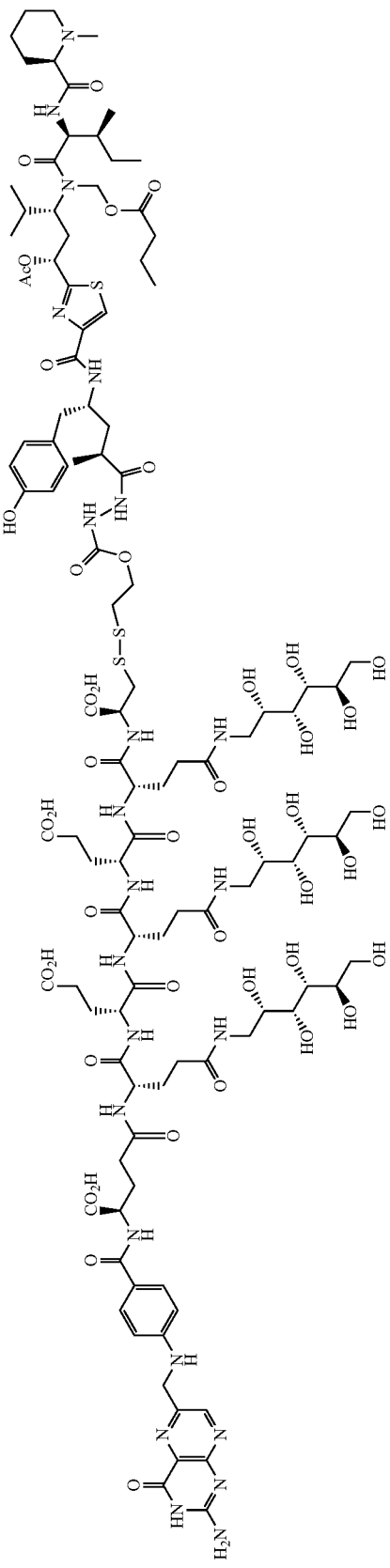

Example
$N^{10}$-TFA Protected EC1454 is prepared according to the following process.
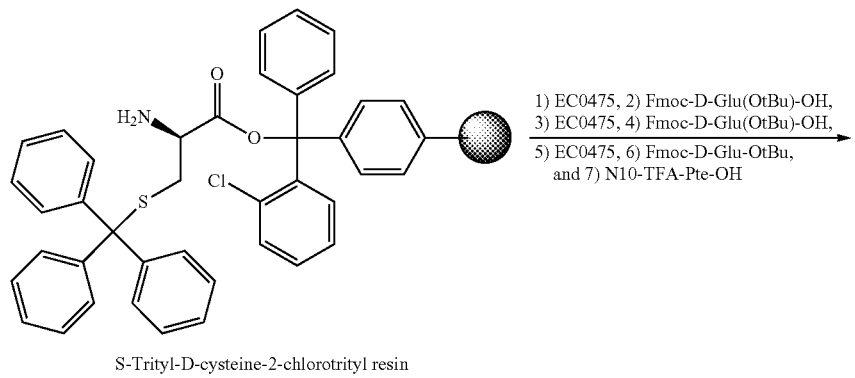
S-Trityl-D-cysteine-2-chlorotrityl resin
1) EC0475, 2) Fmoc-D-Glu(OtBu)-OH,
3) EC0475, 4) Fmoc-D-Glu(OtBu)-OH,
5) EC0475, 6) Fmoc-D-Glu-OtBu,
and 7) N10-TFA-Pte-OH
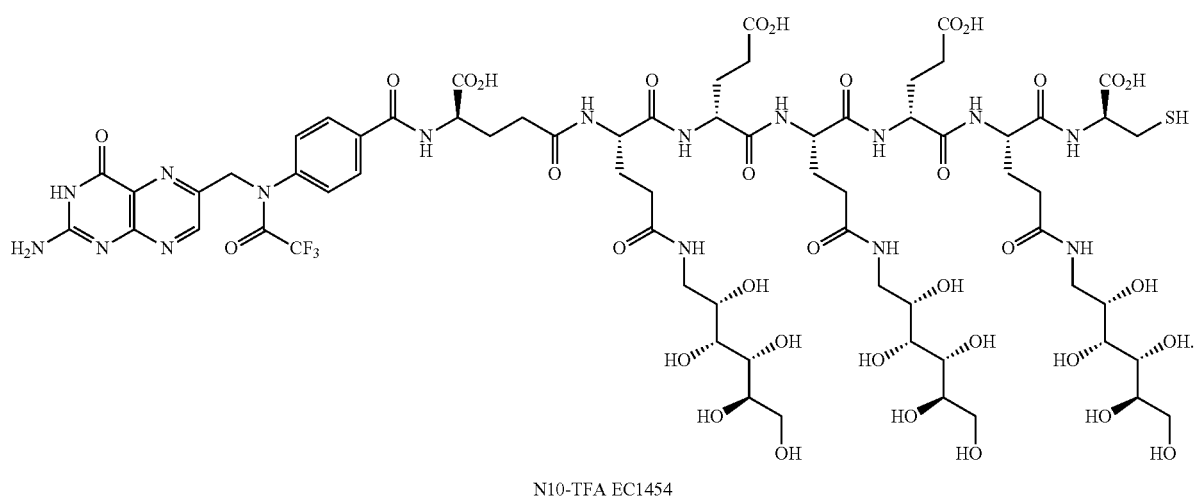
N10-TFA EC1454
Example
EC1454 is prepared according to the following process.
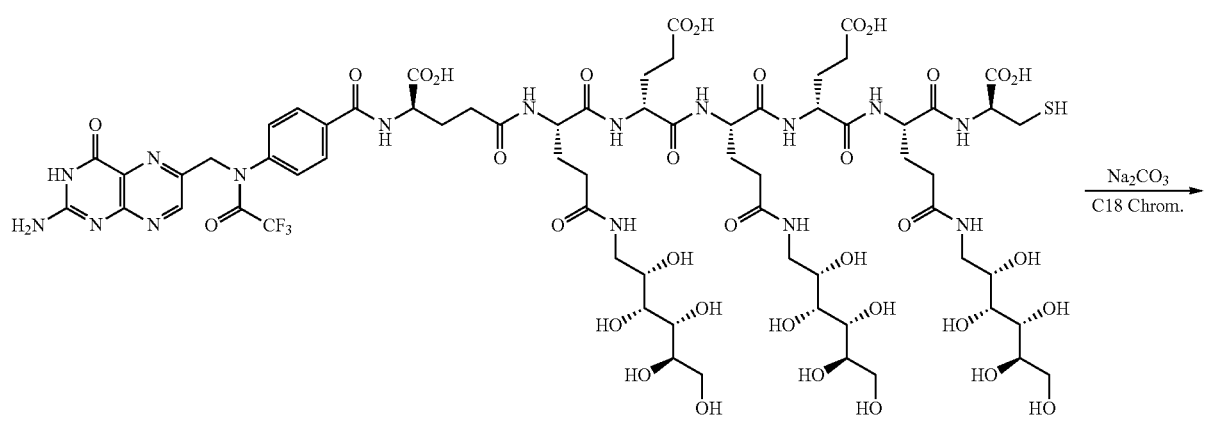
N10-TFA EC1454
$\xrightarrow{\text{Na}_2\text{CO}_3}{\text{C18 Chrom.}}$

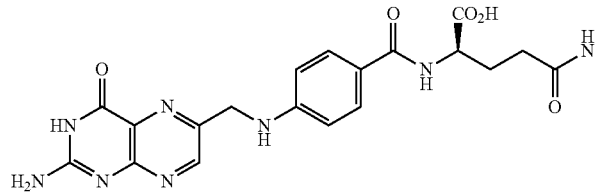
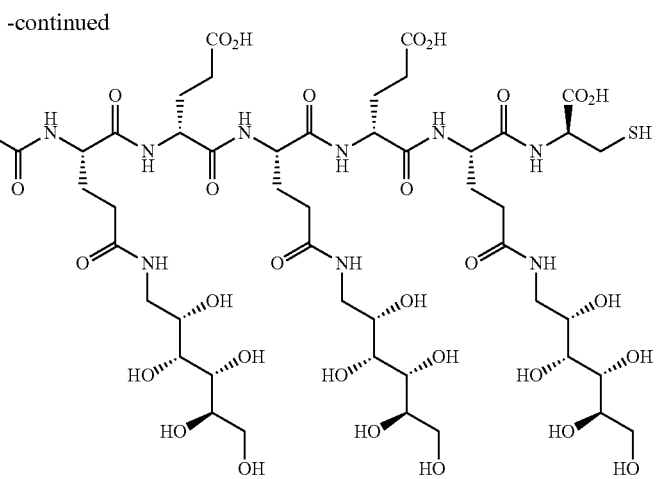
EC1454: MS (ESI, [M+2H]$^{2+}$)=840.90, [M+H]$^{+}$=1681.3. Partial 1H-NMR (DMSO) δ (ppm): 8.6 (s), 7.6 (d), 6.6 (d), 4.45 (s), 4.35 (t), 4.15-4.3 (m), 3.3-3.6 (m), 3.25 (m), 3.0 (m), 2.7-2.9 (m), 2-2.3 (m), 1.6-2 (m).
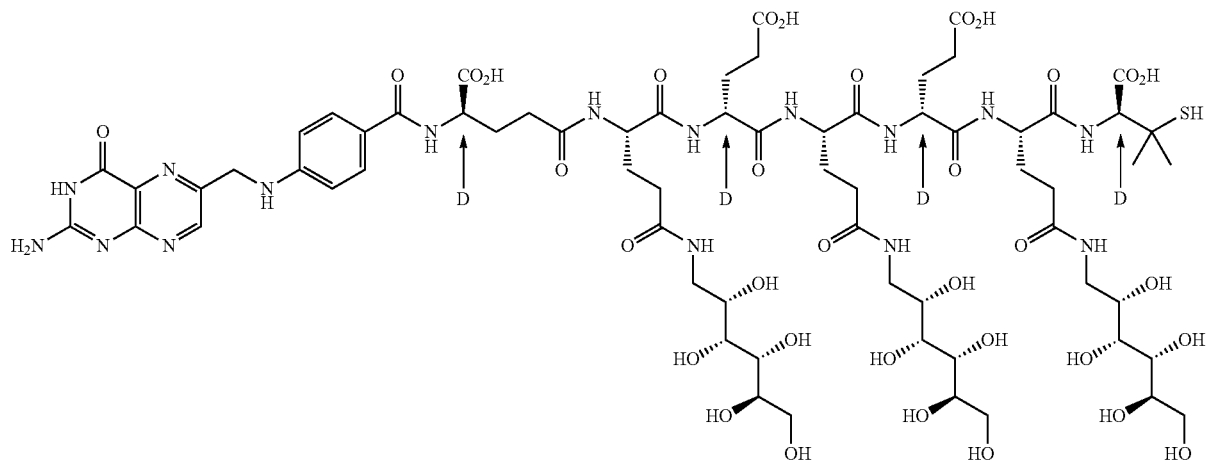
EC1415: [M+H]$^{+}$=1709.69, [M+2H]$^{2+}$=855.22. Partial $^1$H NMR (D$_2$O, 300 MHz) δ(ppm): 8.6 (s, 1H), 7.45 (d, 2H), 6.5 (d, 2H), 4.5 (s, 2H), 4.3-4.1 (m, 6H), 3.95 (t, 1H), 3.8-3.4 (m, 19H), 3.4-2.95 (m, 7H), 2.4-1.7 (m, 26H), 1.6 (m, 1H), 1.25 (s, 2H), 1.05 (s, 3H).
Example
EC1004 is prepared according to the following process.
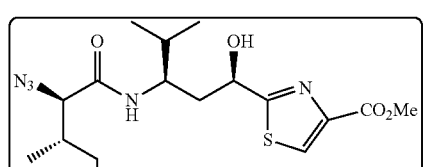
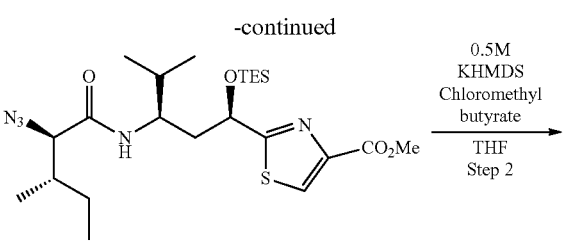
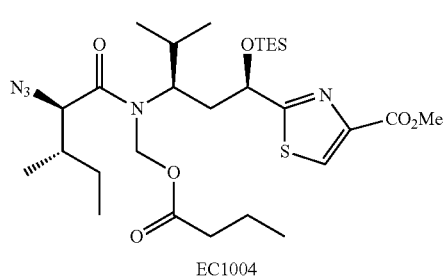

Into a round bottomed flask equipped with magnetic stir bar and temperature probe dipeptide EC1458, imidazole, and methylene chloride is added. Once all the solids have dissolved, the solution is cooled using an ice bath. Chlorotriethylsilane (TESCl) is added drop wise and the ice bath is removed. The reaction is monitored for completion. A second portion of chlorotriethylsilane and/or imidazole is added if necessary. The imidazole HCl salt is removed by filtration and methylene chloride is added. The organics are washed with a saturated solution of sodium chloride (brine), the aqueous layer is back extracted once with methylene chloride, and the combined organic layers are washed with brine. The organic layer is dried over sodium sulfate and concentrated on a rotary evaporator. The residue is dissolved in tetrahydrofuran (THF) and cooled to approximately −45° C. A solution of potassium bis(trimethylsilyl)amide (KHMDS) in toluene is added drop wise. With stirring, chloromethyl butyrate is added and the reaction is monitored. The reaction is quenched with methanol and then ethyl acetate and brine are added. The aqueous layer is discarded and the organics are washed once with brine. The organic layer is concentrated on a rotary evaporator and the oily residue is passed through a short plug of silica gel. The plug is washed with a 20% solution of ethyl acetate in petroleum ether. The combined organics are concentrated on a rotary evaporator until distillation ceases. The crude EC1004 oil is analyzed by LC and NMR and stored in a freezer until use.

Example

EC1005 is prepared according to the following process.

Into an appropriately sized hydrogenation flask place R—N-methyl pipecolinate (MEP), pentafluorophenol, N-methyl pyrrolidinone (NMP), and ethyl dimethylaminopropyl carbodiimide (EDC). The mixture is stirred for at least 16 h. EC1004 dissolved in N-methyl pyrrolidinone (NMP) and 10 wt % Pd/C are added. The reaction mixture is stirred/shaken under hydrogen pressure until the reaction is complete by LC analysis. The Pd/C is removed by filtration through celite. The celite is washed with ethyl acetate and the combined organics are washed three times with a 1% sodium bicarbonate/10% sodium chloride solution. The organic layer is dried over sodium sulfate and concentrated on a rotary evaporator. The residue is dissolved in DCM and purified by silica gel chromatography using ethyl acetate and petroleum ether as eluents. Fractions are collected, checked for purity, combined and dried on a rotary evaporator. The EC1005 oil is assayed by LC and stored in a freezer until use.

Example

EC1008 is prepared according to the following process.

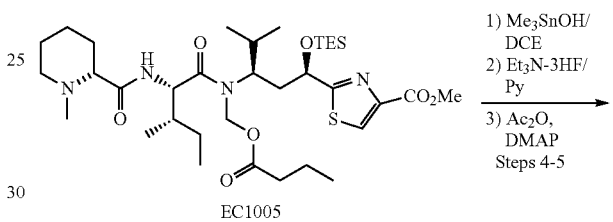

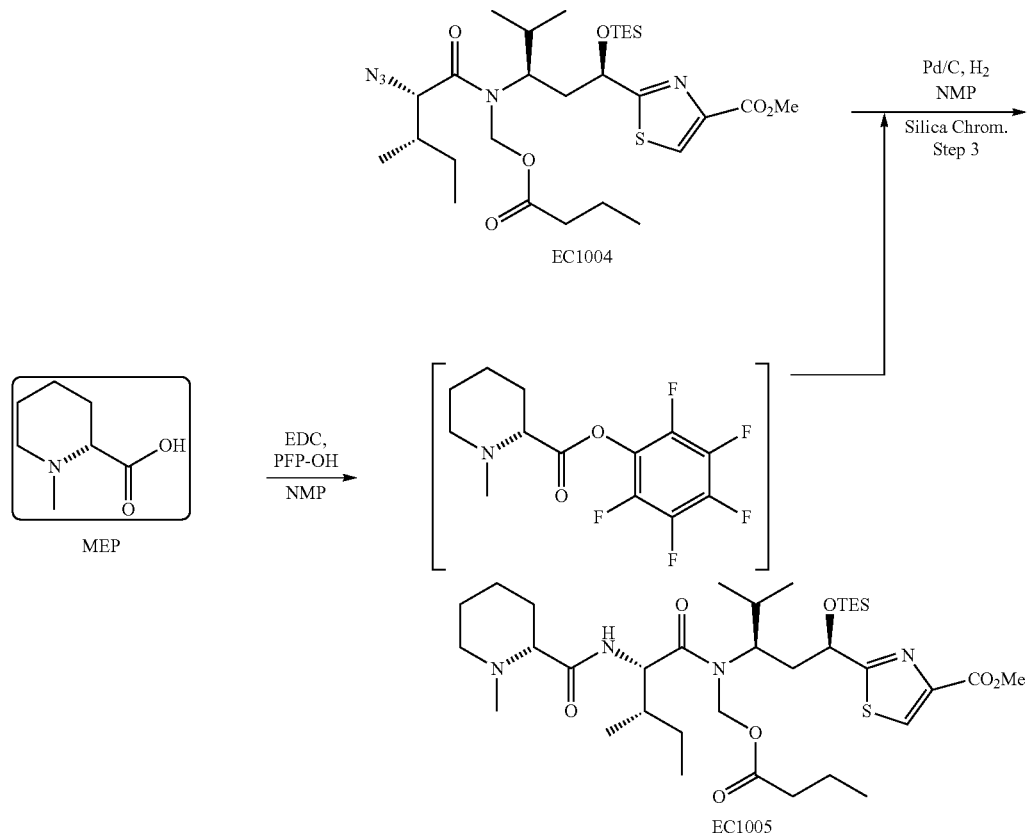

-continued

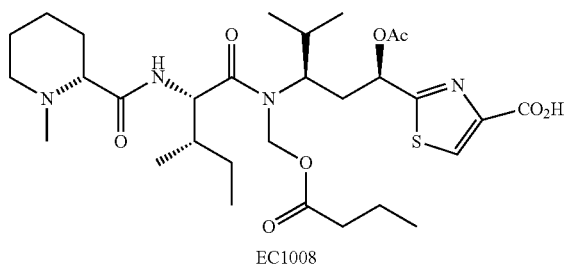
EC1008

EC1005 is dissolved in 1,2-dichloroethane (DCE) and trimethyltin hydroxide is added. The reaction mixture is heated and reaction is monitored by LC. On completion, the mixture is cooled with an ice bath and filtered. The solids are then washed with DCE. The organic layer is washed once with water and dried over sodium sulfate. The solution is concentrated on a rotary evaporator and the residue dissolved in tetrahydrofuran (THF). Triethylamine trihydrofluoride is added and the mixture stirred while monitoring with LC. Pyridine, dimethylaminopyridine (DMAP), and acetic anhydride are added. The reaction is stirred and monitored by LC. The reaction mixture is concentrated to a residue and the product is purified by C18 column chromatography with acetonitrile and water as eluents. Product fractions are collected, concentrated, and lyophilized to yield a white to off-white powder.

Example

EC1426 is prepared according to the following process.

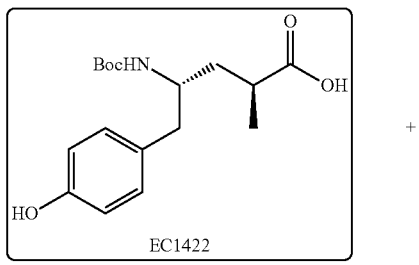
EC1422

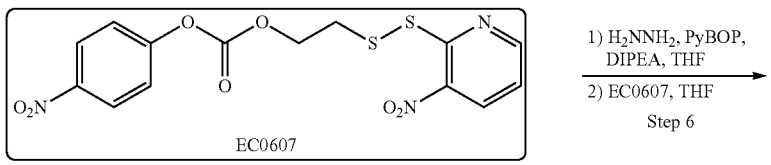
EC0607

1) H$_2$NNH$_2$, PyBOP, DIPEA, THF
2) EC0607, THF
Step 6

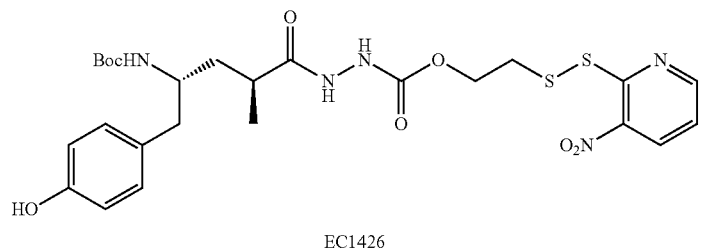
EC1426

EC1422 is dissolved in tetrahydrofuran (THF) and (Benzotriazol-1-yloxy)tripyrrolidinophosphonium hexafluorophosphate (PyBop) and diisopropylethylamine (DIPEA) are added. Once all the solids have dissolved hydrazine is added and the reaction is stirred and monitored for completion. EC0607 is added and the mixture stirred and monitored for completion by LC. Ethyl acetate is added and the organics are washed once with saturated ammonium chloride, twice with saturated sodium bicarbonate, and once with saturated sodium chloride. The organics are dried over sodium sulfate and concentrated on a rotary evaporator. The crude EC1426 is purified by silica column chromatography with dichloromethane and methanol as eluents. Fractions are collected and the combined product fractions are concentrated on a rotary evaporator to yield a yellow solid.

Example

EC1428 is prepared according to the following process.

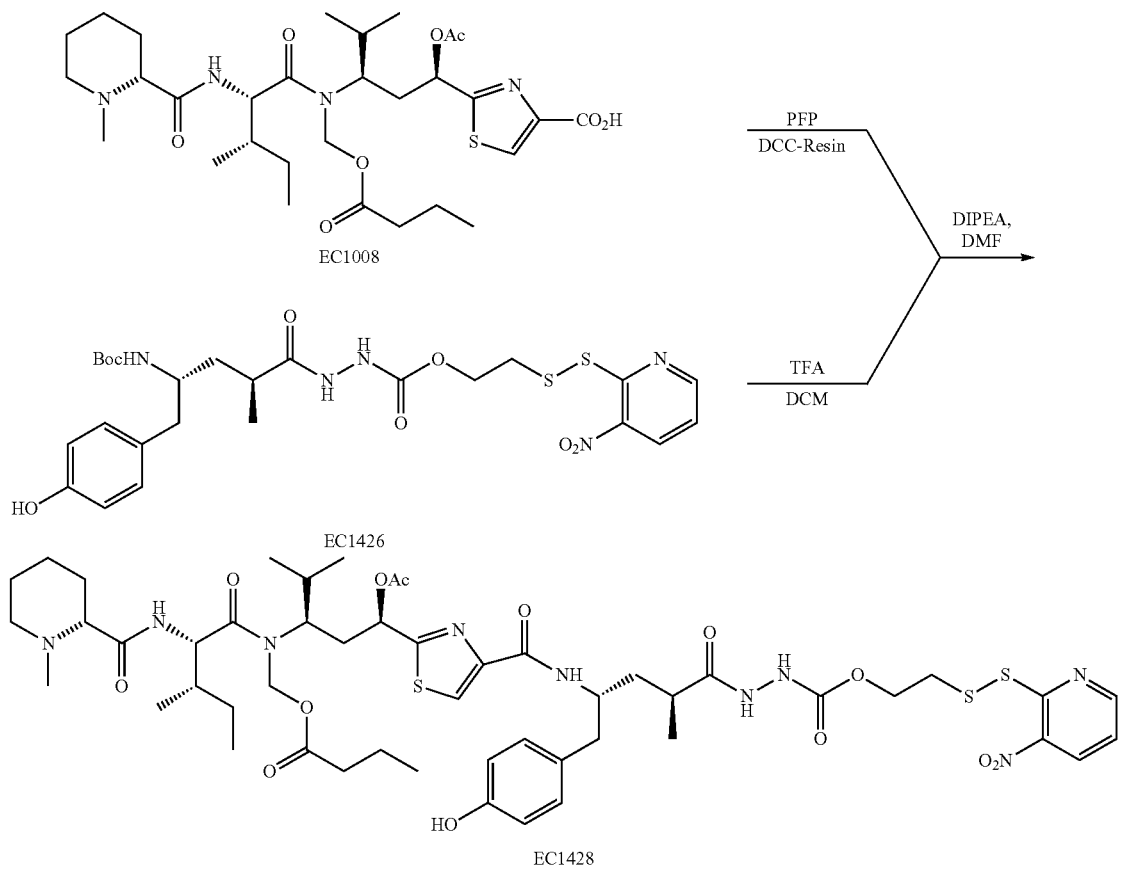

EC1008 is dissolved in dichloromethane and pentafluorophenol dissolved in DCM along with N-cyclohexylcarbodiimide,N'-methyl polystyrene (DCC-resin) are added. The mixture is stirred and reaction completion is monitord by LC. The mixture is filtered to remove the resin and the organic layer is concentrated on a rotary evaporator to yield activated EC1008. In a separate flask, EC1426 is dissolved in dichloromethane and trifluoroacetic acid is added. The reaction mixture is stirred and monitored for completion by LC. The reaction mixture is concentrated on a rotary evaporator to yield deprotected EC1426. The activated EC1008 is dissolved in DMF and diisopropylethylamine (DIPEA) is added. The deprotected EC1426 is dissolved in DMF and added to the reaction mixture. The reaction is stirred and monitored for completion by LC. Ethyl acetate is added and the organics are washed three times with saturated aqueous sodium chloride. The organic layer is dried over sodium sulfate and the volatiles removed by rotary evaporation. The crude EC1428 is purified by silica column chromatography using dichloromethane and methanol as eluents. Fractions are collected, checked for purity, and the combined product fractions are concentrated by rotary evaporation to yield a yellow solid. The EC1428 is stored in a freezer.

Example

Additional tubulsyins and tubulysin intermediates may be prepared according to the processes described in WO 2012/019123, WO 2009/055562, PCT International Application Serial No. US2013/034672, and U.S. Provisional application Ser. No. 61/793,082, the disclosures of each of which are incorporated herein by reference in their entirety.

Example

Illustrative tubulysins are as follows:

| Compound | 100a | 100b | 100c | Tub B |
|---|---|---|---|---|
| R | allyl | n-butyl | n-pentyl | |
| IC50 on FR+ KB cell (nM) | 1.2 | 0.7 | 0.8 | 1.2 |

Example

EC1454 is prepared according to the following process.

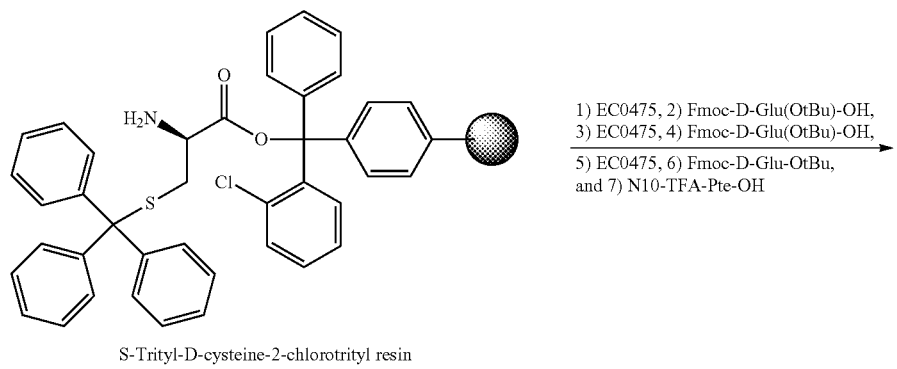

S-Trityl-D-cysteine-2-chlorotrityl resin

1) EC0475, 2) Fmoc-D-Glu(OtBu)-OH,
3) EC0475, 4) Fmoc-D-Glu(OtBu)-OH,
5) EC0475, 6) Fmoc-D-Glu-OtBu,
and 7) N10-TFA-Pte-OH

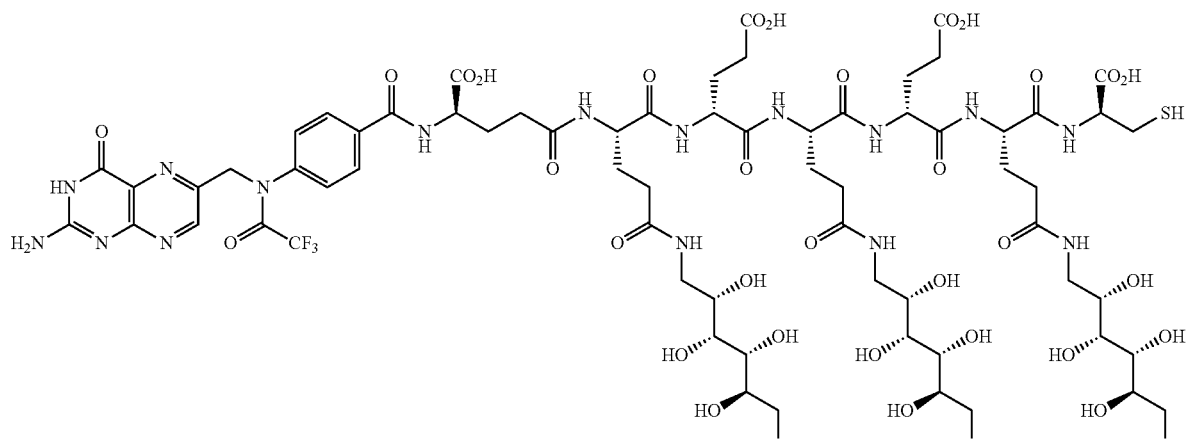

N10-TFA EC1454

The solid phase synthesis of $N^{10}$-TFA protected EC1454 starts with resin bound trityl protected D-cysteine. The resin is suspended in dimethylformamide (DMF) and washed twice with DMF. EC0475 (glucamine modified L-glutamic acid), (Benzotriazol-1-yloxy)tripyrrolidinophosphonium hexafluorophosphate (PyBOP), and diisopropylethylamine (DIPEA) are added to reaction mixture. After at least 1 hour, a Kaiser test is performed to ensure the coupling is complete. The resin is washed three times with DMF, three times with IPA, and three times with DMF. The resin is slowly washed three times with piperidine in DMF, three times with DMF, and three times with IPA. A Kaiser test is performed to confirm deprotection. The resin is washed three times with DMF and the next amino acid in the sequence is coupled following the same process. Monomers are coupled in the following order: 1) EC0475, 2) Fmoc-D-Glu(OtBu)-OH, 3) EC0475, 4) Fmoc-D-Glu(OtBu)-OH, 5) EC0475, 6) Fmoc-D-Glu-OtBu, and 7) $N^{10}$-TFA-Pte-OH.

Once the final coupling is complete, the resin is washed three times with methanol and dried by passing argon through the resin at room temperature. The dried resin is suspended in a mixture of TFA, water, ethanedithiol, and triisopropylsilane. After 1 hour the resin is removed by filtration and washed with TFA. The product is precipitated by addition to cold ethyl ether, filtered, and washed with ether. The solids are dried under vacuum at room temperature and stored in a freezer.

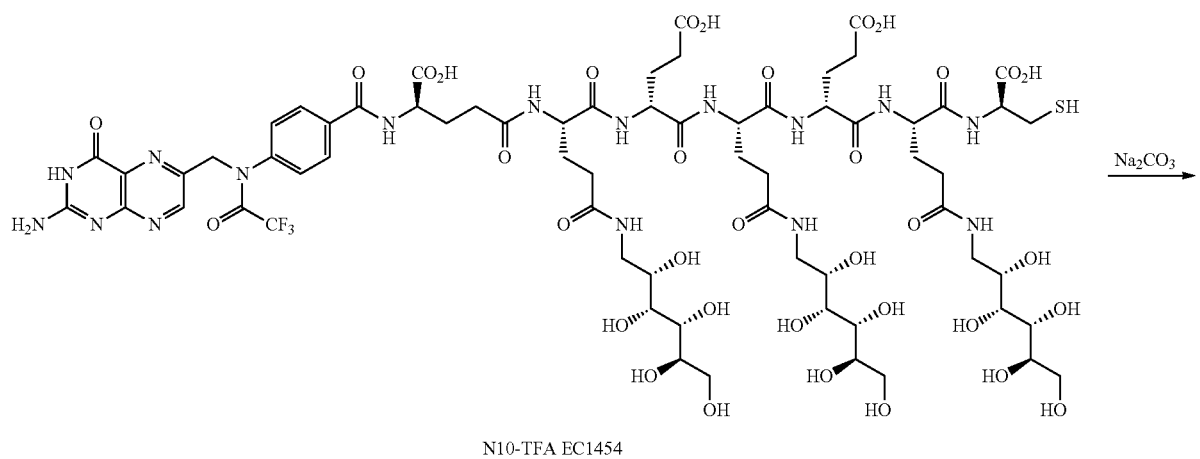

N10-TFA EC1454

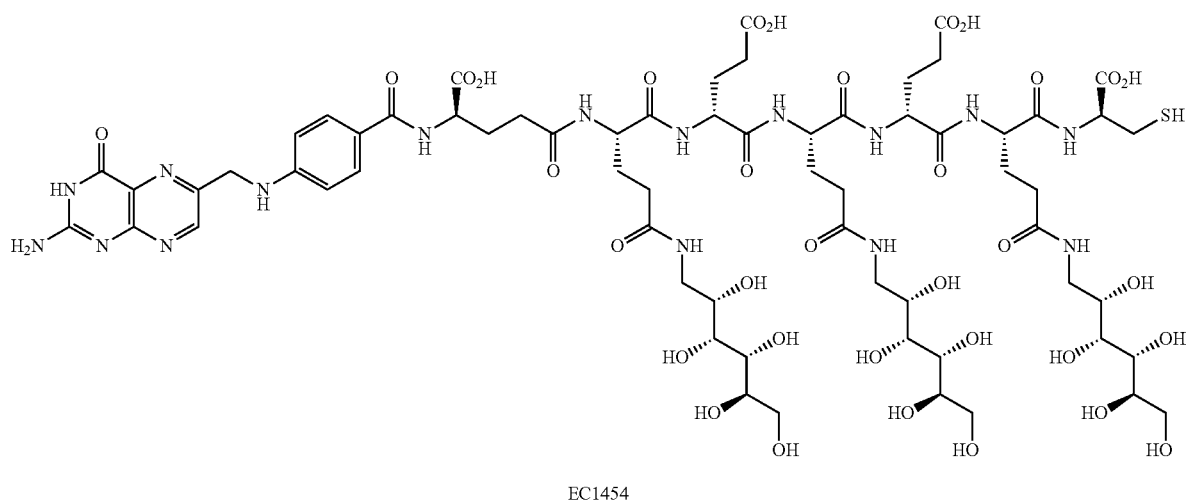 [SMILES: Nc1nc2ncc(CNc3ccc(C(=O)N[C@H](CCC(=O)N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@@H](CS)C(=O)O)C(=O)O)cc3)nc2c(=O)[nH]1]

EC1454

$N^{10}$-TFA EC1454 is dissolved in argon sparged water. Sodium carbonate (1M in water, argon sparged) is added to achieve a pH of 9.4-10.1. The reaction mixture is stirred for at least 20 minutes. Once the reaction is complete as determined by LC, it is quenched by adjusting the pH to 1.9-2.3 with 2M HCl. The product is purified by C18 column chromatography using acetonitrile and pH 5 ammonium acetate buffer as eluents. Fractions are collected and checked for purity by HPLC. The combined product fractions are concentrated on a rotary evaporator and then lyophilized to yield EC1454 as a yellow solid. MS (ESI, $[M+2H]^{2+}$)= 840.90, $[M+H1]^+$=1681.3. Selected 1H-NMR (DMSO, 300 MHz) δ (ppm): 8.6 (s), 7.6 (d), 6.6 (d), 4.45 (s), 4.35 (t), 4.15-4.3 (m), 3.3-3.6 (m), 3.25 (m), 3.0 (m), 2.7-2.9 (m), 2-2.3 (m), 1.6-2 (m). The product is stored at −20° C.

Example

EC1456 is prepared according to the following process.

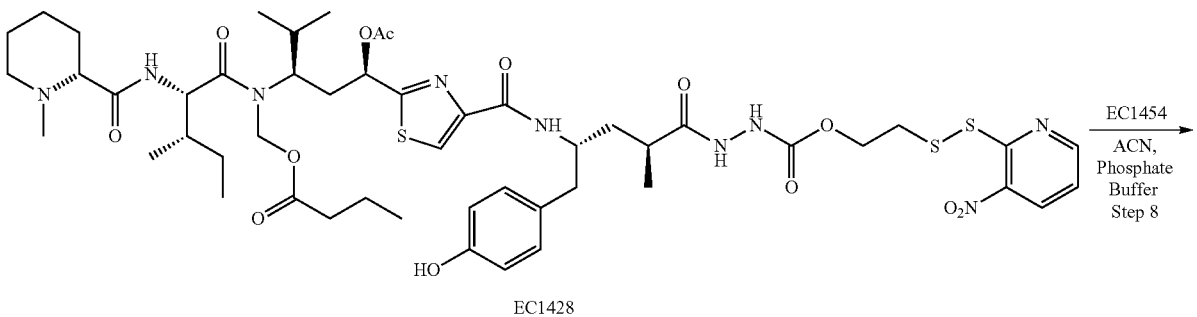

EC1428

-continued

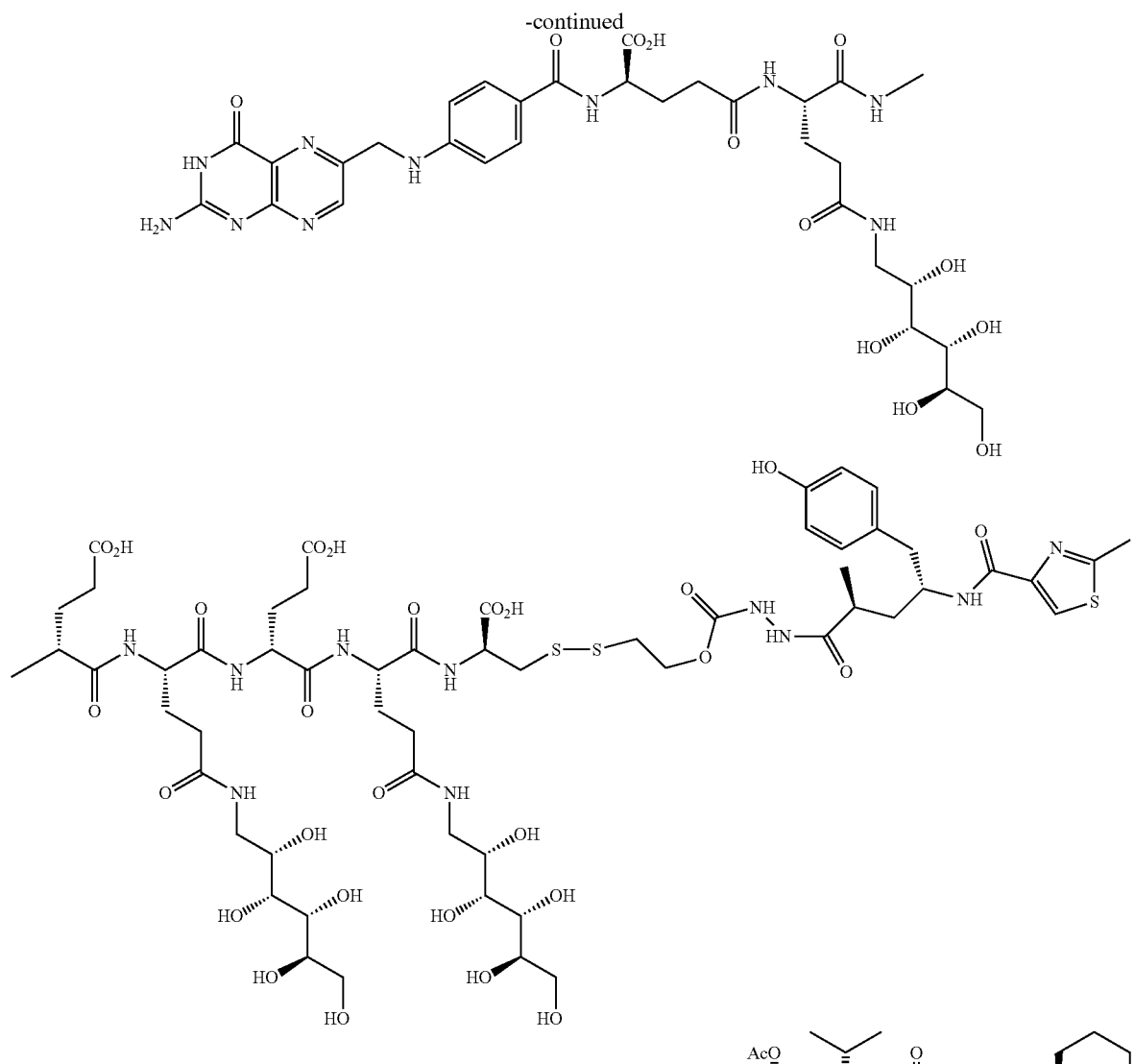

EC1456

EC1428 is dissolved in acetonitrile and a solution of EC1454 in pH 7.4 Sodium phosphate buffer is added. The solutions are sparged with argon before and after addition. The reaction mixture is stirred for at least 15 minutes and then checked for completion. The desired product is purified by C18 column chromatography using acetonitrile and pH 7.4 phosphate buffer as eluents. The product fractions are collected, checked for purity, combined and concentrated by ultra-filtration to yield an aqueous solution that is 10-20 mg/mL EC1456. The final product solution is sampled for assay and then stored in a freezer.

The positive electrospray mass spectrum of EC1456 was obtained on a high resolution Waters Acquity UPLC Xevo Gs-S QTOF mass spectrometer. The spectrum was obtained following separation of the major component on a UPLC inlet system, the resolving power was approximately 35,000. The accurate mass measurement of the M+H monoisotopic peak was 2625.0598, which is 1.1 ppm error difference from the theoretical value of 2625.0570 for an ion of formula $C_{110}H_{166}N_{23}O_{45}S_3$. The isotopic distribution is also consistent with that formula.

Mass spectral features of the ES+ spectrum for EC1456

| Observed Ion | Interpretation |
|---|---|
| 2626.06 | $^{13}C$ isotope of the (M + H)$^+$ ion for the MW 2624 drug substance |

| Observed Ion | Interpretation |
|---|---|
| 1313.54 | $^{13}C$ isotope of the (M + 2H)$^{++}$ ion for the MW 2624 drug substance |
| 1150.43 | $^{13}C$ isotope of the (M + 2H − 326)$^{++}$ fragment, corresponding to the cleavage of the peptide bond at the tertiary nitrogen and the loss of the butyric acid moiety. |
| 876.03 | $^{13}C$ isotope of the (M + 3H)$^{+++}$ ion for the MW 2624 drug substance |
| 657.27 | $^{13}C$ isotope of the (M + 4H)$^{++++}$ ion for the MW 2624 drug substance |

A sample of ~30 mg EC1456 was dissolved in 665 μL of a 9:1 mixture of deuterated dimethylsulfoxide and deuterated water. The $^1H$ NMR spectrum was obtained at 500 MHz at 26 deg. C. on an Agilent model DD2 spectrometer fitted with a 2 channel probe containing both broadband and proton observe coils. The $^{13}C$ NMR spectrum was obtained at 125 MHz on the same instrument under identical conditions. All spectra were referenced to the DMSO solvent residual signals at 2.5 ppm ($^1H$) and 39.50 ppm ($^{13}C$).

All spectral features are assigned for both NMR spectra in the tables below ($^1H$ and $^{13}C$) using the atom numbering in the following figure, where the * symbols indicate the connection for the disulfide bond.

the same chemical shift) could be resolved in the 2D spectra, in these cases the tables reflect the chemical shifts measured from the 2D spectra but summed integrations for the group of co-resonating species. In some cases of 1D overlap (such as the nearly identical glutamic acid and glucamine subunits) there was also overlap in the 2D correlation spectra which precludes unambiguous assignment of single or multiple resonances between multiple atom numbers, in these cases there are multiple entries for chemical shift and/or atom number assignments in a single table row.

NH and OH protons were exchanged by the $D_2O$ deuterium atoms and are mostly absent from the spectrum, except weak broad peaks in the 5-10 ppm region. The $^1H$ peaks in the spectrum that are not listed in the table include a broad HOD peak at 3.75 ppm, and a DMSO peak at 2.50 ppm. The HOD peak does not obscure any resonances, but elevates the integrations for nearby resonances at 4.2 and 3.4-3.7 ppm due to the broad baseline rise. The DMSO peak obscures the resonance for H129, which is not integrated for this reason. The $^{13}C$ peaks in spectrum not listed in the table include the very large DMSO solvent at 39.50 ppm. The DMSO peak obscures both the signals from C91 and C93. The C116 peak is not observable in the $^{13}C$ spectrum due to extensive broadening due to conformational changes around the nearby amide group. All three chemical shifts (C91, C93, C116) are visible in and measured in the proton detected 2D correlation spectra.

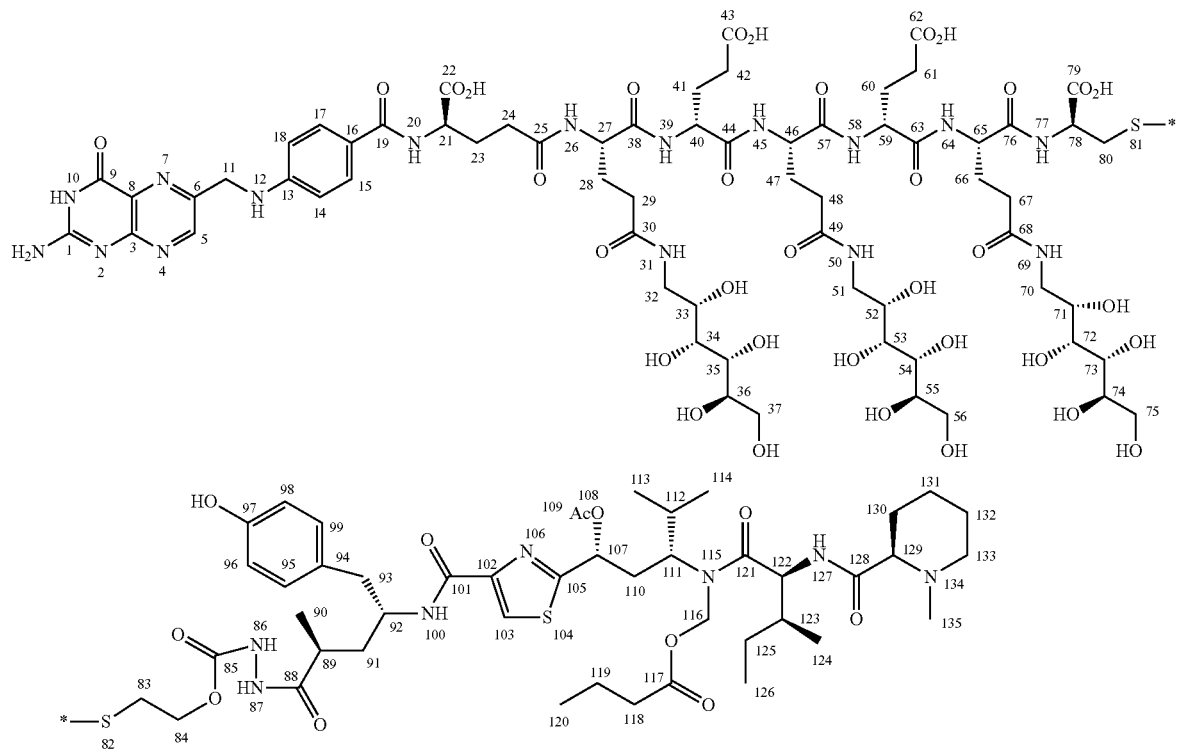

Assignments were made on the basis of both 1D and 2D NMR experiments, including through bond H—H connectivity using the COSY and TCSY 2D experiments, through space H—H proximity using 2D NOESY, carbon multiplicity measurement using the 1D DEPT experiment and through bond C—H connectivity using the proton detected 2D experiments HSQC and HMBC. In most cases of overlap in the 1D spectra (different protons or carbons resonating at Proton NMR assignments for EC1456

| Proton Chemical Shift (ppm) | Assignment | # protons |
|---|---|---|
| 8.61 | 5 | 1 |
| 8.16 | 103 | 1 |
| 7.58 | 15, 17 | 2 |

-continued

| Proton Chemical Shift (ppm) | Assignment | # protons |
|---|---|---|
| 6.96 | 95, 99 | 2 |
| 6.62 | 14, 18 | 4 |
| 6.59 | 96, 98 | |
| 6.18 | 116 Ha | 1 |
| 5.7 | 107 | 1 |
| 5.24 | 116 Hb | 1 |
| 4.47 | 11 | 2 |
| 4.39 | 111, 122 | 2 |
| 4.21 | 78 | 10 |
| 4.21 | 65 | |
| 4.18 | 84 | |
| 4.15 | 46 | |
| 4.15 | 59 | |
| 4.13 | 21 | |
| 4.13 | 40 | |
| 4.09 | 27 | |
| 4.09 | 92 | |
| 3.61 | 33, 52, 71 | 3 |
| 3.56 | 34, 53, 72 | 6 |
| 3.54 | 37Ha, 56Ha, 75Ha | |
| 3.46 | 36, 55, 74 | 3 |
| 3.4 | 35, 54, 73 | 6 |
| 3.38 | 37Hb, 56Hb, 75Hb | |
| 3.21 | 80Ha, 32Ha, 51 Ha, 70 Ha | 4 |
| 3.05 | 32Hb, 51Hb, 70Hb | 3 |
| 2.93 | 80 Hb | 3 |
| 2.91 | 83 | |
| 2.8 | 133Ha | 1 |
| 2.68 | 93 | 2 |
| 2.49 (see text) | 129 | 1 |
| 2.35 | 89 | 2 |
| 2.33 | 110Ha | |
| 2.8 | 133Hb | 37 |
| 2.17 | 118 | |
| 2.14-2.08 | 24, 29, 42, 48, 61, 67 | |
| 2.09 | 110Hb | |
| 2.08 | 109 | |
| 2.02 | 135 | |
| 1.97-1.70 | 28, 41, 47, 60, 66 | |
| 1.92 | 23Ha | |
| 1.88 | 123 | |
| 1.8 | 91Ha | |
| 1.79 | 23Hb | |
| 1.77 | 112 | |
| 1.6 | 131Ha | 9 |
| 1.56 | 130Ha | |
| 1.5 | 132Ha | |
| 1.5 | 91Hb | |
| 1.45 | 125Ha | |
| 1.42 | 119 | |
| 1.4 | 132Hb | |
| 1.33 | 130Hb | |
| 1.14 | 131Hb | 2 |
| 1.07 | 125Hb | |
| 1 | 90 | 3 |
| 0.94 | 114 | 3 |
| 0.79 | 124 | 3 |
| 0.77 | 126 | 3 |
| 0.75 | 120 | 3 |
| 0.64 | 113 | 3 |

Carbon NMR assignments for EC1456

| Carbon Chemical shift (ppm) | Assignment |
|---|---|
| 176.77, 176.32 | 43, 62 |
| 175.74 | 88 |
| 175.42 | 22 |
| 174.75 | 121 |
| 173.87, 172.68, 172.15, 171.94, | 25, 38, 44, 57, 63 |
| 171.84 | |
| 173.43 | 79 |
| 73.3 | 128 |
| 172.79 (2x), 172.72 | 30, 49, 68 |
| 172.46 | 117 |
| 170.87 | 76 |
| 170.39 | 108 |
| 169.3 | 105 |
| 166.09 | 19 |
| 162.4 | 9 |
| 160.7 | 101 |
| 156.4 | 85 |
| 156.09 | 3 |
| 155.71 | 97 |
| 154.59 | 1 |
| 150.84 | 13 |
| 149.63 | 102 |
| 149.11 | 6 |
| 148.99 | 5 |
| 130.44 | 95, 99 |
| 128.99 | 15, 17 |
| 128.89 | 94 |
| 127.99 | 8 |
| 124.97 | 103 |
| 122.24 | 16 |
| 115.25 | 96, 98 |
| 111.86 | 14, 18 |
| 72.17 (3x) | 35, 54, 73 |
| 71.78, 71.74, 71.71 | 33, 52, 71 |
| 71.62, 71.59 (2x) | 36, 55, 74 |
| 69.65, 69.57 (2x) | 34, 53, 72 |
| 69.45 | 107 |
| 69.34 | 116 |
| 68.51 | 129 |
| 63.42 (3x) | 37, 56, 75 |
| 63.03 | 84 |
| 55.08 | 133 |
| 54.05 | 40 |
| 53.88 | 78 |
| 53.46 (2x) | 46, 59 |
| 53.33 | 27 |
| 52.96 (2x) | 122, 111 |
| 52.89 | 21 |
| 52.55 | 65 |
| 49.77 | 92 |
| 46.07 | 11 |
| 44.02 | 135 |
| 42.85 | 80 |
| 42.34 (2x), 42.29 | 32, 51, 70 |
| 39.52 | 93 |
| 38.95 | 91 |
| 37.43 | 83 |
| 35.95 | 118 |
| 35.43 | 123 |
| 35.38 | 89 |
| 34.86 | 110 |
| 32.56, 32.36, 32.16, 32.09 (2x), 31.81 | 24, 29, 42, 48, 61, 67 |
| 30.5 | 112 |
| 29.95 | 130 |
| 28.60, 28.04, 27.78 (2x), 27.66 | 28, 41, 47, 60, 66 |
| 27 | 23 |
| 25.01 | 132 |
| 24.43 | 125 |
| 23.04 | 131 |
| 20.86 | 109 |
| 20.56 | 114 |
| 19.64 | 113 |
| 18.36 | 90 |

-continued

| Carbon Chemical shift (ppm) | Assignment |
|---|---|
| 18.04 | 119 |
| 15.64 | 124 |
| 13.72 | 120 |
| 10.28 | 126 |

The IR spectrum of EC1456 was acquired on a Nexus 6700® Fourier transform infrared (FT-IR) spectrophotometer (Thermo Nicolet) equipped with an Ever-Glo mid/far IR source, an extended range potassium bromide (KBr) beam splitter, and a deuterated triglycine sulfate (DTGS) detector. An attenuated total reflectance (ATR) accessory (Thunderdome™, Thermo Spectra-Tech), with a germanium (Ge) crystal was used for data acquisition. The spectrum represents 256 co-added scans collected at a spectral resolution of 4 cm-1. A background data set was acquired with a clean Ge crystal. A Log 1/R (R=reflectance) spectrum was acquired by taking a ratio of these two data sets against each other. Wavelength calibration was performed using polystyrene. Infrared band assignments for EC1456 reference substance

| Characteristic Absorption(s) (cm$^{-1}$) | Functional Group |
|---|---|
| 1700-1500 (m, m) | Aromatic C=C Bending |
| 2950-2850 (m or s) | Alkyl C—H Stretch |
| ~3030 (v) | Aromatic C—H Stretch |
| 3550-3200 (broad, s) | Alcohol/Phenol O—H Stretch |
| 3700-3500 (m) | Amide C=O Stretch |

The ultraviolet spectrum EC1456 acquired on a Perkin-Elmer Lambda 25 UV/Vis spectrometer. The spectrum was recorded at 40.7 uM in 0.1M NaOH solvent on a 1 cm path-length cell at 25 deg. C. The local maxima at 366 nm, 288 nm and 243 nm are due primarily to the Pteroic acid, benzamide/phenol and thiazole-amide substructures, respectively, although the molecule contains dozens of chromaphores with overlapping absorption in the UV region.

Example $N^{10}$-TFA Protected EC1579 is prepared according to the following process.

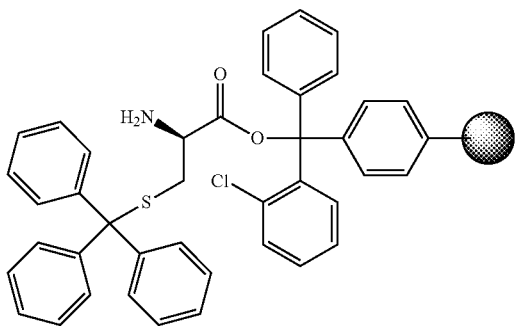

S-Trityl-D-cysteine-2-chlorotrityl resin

1) EC0475, 2) Fmoc-D-Glu(OtBu)-OH,
3) EC0475, 4) Fmoc-D-Glu(OtBu)-OH,
5) EC0475, 6) Fmoc-D-Glu-OtBu,
7) N10-TFA-Pte-OH

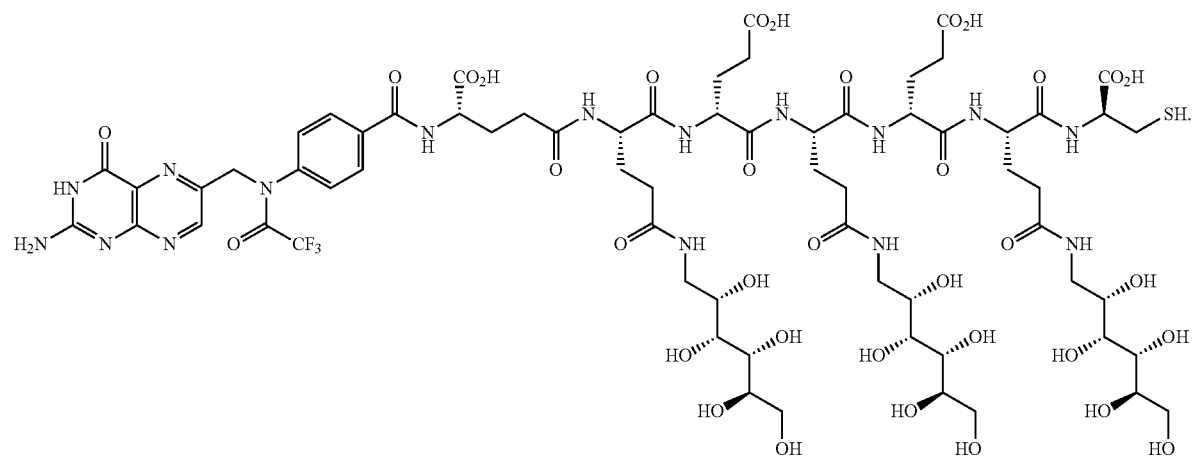

N10-TFA EC1579

Example
EC1579 is prepared according to the following process.
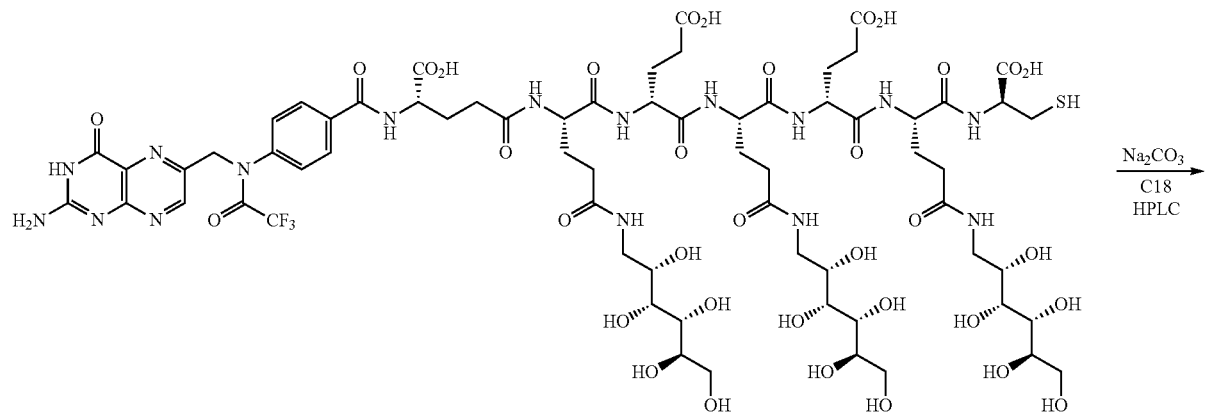
N10-TFA EC1579
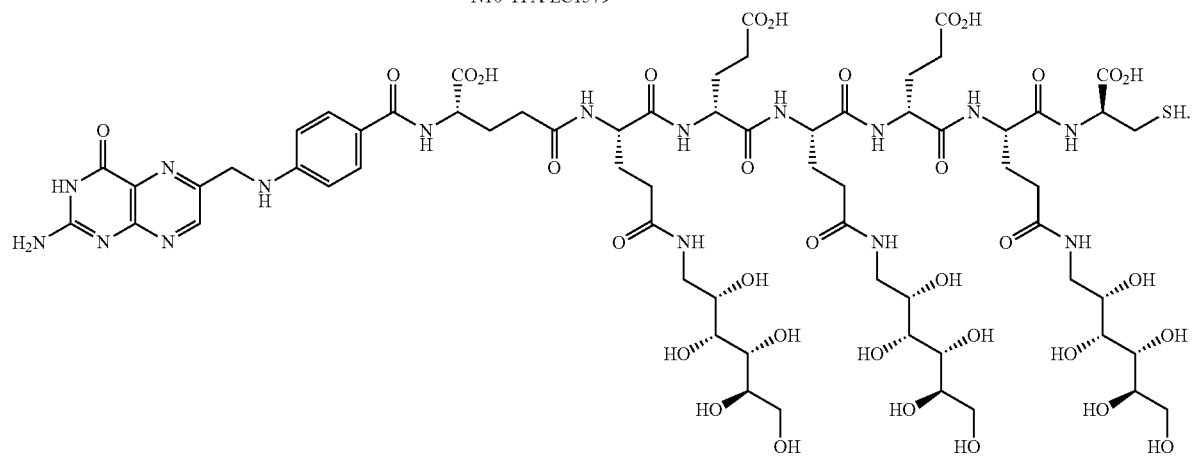
EC1579
EC1579 MS (ESI, $[M+2H]^{2+}$)=840.89 $(M+1H)1+$= 1681.0. Partial 1H-NMR ($D_2O$) δ(ppm): 8.6 (s), 7.5 (d), 6.65 (d), 4.4-4.8 (m), 4-4.2 (m), 3.4-3.8 (m) 3-3.3 (m) 2.75 (s), 1.6-2.4 (m).
Example
EC0948 is made by the processes described herein.
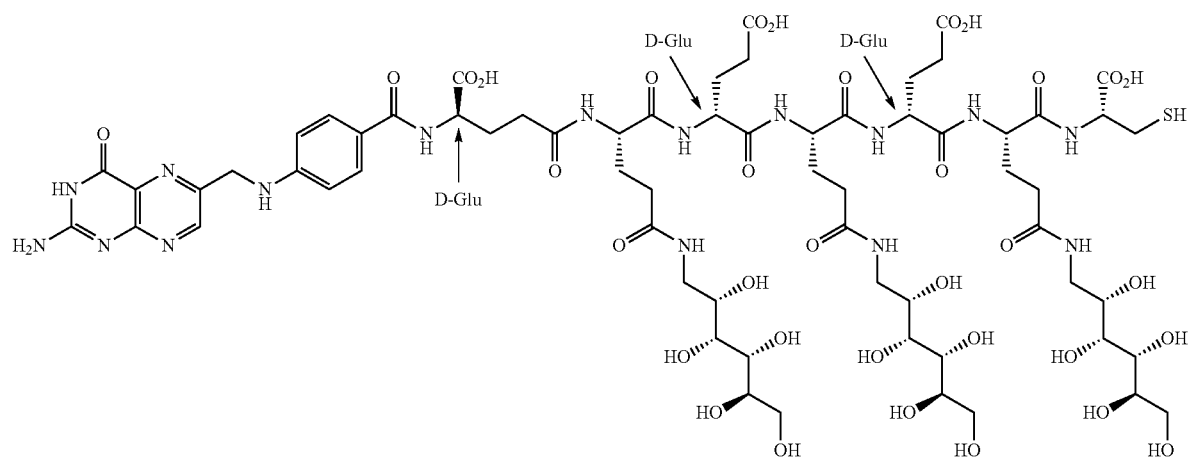
EC0848

EC0848: MS (ESI, [M+2H]2+)=840.8. [M+H]+=1681.1. Selected 1H-NMR (DMSO) δ (ppm): s, 8.6; d, 7.6; d, 6.6; s, 4.45; m, 4-4.2; m, 3.3-3.8; m, 3.1-3.3; m, 3-3.1; m, 2.7-2.9; m, 1.7-2.3; s, 1.15

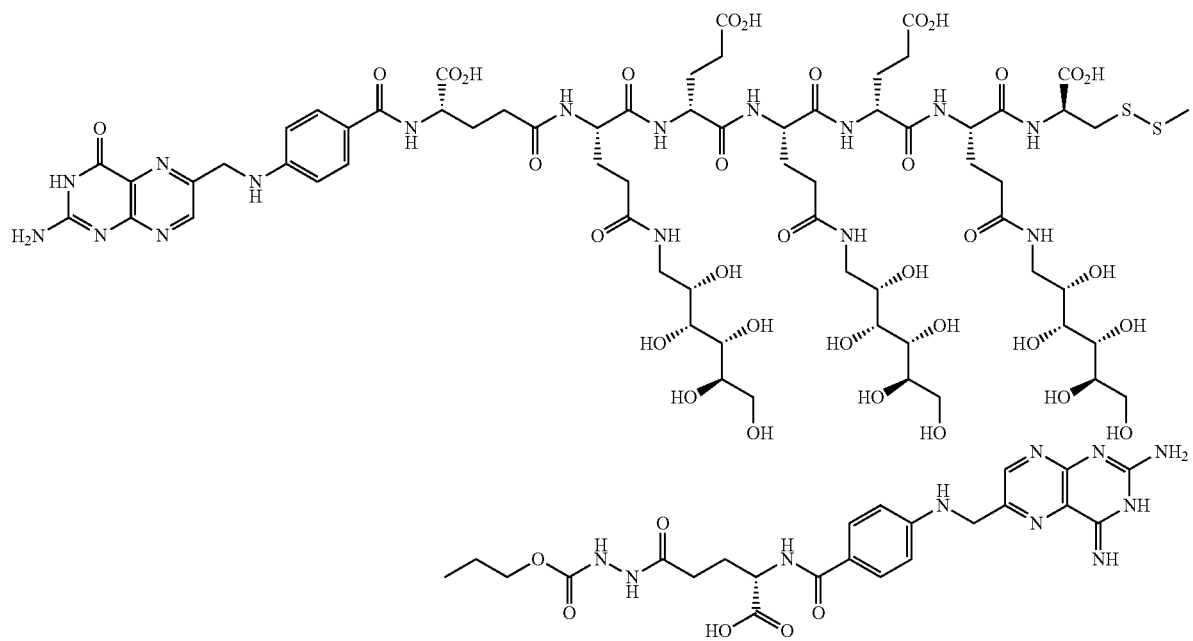

Example

EC1669 is prepared according to the processes described herein from EC1579 and EC0469 as follows:

EC1579 +

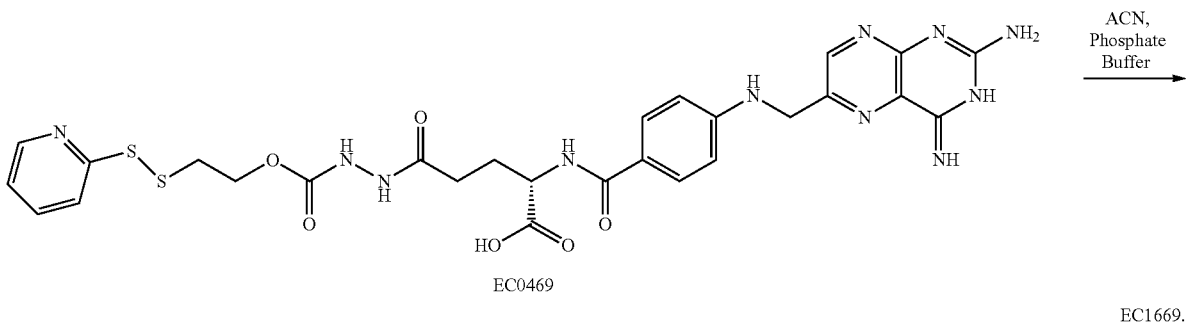

EC0469

EC1669.

EC1579 (200 mg, 1.0 eq) is dissolved in deoxygenated (bubbling argon) 20 mM PO$_4$ (pH=7) buffer (4.0 mL) and added dropwise to a stirring solution of EC0469 (80 mg, 1.0 eq) in dry dimethylsulfoxide (4.0 mL) at room temperature with argon bubbling. After 30 min, EC1669 (132 mg) is purified by preparative HPLC in 0-30% acetonitrile/50 mM NH$_4$HCO$_3$ pH7 buffer and lyophilized (49% yield). Chemical Formula: C$_{87}$H$_{122}$N$_{26}$O$_{40}$S2; Exact Mass: 2234.78; MW 2236.18. MS (ESI, [M+2H]$^{2+}$) Predicted 1118.39. Found 1119.52. Partial $^1$H NMR (DMSO w/10% D$_2$O) δ (ppm) 8.67 (s), 8.59 (2), 7.61 (d), 7.56 (d), 6.71 (d), 6.61 (d), 3.34-3.39 (m)'

Example
The following additional compounds are described and are prepared according to the general processes described herein.
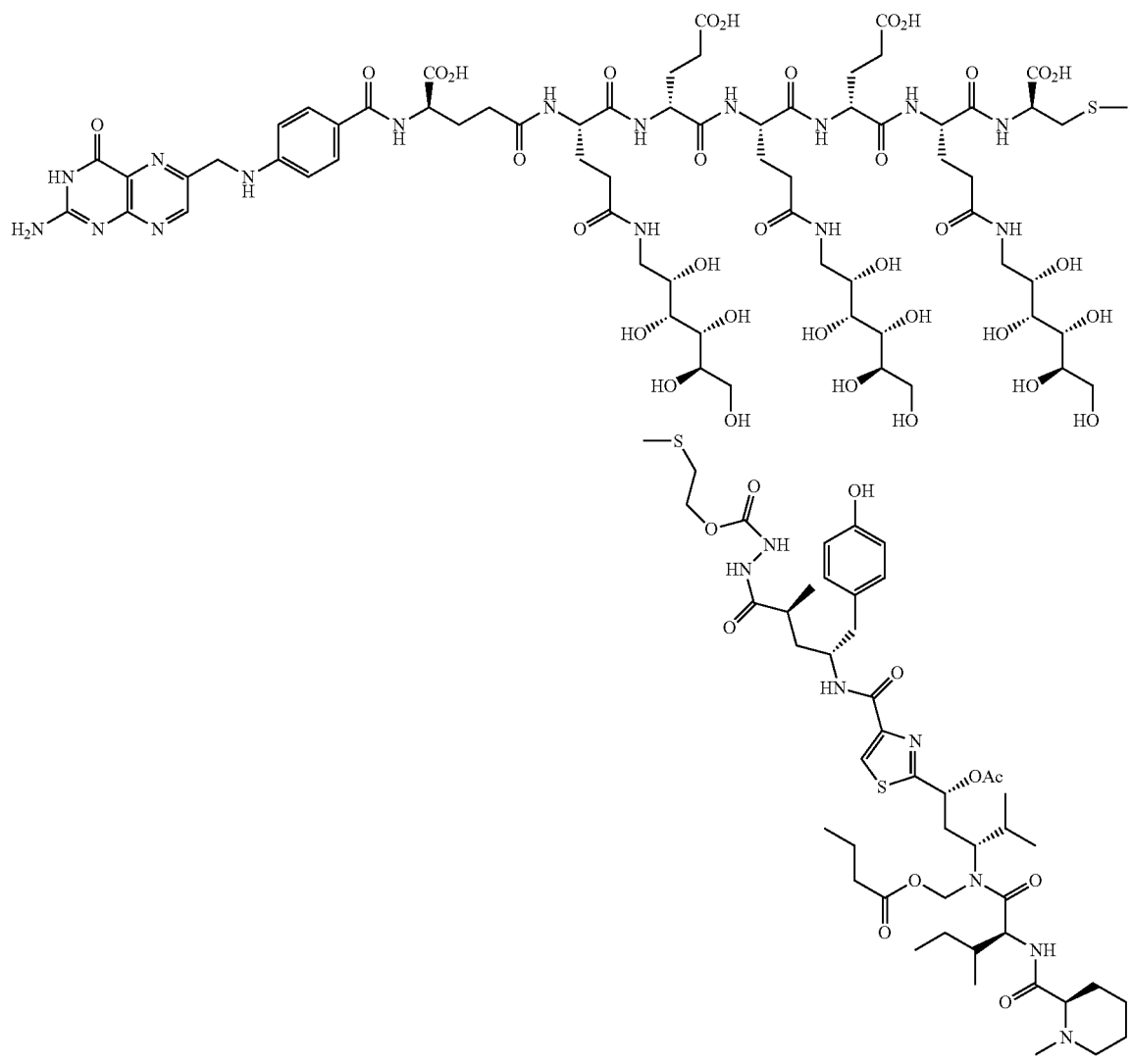
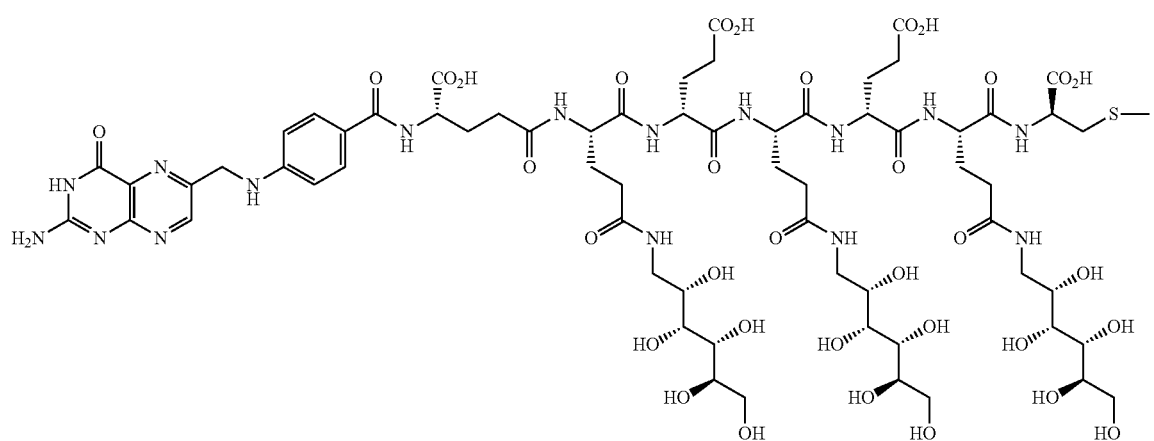

-continued
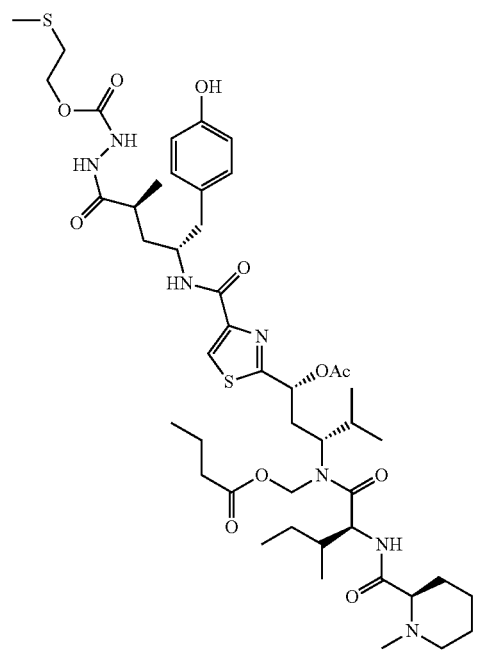
EC1739
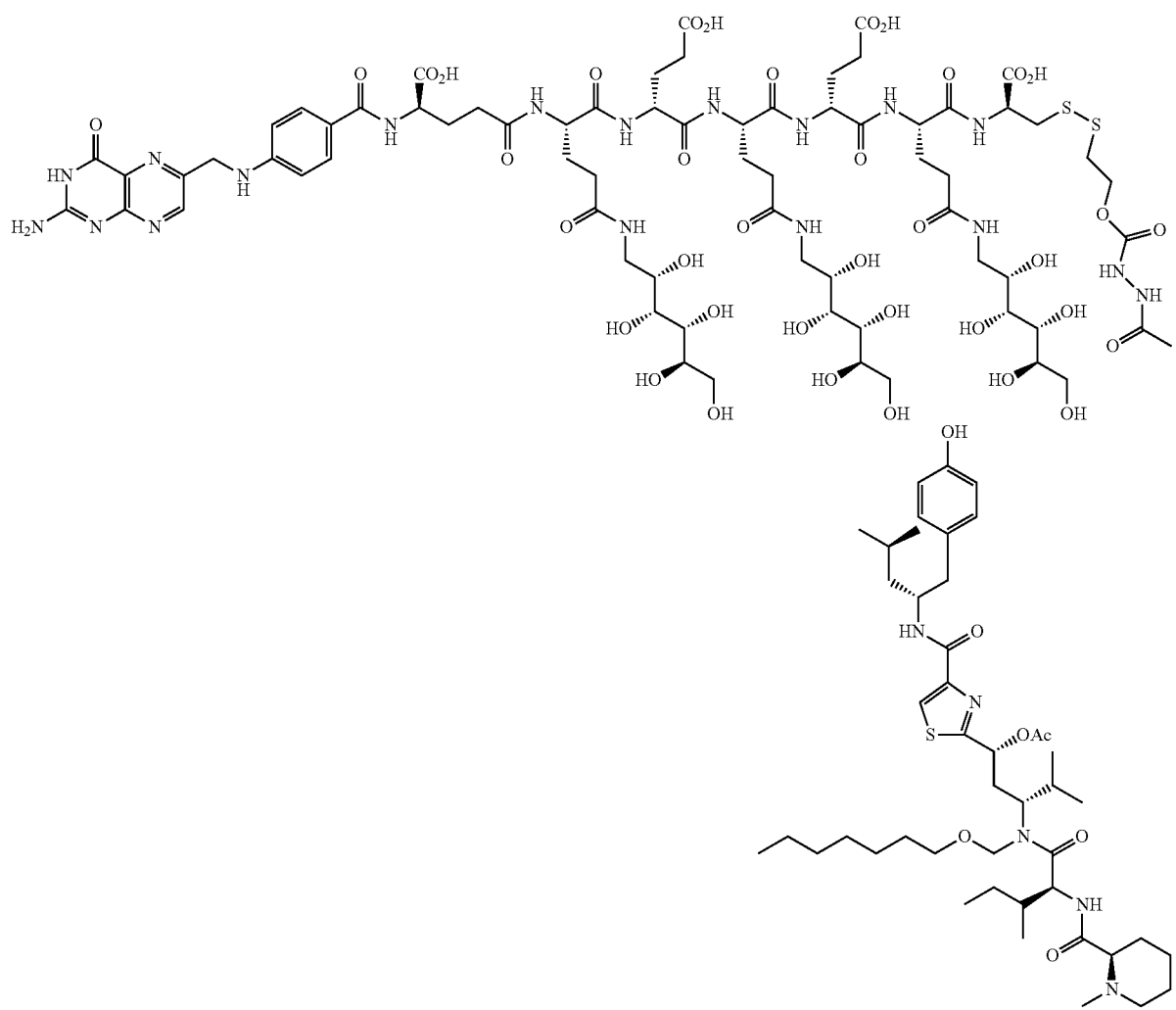
($C_{113}H_{173}N_{23}O_{44}S_3$; MW 2653.91)

EC1454 (8.5 mg, 1.5 eq) was dissolved in degassed (Ar bubbling) 20 mM phosphate pH7 buffer (2.0 mL) and added dropwise to a stirring solution of EC1717 (3.8 mg, 1.0 eq) in dry dimethylsulfoxide (2.0 mL, Aldrich) at room temperature with Ar bubbling. After 30 min, EC1739 (5.3 mg, 59%) was purified by preparative HPLC in 10-100% acetonitrile/50 mM $NH_4HCO_3$ pH7 buffer and lyophilized. MS (ESI, $[M+2H]^{2+}$)=1327.06. Found 1327.73
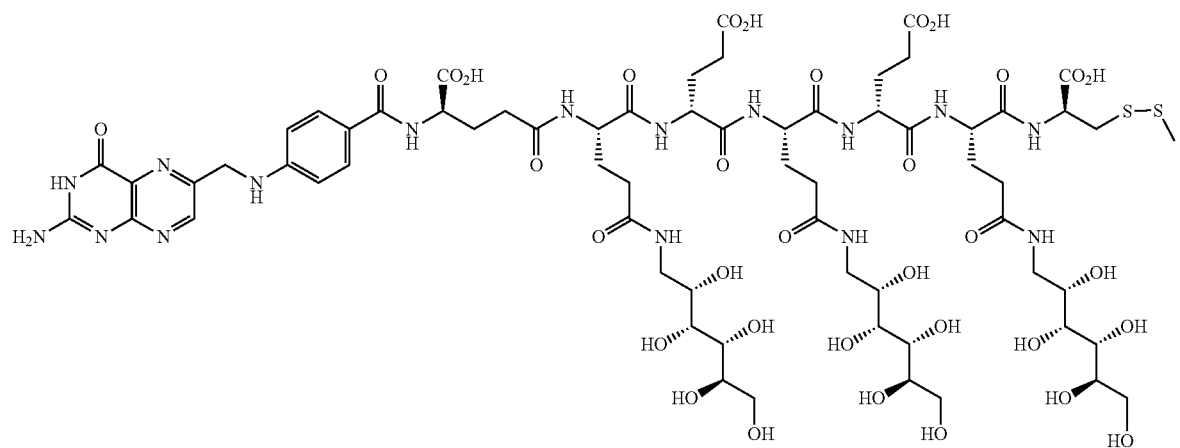
EC1664
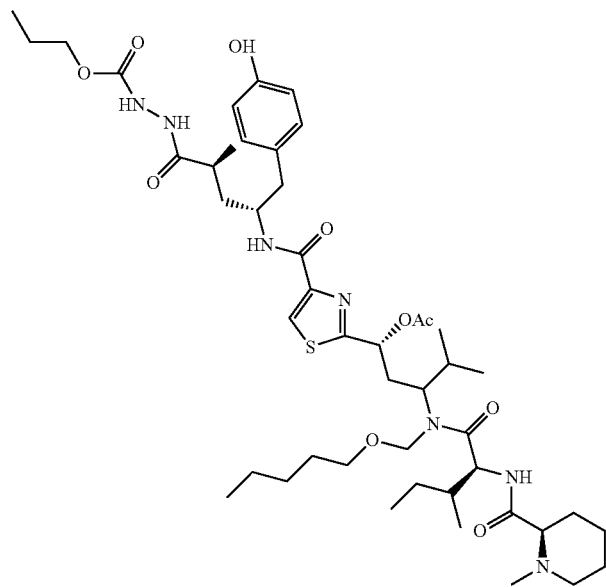
($C_{111}H_{169}N_{23}O_{44}S_3$; Molecular Weight 2625.85)

C1454 (5.5 mg, 1.0 eq) was dissolved in degassed (Ar bubbling) 20 mM phosphate pH7 buffer (2.0 mL) and added dropwise to a stirring solution of EC1662 (3.6 mg, 1.0 eq) in dry dimethylsulfoxide (2.0 mL, Aldrich) at room temperature with Ar bubbling. After 30 min, EC1664 (4.6 mg, 54%) was purified by preparative HPLC in 10-100% acetonitrile/50 mM $NH_4HCO_3$ pH7 buffer and lyophilized. MS (ESI, $[M+2H]^{2+}$) Predicted 1313.05. Found 1313.37. Partial $^1$H NMR (DMSO w/10% $D_2O$, 300 MHz) δ (ppm) 8.61 (s), 8.15 (s), 7.58 (d), 6.94 (d), 6.60 (m), 5.78 (d), 5.22 (d), 4.47 (m), 4.09-4.33 (m), 0.99 (d), 0.93 (d), 0.76 (t), 0.71 (t), 0.61 (d).

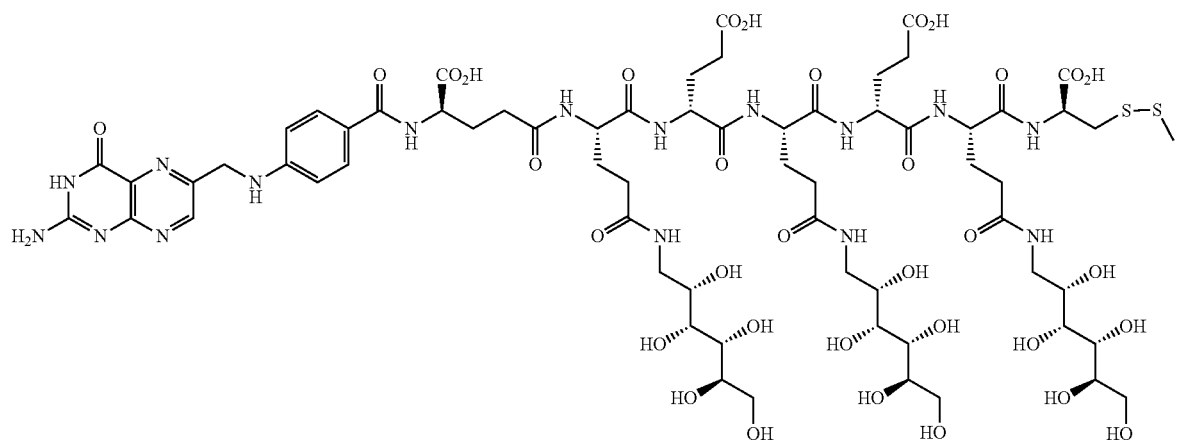

EC1663

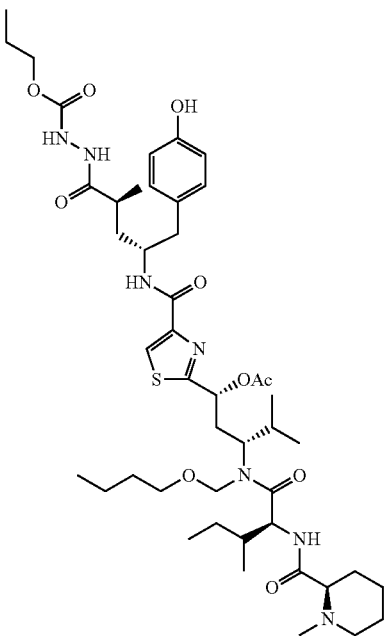

(Chemical Formula: $C_{110}H_{167}N_{23}O_{44}S_3$; MW 2611.83)

EC1454 (16.1 mg, 1.2 eq) was dissolved in degassed (Ar bubbling) 20 mM phosphate pH7 buffer (2.0 mL) and added dropwise to a stirring solution of EC1661 (8.7 mg, 1.0 eq) in dry dimethylsulfoxide (2.0 mL, Aldrich) at room temperature with Ar bubbling. After 30 min, EC1663 (15.8 mg, 76%) was purified by preparative HPLC in 10-100% acetonitrile/50 mM $NH_4HCO_3$ pH7 buffer and lyophilized. MS (ESI, $[M+2H]^{2+}$) Predicted 1306.04. Found 1306.82.

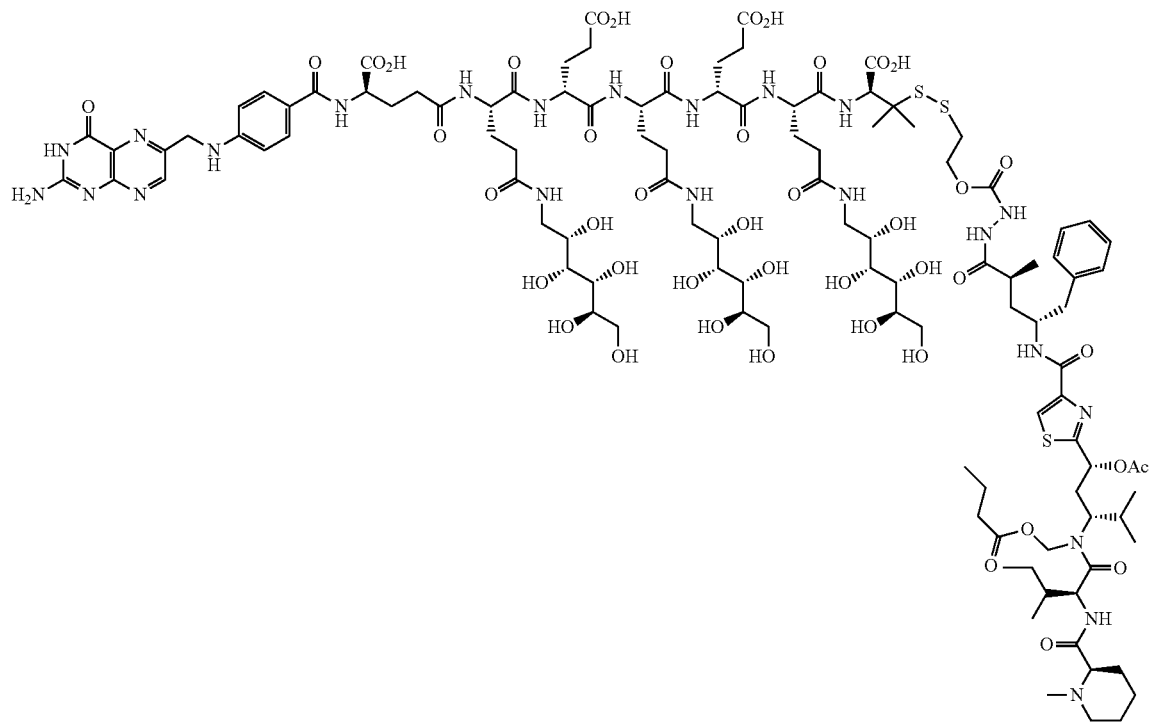

EC1416

($C_{112}H_{169}N_{23}O_{45}S_3$; MW 2653.87)

EC1415 (20 mg) was dissolved in pH7 phosphate (pH 7.75, purged with argon). To this solution was added a suspension of ECO312 (14 mg) in equal volume of MeOH. The reaction mixture was stirred at ambient temperature under argon for 45 min, and then loaded onto a preparatory HPLC (Mobile phase A=50 mM $NH_4HCO_3$ buffer, pH=7.0. B=ACN. Method: 5-80% B in 20 min.) for purification. Fractions containing the desired product were collected, combined, and freeze-dried to afford the product (18 mg) as a pale yellow solid. MS(ESI, $[M+2H]^{2+}$) 1328, 1H NMR (DMSO-d6, $D_2O$, 300 MHz): 8.6 (s, 1H), 8.15 (s, 1H), 7.85 (bd, 1H), 7.55 (d, 2H), 6.95 (d, 2H), 6.6 (m, 4H), 6.2 (d, 1H), 5.68 (d, 1H), 5.2 (d, 1H), 4.5 (bs, 3H), 4.5-4.3 (m, 4H), 4.3-4.0 (m, 10H), 3.5-3.3 (m, 13H), 3.2 (bd, 5H), 3.1-2.8 (m, 8H), 2.75 (bs, 5H), 2.6-1.6 (m, 50H), 1.4 (m, 9H), 1.2 (m, 9H), 1.0 (dd, 9H), 0.7 (m, 11H), 0.6 (d, 3H).

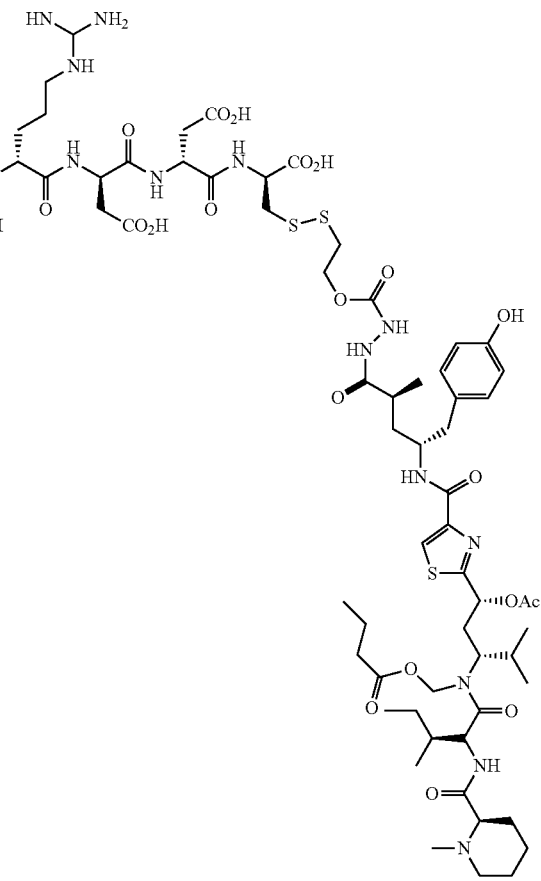

EC1299

($C_{85}H_{118}N_{22}O_{28}S_3$; MW 1992.18)

A solution of EC0259 (35 mg) in 20 mM pH7 phosphate buffer (3.0 mL) and a saturated $NaHCO_3$ solution (1.5 mL) were added to a solution of EC0312 (39 mg) in MeOH (5.5 mL) in tandem. The resulting homogeneous solution was stirred at ambient temperature under argon for 20 min. and then loaded directly onto a preparatory HPLC (Mobile phase A=50 mM $NH_4HCO_3$ buffer, pH=7.0. B=ACN. Method: 5-80% B in 20 min.) for purification. Fractions containing the desired product were collected, combined, and freeze-dried to afford the product (25 mg) as a pale yellow solid. MS (ESI, [M+H]$^+$) 1993.

EC1549

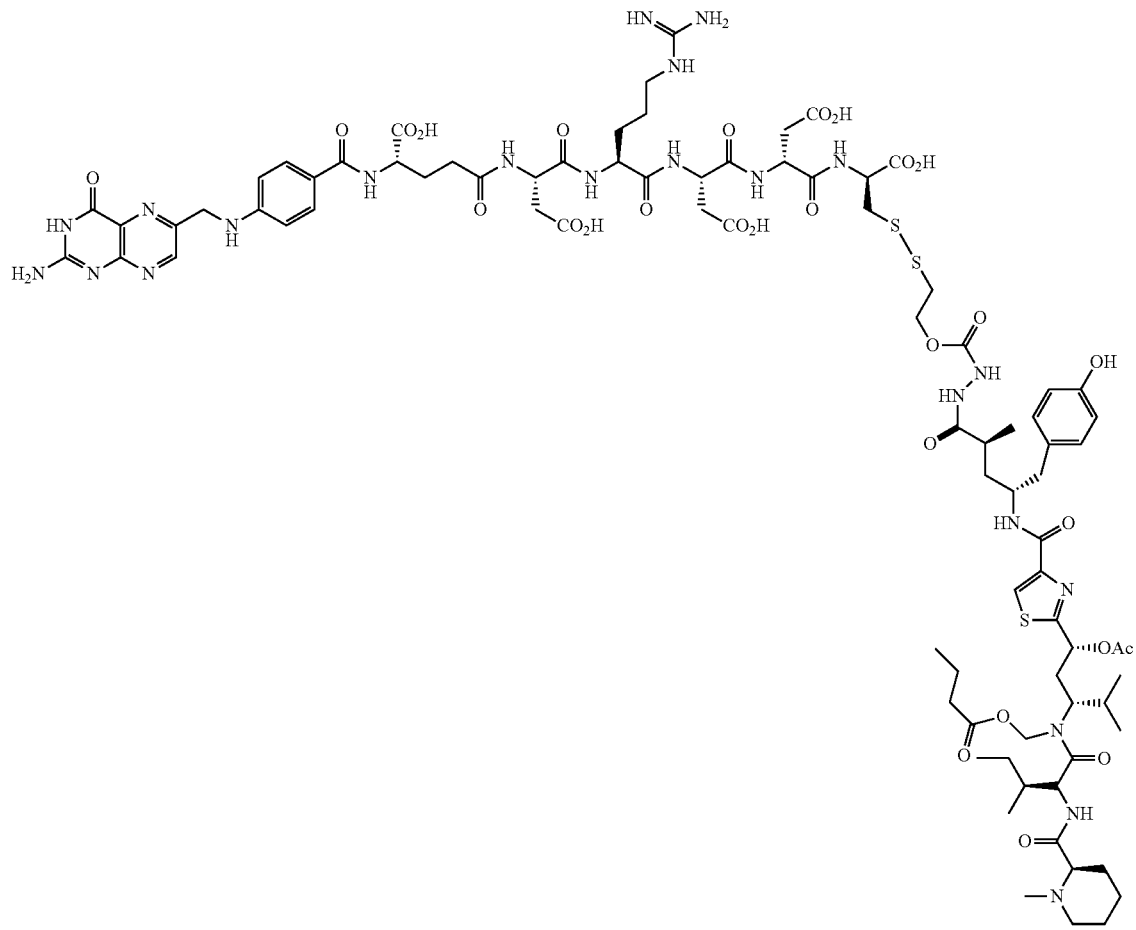

($C_{85}H_{118}N_{22}O_{28}S_3$; MW 1992.17)

A solution of EC0259 (35 mg) in 20 mM pH7 phosphate buffer (3.0 mL) and a saturated NaHCO₃ solution (1.5 mL) were added to a solution of EC0312 (39 mg) in MeOH (5.5 mL) in tandem. The resulting homogeneous solution was stirred at ambient temperature under argon for 20 min. and then loaded directly onto a preparatory HPLC (Mobile phase A=50 mM NH₄HCO₃ buffer, pH=7.0. B=ACN. Method: 5-80% B in 20 min.) for purification. Fractions containing the desired product were collected, combined, and freeze-dried to afford the product (25 mg) as a pale yellow solid. MS (ESI, [M+H]⁺) 1993.

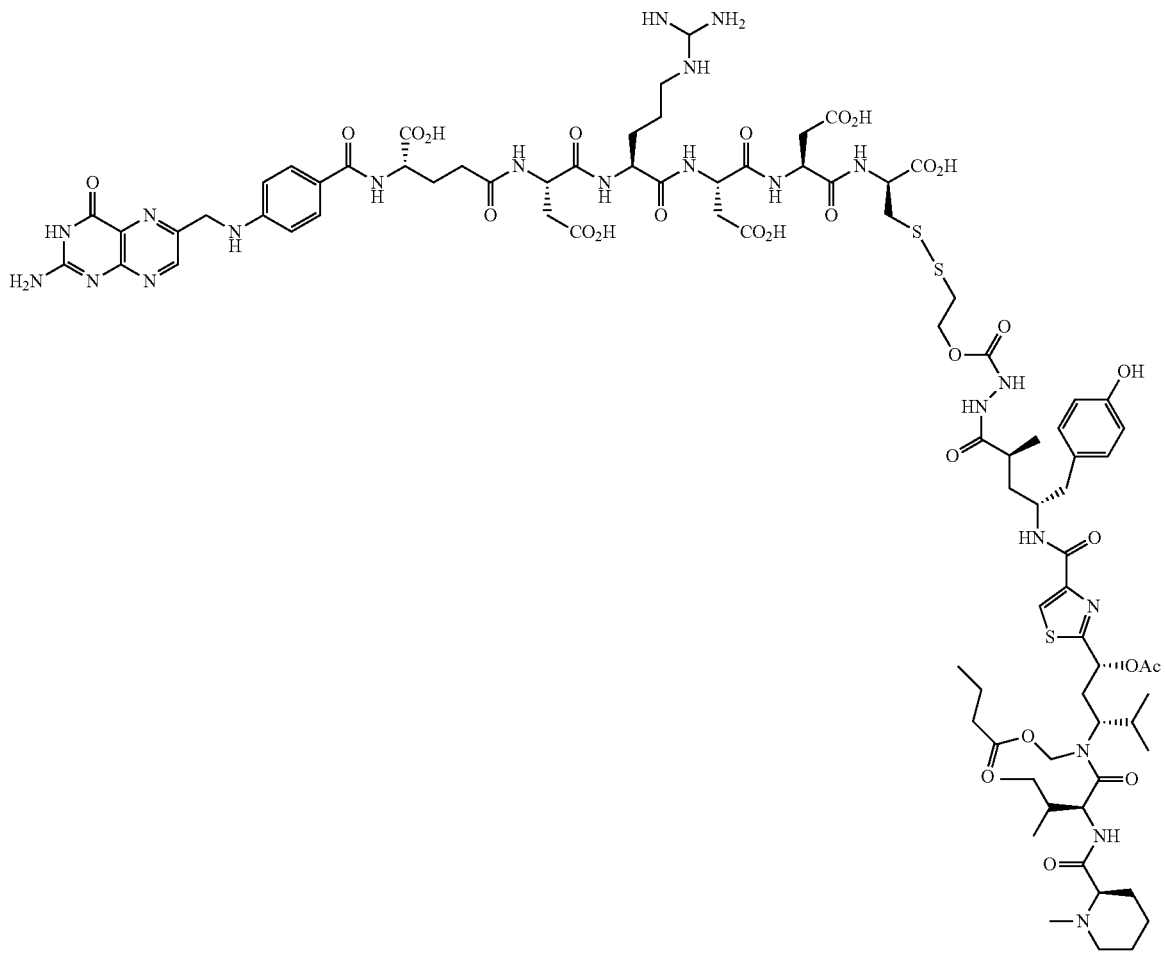

EC1548

($C_{85}H_{118}N_{22}O_{28}S_3$; MW 1992.17)

A solution of EC1544 (55.1 mg) in 20 mM pH7 phosphate buffer (1.95 mL) and a saturated NaHCO$_3$ solution (0.30 mL) were added to a solution of EC1248 (58.0 mg) in MeOH (2.30 mL) in tandem. The resulting homogeneous solution was stirred at ambient temperature under argon for 20 min. and then loaded directly onto a preparatory HPLC (Mobile phase A=50 mM NH$_4$HCO$_3$ buffer, pH=7.0. B=ACN. Method: 5-80% B in 20 min.) for purification. Fractions containing the desired product were collected, combined, and freeze-dried to afford the product (61.5 mg) as a pale yellow solid. MS (ESI, [M+H]$^+$) 1993.

EC1393

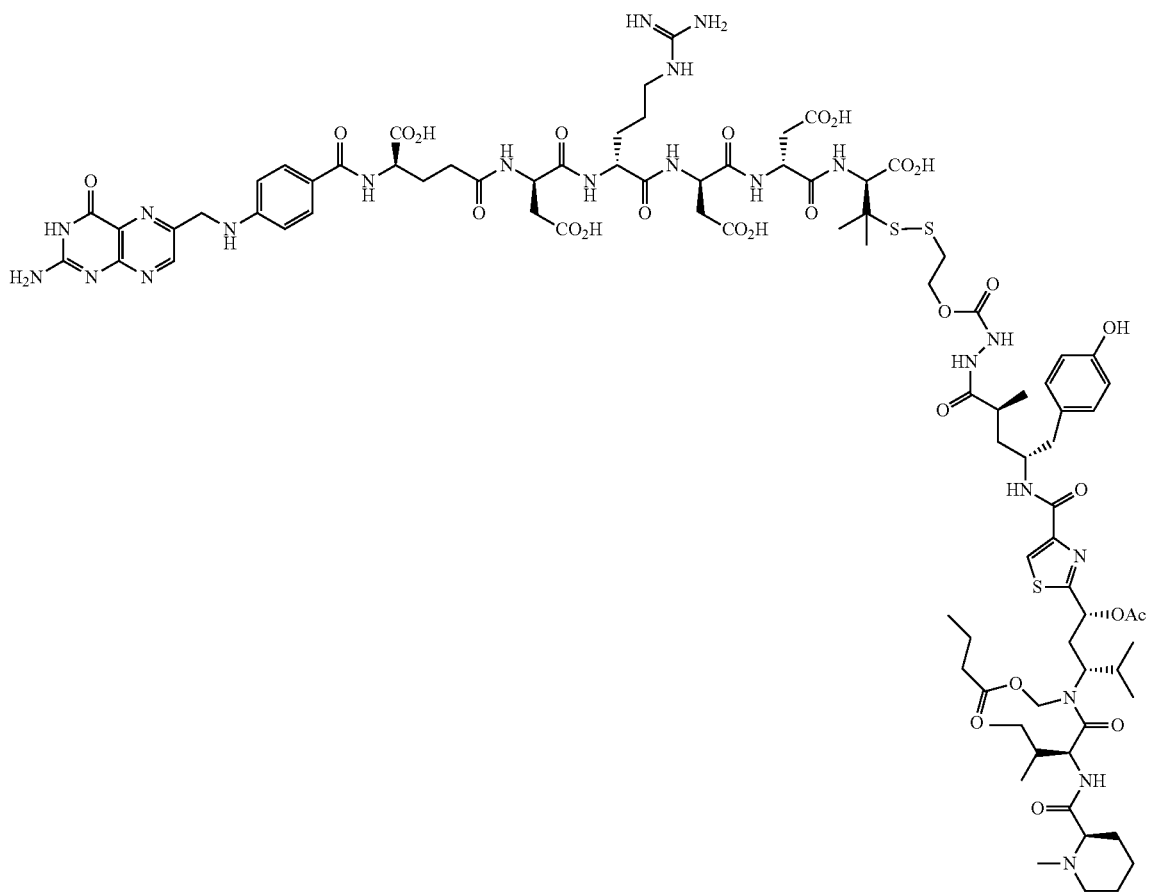

($C_{87}H_{122}N_{22}O_{28}S_3$; MW 2020.23)

The pH of a solution of EC1392 (20 mg) in 40 mM pH7 phosphate buffer was adjusted to 8 with a saturated $NaHCO_3$ solution. To the solution was added a suspension of ECO312 (20 mg) in equal volume of MeOH. The reaction mixture was stirred at ambient temperature under argon for 30 min, and then loaded onto a preparatory HPLC (Mobile phase A=50 mM $NH_4HCO_3$ buffer, pH=7.0. B=ACN. Method: 5-80% B in 20 min.) for purification. Fractions containing the desired product were collected, combined, and freeze-dried to afford the product (15 mg) as a pale yellow solid. MS(ESI, $[M+2H]^{2+}$) 1011.39. $^1H$ NMR (DMSO-d6, $D_2O$, 300 MHz): 8.6 (s, 1H), 8.15 (s, 1H), 7.85 (bd, 1H), 7.55 (d, 2H), 6.95 (d, 2H), 6.6 (m, 4H), 6.2 (d, 1H), 5.68 (d, 1H), 5.2 (d, 1H), 4.6 (t, 1H), 4.5 (m, 3H), 4.5-4.0 (m, 11H), 3.2-2.8 (m, 6H), 2.8-2.5 (m, 8H), 2.4 (m, 5H), 2.2-2.0 (m, 14H), 2.0-1.7 (m, 7H), 1.6-1.3 (m, 13H), 1.25 (d, 8H), 1.1-0.95 (dd, 8H), 0.75 (m, 10H), 0.6 (d, 2H).

Example

The compounds described herein can also be prepared by following two methods:

Method A: Folate spacer is dissolved in water by adjusting the pH of the solution with $NaHCO_3$ solution to a pH=7 with argon purging. The thiophilic agent in organic solvent (MeOH, ACN, THF or DMSO) is then added. The reaction mixture is stirred at room temperature with argon purging. The progress of reaction is monitored by analytical HPLC (Mobile phase A=50 mM $NH_4HCO_3$ buffer, pH=7.0; B=ACN). After the reaction is complete, the organic solvent is evaporated and the resulted solution is then purified by prep-HPLC with C18 column (Mobile phase A=50 mM $NH_4HCO_3$ buffer or 2 mM phosphate buffer, pH=7.0; B=ACN).

Method B: Folate spacer is dissolved in water and the pH is adjusted to 2 with acid (AcOH or dilute HCl). The resulting pH adjusted spacer is lyophilized, and then redissolved in DMSO. The reaction mixture is purged with argon, and 10 molar equivalents of $Et_3N$ (or DIPEA) are added. To this solution is added the thiophilic agent in organic solvent (DMSO, THF, ACN, etc.). The progress of the reaction is monitored by HPLC (Mobile phase A=50 mM $NH_4HCO_3$ buffer or 2 mM phosphate buffer, pH=7.0. B=ACN). After the reaction is complete, the reaction mixture is purified by prep-HPLC with C18 column (Mobile phase A=50 mM $NH_4HCO_3$ buffer or 2 mM phosphate buffer, pH=7.0; B=ACN).

Example

Additional illustrative linker intermediates (also referred as folate spacers) are described herein:

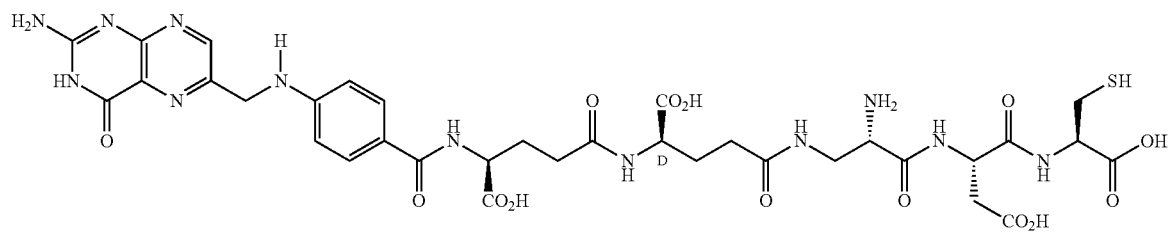

EC 014

EC0014: ¹H NMR (D$_2$O, 500 MHz) δ (ppm) 8.73 (s, 1H, FA H-7), 7.56 (d, 2H, FA H-12&H16), 6.73 (d, 2H, FA H-13&H15), 4.45 (m, 2H), 4.1 (m, 2H), 3.61 (d, 2H), 2.82 (m, 3H), 2.74 (dd, 1H), 2.37 (m, 2H), 2.18 (m, 1H), 2.09 (m, 3H), 1.74 (m, 1H)

Example

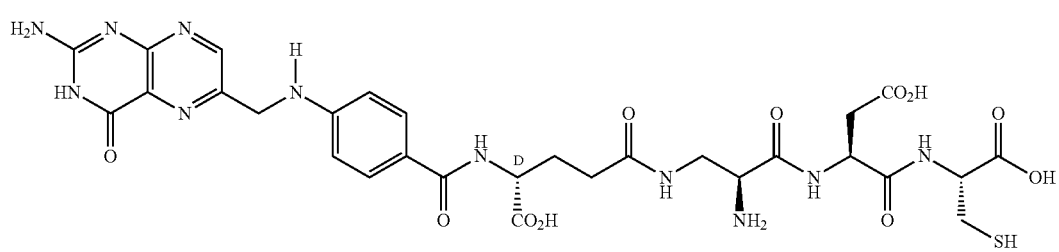

EC 20

Pte-γ-D-Glu-β-Dap-Asp-Cys

EC0020: MS (ESI, [M+H]⁺) 746. ¹H NMR (D$_2$O, 500 MHz) δ(ppm) 8.76 (s, 1H, FA H-7), 7.68 (d, 2H, FA H-12&H16), 6.8 (d, 2H, FA H-13&H15), 4.71 (dd, 1H, Asp H-2), 4.64 (s, 2H FA H-9), 4.41 (dd, 1H, D-Glu H-2), 4.3 (dd, 1H, Cys H-2), 4.1 (dd, Dpr H-2), 3.72 (dd, 1H, Dpr H-3A), 3.52 (dd, 1H, Dpr H-3B), 2.89 (dd, 1H, Cys H-3A), 2.85 (dd, 1H, Cys H-3B), 2.81 (dd, 1H, Asp H-3A), 2.62 (dd, 1H, Asp H-3B), 2.44 (dd, 2H, D-Glu H-4), 2.27 (m, 1H, D-Glu H-3A), 2.08 (m, 1H, D-Glu H-3B). ¹³C NMR (DMSO-d6+D$_2$O, 75 MHz): δ 174.78, 174.42, 172.68 (2C), 170.45, 168.25, 167.08, 162.24, 156.24, 154.38, 151.24, 149.41 (2C), 129.52, 128.14, 121.74, 111.98, 55.76, 53.02 (2C), 52.77, 50.89, 46.16, 36.61, 32.26, 27.32, 26.60

Examples

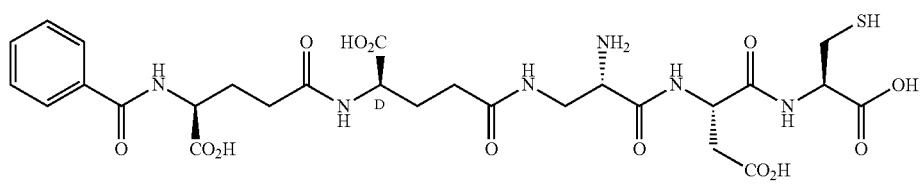

EC0028

EC0028

-continued
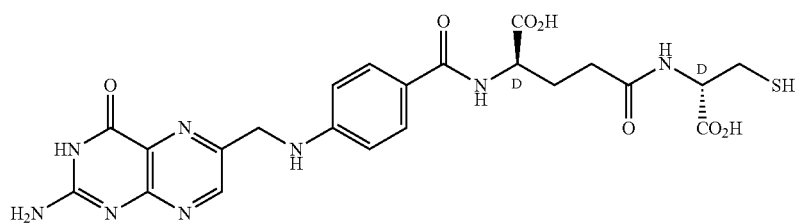
EC0048
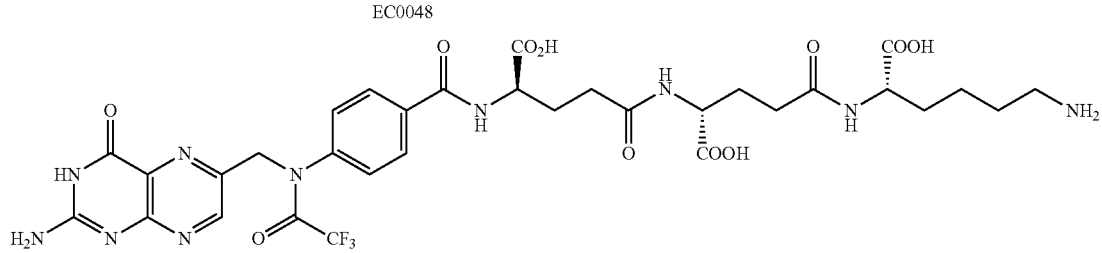
EC0049: MS (ESI, [M + H]$^+$) 795.
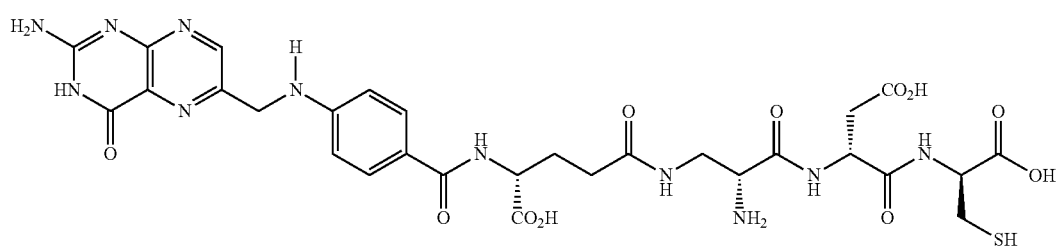
Pte-γ-D-Glu-β-D-Dap-D-Asp-D-Cys
EC0053: MS (ESI, [M + H]$^+$) 746
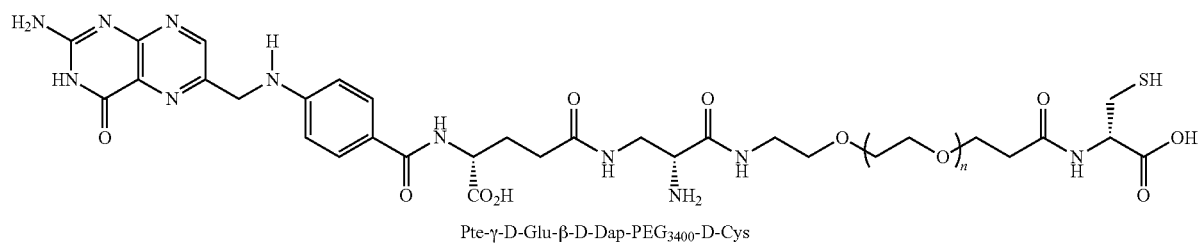
Pte-γ-D-Glu-β-D-Dap-PEG$_{3400}$-D-Cys
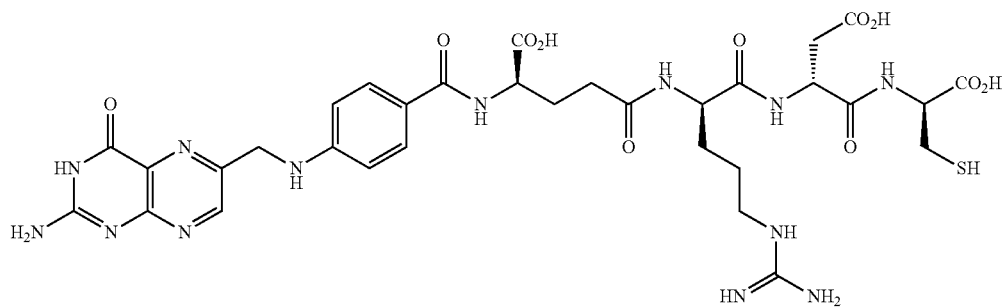
EC0059: MS (ESI, [M + H]$^+$) 816

-continued
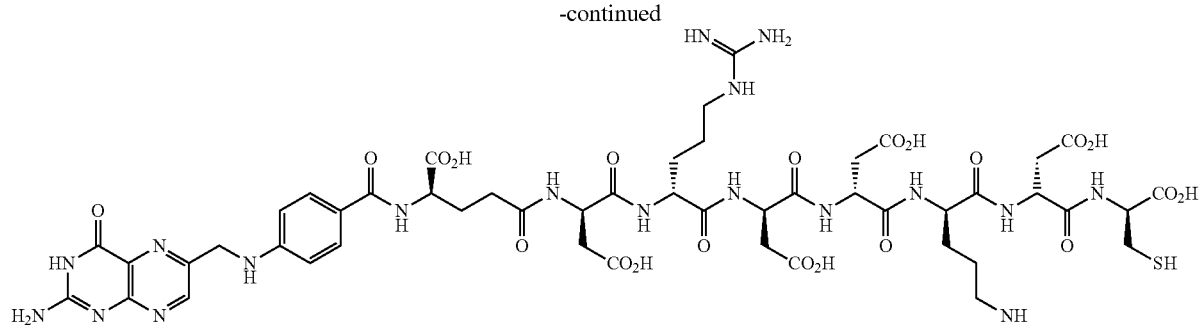
EC0066: MS (ESI, [M + H]⁺) 1317
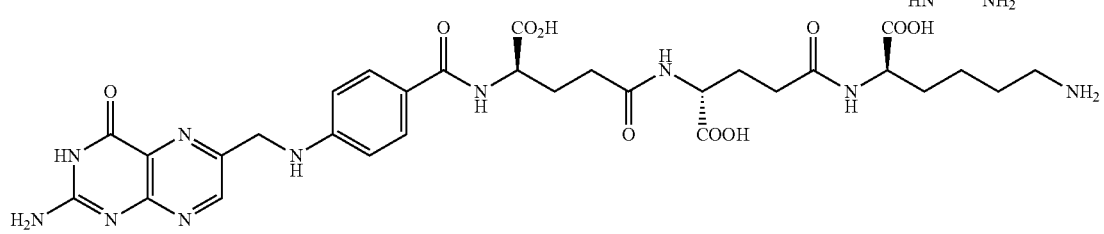
EC0067: MS (ESI, [M + H]⁺) 699
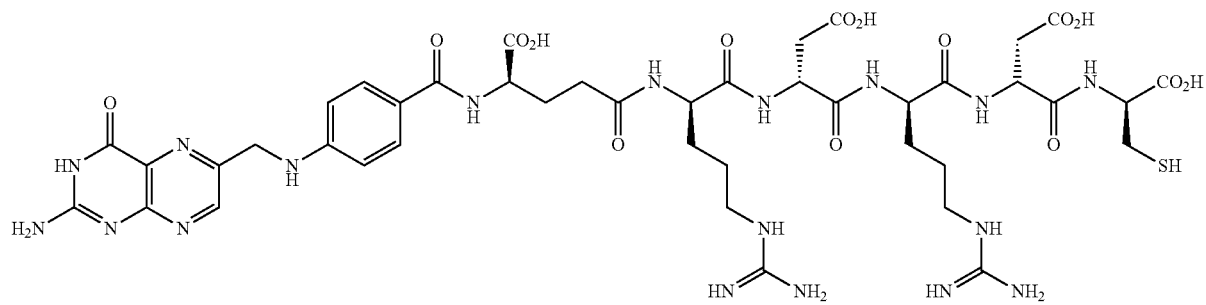
EC0073: N¹⁰-TFA-EC073 MS (ESI, [M + H]⁺) 1183.
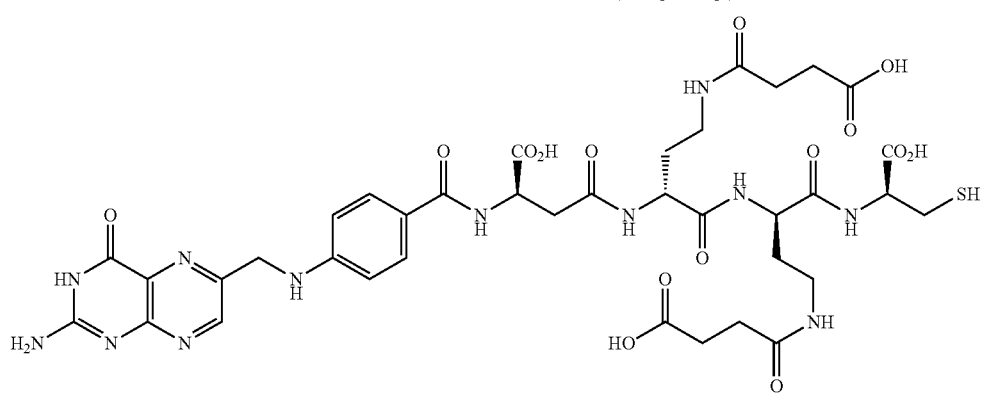
EC0075: MS (ESI, [M + H]⁺) 931
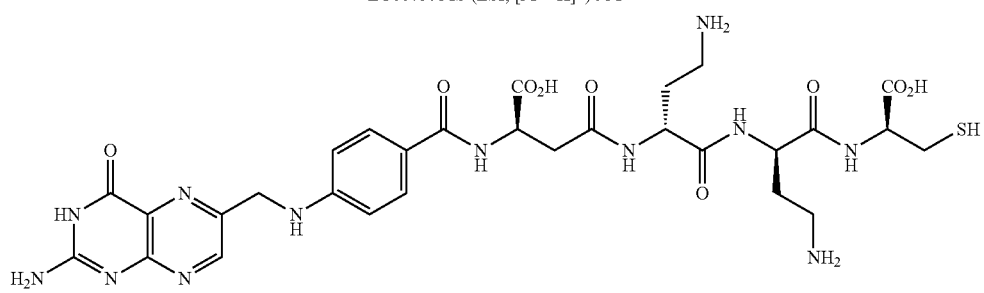
EC0076: MS (ESI, [M + H]⁺) 731

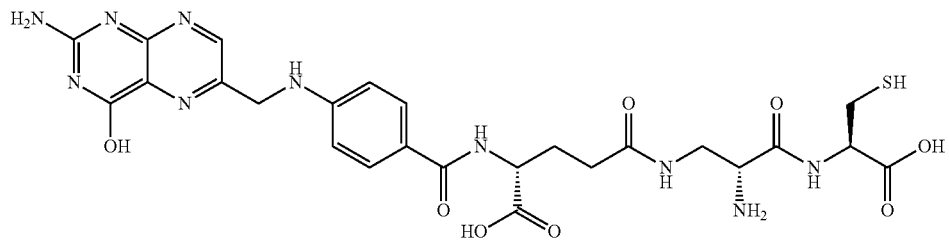
Pte-Glu-D-Dap-D-Glu-Pte
EC0149: [M+H]⁺=631. $^1$H NMR (D$_2$O): 8.55 (s, 1H), 7.5 (d, 2H), 6.61 (d, 2H), 4.42 (s, 2H), 4.35 (dd, 1H), 4.25 (m, 2H), 4.1 (s, 1H), 3.68 (m, 1H), 3.5 (m, 1H), 3.35-3.2 (m, 3H), 3.1 (dd, 1H), 2.4-2.1 (m, 3H), 2.1-1.9 (m, 4H).
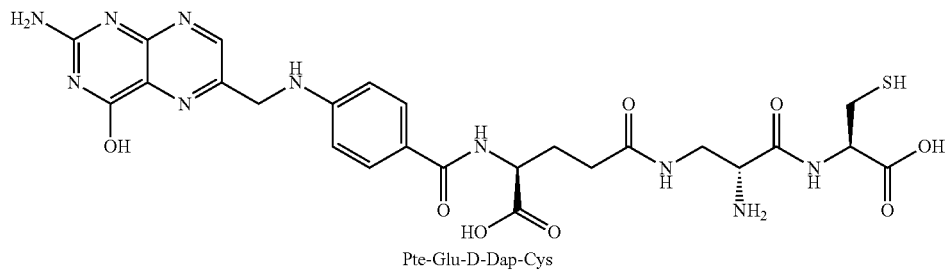
Pte-Glu-D-Dap-Cys
EC0150: MS (ESI, [M+H]⁺) 631. Selected $^1$H NMR (D$_2$O) δ (ppm) 8.42 (s, 1H, FA H-7), 7.50 (d, 2H, FA H-12&16), 6.65 (d, 2H, FA H-13&15), 4.42 (s, 2H), 4.3-4.1 (m, 2H), 4.0-3.85 (m, 1H), 3.35-3.30 (m, 1H), 3.30-3.10 (m, 2H), 3.10-2.90 (m, 2H), 2.80-2.70 (m, 1H), 2.65-2.50 (m, 2H), 2.30-2.10 (m, 3H), 2.10-1.85 (m, 2H), 1.95-1.80 (m, 2H).
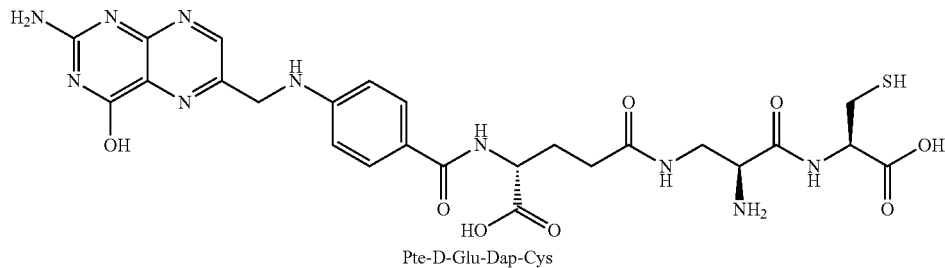
Pte-D-Glu-Dap-Cys
EC0151: MS (ESI, [M+H]⁺) 630. Selected $^1$H NMR (D$_2$O) δ (ppm) 8.42 (s, 1H, FA H-7), 7.50 (d, 2H, FA H-12&16), 6.65 (d, 2H, FA H-13&15), 4.42 (s, 2H), 4.3-4.1 (m, 2H), 4.0-3.85 (m, 1H), 3.35-3.30 (m, 1H), 3.30-3.10 (m, 2H), 3.10-2.90 (m, 2H), 2.80-2.70 (m, 1H), 2.65-2.50 (m, 2H), 2.30-2.10 (m, 3H), 2.10-1.85 (m, 2H), 1.95-1.80 (m, 2H).

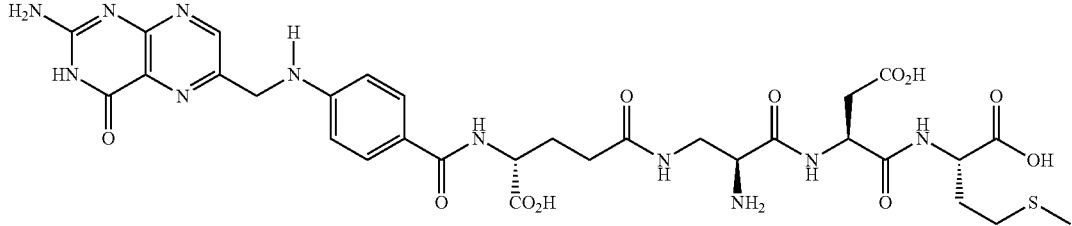
EC 232
EC0232: MS (ESI, [M+H]⁺) 774. $^1$H NMR (D$_2$O): 8.56 (s), 7.50 (d), 6.65 (d), 4.48-4.41 (m), 4.21 (dd), 4.08 (dd), 3.48-3.42 (m), 3.28-3.09 (m), 2.61-2.35 (m), 2.28-2.18 (m), 2.16-2.02 (m), 1.97-1.62 (m).
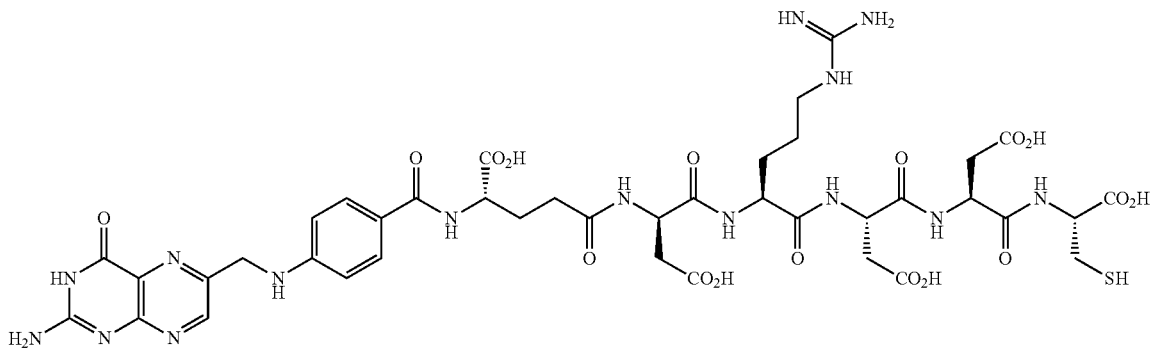
EC 252
EC0252: [M+H]⁺=1046.83. 1H NMR (D$_2$O): 8.58 (s, 1H), 7.5 (d, 2H), 6.6 (d, 2H), 3.05-2.6 (m, 5H), 2.3-1.9 (m, 4H), 1.8-1.2 (m, 7H).
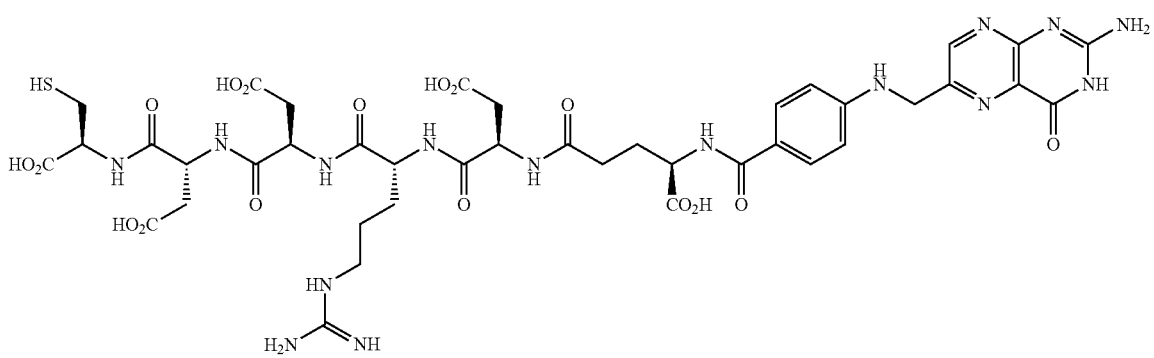
EC 259
(All D-EC119)
EC0259: [M+H]⁺=1047.52. 1H NMR (D$_2$O): 8.6 (s, 1H), 7.5 (d, 2H), 6.65 (d, 2H), 4.4 (dd, 2H), 4.18 (m, 4H), 2.9 (t, 2H), 2.75 (t, 2H), 2.6-2.15 (m, 10H), 2.1-1.8 (m, 3H), 1.7-1.4 (m, 3H), 1.3 (m, 3H).

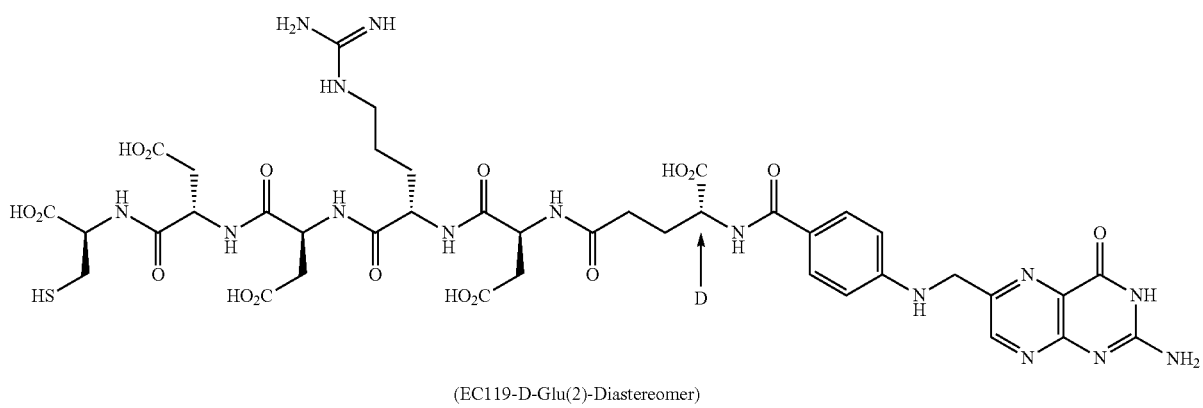
(EC119-D-Glu(2)-Diastereomer)
EC1213: LCMS (ESI [M+H]$^+$): 1046. Selected $^1$H NMR data (D$_2$O, 300 MHz): δ 8.68 (s, 1H, FA H-7), 7.57 (d, 2H, J=8.4 Hz, FA H-12 &16), 6.67 (d, 2H, J=9 Hz, FA H-13 &15).
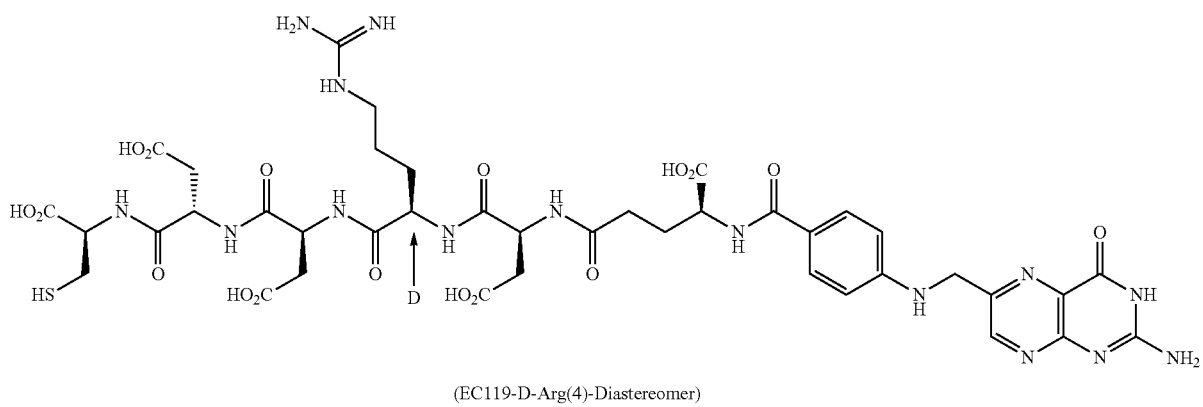
(EC119-D-Arg(4)-Diastereomer)
EC1214: LCMS (ESI [M+H]$^+$): 1046. Selected $^1$H NMR data (D$_2$O, 300 MHz): δ 8.68 (s, 1H, FA H-7), 7.57 (d, 2H, J=8.4 Hz, FA H-12 &16), 6.67 (d, 2H, J=9 Hz, FA H-13 &15).
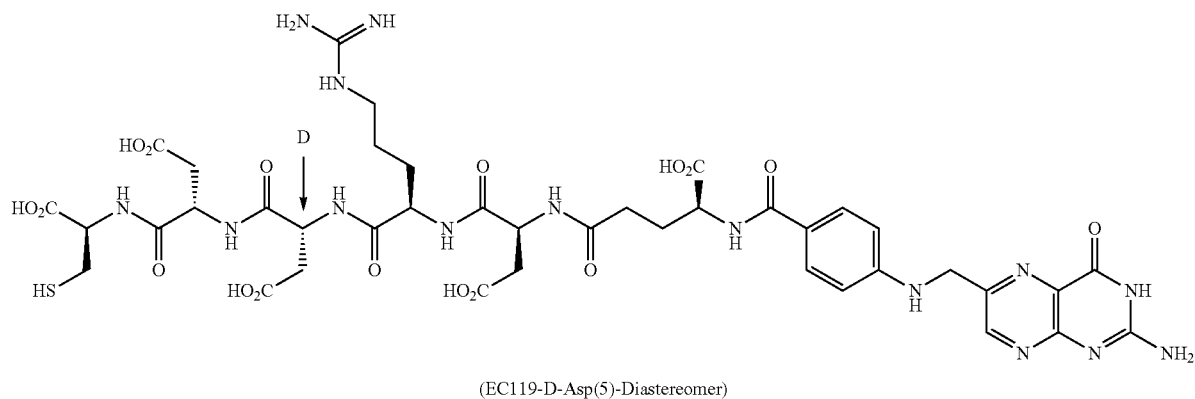
(EC119-D-Asp(5)-Diastereomer)
EC1215: LCMS (ESI [M+H]$^+$): 1046. Selected $^1$H NMR data (D$_2$O, 300 MHz): δ 8.68 (s, 1H, FA H-7), 7.57 (d, 2H, J=8.4 Hz, FA H-12 &16), 6.67 (d, 2H, J=9 Hz, FA H-13 &15).

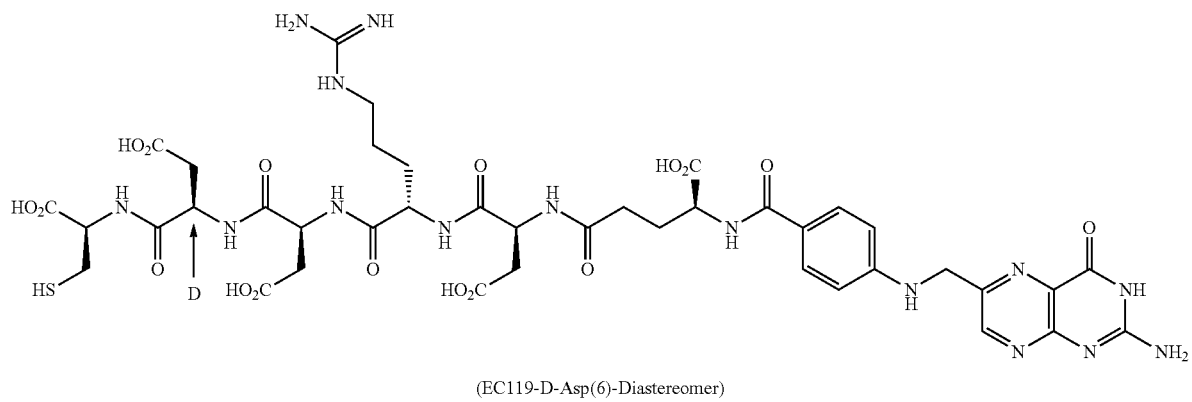
(EC119-D-Asp(6)-Diastereomer)
EC1216: LCMS (ESI [M+H]$^+$): 1046
Selected $^1$H NMR data (D$_2$O, 300 MHz): δ 8.68 (s, 1H, FA H-7), 7.57 (d, 2H, J=8.4 Hz, FA H-12 &16), 6.67 (d, 2H, J=9 Hz, FA H-13 &15).
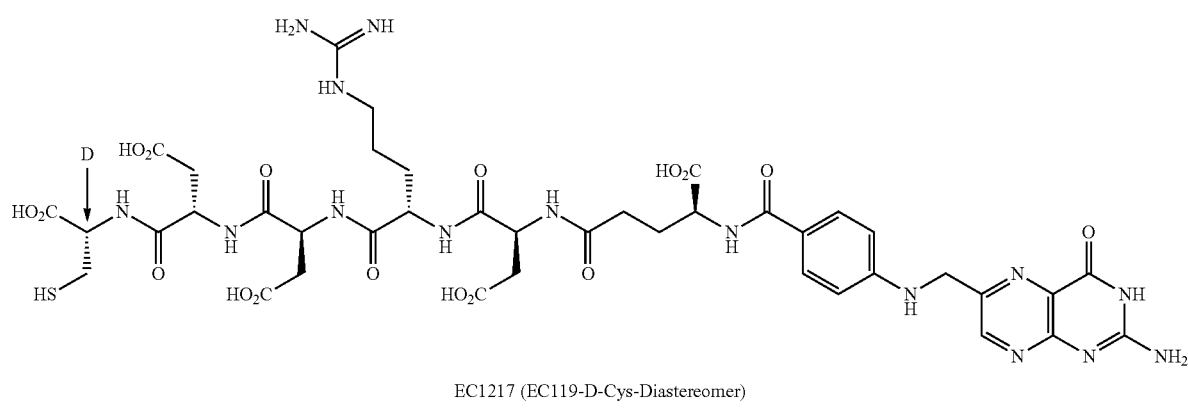
EC1217 (EC119-D-Cys-Diastereomer)
EC1217: LCMS (ESI [M+H]$^+$): 1046. Selected $^1$H NMR data (D$_2$O, 300 MHz): δ 8.68 (s, 1H, FA H-7), 7.57 (d, 2H, J=8.4 Hz, FA H-12 &16), 6.67 (d, 2H, J=9 Hz, FA H-13 &15).
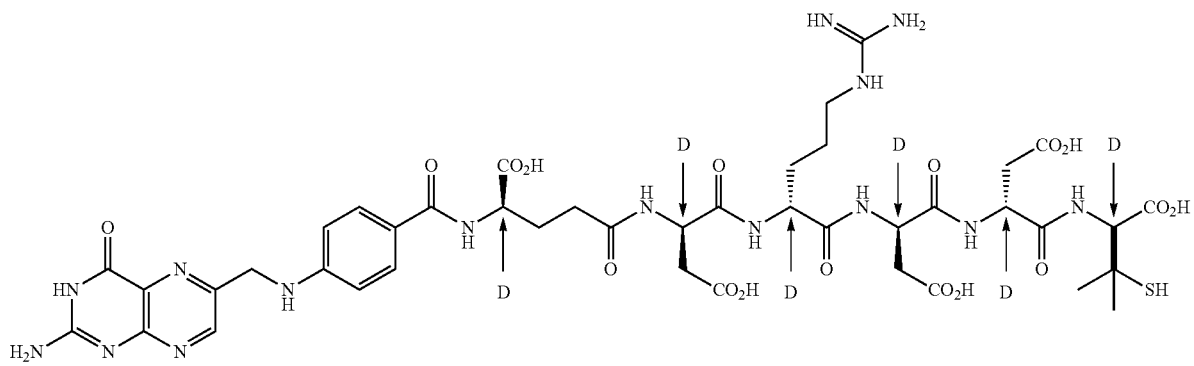
EC1392
EC1392: [M+H]$^+$=1074.85. 1H NMR (D$_2$O, 300 MHz) δ(ppm): 8.55 (s, 1H), 7.45 (d, 2H), 6.5 (d, 2H), 4.6 (m, 2H), 4.45 (t, 1H), 4.35 (bs, 2H), 4.2 (m, 1H), 4.1 (s, 1H), 4.05 (m,1H), 2.9 (t, 2H), 2.75-2.4 (m, 6H), 2.3 (m, 2H), 2.2-1.9 (m, 2H), 1.8-1.4 (m, 2H), 1.2 (m, 2H), 1.3 (s, 3H), 1.2 (s, 3H).

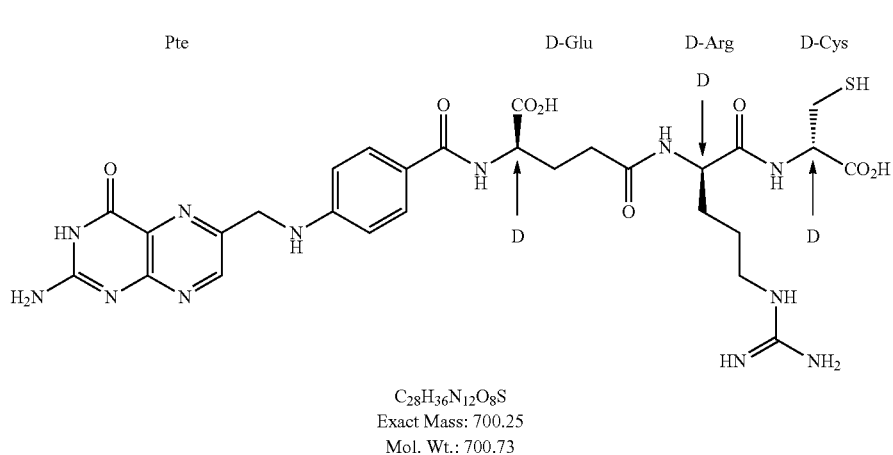
EC1347: MS (ESI, [M+H]⁺)=701.57. Selected 1H-NMR (DMSO, 300 MHz) δ (ppm): 8.65 (s), 7.6 (d), 6.6 (d), 4.2-4.6 (m), 2.6-3.2 (m), 1.8-2.6 (m), 1.1-1.7 (m)
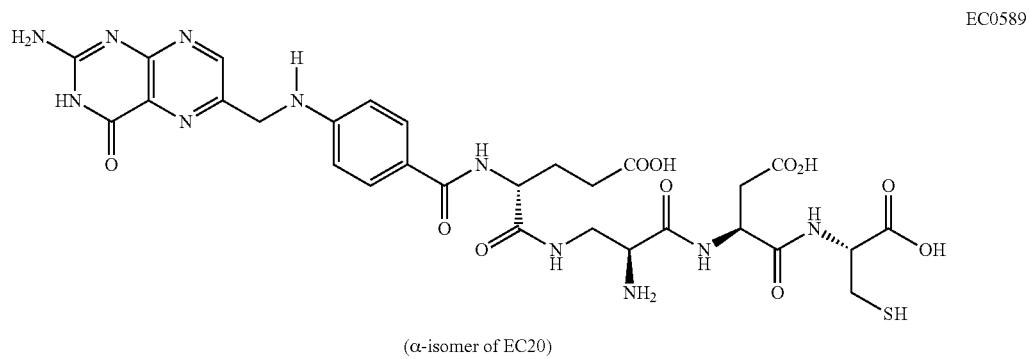 [SMILES: Nc1nc2ncc(CNc3ccc(C(=O)N[C@H](CCC(=O)O)C(=O)NC[C@H](N)C(=O)N[C@@H](CC(=O)O)C(=O)N[C@@H](CS)C(=O)O)cc3)nc2c(=O)[nH]1]
EC0589: MS (ESI, [M+H]⁺) 746. Selected ¹H NMR (DMSO-d6+D₂O, 300 MHz): δ 8.46 (s, 1H), 7.45 (d, J=8.4 Hz, 2H), 6.47 (d, J=8.4 Hz, 2H), 4.39 (t, J=6.6 Hz, 1H).
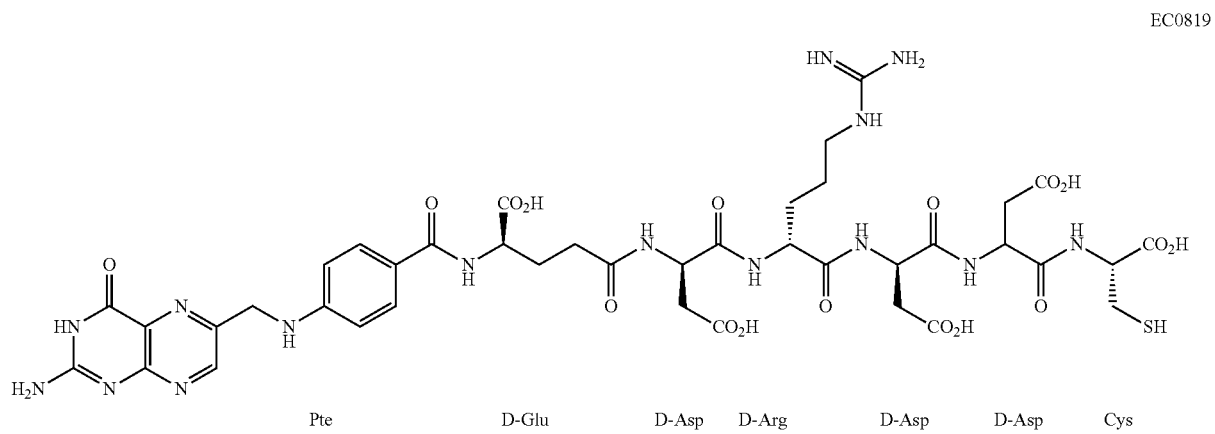 [SMILES: N=C(N)NCCC[C@@H](NC(=O)[C@@H](CC(=O)O)NC(=O)CC[C@@H](NC(=O)c1ccc(NCc2cnc3nc(N)[nH]c(=O)c3n2)cc1)C(=O)O)C(=O)N[C@H](CC(=O)O)C(=O)NC(CC(=O)O)C(=O)N[C@@H](CS)C(=O)O]
EC0819: MS (ESI, [M+H]⁺)=1046.4. Selected 1H-NMR (DMSO) δ (ppm): 8.6 (s), 7.6 (d), 6.6 (d), 4-4.6 (m), 3.4-3.8 (m), 3-3.15 (m), 1-2.8 (m).

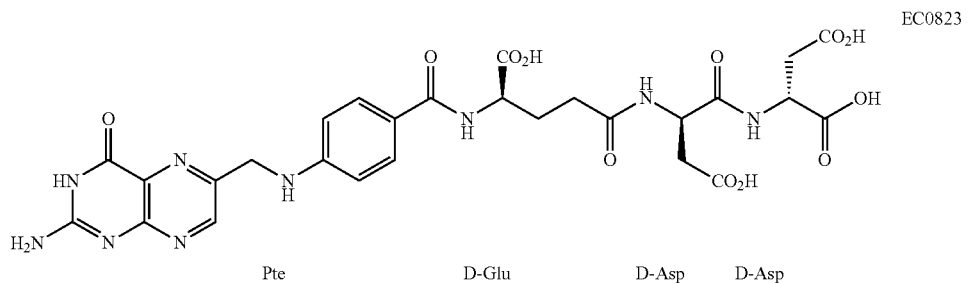 [SMILES: Nc1nc2ncc(CNc3ccc(C(=O)N[C@H](CCC(=O)N[C@H](CC(=O)O)C(=O)N[C@H](CC(=O)O)C(=O)O)C(=O)O)cc3)nc2c(=O)[nH]1]
EC0823: MS (ESI, [M+H]$^+$)=672.3. Selected 1H-NMR (DMSO) δ (ppm): 8.8 (s), 7.6 (d), 6.6 (d), 4.4-4.6 (m), 4.2-4.4 (m), 3.4-3.8 (m), 1.8-2.8 (m), 1.15 (s)
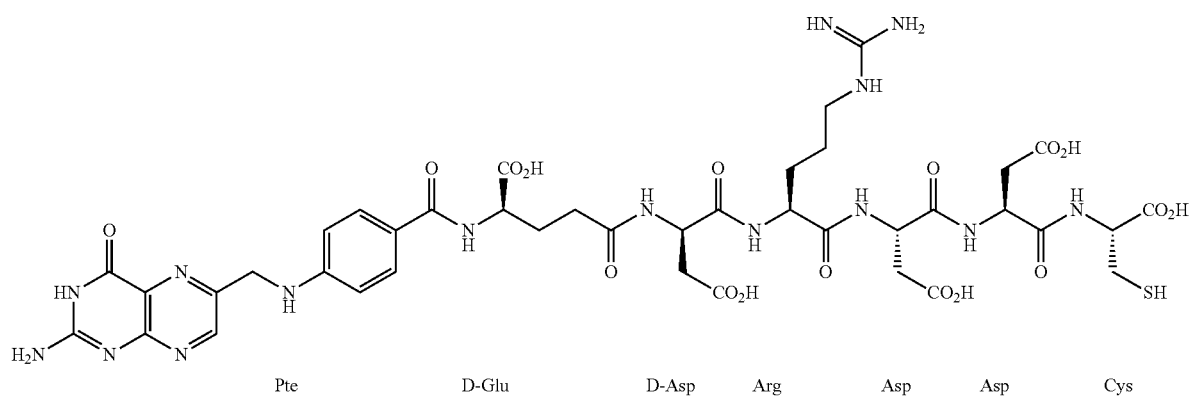
EC0835: MS (ESI, [M+H]$^+$)=1046.5. Selected 1H-NMR (DMSO) δ (ppm): 8.6 (s), 7.5 (d), 6.6 (d), 3.8-4.6 (m), 2.8-3.2 (m), 2.2-2.8 (m), 1-2.2 (m)

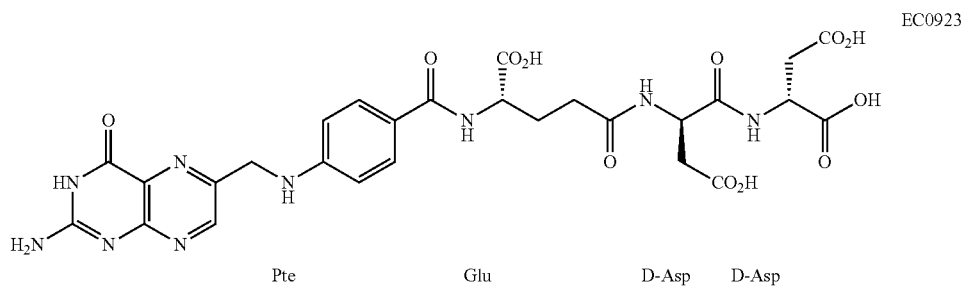 [SMILES: Nc1nc2ncc(CNc3ccc(C(=O)N[C@@H](CCC(=O)N[C@H](CC(=O)O)C(=O)N[C@H](CC(=O)O)C(=O)O)C(=O)O)cc3)nc2c(=O)[nH]1]
EC0923: MS (ESI, [M+H]$^+$)=672.3. Selected 1H-NMR (D$_2$O) δ(ppm): 8.8 (s), 7.75 (d), 6.85 (d), 4.4-5 (m), 2.6-2.9 (m), 2.4-2.6 (m), 2-2.6 (m)
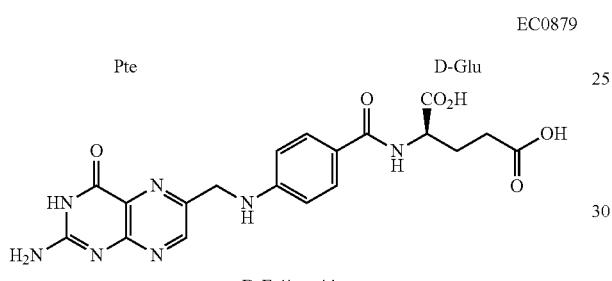
EC0879: MS (ESI, [M+H]$^+$)=442.3. Selected 1H-NMR (DMSO) δ (ppm): 8.7 (s), 7.6 (d), 6.6 (d), 4.55 (s), 4.3 (m), 2.2-2.6 (m), 1.8-2.2 (m), 1-1.2 (m)
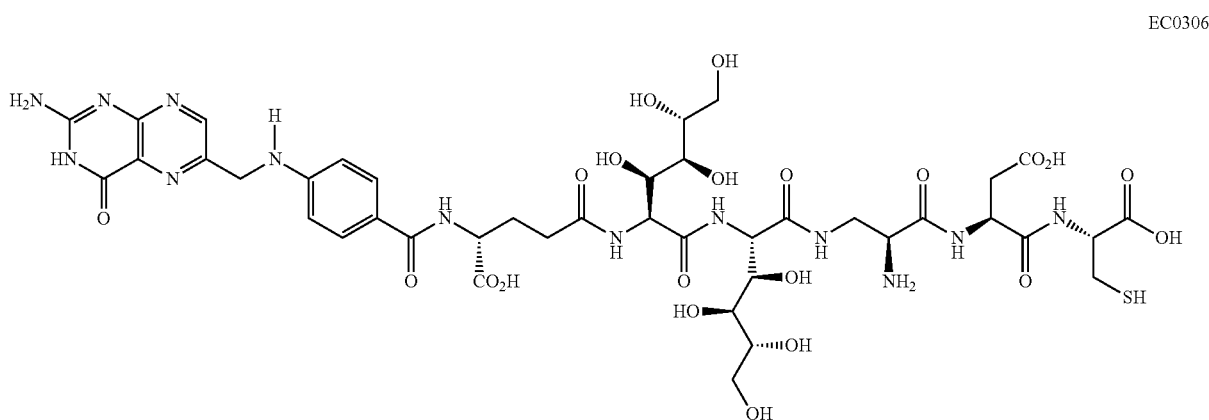 [SMILES: Nc1nc2ncc(CNc3ccc(C(=O)N[C@H](CCC(=O)N[C@H](C(=O)N[C@H](C(=O)NC[C@H](N)C(=O)N[C@@H](CC(=O)O)C(=O)N[C@@H](CS)C(=O)O)[C@@H](O)[C@H](O)[C@H](O)CO)[C@@H](O)[C@H](O)[C@H](O)CO)C(=O)O)cc3)nc2c(=O)[nH]1]
EC0306: [M+H]$^+$=1100.51. 1H NMR (D$_2$O): δ 8.75 (s, 1H), 7.6 (d, 2H), 6.75 (d, 2H), 4.7-4.5 (m, 5H), 4.38 (m, 2H), 4.2 (m, 2H), 4.1 (d, 1H), 3.85-3.5 (m, 10H), 2.95-2.6 (m, 4H), 2.45 (m, 2H), 2.3-2.0 (m, 2H).

195
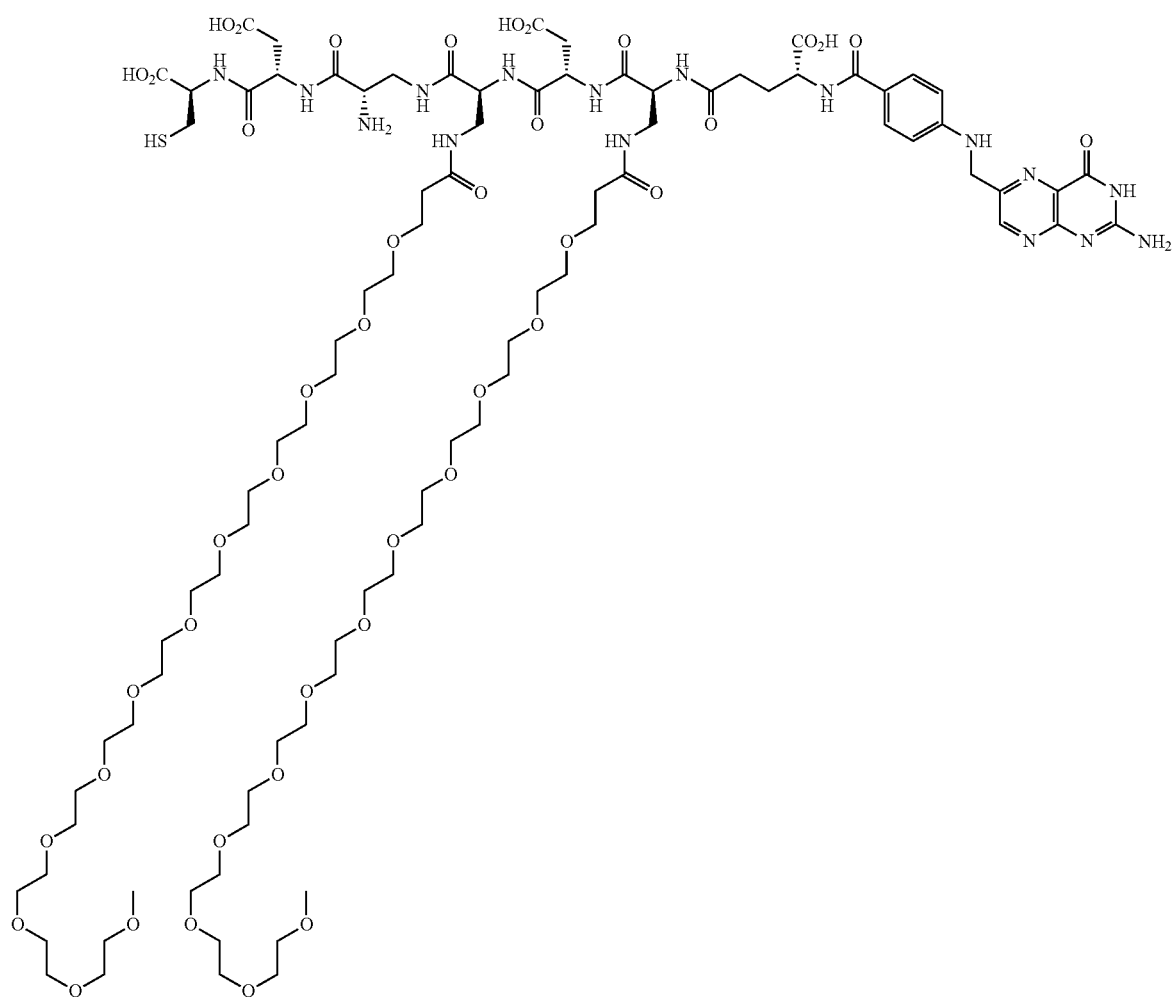
EC0368
EC0368: [M+H]+=2175.5. 1H NMR (D₂O): 8.6 (s, 1H), 7.5 (d, 2H), 6.6 (d, 2H), 4.45 (bs, 3H), 4.35-4.2 (m, 4H), 4.05 (t, 1H), 3.6-3.35 (bs, 114H), 3.2 (s, 6H), 2.77 (t, 2H), 2.65 (dd, 1H), 2.55-2.45 (m, 3H), 2.4-2.2 (m, 6H), 2.1-1.8 (m, 2H).
196
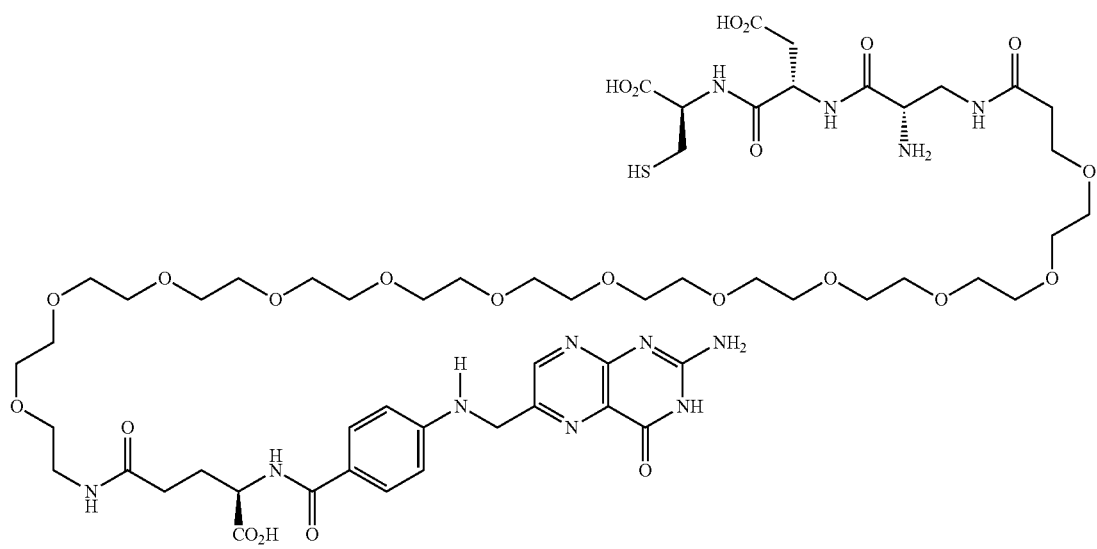
EC0373

EC0373: [M+H]$^+$=1346.0. 1H NMR (D$_2$O): 8.55 (s, 1H), 7.5 (d, 2H), 6.6 (d, 2H), 4.4 (s, 2H), 4.25 (m, 2H), 4.05 (t, 1H), 3.7 (dd, 1H), 3.6-3.3 (m, 50H), 3.25 (dd, 3H), 3.05 (dd, 3H), 2.8 (t, 2H), 2.7 (dd, 2H), 2.6 (dd, 1H), 2.4 (t, 2H), 2.2-1.9 (m, 4H).
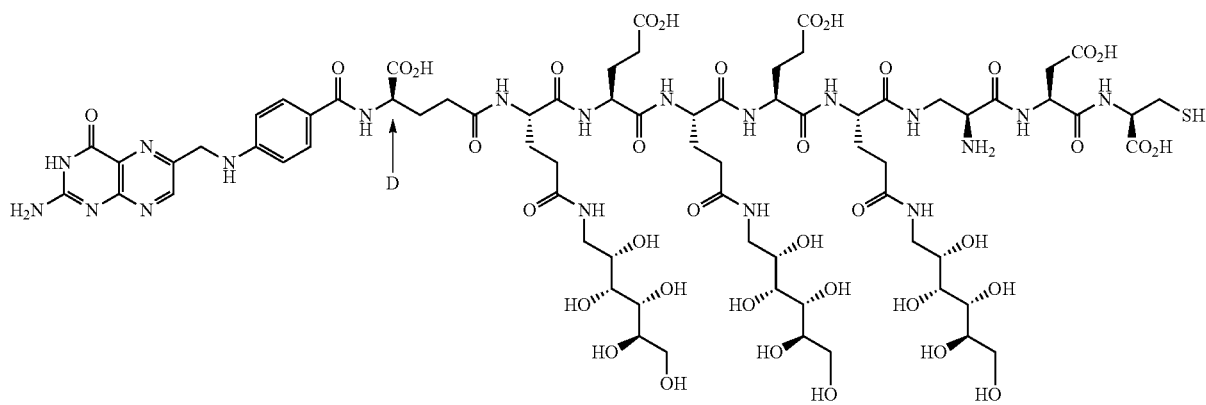
EC0536: [M+2H]$^{2+}$=941.2. 1H NMR (D$_2$O): 8.55 (s, 1H), 7.5 (d, 2H), 6.6 (d, 2H), 4.4 (s, 2H), 4.25 (m, 2H), 4.1 (m, 5H), 3.85 (t, 1H), 3.8-3.4 (m, 21H), 3.4-2.95 (m, 7H), 2.8 (s, 2H), 2.7-2.4 (ddd, 2H), 2.4-1.7 (m, 22H), 1.55 (m, 1H).
Example
Additional illustrative compounds and processes for preparing the compounds are described herein:
Conjugates of EC1579
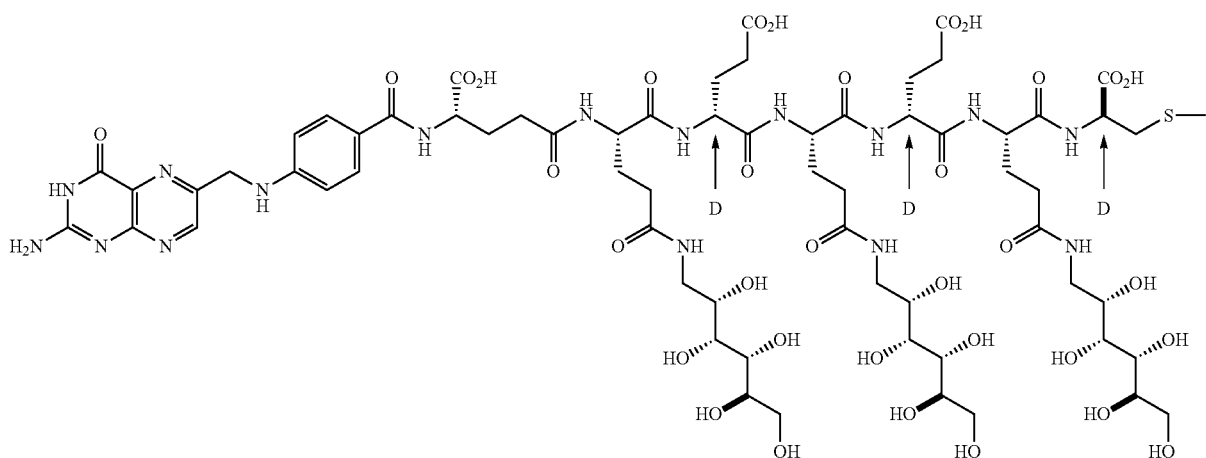

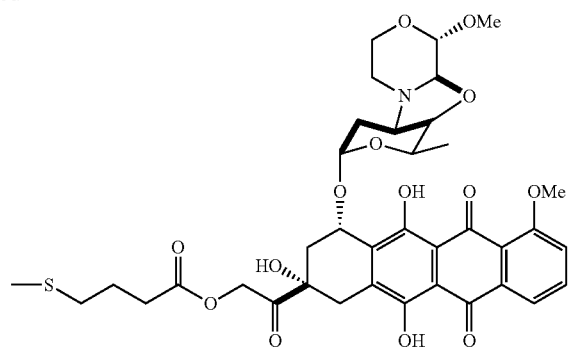
EC1840
Chemical Formula: $C_{101}H_{137}N_{17}O_{48}S_2$
Exact Mass: 2419.82
Molecular Weight: 2421.38
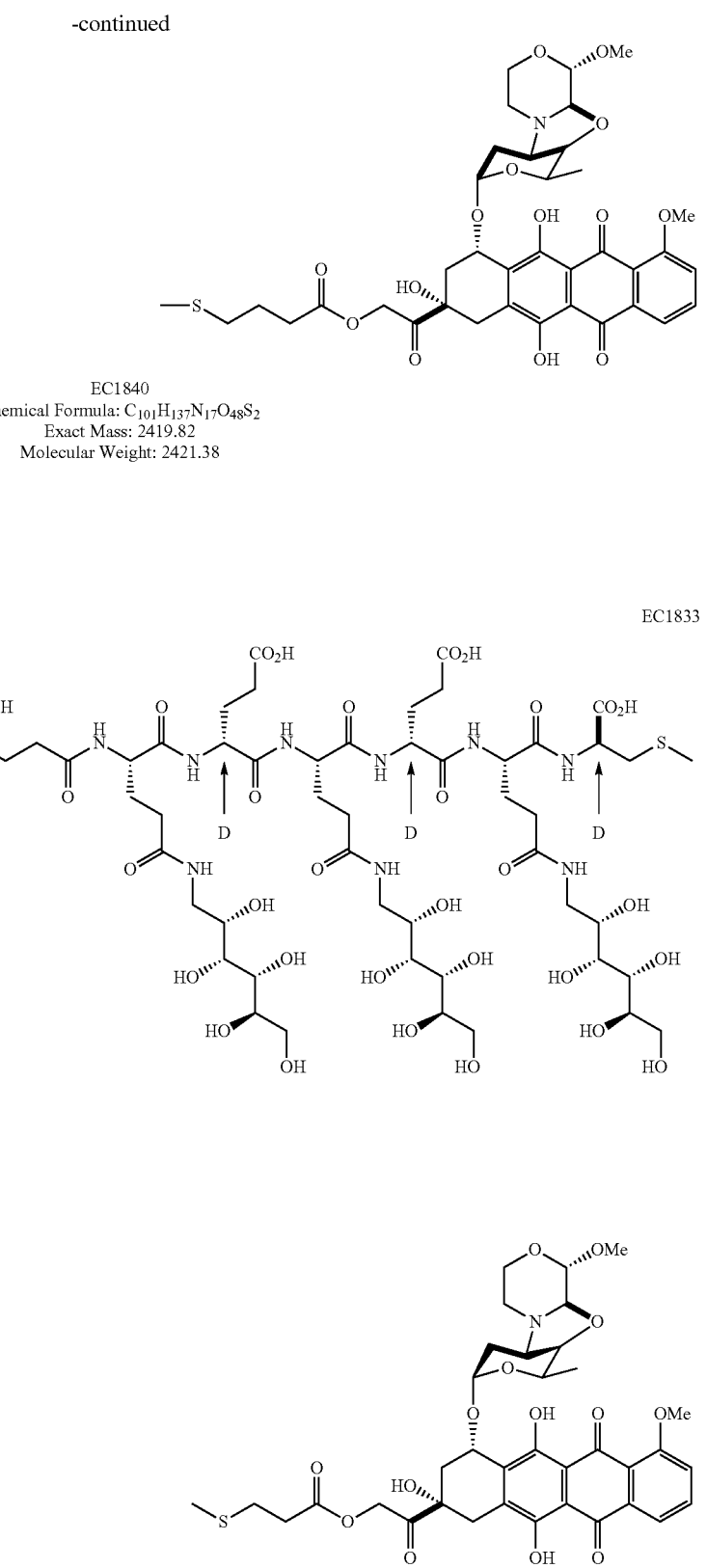
EC1833
Chemical Formula: $C_{100}H_{135}N_{17}O_{48}S_2$
Exact Mass: 2405.81
Molecular Weight: 2407.36

-continued
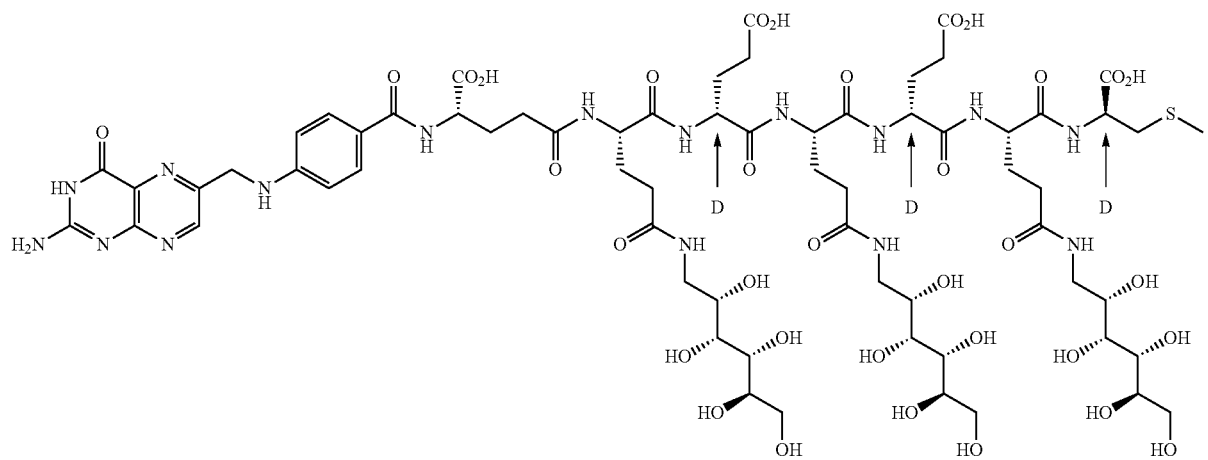
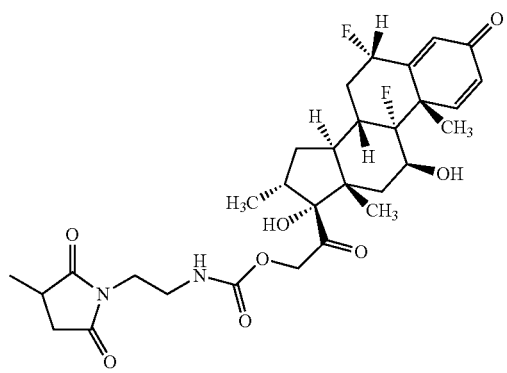
EC1828
C$_{94}$H$_{132}$F$_2$N$_{18}$O$_{42}$S
Exact Mass: 2254.84
Mol. Wt.: 2256.21
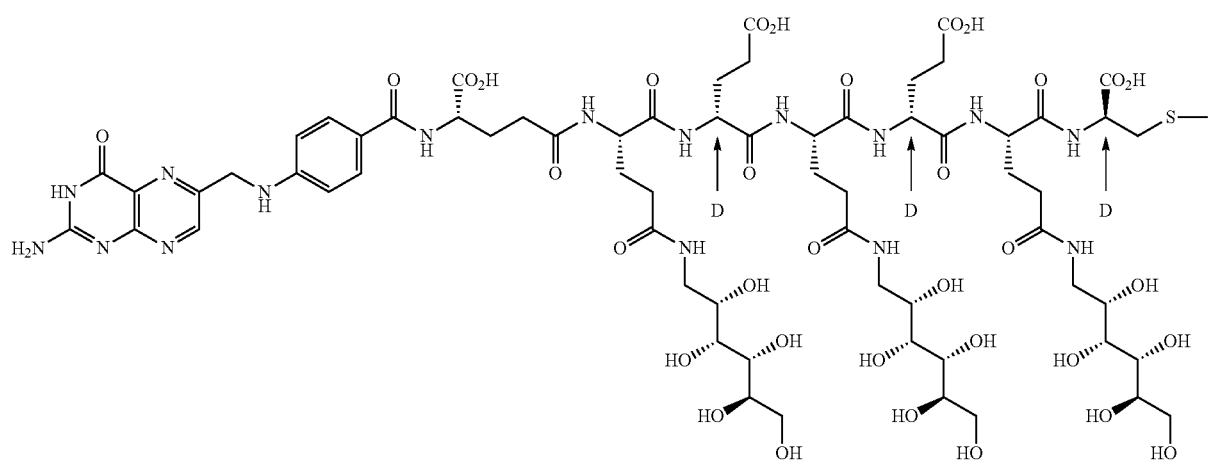

-continued

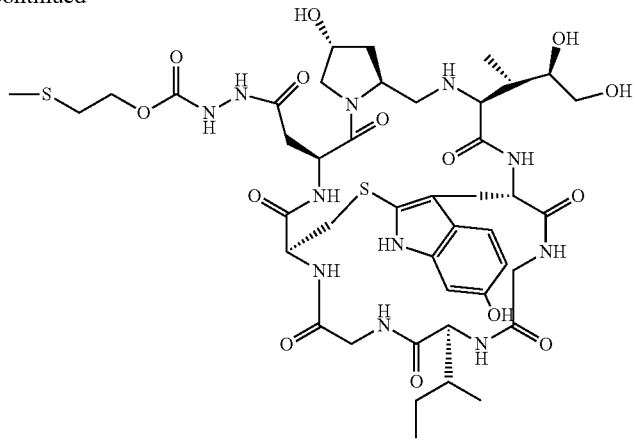

EC1824

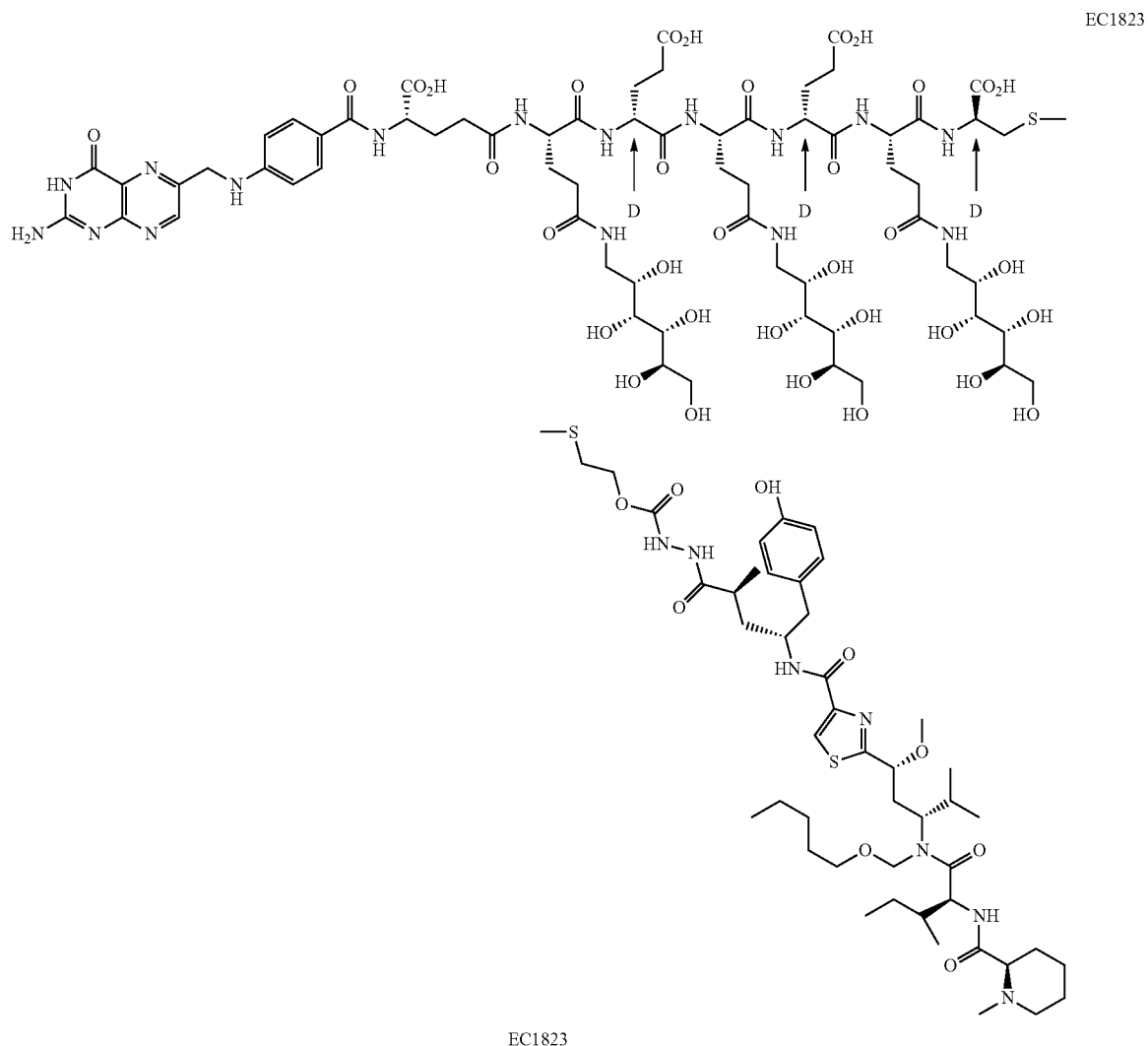

EC1823

EC1823

A solution of EC1579 (acidified, 13.0 mg, 0.0077 mmole) in DMSO (0.4 mL) and 12 µL of DIPEA (0.070 mmole, 13.5 eq.) were added to a solution of EC1822 (5.6 mg, 0.0052 mmole) in DMSO (0.2 mL) in tandem. The resulting homogeneous solution was stirred at ambient temperature under argon for 20 min. and then loaded directly onto a preparatory HPLC (Mobile phase A=50 mM NH$_4$HCO$_3$ buffer, pH=7.0. B=ACN. Method: 5-80% B in 20 min.) for purification. Fractions containing the desired product were collected, combined, and freeze-dried to afford the product (12.4 mg)

as a pale yellow solid. Selected $^1$H NMR (DMSO-d6) δ (ppm) 8.62 (s, 1H), 8.20 (s, 1H), 7.60 (d, 2H), 7.56 (d), 6.93 (d, 2H), 6.61 (m, 3H), 5.25 (d, 1H), 4.51 (d, 1H), 4.50-4.40 (m, 3H), 4.32-4.10 (m, 10H), 3.65-3.50 (m, 10H), 3.40-3.30 (m, 10H), 3.30-3.10 (m, 7H), 3.10-2.95 (m, 3H), 2.95-2.80 (m, 3H), 2.75-2.60 (br, 3H), 2.40-2.00 (m, 14H), 2.0-1.3 (m, 24H), 1.30-1.05 (m, 6H), 0.99 (d, 3H), 0.88 (d, 3H), 0.86 (d, 3H), 0.79 (t, 6H), 0.73 (t, 3H), 0.64 (br, 3H)
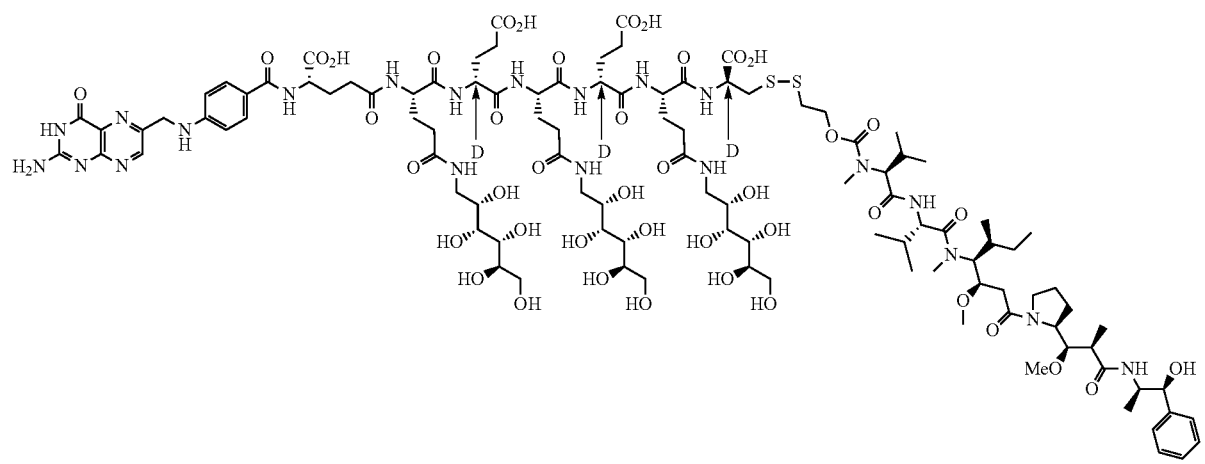
EC1818
Chemical Formula: $C_{107}H_{167}N_{21}O_{43}S_2$
Exact Mass: 2498.10
Molecular Weight: 2499.72
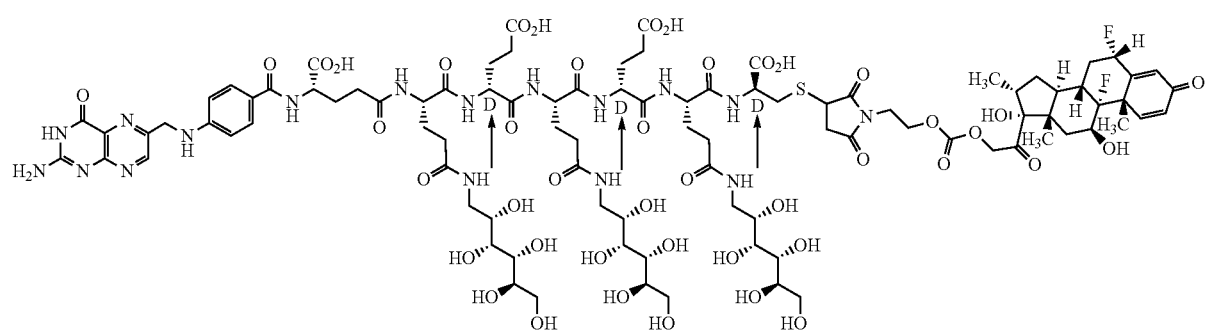
EC1756
$C_{94}H_{131}F_2N_{17}O_{43}S$
Exact Mass: 2255.83
Mol. Wt.: 2257.20

Example

Synthesis of EC1746

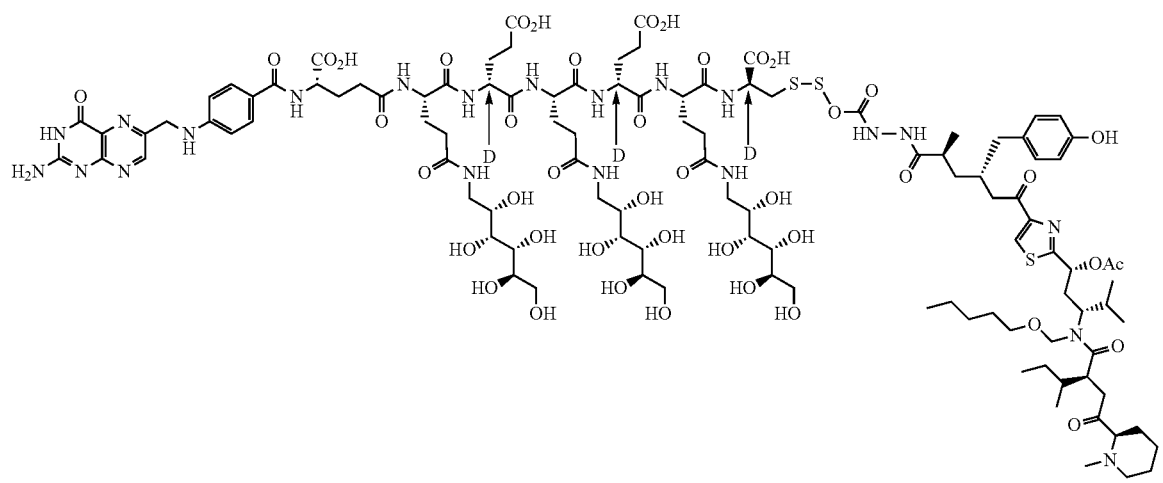

EC1746

Chemical Formula: $C_{111}H_{169}N_{23}O_{44}S_3$
Exact Mass: 2624.09
Molecular Weight: 2625.85

A solution of EC1579 (30.9 mg) in 20 mM pH7 phosphate buffer (4.2 mL) and a saturated $NaHCO_3$ solution (0.30 mL) were added to a solution of EC1662 (16.9 mg) in MeOH (4.8 mL) in tandem. The resulting homogeneous solution was stirred at ambient temperature under argon for 20 min. and then loaded directly onto a preparatory HPLC (Mobile phase A=50 mM $NH_4HCO_3$ buffer, pH=7.0. B=ACN. Method: 5-80% B in 20 min.) for purification. Fractions containing the desired product were collected, combined, and freeze-dried to give the product (33.1 mg) as a fluffy yellow solid. MS (ESI, M+H)=2627. EC1746 $^1$H NMR ($D_2O$): 8.66 (s), 8.10 (s), 7.62 (b), 6.99 (b), 6.69 (b), 5.81 (b), 5.18 (b), 4.60-4.18 (m), 3.91-0.57 (m).

Example

Synthesis of EC1669

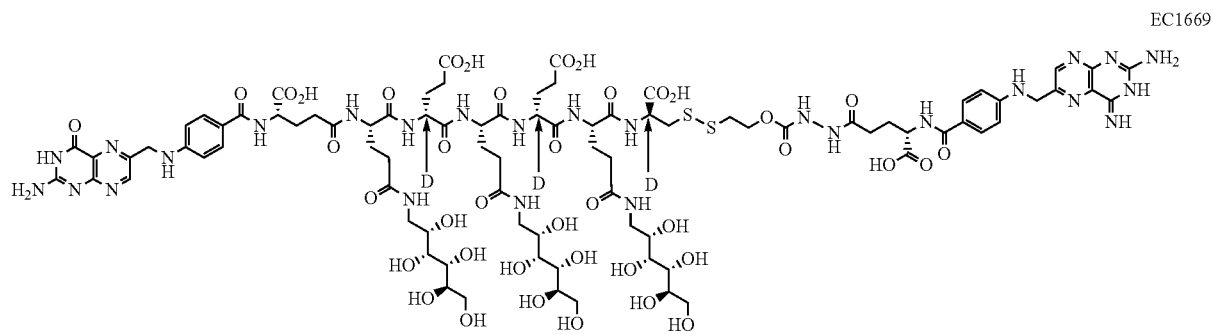

EC1669

Chemical Formula: $C_{87}H_{122}N_{26}O_{40}S_2$
Exact Mass: 2234.78
Molecular Weight: 2236.18

EC1579 (200 mg, 1.0 eq) was dissolved in degassed (Ar bubbling) 20 mM $PO_4$ pH7 buffer (4.0 mL) and added dropwise to a stirring solution of crude EC0469 (80 mg, 1.0 eq) in dry dimethylsulfoxide (4.0 mL, Aldrich) at room temperature with Ar bubbling. After 30 min, EC1669 (132 mg, 49%) was purified by preparative HPLC in 0-30% acetonitrile/50 mM $NH_4HCO_3$ pH7 buffer and lyophilized. MS (ESI, $[M+2H]^{2+}$) Predicted 1118.39. Found 1119.52. Partial $^1H$ NMR (DMSO w/10% $D_2O$) d (ppm) 8.67 (s), 8.59 (2), 7.61 (d), 7.56 (d), 6.71 (d), 6.61 (d), 3.34-3.39 (m).

Example

Synthesis of EC1665

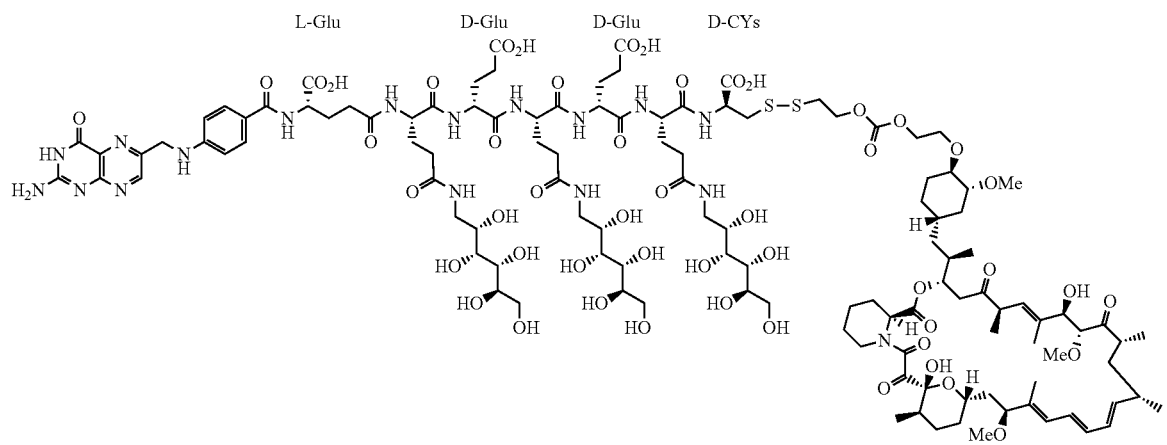

EC1665

Chemical Formula: $C_{121}H_{183}N_{17}O_{50}S_2$
Exact Mass: 2738.17
Molecular Weight: 2739.96

EC1579 (15 mg, 1.0 eq) was dissolved in degassed (Ar bubbling) 20 mM $PO_4$ pH7 buffer (2.0 mL) and added dropwise to a stirring solution of EC0564 (10.5 mg, 1.0 eq) in dry dimethylsulfoxide (4.0 mL, Aldrich) at room temperature with Ar bubbling. After 30 min, EC1665 (13.4 mg, 55%) was purified by preparative HPLC in 10-100% acetonitrile/10 mM $NH_4OAc$ pH5 buffer and lyophilized. MS (ESI, $[M+2H]^{2+}$) Predicted 1368.09. Found 1368.30

Conjugates of EC1454

Example

Synthesis of EC1751

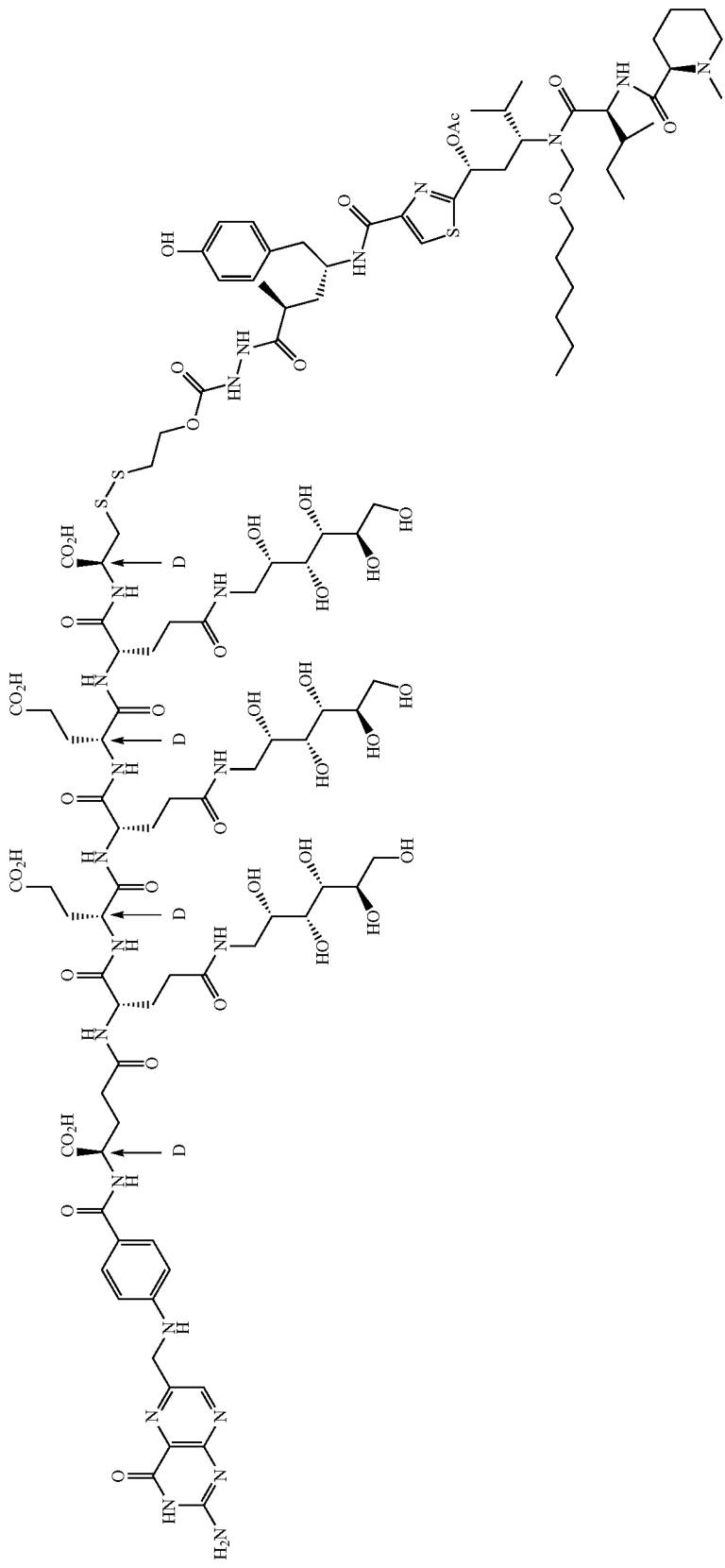

EC1454 (21.1 mg, 1.3 eq) was dissolved in degassed (Ar bubbling) 20 mM PO$_4$ pH7 buffer (2.0 mL) and added dropwise to a stirring solution of EC1716 (10.8 mg, 1.0 eq) in dry dimethylsulfoxide (2.0 mL, Aldrich) at room temperature with Ar bubbling. After 30 min, EC1751 (8.5 mg, 33%) was purified by preparative HPLC in 10-100% acetonitrile/50 mM NH$_4$HCO$_3$ pH7 buffer and lyophilized. MS (ESI, [M+2H]$^{2+}$) Predicted 1320.05. Found 1320.72. Selected $^1$H NMR (DMSO w/10% D$_2$O) δ (ppm) 8.61 (s), 8.15 (s), 7.58 (d), 6.94 (d), 6.60 (m), 5.79 (d), 5.22 (d), 4.47 (m), 4.09-4.33 (m), 0.98 (d), 0.93 (d), 0.75 (m), 0.61 (d)

Example

Synthesis of EC1750

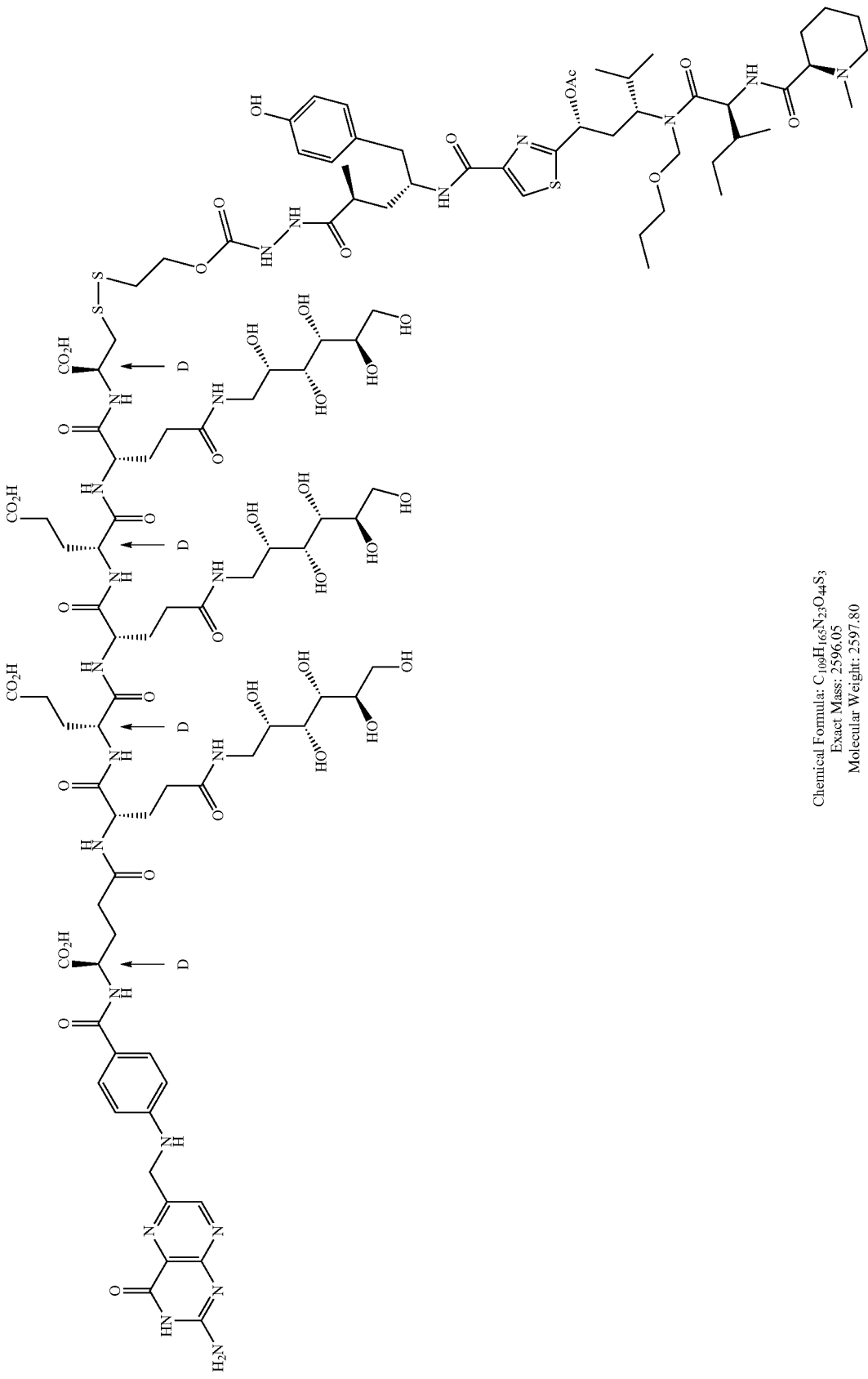

EC1454 (31.1 mg, 1.3 eq) was dissolved in degassed (Ar bubbling) 20 mM $PO_4$ pH7 buffer (2.0 mL) and added dropwise to a stirring solution of EC1715 (15.3 mg, 1.0 eq) in dry dimethylsulfoxide (2.0 mL, Aldrich) at room temperature with Ar bubbling. After 30 min, EC1750 (18.0 mg, 97%) was purified by preparative HPLC in 10-100% acetonitrile/50 mM $NH_4HCO_3$ pH7 buffer and lyophilized. MS (ESI, $[M+2H]^{2+}$) Predicted 1299.03. Found 1299.19. Partial $^1$H NMR (DMSO w/10% $D_2O$) δ (ppm) 8.61 (s), 8.14 (s), 7.57 (d), 6.93 (d), 6.60 (m), 5.77 (d), 5.23 (d), 4.47 (m), 0.98 (d), 0.92 (d), 0.76 (m), 0.71 (t), 0.61 (d)

Example

Synthesis of EC1739

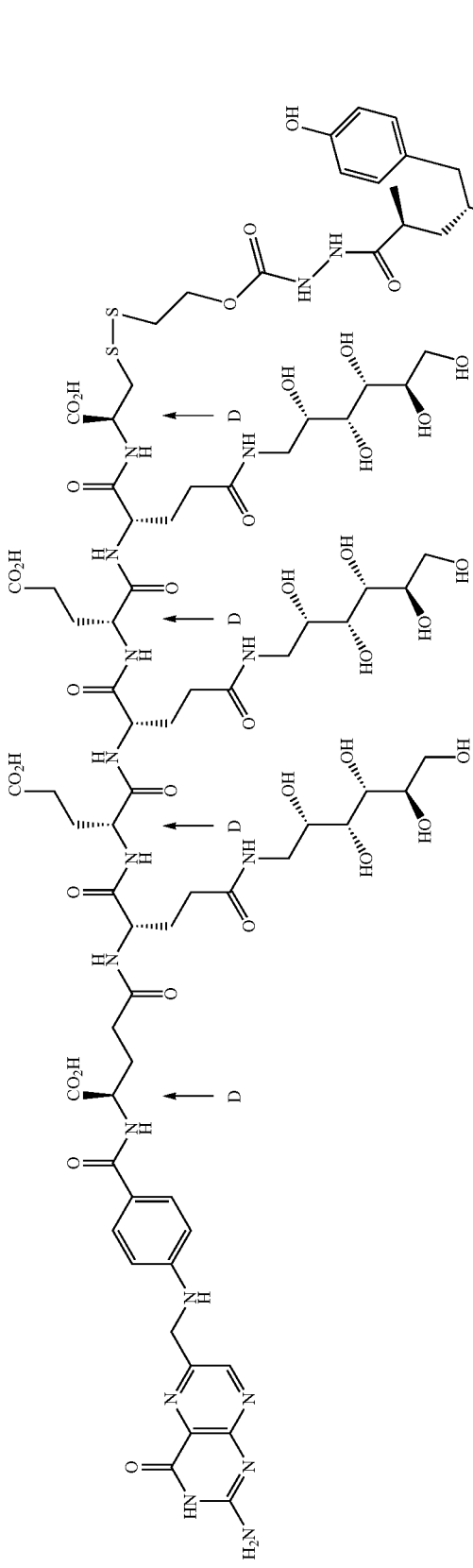
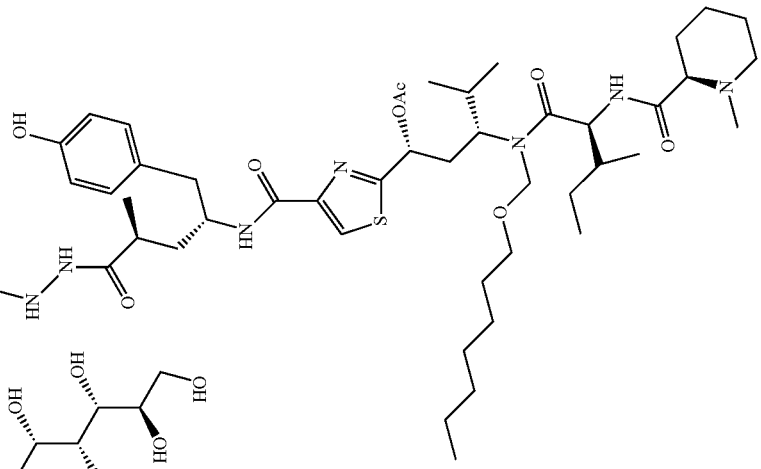
EC1454-EC1717
Chemical Formula: $C_{113}H_{173}N_{23}O_{44}S_3$
Exact Mass: 2652.12
Molecular Weight: 2653.91

EC1454 (8.5 mg, 1.5 eq) was dissolved in degassed (Ar bubbling) 20 mM $PO_4$ pH7 buffer (2.0 mL) and added dropwise to a stirring solution of EC1717 (3.8 mg, 1.0 eq) in dry dimethylsulfoxide (2.0 mL, Aldrich) at room temperature with Ar bubbling. After 30 min, EC1739 (5.3 mg, 59%) was purified by preparative HPLC in 10-100% acetonitrile/50 mM $NH_4HCO_3$ pH7 buffer and lyophilized. MS (ESI, $[M+2H]^{2+}$) predicted 1327.06. Found 1327.73

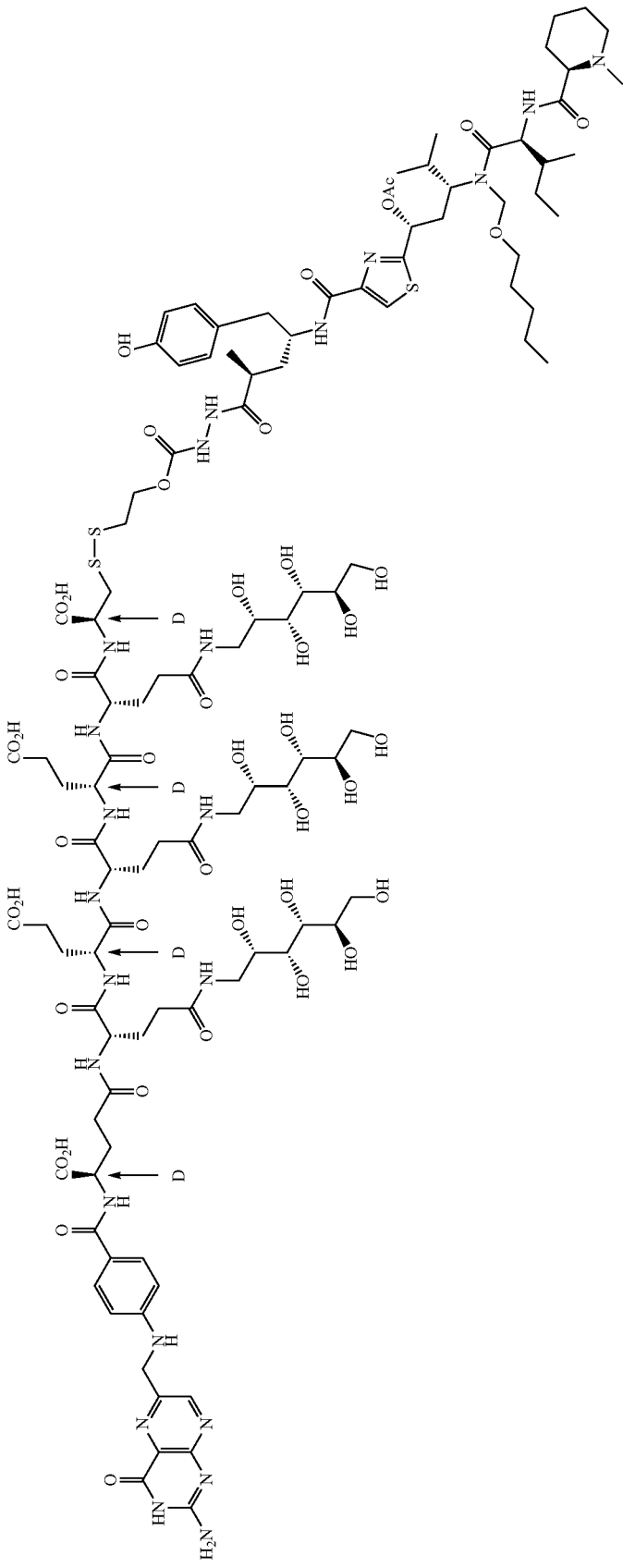

MS (ESI, [M+2H]$^{2+}$) Predicted 1313.05. Found 1313.37. Selected $^1$H NMR (DMSO w/10% D$_2$O) δ (ppm) 8.61 (s), 8.15 (s), 7.58 (d), 6.94 (d), 6.60 (m), 5.78 (d), 5.22 (d), 4.47 (m), 4.09-4.33 (m), 0.99 (d), 0.93 (d), 0.76 (t), 0.71 (t), 0.61 (d)

Example

Synthesis of EC1664

EC1454 (5.5 mg, 1.0 eq) was dissolved in degassed (Ar bubbling) 20 mM PO$_4$ pH7 buffer (2.0 mL) and added dropwise to a stirring solution of EC1662 (3.6 mg, 1.0 eq) in dry dimethylsulfoxide (2.0 mL, Aldrich) at room temperature with Ar bubbling. After 30 min, EC1664 (4.6 mg, 54%) was purified by preparative HPLC in 10-100% acetonitrile/50 mM NH$_4$HCO$_3$ pH7 buffer and lyophilized.

Example

Synthesis of EC1663

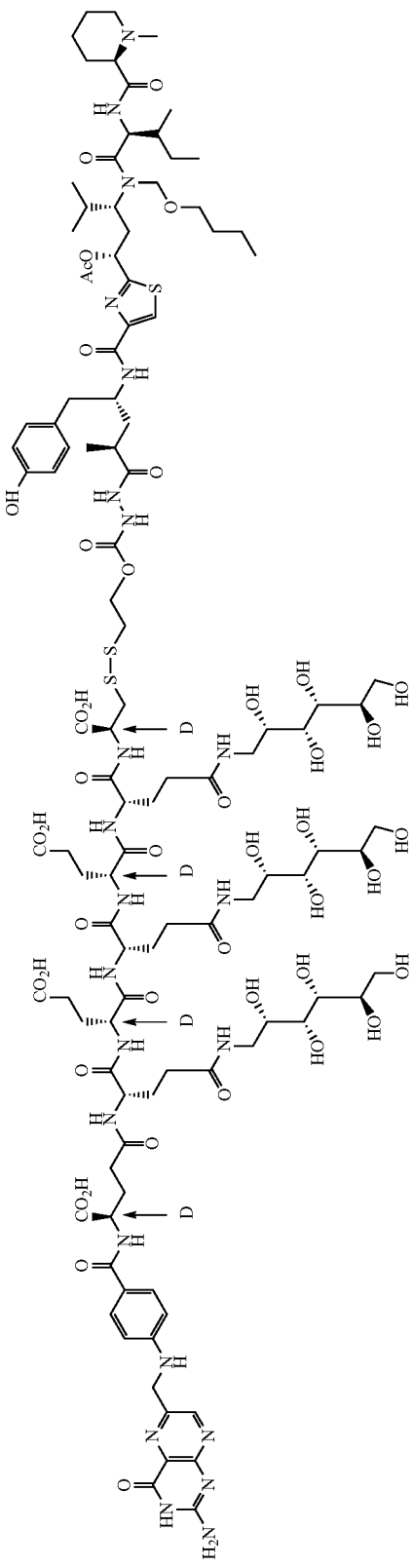

EC1454 (16.1 mg, 1.2 eq) was dissolved in degassed (Ar bubbling) 20 mM $PO_4$ pH7 buffer (2.0 mL) and added dropwise to a stirring solution of EC1661 (8.7 mg, 1.0 eq) in dry dimethylsulfoxide (2.0 mL, Aldrich) at room temperature with Ar bubbling. After 30 min, EC1663 (15.8 mg, 76%) was purified by preparative HPLC in 10-100% acetonitrile/50 mM $NH_4HCO_3$ pH7 buffer and lyophilized. MS (ESI, $[M+2H]^{2+}$) Predicted 1306.04. Found 1306.82

Example 10

Synthesis of EC1653

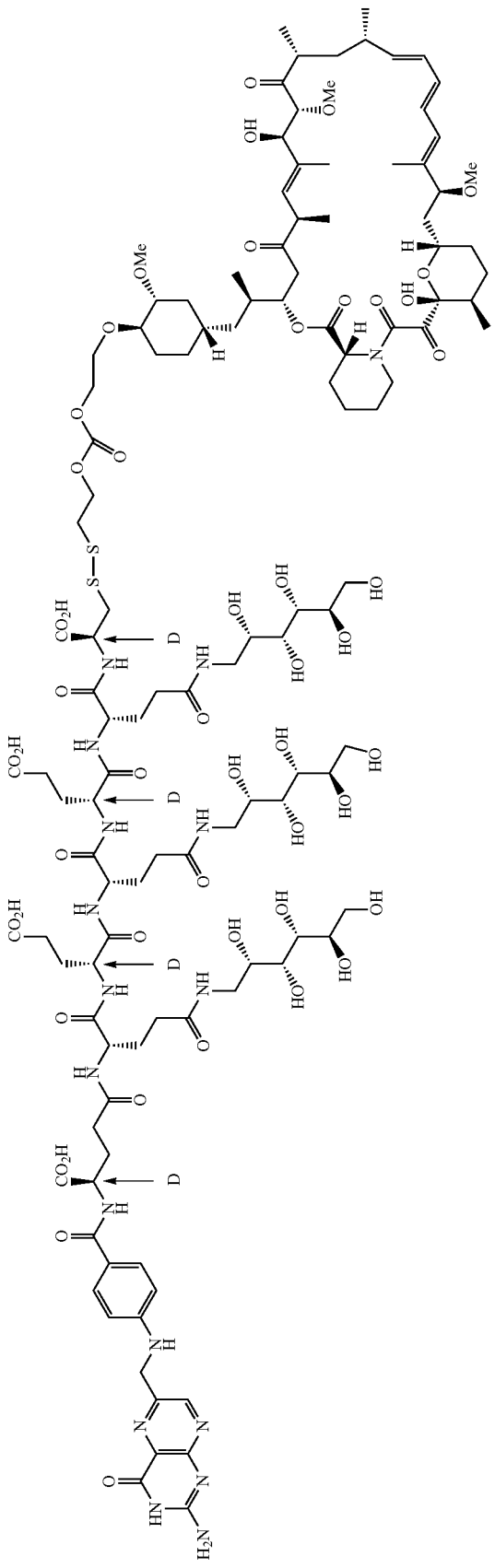

EC1454 (8.3 mg, 1.0 eq) was dissolved in degassed (Ar bubbling) 20 mM $PO_4$ pH7 buffer (2.0 mL) and added dropwise to a stirring solution of EC0564 (5.8 mg, 1.0 eq) in dry dimethylsulfoxide (4.0 mL, Aldrich) at room temperature with Ar bubbling. After 30 min, EC1653 (6.3 mg, 46%) was purified by preparative HPLC in 10-100% acetonitrile/10 mM $NH_4OAc$ pH5 buffer and lyophilized. MS (ESI, ((M-2)/2)) Predicted 1368.09. Found 1368.74

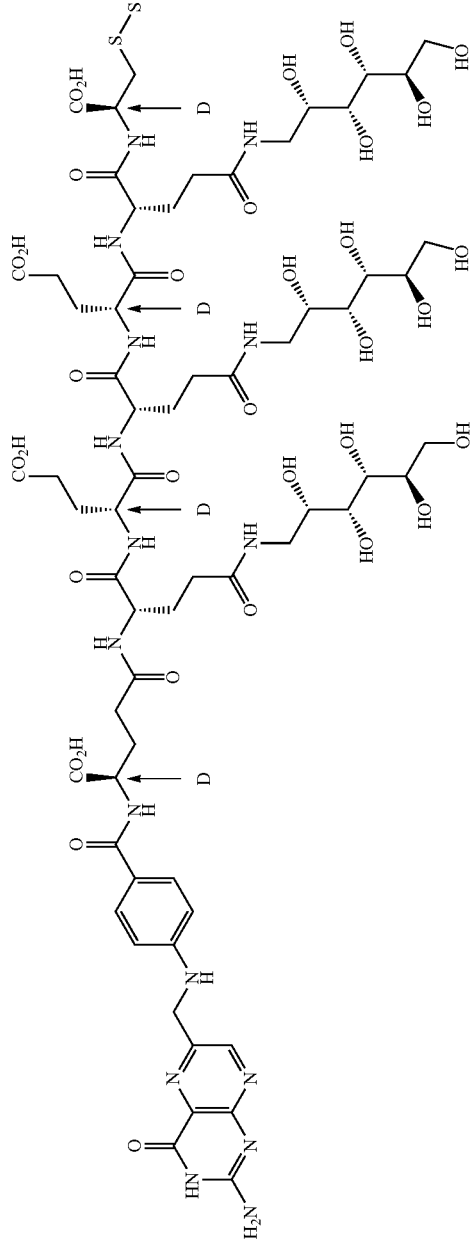

-continued
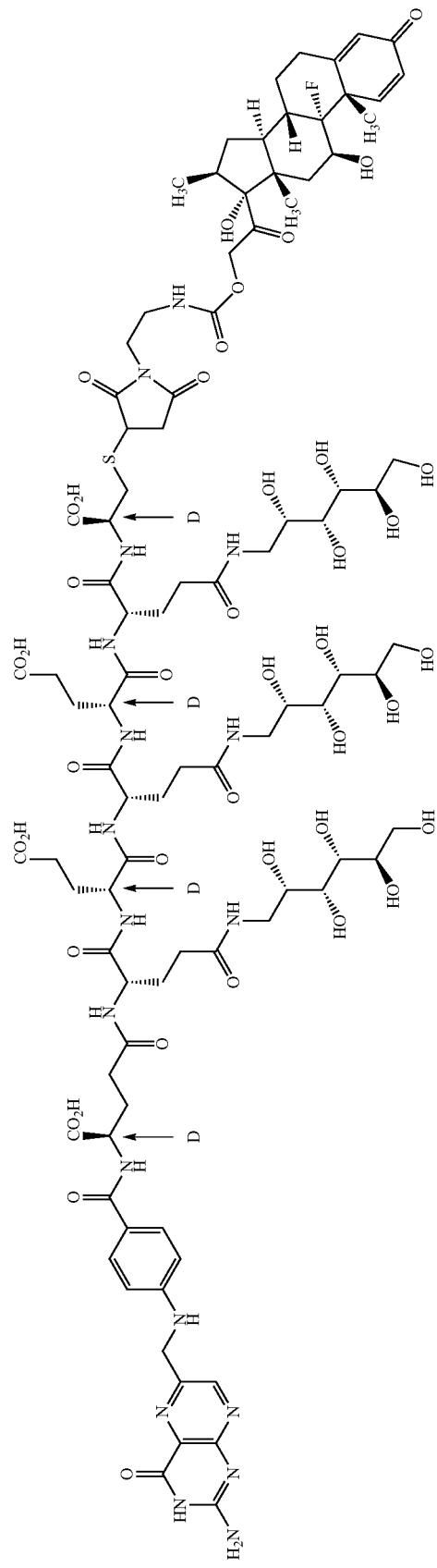

Example

Synthesis of EC1496

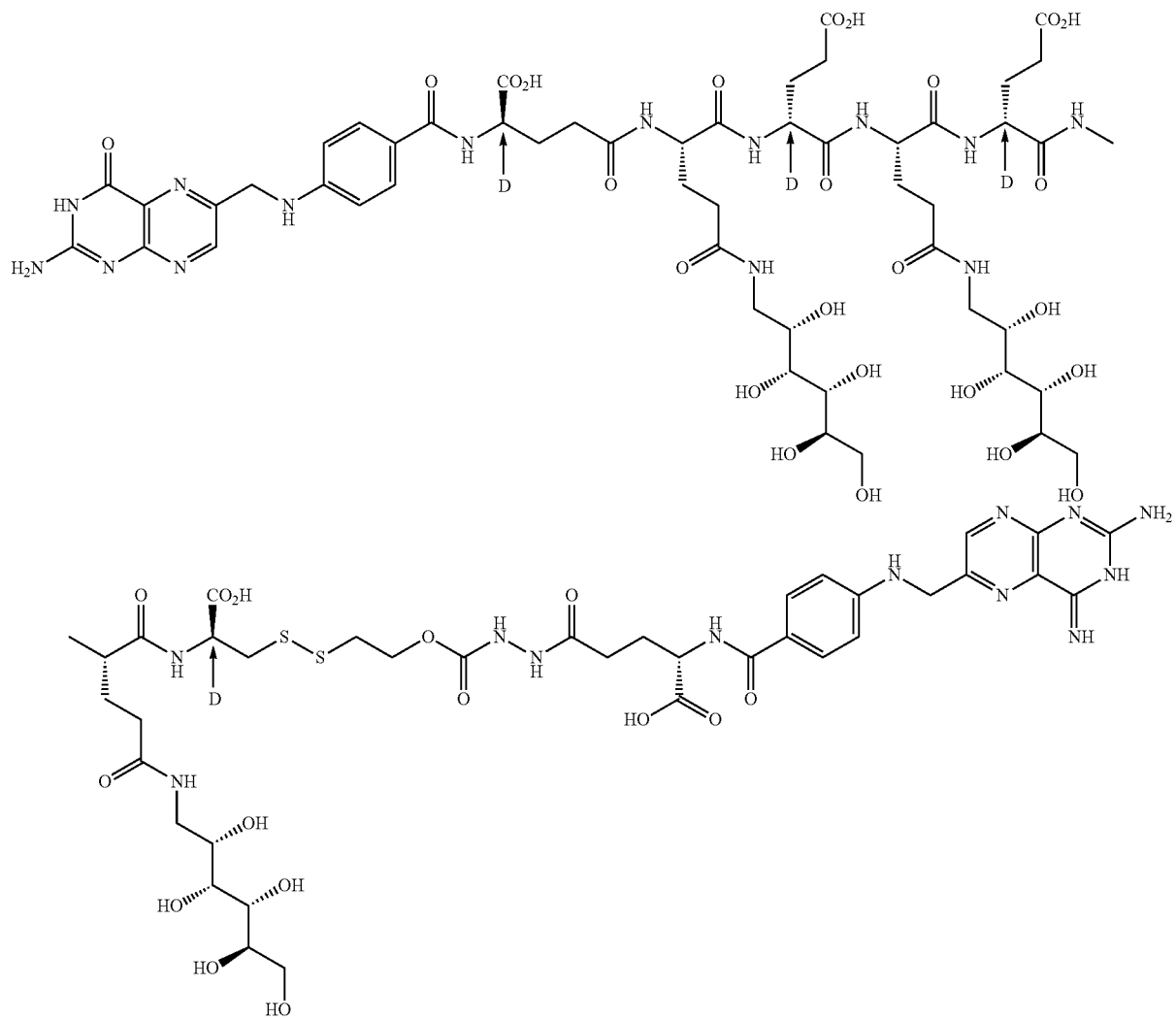

EC1496
$C_{87}H_{122}N_{26}O_{40}S_2$
Exact Mass: 2234.78
Mol. Wt: 2236.18

EC1454 (324 mg, 1.0 eq) was dissolved in degassed (Ar bubbling) 20 mM PO$_4$ pH7 buffer (4.0 mL) and added dropwise to a stirring solution of crude EC0469 (142 mg, 1.1 eq) in dry dimethylsulfoxide (4.0 mL, Aldrich) at room temperature with Ar bubbling. After 30 min, EC1496 (221 mg, 51%) was purified by preparative HPLC in 0-30% acetonitrile/50 mM NH$_4$HCO$_3$ pH7 buffer and lyophilized. MS (ESI, ((M+2)/2)) Predicted 1118.39. Found 1119.02

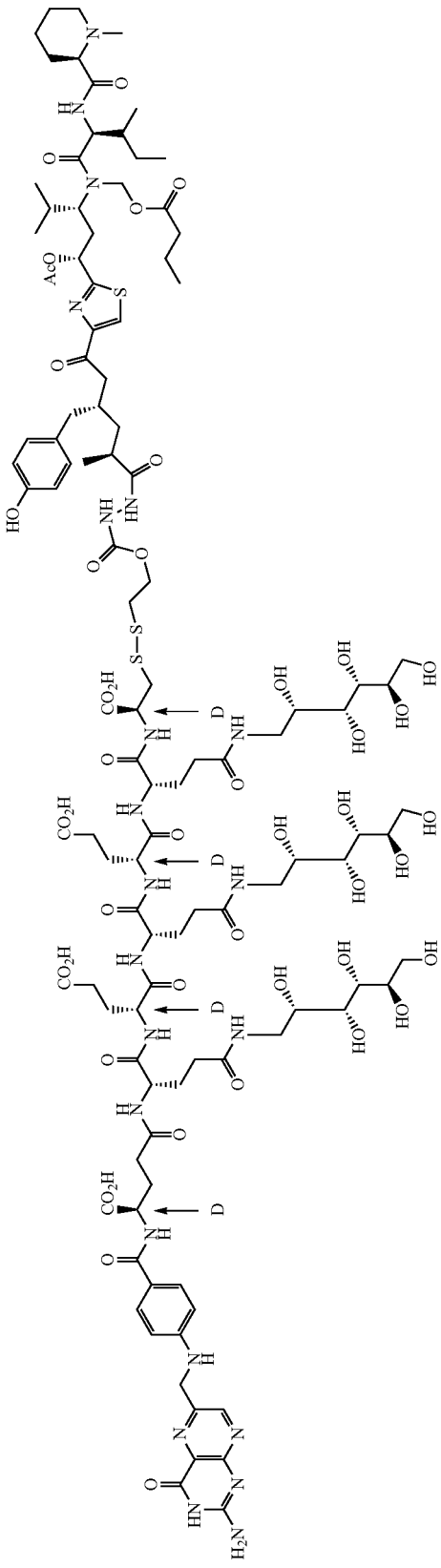

Examples
Conjugates of EC1415
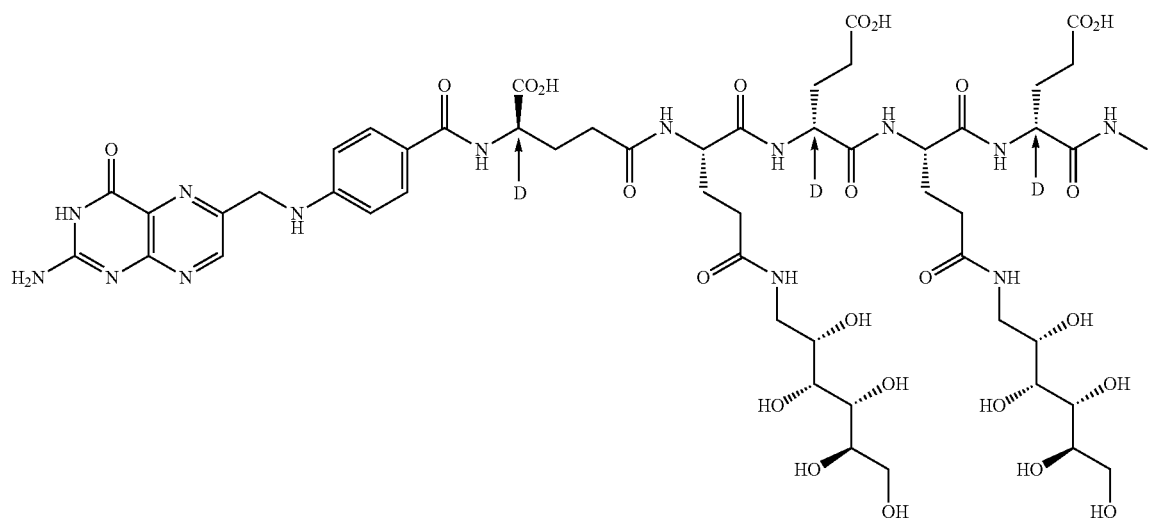
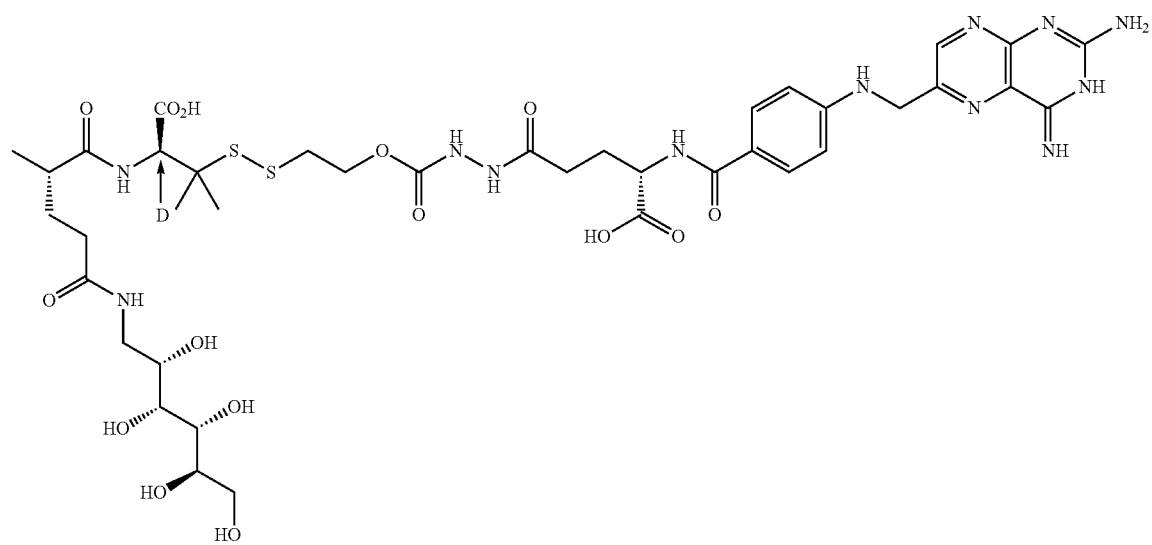
C₈₈H₁₂₆N₂₆O₄₀S₂
Exact Mass: 2262.81
Mol. Wt: 2264.24

Example

Synthesis of EC1416

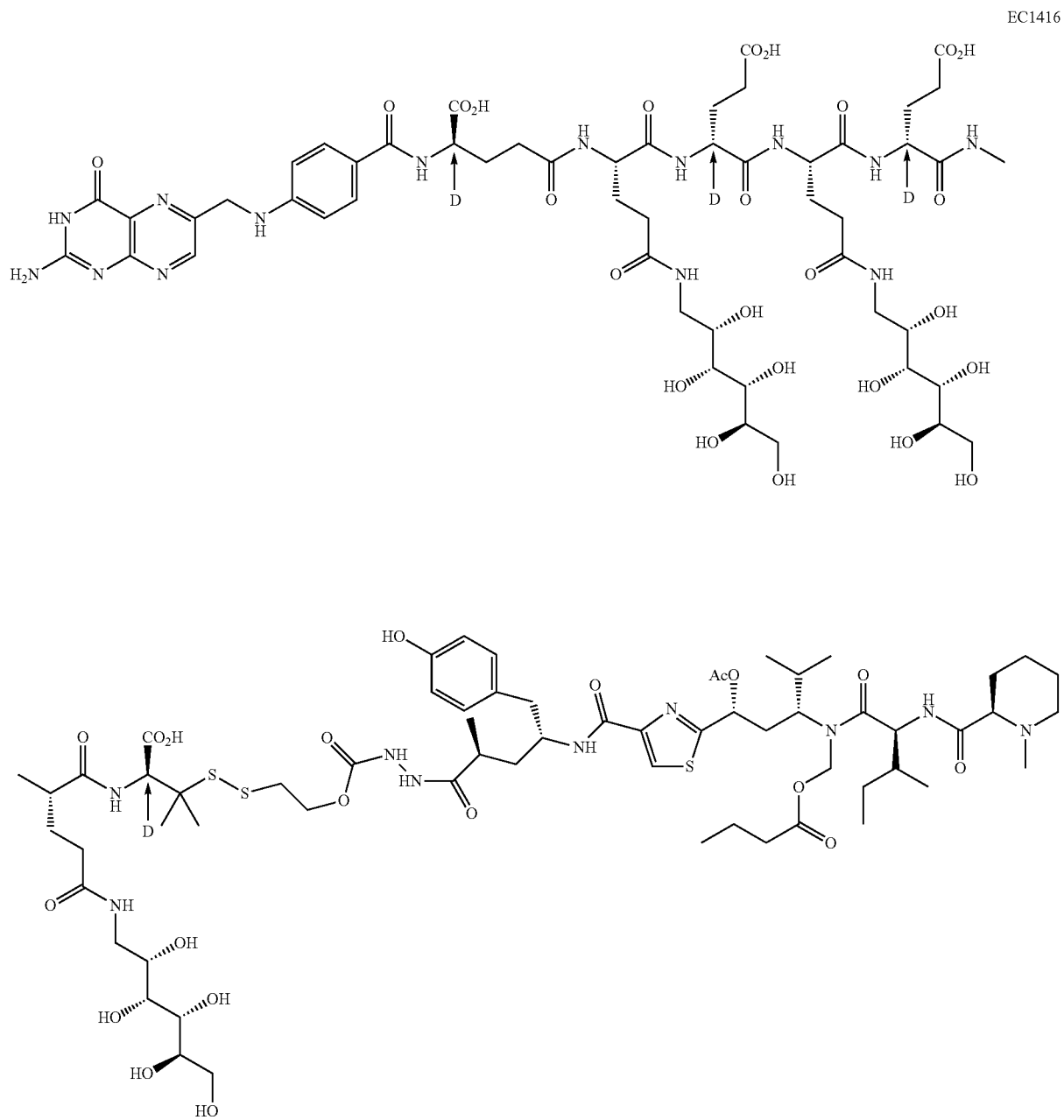

EC1415 (20 mg) was dissolved in pH7 phosphate (pH 7.75, purged with argon). To this solution was added a suspension of EC0312 (14 mg) in equal volume of MeOH. The reaction mixture was stirred at ambient temperature under argon for 45 min, and then loaded onto a preparatory HPLC (Mobile phase A=50 mM $NH_4HCO_3$ buffer, pH=7.0. B=ACN. Method: 5-80% B in 20 min.) for purification. Fractions containing the desired product were collected, combined, and freeze-dried to afford the product (18 mg) as a pale yellow solid. MS(ESI, $[M+2H]^{2+}$) 1328. 1H NMR (DMSO-d6, $D_2O$, 300 MHz): 8.6 (s, 1H), 8.15 (s, 1H), 7.85 (bd, 1H), 7.55 (d, 2H), 6.95 (d, 2H), 6.6 (m, 4H), 6.2 (d, 1H), 5.68 (d, 1H), 5.2 (d, 1H), 4.5 (bs, 3H), 4.5-4.3 (m, 4H), 4.3-4.0 (m, 10H), 3.5-3.3 (m, 13H), 3.2 (bd, 5H), 3.1-2.8 (m, 8H), 2.75 (bs, 5H), 2.6-1.6 (m, 50H), 1.4 (m, 9H), 1.2 (m, 9H), 1.0 (dd, 9H), 0.7 (m, 11H), 0.6 (d, 3H).

Examples

Conjugates of EC1392

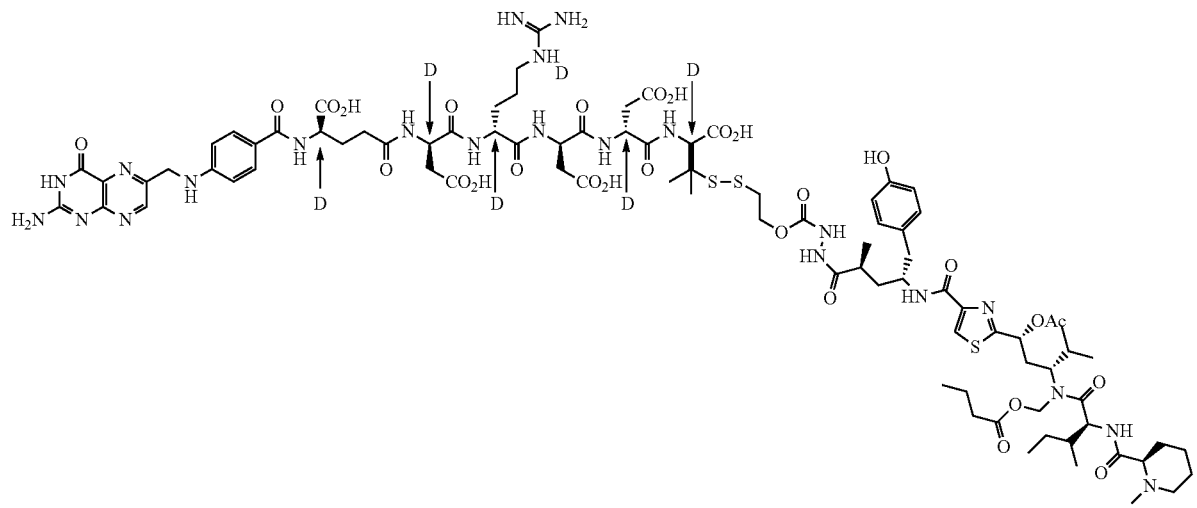

EC1393

$C_{87}H_{122}N_{22}O_{28}S_3$
Exact Mass: 2018.80
Mol. Wt.: 2020.23
MS(ESI, [M + 2H]$^{2+}$) 1011.39

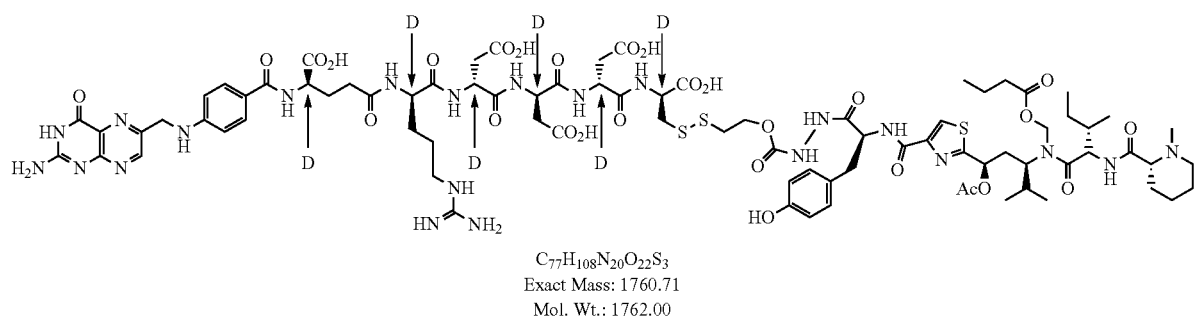

EC1391

$C_{77}H_{108}N_{20}O_{22}S_3$
Exact Mass: 1760.71
Mol. Wt.: 1762.00

Example

Conjugates of EC59

A solution of EC59 (13.2 mg) in 20 mM pH7.1 phosphate buffer (2.4 mL) was added to a solution of EC0312 (14.2 mg) in MeOH (2.4 mL). The resulting homogeneous solution was stirred at ambient temperature under argon for 20 min. and then loaded directly onto a preparatory HPLC (Mobile phase A=50 mM NH$_4$HCO$_3$ buffer, pH=7.0. B=ACN. Method: 5-80% B in 20 min.) for purification. Fractions containing the desired product were collected, combined, and freeze-dried to give the product (15.3 mg) as a fluffy yellow solid.

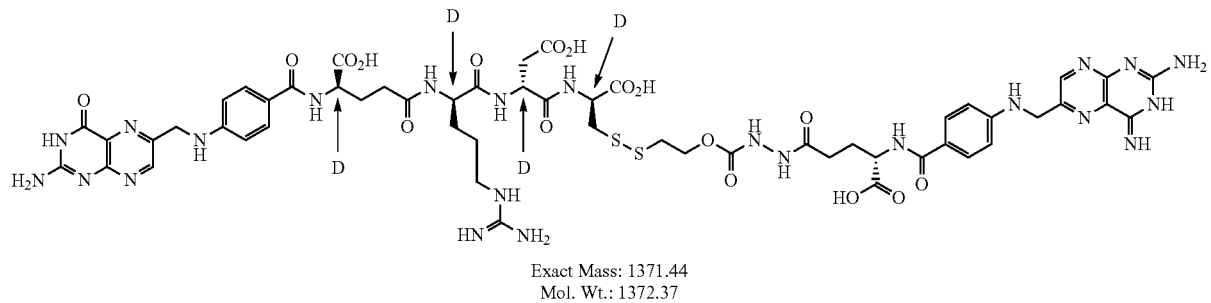

EC1390

Exact Mass: 1371.44
Mol. Wt.: 1372.37

Examples

Conjugates of EC1347

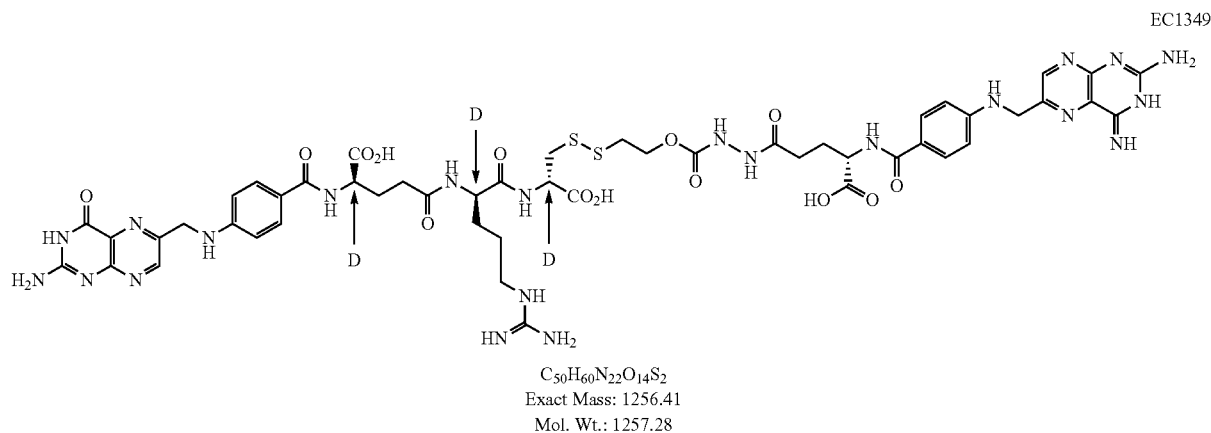

EC1349

C₅₀H₆₀N₂₂O₁₄S₂
Exact Mass: 1256.41
Mol. Wt.: 1257.28

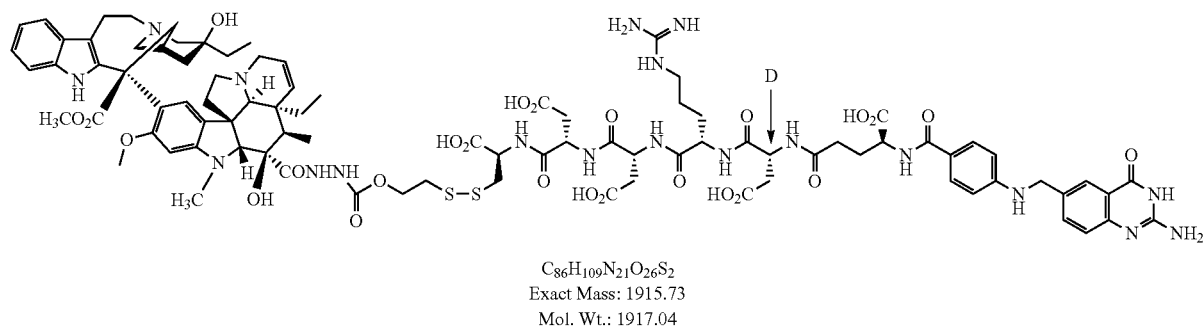

EC1208

C₈₆H₁₀₉N₂₁O₂₆S₂
Exact Mass: 1915.73
Mol. Wt.: 1917.04

EC1208: LCMS [ESI (M+H)⁺: 1918]. ¹H NMR data for EC145 (D₂O, 300 MHz): δ 8.67 (s, 1H, FA H-7), 7.50 (br s, 1H, VLB H-11'), 7.30-7.40 (br s, 1H, VLB H-14'), 7.35 (d, 2H, J=7.8 Hz, FA H-12 &16), 7.25 (m, 1H, VLB H-13'), 7.05 (br s, 1H, VLB H-12'), 6.51 (d, 2H, J=8.7 Hz, FA H-13 &15), 6.4 (s, 2H, VLB H-14 & 17), 5.65 (m, 1H, VLB H-7), 5.5 (m, 1H, VLB H-6), 4.15 (m, 1H, VLB H-8'), 3.82 (s, 3H, VLB C₁₈'—CO₂CH₃), 3.69 (s, 3H, VLB C₁₆—OCH₃), 2.8 (s, 3H, VLB N—CH₃), 1.35 (br s, 1H, VLB H-3'), 1.15 (m, 1H, VLB H-2'), 0.9 (t, 3H, J=7 Hz, VLB H-21'), 0.55 (t, 3H, J=6.9 Hz, VLB H-21) ppm.

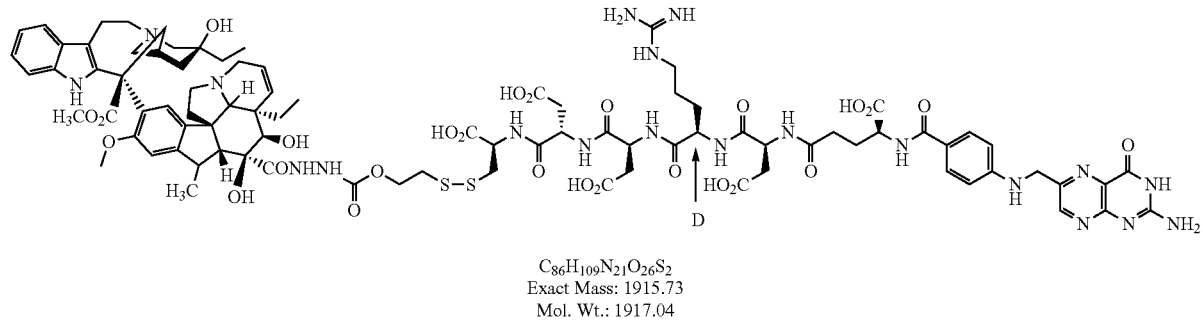

EC1209

C₈₆H₁₀₉N₂₁O₂₆S₂
Exact Mass: 1915.73
Mol. Wt.: 1917.04

EC1209: LCMS [ESI (M+H)$^+$: 1918]. $^1$Selected $^1$H NMR data for EC145 (D$_2$O, 300 MHz): δ 8.67 (s, 1H, FA H-7), 7.50 (br s, 1H, VLB H-11'), 7.30-7.40 (br s, 1H, VLB H-14'), 7.35 (d, 2H, J=7.8 Hz, FA H-12 &16), 7.25 (m, 1H, VLB H-13'), 7.05 (br s, 1H, VLB H-12'), 6.51 (d, 2H, J=8.7 Hz, FA H-13 &15), 6.4 (s, 2H, VLB H-14 & 17), 5.65 (m, 1H, VLB H-7), 5.5 (m, 1H, VLB H-6), 4.15 (m, 1H, VLB H-8'), 3.82 (s, 3H, VLB C$_{18'}$—CO$_2$CH$_3$), 3.69 (s, 3H, VLB C$_{16}$—OCH$_3$), 2.8 (s, 3H, VLB N—CH$_3$), 1.35 (br s, 1H, VLB H-3'), 1.15 (m, 1H, VLB H-2'), 0.9 (t, 3H, J=7 Hz, VLB H-21'), 0.55 (t, 3H, J=6.9 Hz, VLB H-21) ppm.

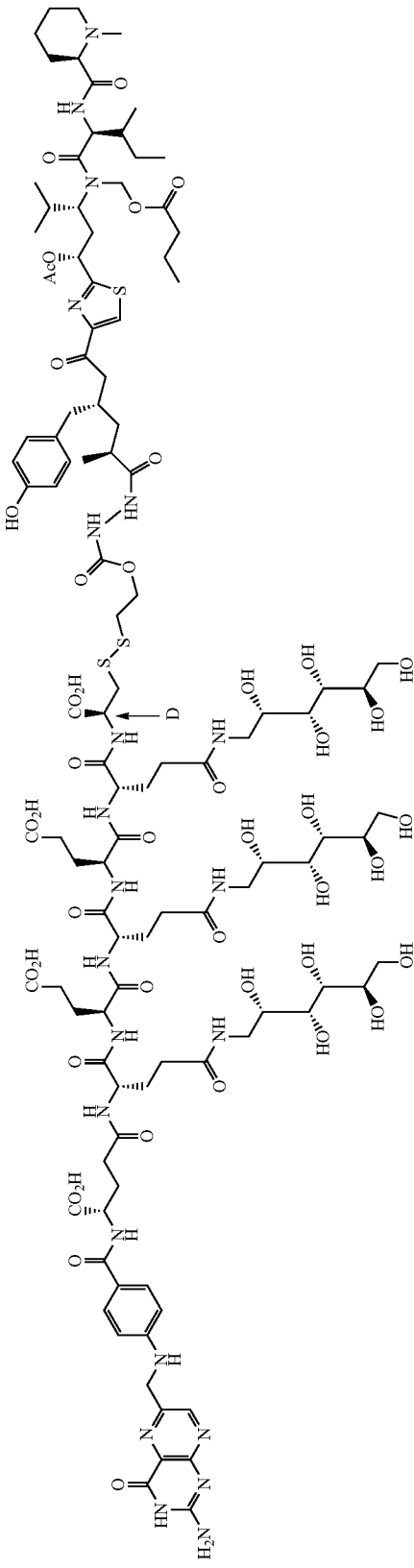

EC1575: A solution of EC1577 (9.5 mg) in 20 mM pH7 phosphate buffer (2.0 mL) and a saturated NaHCO$_3$ solution (0.50 mL) were added to a solution of EC0312 (10.1 mg) in MeOH (2.0 mL) in tandem. The resulting homogeneous solution was stirred at ambient temperature under argon for 20 min. and then loaded directly onto a preparatory HPLC (Mobile phase A=50 mM NH$_4$HCO$_3$ buffer, pH=7.0. B=ACN. Method: 5-80% B in 20 min.) for purification. Fractions containing the desired product were collected, combined, and freeze-dried to afford the product (9.5 mg) as a pale yellow solid. LCMS [ESI (M+H)$^+$: 2627]. $^1$H NMR (D$_2$O, 300 MHz): 8.70 (s), 8.11 (s), 7.62 (d), 7.00 (d), 6.71 (dd), 6.11 (d), 5.80 (d), 5.33 (d), 4.60-4.50 (m), 4.40-4.15 (m), 3.88-3.51 (m), 3.50-3.20 (m), 3.19-2.80 (m), 2.76 (s), 2.60-1.43 (m), 1.40-1.27 (m), 1.18 (d), 1.02 (d), 0.97-0.82 (m), 0.76-0.63 (m).

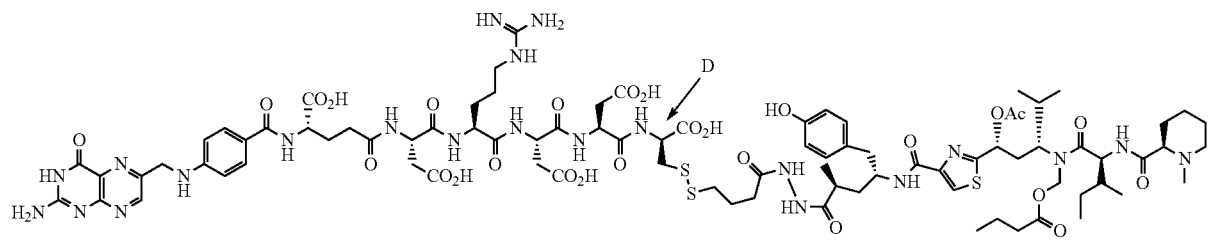

EC1548

Chemical Formula: C$_{85}$H$_{118}$N$_{22}$O$_{28}$S$_3$
Exact Mass: 1990.76
Mol. Wt: 1992.17

EC1548: A solution of EC1544 (55.1 mg) in 20 mM pH7 phosphate buffer (1.95 mL) and a saturated NaHCO$_3$ solution (0.30 mL) were added to a solution of EC1248 (58.0 mg) in MeOH (2.30 mL) in tandem. The resulting homogeneous solution was stirred at ambient temperature under argon for 20 min. and then loaded directly onto a preparatory HPLC (Mobile phase A=50 mM NH$_4$HCO$_3$ buffer, pH=7.0. B=ACN. Method: 5-80% B in 20 min.) for purification. Fractions containing the desired product were collected, combined, and freeze-dried to afford the product (61.5 mg) as a pale yellow solid. MS (ESI, M+1) 1993

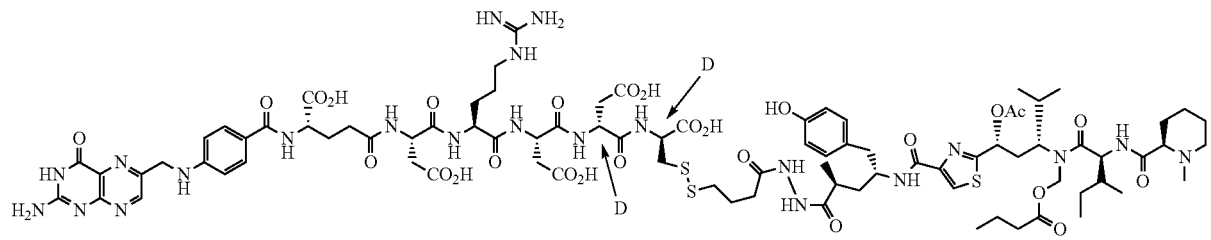

EC1549

Chemical Formula: C$_{85}$H$_{118}$N$_{22}$O$_{28}$S$_3$
Exact Mass: 1990.76
Mol. Wt: 1992.17

EC1549: A solution of EC1547 (23.5 mg) in 20 mM pH7 phosphate buffer (2.0 mL) and a saturated NaHCO$_3$ solution (0.30 mL) were added to a solution of EC1248 (24.7 mg) in MeOH (2.3 mL) in tandem. The resulting homogeneous solution was stirred at ambient temperature under argon for 20 min. and then loaded directly onto a preparatory HPLC (Mobile phase A=50 mM NH$_4$HCO$_3$ buffer, pH=7.0. B=ACN. Method: 5-80% B in 20 min.) for purification. Fractions containing the desired product were collected, combined, and freeze-dried to afford the product (29.2 mg) as a pale yellow solid. MS (ESI, M+1) 1993

Example

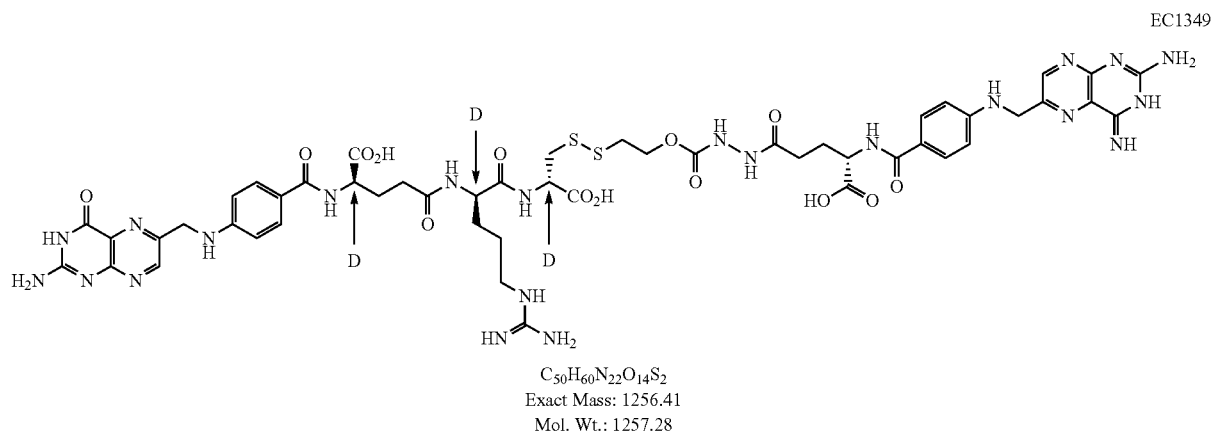

EC1349

Example 25

EC1299

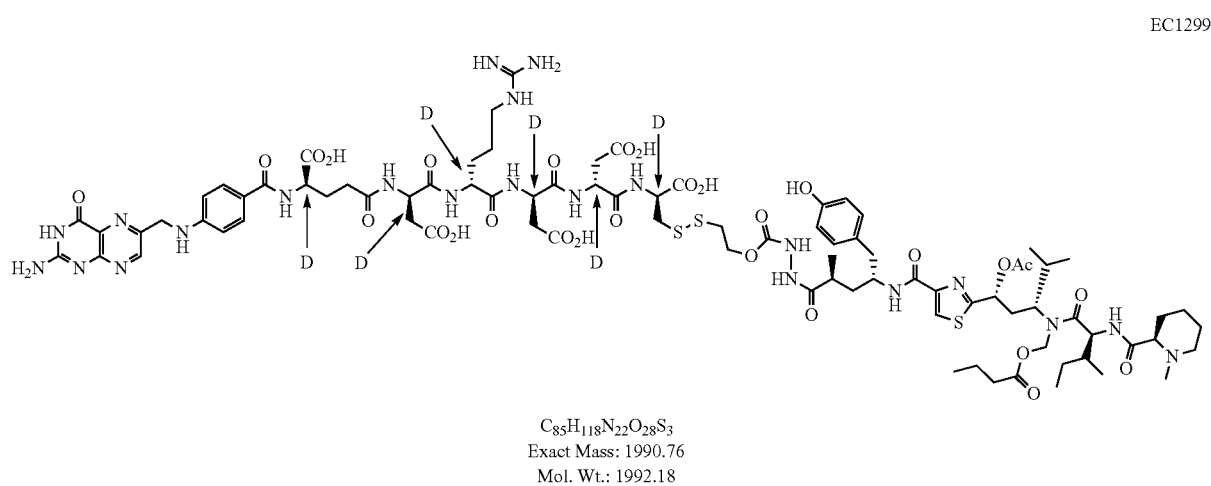

EC1299

A solution of EC0259 (35 mg) in 20 mM pH7 phosphate buffer (3.0 mL) and a saturated $NaHCO_3$ solution (1.5 mL) were added to a solution of EC0312 (39 mg) in ACN (5.5 mL) in tandem. The resulting homogeneous solution was stirred at ambient temperature under argon for 20 min. and then loaded directly onto a preparatory HPLC (Mobile phase A=50 mM $NH_4HCO_3$ buffer, pH=7.0. B=ACN. Method: 5-80% B in 20 min.) for purification. Fractions containing the desired product were collected, combined, and freeze-dried to afford the product (25 mg) as a pale yellow solid. MS (ESI, M+1) 1993

Example
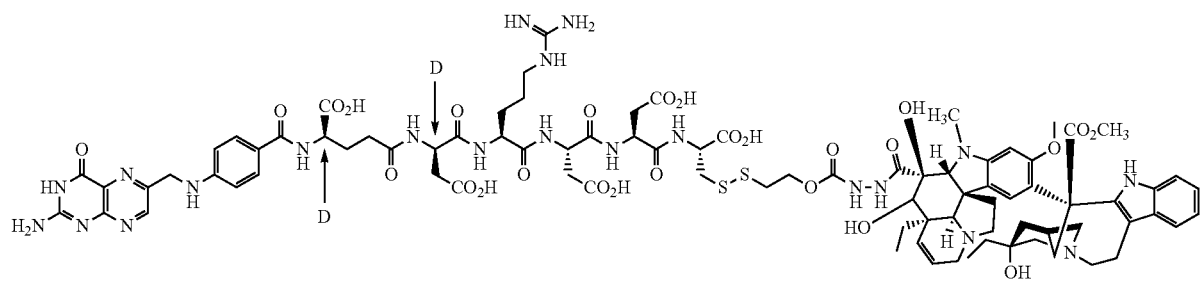
EC0836
Chemical Formula: $C_{86}H_{109}N_{21}O_{26}S_2$
Exact Mass: 1915.73
Mol. Wt: 1917.04
Example 20
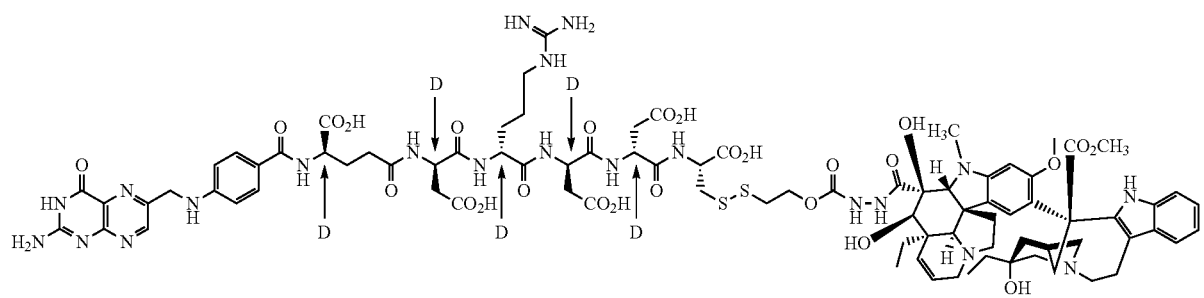
EC0821
Chemical Formula: $C_{86}H_{109}N_{21}O_{26}S_2$
Exact Mass: 1915.73
Mol. Wt: 1917.04
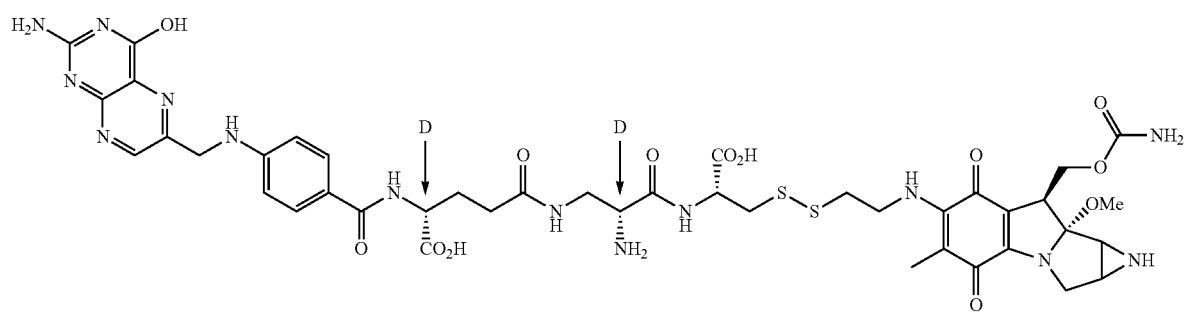
EC 153
EC153: MS(ESI, [M+H]$^+$) 1023; (ESI, [M−H]$^−$) 1021; $^1$H NMR (DMSO-d6, 300 MHz): 8.84 (s, 1H), 7.70 (d, 2H), 6.80 (d, 2H), 4.60 (m, 1H), 4.56 (s, 2H), 4.34 (m, 2H), 4.10 (m, 2H), 3.85 (m, 2H), 3.60-3.30 (m, 5H), 3.20 (s, 2H), 3.18-3.05 (m, 1H), 3.0 (br, 2H), 2.90-2.70 (m, 2H), 2.40-2.00 (m, 4H), 1.95 (m, 3H).

Examples
The following compounds were prepared according to the processes described herein starting from EC0059:
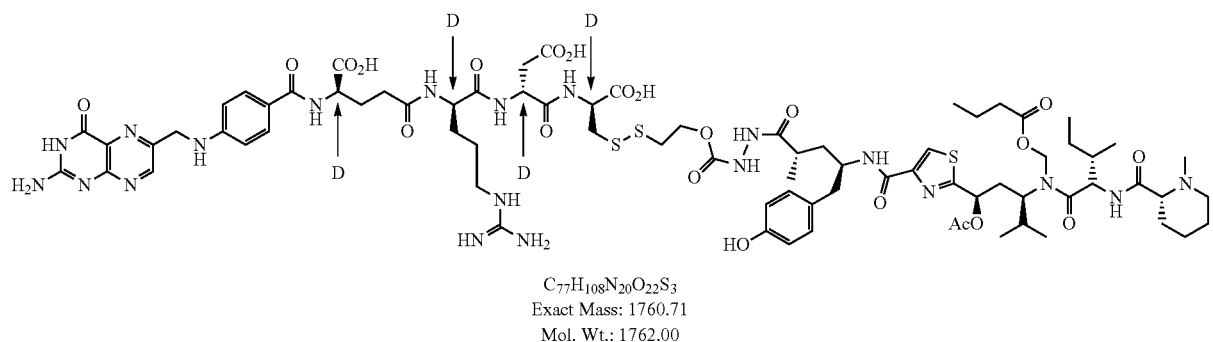
EC1391
C₇₇H₁₀₈N₂₀O₂₂S₃
Exact Mass: 1760.71
Mol. Wt.: 1762.00
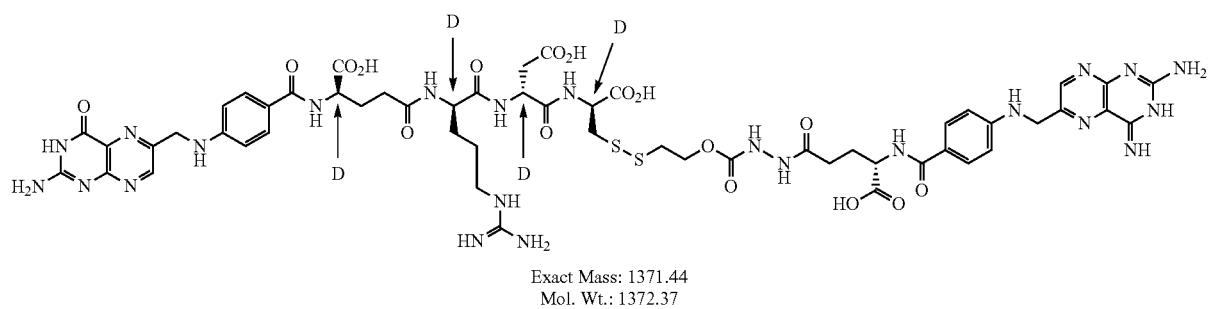
EC1390
Exact Mass: 1371.44
Mol. Wt.: 1372.37
Example 40
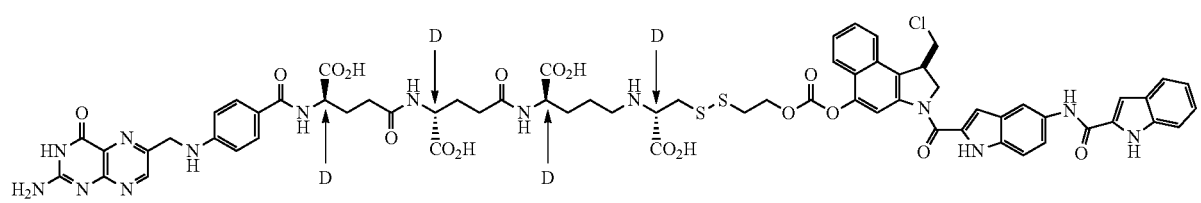
EC74: MS(ESI, [M + H]⁺) 1438.3; (ESI, [M − H]⁻) 1436.4
Comparative Examples
The following comparative compounds are disclosed:
Comparative Example

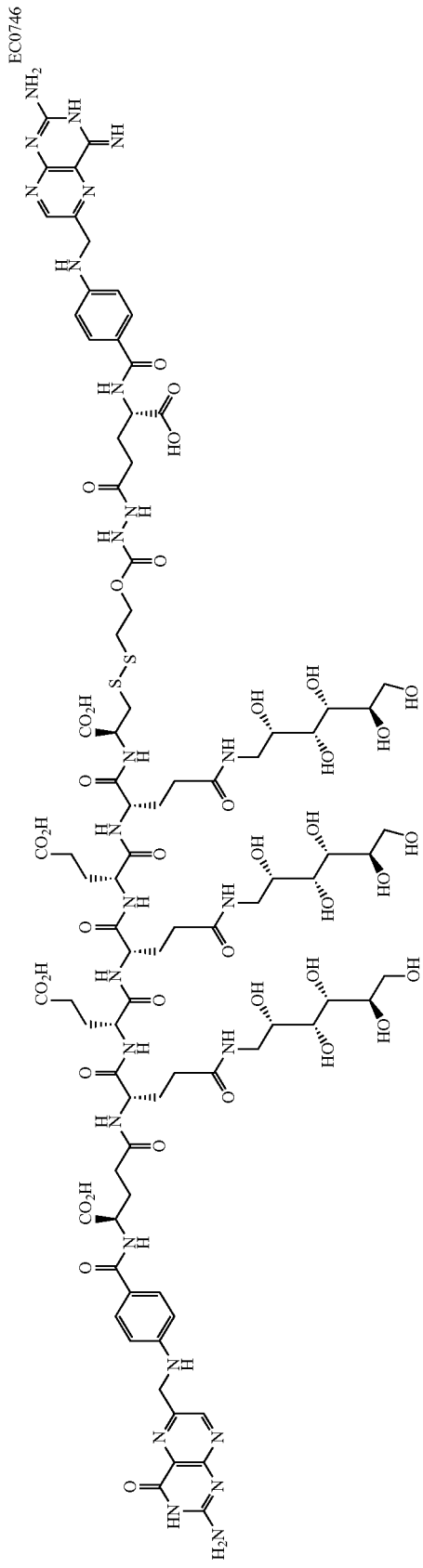

Comparative Example

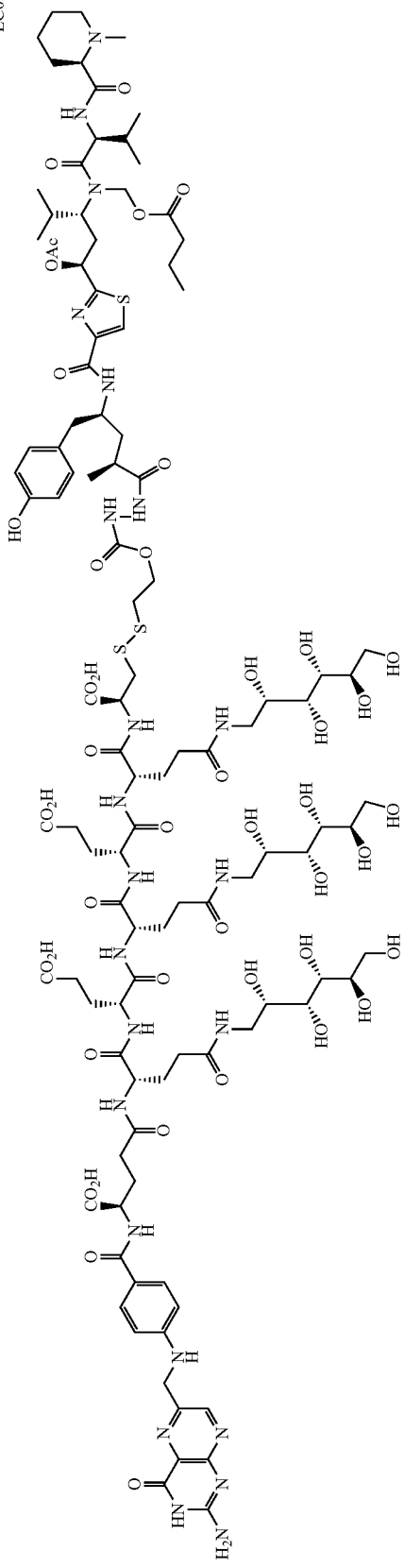

Comparative Example

EC0923

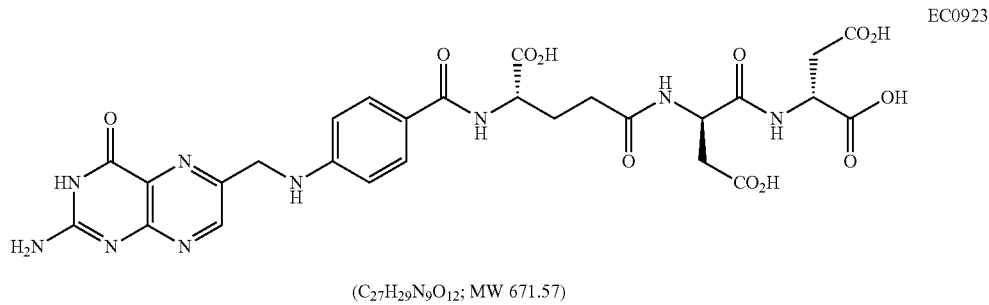 [SMILES: Nc1nc2ncc(CNc3ccc(C(=O)N[C@@H](CCC(=O)N[C@H](CC(=O)O)C(=O)N[C@H](CC(=O)O)C(=O)O)C(=O)O)cc3)nc2c(=O)[nH]1]

($C_{27}H_{29}N_9O_{12}$; MW 671.57)

METHODS AND EXAMPLES

General. The following abbreviations are used herein: partial response (PR); complete response (CR), three times per week (M/W/F) (TIW).

Method

Relative Affinity Assay. The affinity for folate receptors (FRs) relative to folate is determined according to a previously described method (Westerhof, G. R., J. H. Schornagel, et al. (1995) Mol. Pharm. 48: 459-471) with slight modification. Briefly, FR-positive KB cells are heavily seeded into 24-well cell culture plates and allowed to adhere to the plastic for 18 h. Spent incubation media is replaced in designated wells with folate-free RPMI (FFRPMI) supplemented with 100 nM $^3$H-folic acid in the absence and presence of increasing concentrations of test article or folic acid. Cells are incubated for 60 min at 37° C. and then rinsed 3 times with PBS, pH 7.4. Five hundred microliters of 1% SDS in PBS, pH 7.4, is added per well. Cell lysates are then collected and added to individual vials containing 5 mL of scintillation cocktail, and then counted for radioactivity. Negative control tubes contain only the $^3$H-folic acid in FFRPMI (no competitor). Positive control tubes contain a final concentration of 1 mM folic acid, and CPMs measured in these samples (representing non-specific binding of label) are subtracted from all samples. Relative affinities are defined as the inverse molar ratio of compound required to displace 50% of $^3$H-folic acid bound to the FR on KB cells, where the relative affinity of folic acid for the FR is set to 1.

Example

EC1669 shows high binding affinities towards folate receptors as determined by an in vitro competitive binding assay that measures the ability of the ligand to compete against $^3$H-folic acid for binding to cell surface folate receptors (FR). EC1669 ( ). The relative affinity values of EC1669 (normalized against folic acid, which is set to (1) are determined to be 0.53 and 0.13 on KB and CHO-FRβ cells, respectively (see, FIG. 1A and FIG. 1B). In comparison, methotrexate (MTX) showed poor binding to the cell surface FRs. Without being bound by theory, it is believed herein that the high binding affinity of EC1669 allows for efficient cellular uptake via FR-mediated endocytosis.

Method

Inhibition of Cellular DNA Synthesis. The compounds described herein are evaluated using an in vitro cytotoxicity assay that predicts the ability of the drug to inhibit the growth of folate receptor-positive cells, such as KB cells, RAW264.7 macrophages, and the like. It is to be understood that the choice of cell type can made on the basis of the susceptibility of those selected cells to the drug that forms the conjugate. The test compounds are comprised of folate linked to a respective chemotherapeutic drug, as prepared according to the processes described herein. The test cells are exposed to varying concentrations of folate-drug conjugate, and also in the absence or presence of at least a 100-fold excess of folic acid to assess activity as being specific to folate receptor mediation.

Example

Conjugates of cytotoxic drugs described herein are active against KB cells. The activity is mediated by the folate receptor as indicated by competition experiments using co-administered folic acid. KB cells are exposed for up to 7 h at 37° C. to the indicated concentrations of folate-drug conjugate in the absence or presence of at least a 100-fold excess of folic acid. The cells are then rinsed once with fresh culture medium and incubated in fresh culture medium for 72 hours at 37° C. Cell viability was assessed using a $^3$H-thymidine incorporation assay. For compounds described herein, dose-dependent cytotoxicity is generally measurable, and in most cases, the $IC_{50}$ values (concentration of drug conjugate required to reduce $^3$H-thymidine incorporation into newly synthesized DNA by 50%) are in the low nanomolar range. Though without being bound by theory, when the cytotoxicities of the conjugates are reduced in the presence of excess free folic acid, it is believed herein that such results indicate that the observed cell death is mediated by binding to the folate receptor.

Example

Figure 2:
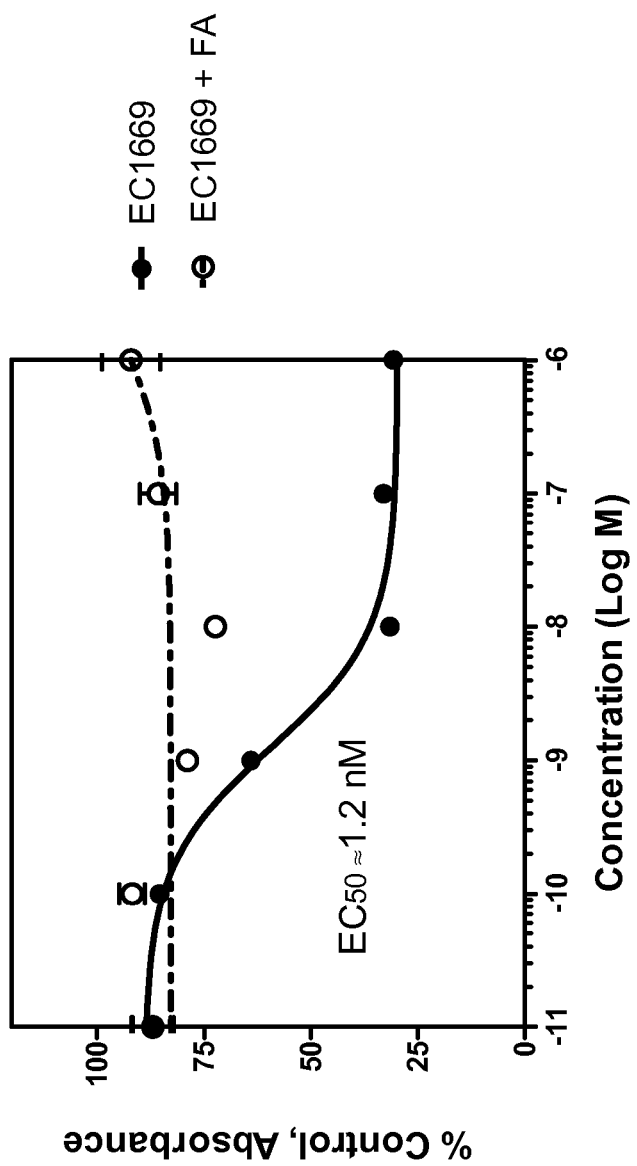
FIG. 2 shows the cytostatic effect of EC1669 on RAW264.7 cells, as determined by XTT cell viability at 2 h and 72 h.

EC1669 shows a potent cytostatic effect against murine RAW264.7 macrophages. The anti-proliferative activity of EC1669 is measured in a XTT cell viability assay (FIG. 2) on RAW264.7 cells after a 2-h exposure and a total of 72 h incubation. RAW264.7 macrophages are susceptible to the drug forming the EC1669 conjugate, aminopterin. The cell viability is assessed by adding XTT (2,3-bis(2-methoxy-4-nitro-5-sulfo-phenyl)-2H-tetrazolium-5-carboxanilide) following the manufacturer's instructions. EC1669 showed a dose-dependent inhibition of cell proliferation with a relative $IC_{50}$ value of ~1.2 nM. The observed anti-proliferative effect was 100% competable in the presence of 100-fold excess folic acid (FA), indicating a FR-specific mode of action for EC1669.

Method

In vitro activity against various cancer cell lines. $IC_{50}$ values are generated for various cell lines. Cells are heavily seeded in 24-well Falcon plates and allowed to form nearly confluent monolayers overnight. Thirty minutes prior to the addition of the test compound, spent medium is aspirated from all wells and replaced with fresh folate-deficient RPMI medium (FFRPMI). A subset of wells are designated to receive media containing 100 µM folic acid. The cells in the designated wells are used to determine the targeting specificity. Without being bound by theory it is believed herein that the cytotoxic activity produced by test compounds in the presence of excess folic acid, i.e. where there is competition for FR binding, corresponds to the portion of the total activity that is unrelated to FR-specific delivery. Following one rinse with 1 mL of fresh FFRPMI containing 10% heat-inactivated fetal calf serum, each well receives 1 mL of medium containing increasing concentrations of test compound (4 wells per sample) in the presence or absence of 100 µM free folic acid as indicated. Treated cells are pulsed for 2 h at 37° C., rinsed 4 times with 0.5 mL of media, and then chased in 1 mL of fresh medium up to 70 h. Spent medium is aspirated from all wells and replaced with fresh medium containing 5 µCi/mL $^3$H-thymidine. Following a further 2 h 37° C. incubation, cells are washed 3 times with 0.5 mL of PBS and then treated with 0.5 mL of ice-cold 5% trichloroacetic acid per well. After 15 min, the trichloroacetic acid is aspirated and the cell material solubilized by the addition of 0.5 mL of 0.25 N sodium hydroxide for 15 min. A 450 µL aliquot of each solubilized sample is transferred to a scintillation vial containing 3 mL of Ecolume scintillation cocktail and then counted in a liquid scintillation counter. Final results are expressed as the percentage of $^3$H-thymidine incorporation relative to untreated controls.

Example

Compounds described herein exhibit potent in vitro activity against pathogenic cells, such as KB cells. Compounds described herein exhibit greater specificity for the folate receptor compared to compounds that do not include at least one unnatural amino acid. For Example, EC1456 exhibits ca. 1000-fold specificity for the folate receptor as determined by folic acid competition (specificity=difference in $IC_{50}$ between competed group and non-competed group), and a 4-fold improvement in specificity compared to comparator compound EC0531, which does not include a linker L having an unnatural amino acid.

Example

Selectivity for folate receptor expressing cells. Compounds described herein show high activity for folate receptor expressing cells. Compounds described herein do not show significant binding to folate receptor negative cells. EC1456 show high competable binding to low and high FR expressing cells (FR+), and does not show binding to cells that do not express FR (FR−).

| Activity of EC1456 in (FR+) and (FR−) Cell Lines | | | |
|---|---|---|---|
| Cell Line | | FR Expression | Activity ($IC_{50}$) | Competable up to 100 nM |
| KB | Human Cervical Carcinoma | +++ | 2.3 nM | Yes |
| NCI/ADR-RES-Cl$_2$ | Human ovarian Carcinoma | ++ | 1.4 nM | Yes |
| IGROV1 | Human ovarian adenocarcinoma | + | 0.72 nM | Yes |
| MDA-MB-231 | Human breast adenocarcinoma (triple negative) | + | 0.47 nM | Yes |
| A549 | Human Lung Carcinoma | − | Inactive (a) | NA |
| H23 | Human Lung adenocarcinoma | − | Inactive | NA |
| HepG2 | Human hepatocellular Carcinoma | − | Inactive | NA |
| AN3CA | Human endometrial adenocarcinoma | − | Inactive | NA |
| LNCaP | Human prostate adenocarcinoma | − | ~850 nM | NA |

(a) activity was evaluated from 0.1-100 nM against these specifically selected (FR−) cell lines (A549, H23, HepG2, AN3CA, LNCaP);
NA = not applicable.

Method

Inhibition of Tumor Growth in Mice. Four to seven week-old mice (Balb/c or nu/nu strains) are purchased from Harlan Sprague Dawley, Inc. (Indianapolis, Ind.). Normal rodent chow contains a high concentration of folic acid (6 mg/kg chow); accordingly, test animals are maintained on a folate-free diet (Harlan diet #TD00434) for about 1 week before tumor implantation to achieve serum folate concentrations close to the range of normal human serum, and during the Method. For tumor cell inoculation, $1\times10^6$ M109 cells (a syngeneic lung carcinoma) in Balb/c strain, or $1\times10^6$ KB cells in nu/nu strain, in 100 µL are injected in the subcutis of the dorsal medial area (right axilla). Tumors are measured in two perpendicular directions every 2-3 days using a caliper, and their volumes are calculated as $0.5 \times L \times W^2$, where L=measurement of longest axis in mm and W=measurement of axis perpendicular to L in mm. Log cell kill (LCK) and treated over control (T/C) values are then calculated according to published procedures (see, e.g., Lee et al., "BMS-247550: a novel epothilone analog with a mode of action similar to paclitaxel but possessing superior antitumor efficacy" *Clin Cancer Res* 7:1429-1437 (2001); Rose, "Taxol-based combination chemotherapy and other in vivo preclinical antitumor studies" *J Natl Cancer Inst Monogr* 47-53 (1993)).

Dosing is initiated when the s.c. tumors have an average volume between 50-100 mm³ ($t_0$), typically 8 days post tumor inoculation (PTI) for KB tumors, and 11 days PTI for M109 tumors. Test animals (5/group) are injected i.v., generally three times a week (TIW), for 3 weeks with varying doses, such as with 1 µmol/kg to 5 µmol/kg, of the drug delivery conjugate or with an equivalent dose volume of PBS (control), unless otherwise indicated. Dosing solutions are prepared fresh each day in PBS and administered through the lateral tail vein of the mice.

Method

General 4T-1 Tumor Assay. Six to seven week-old mice (female Balb/c strain) are obtained from Harlan, Inc., Indianapolis, Ind. The mice are maintained on Harlan's folate-free chow for a total of three weeks prior to the onset of and during the method. Folate receptor-negative 4T-1 tumor cells ($1\times10^6$ cells per animal) are inoculated in the subcutis of the right axilla. Approximately 5 days post tumor inoculation when the 4T-1 tumor average volume is ~100 mm³ ($t_0$), mice (5/group) are injected i.v. three times a week (TIW), for 3 weeks with varying doses, such as 3 µmol/kg, of drug delivery conjugate or with an equivalent dose volume of PBS (control), unless otherwise indicated herein. Tumor growth is measured using calipers at 2-day or 3-day intervals in each treatment group. Tumor volumes are calculated using the equation $V=a \times b^2/2$, where "a" is the length of the tumor and "b" is the width expressed in millimeters.

Method

Drug Toxicity. Persistent drug toxicity is assessed by collecting blood via cardiac puncture and submitting the serum for independent analysis of blood urea nitrogen (BUN), creatinine, total protein, AST-SGOT, ALT-SGPT plus a standard hematological cell panel at Ani-Lytics, Inc. (Gaithersburg, Md.). In addition, histopathologic evaluation of formalin-fixed heart, lungs, liver, spleen, kidney, intestine, skeletal muscle and bone (tibia/fibula) is conducted by board-certified pathologists at Animal Reference Pathology Laboratories (ARUP; Salt Lake City, Utah).

Method

Toxicity as Measured by Weight Loss. The percentage weight change of the test animals is determined on selected days post-tumor inoculation (PTI), and during dosing. The results are graphed.

Example

Figure 3:
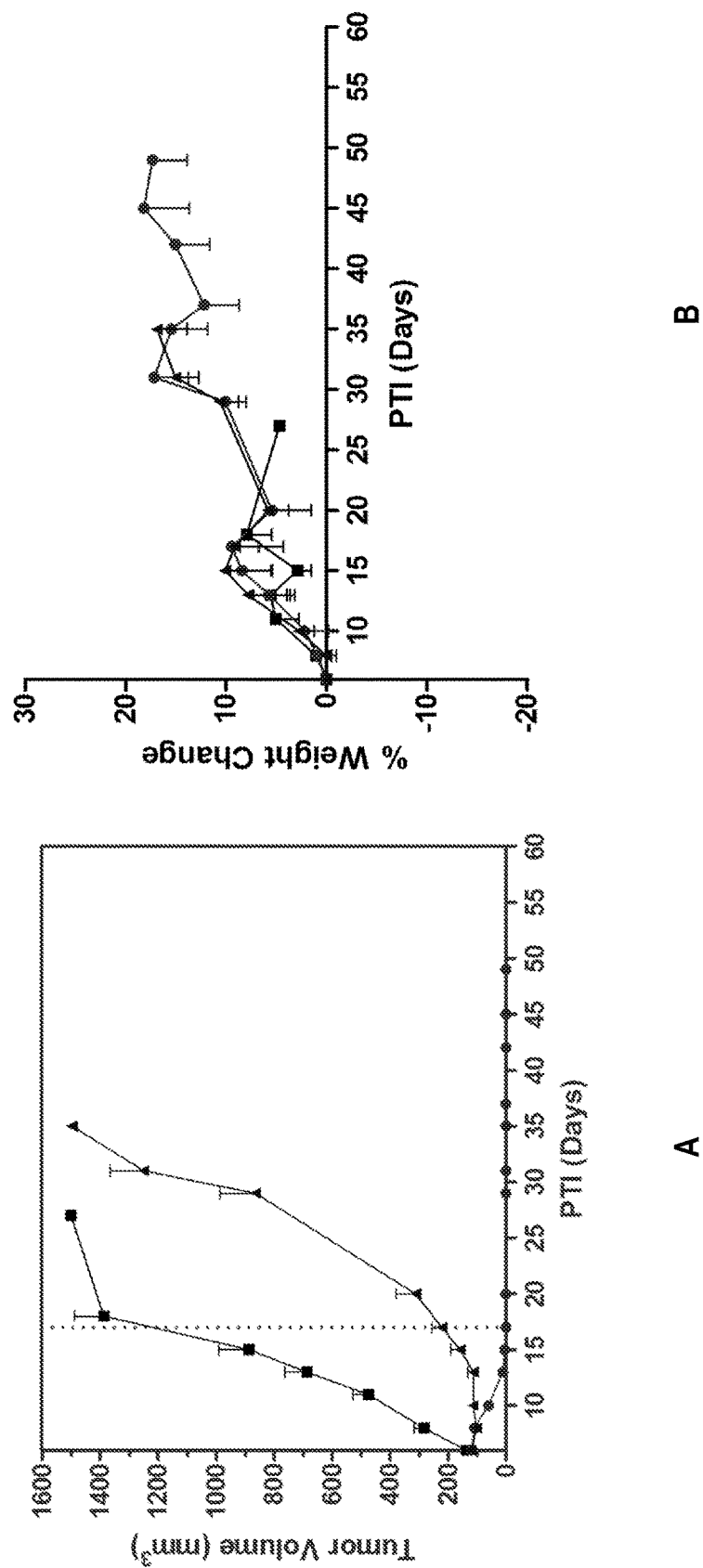
FIG. 3A shows in vivo activity of EC1456 against KB tumors in nu/nu mice dosed at 1 μmol/kg three times per week (M/W/F) (TIW) for two consecutive weeks (●), compared to EC1456 co-dosed with EC0923 at 100 μmol/kg (▲A), and untreated (PBS) controls (■). The dotted vertical line represents the day of the final dose.
FIG. 3B shows that EC1456 did not result in any observable whole animal toxicity as determined by animal body weight.

In vivo activity against tumors. Compounds described herein show high potency and efficacy against KB tumors in nu/nu mice. Compounds described herein show specific activity against folate receptor expressing tumors, with low host animal toxicity. For example, EC1456 shows a complete response in 4/4 test animals when administered intravenously at 1 µmol/kg TIW, 2 wk. EC1456 also shows specific activity mediated by the folate receptor as evidenced by being compatable with excess comparator compound EC0923 (50 or 100 µmol/kg), as shown in FIG. 3A. EC1456 does not show any evidence of whole animal toxicity, as shown in FIG. 3B.

Example

Figure 4:
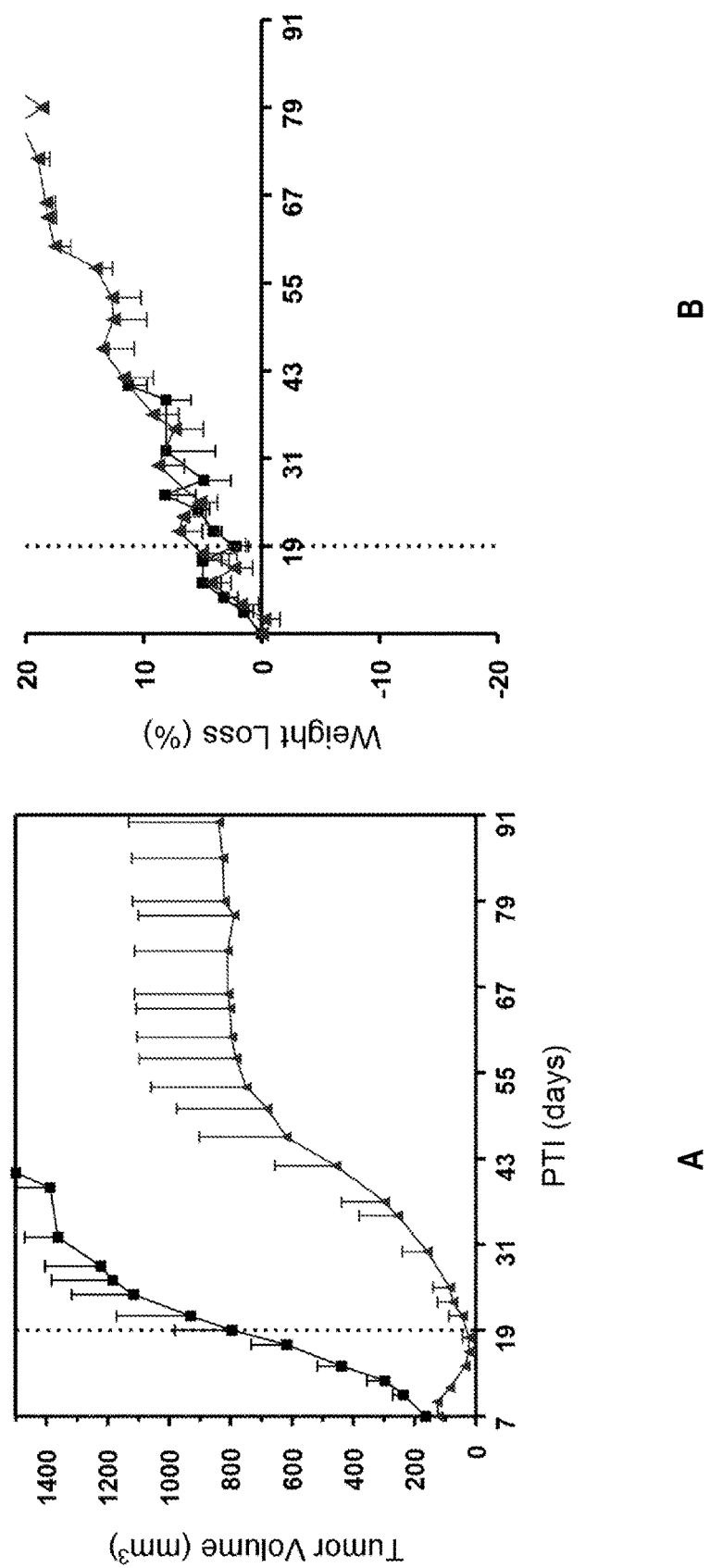
FIG. 4A shows the activity of EC1663 in nu/nu mice bearing s.c. KB tumors, where EC1663 was administered i.v. starting on Day 7 with 0.5 μmol/kg (▲), three times per week (M/W/F) for a 2 week period, and compared to untreated controls (■), N=5 animals per cohort. Dotted vertical line=day of final dosing day.
FIG. 4B shows that EC1663 did not exhibit significant host animal toxicity.

The therapeutic performance of EC1663 was evaluated against the human KB tumors. The data in FIG. 4A show 4/4 partial responses where the tumor volume was significantly decreased compared to control, but did not go to zero, and the tumor began to regrow after dosing ended. It is believed herein that a higher dose may result in a complete response and/or cure. The data in FIG. 4B show that at the administered efficacious dose, whole animal toxicity was not observed.

Method

TNBC Tumor Assay. Triple negative breast cancer (TNBC) is a subtype characterized by lack of gene expression for estrogen, progesterone and Her2/neu. TNBC is difficult to treat, and the resulting death rate in patients is reportedly disproportionately higher than for any other subtype of breast cancer. A TNBC xenograft model was generated in an analogous way to the KB and M109 models described herein by implanting MDA-MB-231 breast cancer cells in nu/nu mice. Dosing is initiated when the s.c. tumors have an average volume between 110-150 (generally 130) mm³ ($t_0$), typically 17 days post tumor inoculation (PTI). Test animals (5/group) are injected i.v., generally three times a week (TIW), for 2-3 weeks with varying doses, such as with 1 µmol/kg to 5 µmol/kg, of the drug delivery conjugate or with an equivalent dose volume of PBS (control), unless otherwise indicated. Dosing solutions are prepared fresh each day in PBS and administered through the lateral tail vein of the mice.

Example

Figure 5:
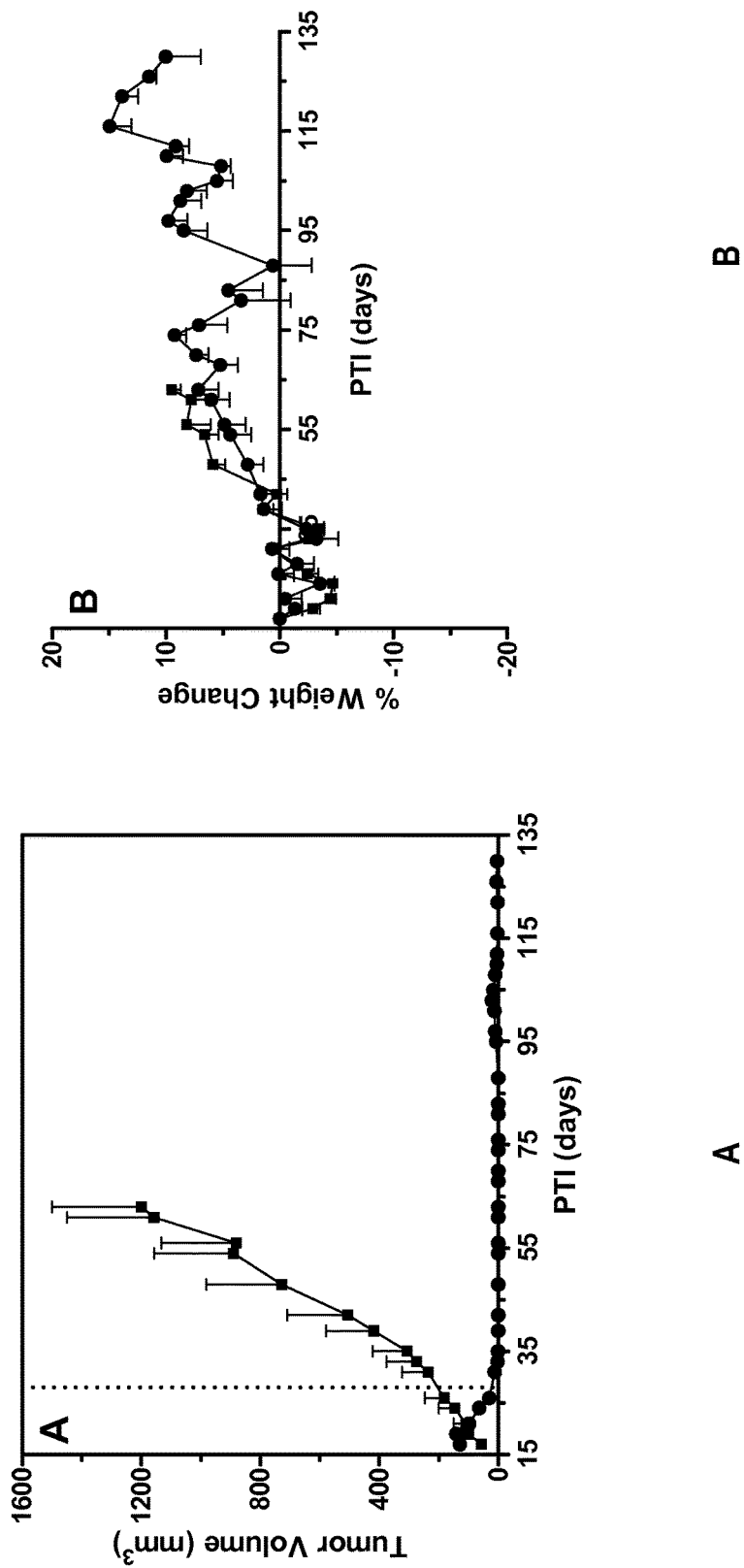
FIG. 5A shows the activity of EC1456 against established subcutaneous MDA-MB-231 tumors. Animals bearing s.c. MDA-MB-231 tumors (94-145 mm$^3$) were treated i.v. starting on Day 17 with 2 μmol/kg (panel A) of EC1456 (●), three times per week (M/W/F) for a 2 week period, and compared to untreated animals (■), as shown in FIG. 5A. N=5 animals per cohort. Dotted vertical line=day of final dose.
FIG. 5B shows that EC1456 did not cause gross whole animal toxicity as determined by % weight change.

When tested against an established triple negative FR-positive subcutaneous MDA-MB-231 breast cancer xenografts, EC1456 is found to be highly active at 2 µmol/kg intravenous dose administered on a three times per week, 2 consecutive week schedule. The treatment produced 4 of 5 complete responses, where tumor volume was reduced to zero, and regrowth did not occur during the observation window over nearly 135 days. Without being bound by theory, it is believed herein that the test animals were cured of the triple negative breast cancer. The results for EC1456 are shown in FIG. 5A. The anti-tumor activity was not accompanied by significant weight loss in the test animals, as shown in FIG. 5B.

Method

Figure 6:
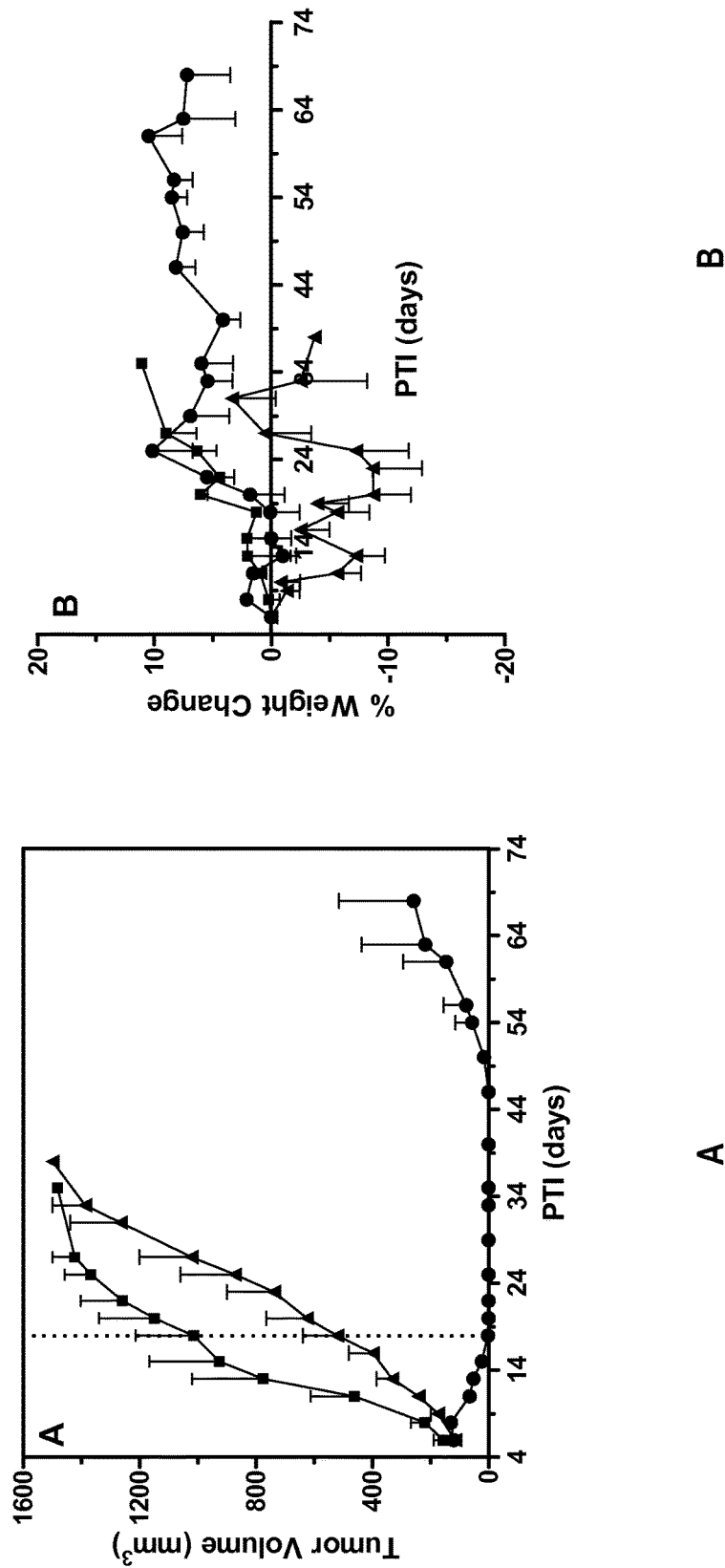
FIG. 6A shows the activity of EC1456 in animals bearing s.c. KB-CR2000 (cisplatin resistant) tumors (98-148 mm3), where EC1456 was administered i.v. starting on Day 6 with 2 μmol/kg (●), three times per week (M/W/F) for a 2 week period, or with 3 mg/kg of cisplatin (▲), twice per week (T/Th) for a 2 week period, and compared to untreated controls (■), N=5 animals per cohort. Dotted vertical line=day of final dosing day.
FIG. 6B shows that EC1456 did not exhibit significant host animal toxicity. In contrast, cisplatin treatment resulted in substantial host animal toxicity during the dosing period.

Human cisplatin-resistant cell line. A human cisplatin-resistant cell line is created by culturing FR-positive KB cells in the presence of increasing cisplatin concentrations (100→2000 nM; over a >12 month period). The cisplatin-resistant cells, labeled as KB-CR2000 cells, are found to be tumorigenic, and are found to retain their FR expression status in vivo. KB-CR2000 tumors are confirmed to be resistant to cisplatin therapy. Treatment with a high, toxic dose of cisplatin (average weight loss of 10.3%, as shown in FIG. 6B), did not produce even a single partial response (PR), as shown in FIG. 6A. In contrast, EC1456 is found to be very active against KB-CR tumors, where 5/5 CRs are observed. In addition, regrowth of the tumor was only observed in 1/5 test animals. Without being bound by theory, it is believed herein that 4/5 test animals were cured of the cisplatin-resistant cancer, where regrowth did not occur during the nearly 70 day observation period. Furthermore, unlike cisplatin, EC1456 did not cause any weight loss in this cohort of mice, and therefore did not display any evidence of gross animal toxicity during the dosing period.

Example

Comparison of conjugated and unconjugated drugs. The therapeutic performance of unconjugated tubulysin B and unconjugated TubB-H (EC0347) drugs is evaluated in vivo against human KB tumors in mice. The anti-tumor efficacy and gross toxicity, as determined by body weight changes, of each unconjugated drug are compared to the EC1456 conjugate. EC1456 produced dose responsive anti-tumor activity in this model. Complete responses were observed under treatment conditions that produced little to no weight loss. In contrast, both unconjugated tubulysin-based drugs failed to yield any anti-tumor response, even when very toxic doses were administered to the mice. The results are shown in the following table.

| Example | Dose (μmol/kg) | Dosing Schedule | PR (%) | CR (%) | Cures (%) | Deaths (%) | Avg. Weight Loss (Toxicity) |
|---|---|---|---|---|---|---|---|
| EC1456 | 0.5 | TIW, 3 weeks | 60 | 0 | 0 | 0 | <5%* |
|  | 0.67 | TIW, 2 weeks | 60 | 20 | 0 | 0 | <2% |
|  | 1.0 | TIW, 2 weeks | 40 | 60 | 60 | 0 | <1.5% |
|  | 2.0 | TIW, 2 weeks | 0 | 100 | 100 | 0 | <3% |
| Tubulysin B | 0.1 (4 doses) | TIW, 2 weeks | 0 | 0 | 0 | 100 | >20% |
|  | 0.2 (3 doses) | TIW, 2 weeks | 0 | 0 | 0 | 100 | >18% |
| TubB-H | 0.5 (1 dose) | TIW, 2 weeks | 0 | 0 | 0 | 100 | >15% |
|  | 0.5 | TIW, 2 weeks | 0 | 0 | 0 | 0 | <5.5% |
|  | 0.75 | TIW, 2 weeks | 0 | 0 | 0 | 20 | >10% |
|  | 1.0 (2 doses)[1] | TIW, 2 weeks | 0 | 0 | 0 | 20 | >15% |

*Untreated control group had an average weight loss of 2.4%
[1]Group received only 2 doses due to toxicity.

These results confirm that despite tubulysin B and TubBH being highly cytotoxic to cells in culture (typical $IC_{50}$~1 nM), both agents yielded dose-limiting toxicities in mice at levels that did not produce measurable anti-tumor effect. Thus, the unconjugated compounds do not exhibit a therapeutic window. In contrast, the conjugated forms of the drugs, such as conjugated TubBH (EC1456) produce anti-tumor responses without significant toxicity to mice bearing well-established human tumor xenografts. Conjugation as described herein provides a therapeutic window to highly toxic drugs.

Example

Compounds described herein exhibit high folate receptor affinity compared to folic acid (relative affinity=1) in 10% serum/FDRPMI, potent in vitro activity, potent in vivo activity, specificity for the folate receptor, and a sufficiently high therapeutic index compared to unconjugated drug.

| Example | Relative Affinity (a) | In vitro IC50 (nM) (b) | 50% competition (nM) (c) | In vitro specificity (fold) (d) | In vivo activity (e) | Therapeutic index over unconjugated drug (f) |
|---|---|---|---|---|---|---|
| EC1299 | 0.29 | 0.9 | 700 | 778 | CR | Yes |
| EC1393 | 0.25 | 2.2 | 600 | 300 | NT | NT |
| EC1456 | 0.27 | 1.5 | 1416 | 944 | CR | Yes |
| EC1548 | 0.23 | 4.4 | 350 | 78 | CR | Yes |
| EC1549 | 0.90 | 4.5 | 350 | 78 | CR | Yes |
| EC1586 | 0.56 | NT | NT | NT | NT | NT |
| EC0531 (comparator example) | NT | 1.5 | 355 | 237 | CR | Yes |

(a) compared to folic acid;
(b) as determined by thymidine incorporation;
(c) IC50 for test compound when competed with excess folic acid; the higher the IC50 the more specific is the folate mediation.;
(d) in vitro specificity = difference in $IC_{50}$ between competed group and non-competed group;
(e) as determined in subcutaneous KB tumor in nu/nu mice;
CR = complete response, where tumor volume, as defined herein, during the observation period was zero for all test animals in the group;
(f) parent tubulysin;
NT = not tested.

Method

Adjuvant-Induced Arthritis (AIA) Model. Female Lewis rats are fed a folate-deficient diet (Harlan Teklad, Indianapolis, Ind.) for 9-10 days prior to arthritis induction. The adjuvant-induced arthritis (AIA) is induced by intradermal inoculation (at the base of tail) of 0.4-0.5 mg of heat-killed *Mycobacteria butyricum* (BD Diagnostic Systems, Sparks, Md.) in 100 μL light mineral oil (Sigma). Ten days after arthritis induction, paw edema (degree of arthritis) in rats is assessed using a modified arthritis scoring system: 0=no arthritis; 1=swelling in one type of joint; 2=swelling in two types of joint; 3=swelling in three types of joint; 4=swelling of the entire paw. A total score for each rat is calculated by summarizing the scores for each of the four paws, giving a maximum score of 16 for each rat. On Day 10 post arthritis induction, rats with a total arthritis score of ≥2 were removed from the study and the remaining rats are distributed evenly across the control and treatment groups (n=5 for all groups except that n=2-3 for healthy controls). All treatments are started on Day 10 unless indicated otherwise. Rat paws are also evaluated radiographically to assess and determine bone damage.

Example

Figure 7:
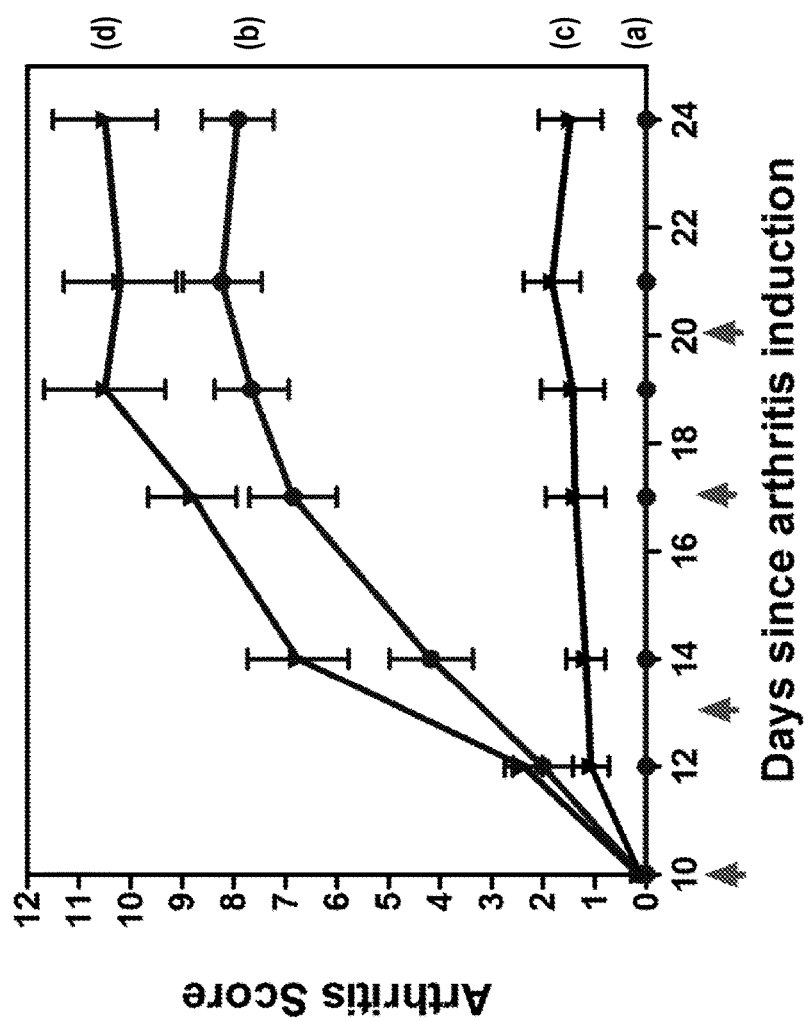
FIG. 7 shows the in vivo efficacy of EC1496 against adjuvant-induced arthritis. The arrows indicate the treatment days. (a) healthy control, (b) untreated control, (c) EC1496, (d) EC1496+excess EC0923 (comparator/competition compound).
Figure 8:
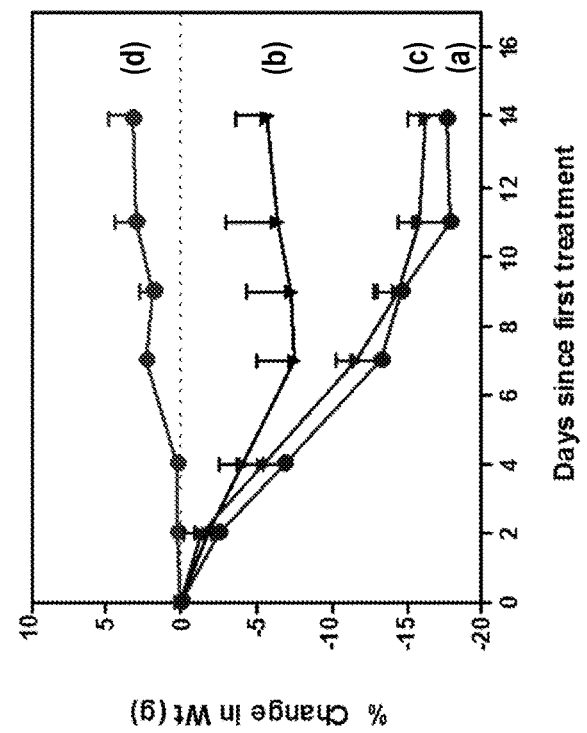
FIG. 8A shows the in vivo efficacy of EC1669 against arthritis, (a) healthy control, (a) untreated control, (b) EC1669 (375 nmol/kg), (c) EC1669+500x EC0923.
FIG. 8B shows that EC1669 does not exhibit whole animal toxicity, (a) untreated control, (b) EC1669 (375 nmol/kg), (c) EC1669+500x EC0923, (d) healthy control.
Figure 8:
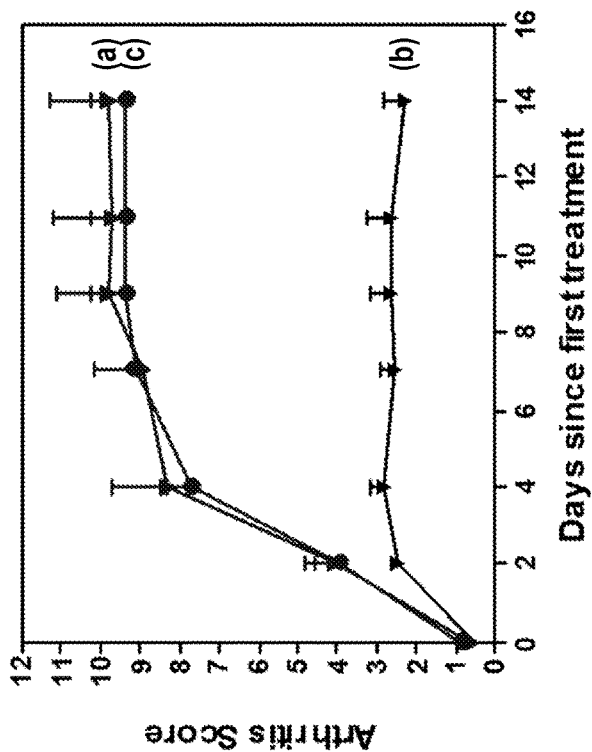
Figure 9:
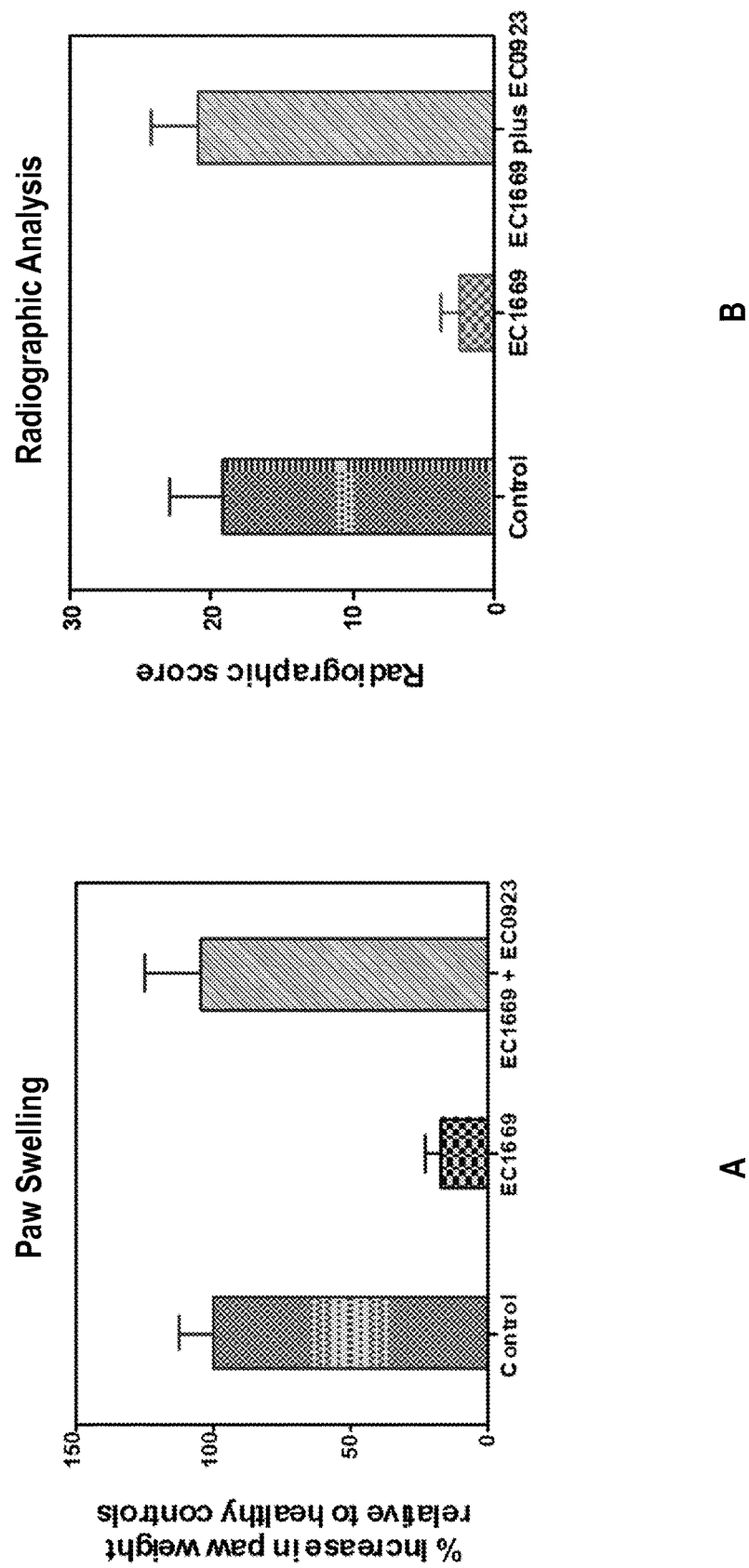
FIG. 9A shows the in vivo efficacy of EC1669 against arthritis, as determined by paw swelling.
FIG. 9B shows the in vivo efficacy of EC1669 against arthritis, as determined by bone radiography.

Compounds described herein are potent in treating inflammatory diseases, such as inflammation and bone damage accompanying arthritis. EC1496 is potent and efficacious in the reducing paw inflammation in a rat model of adjuvant-induced arthritis, as shown in FIG. 7. FIG. 7 shows that EC1496 is efficacious in preventing the development of arthritis based on the evaluation of paw edema. EC1496 (trace (d)) is significantly different from untreated control (trace (b)). In addition, the data indicate that the effect is folate receptor mediated because EC1496 (trace (d)) is also significantly different from the competition control group where EC1496 is co-administered with excess folic acid (trace (d)).

Example

Compounds described herein are potent in treating inflammatory diseases, such as inflammation and bone damage accompanying arthritis. Illustratively, EC1496 is potent and efficacious in reducing and/or preventing bone damage in a rat model of adjuvant-induced arthritis, as determined by radiographic analysis. The radiography shows that the treated animals do not exhibit the bone damage seen in the untreated control animals, based on visual scoring. Instead, the treated animals and the healthy animals show similar bone structure.

Example

EC1669 displays folate receptor-specific activity against adjuvant arthritis. Starting 9 days after induction, rats with developing AIA are distributed according to arthritis scores into three groups (n=5): (1) the untreated AIA control, (2) the EC1669 treated group, and (3) the EC1669 plus EC0923 competition group. All treatments last for 2 consecutive weeks. The animals in the AIA control group are left untreated. The animals in the EC1669 treatment group are given twice-a-week subcutaneous doses of EC1669 at a dosage of 375 nmol/kg. The animals in the EC1669 plus EC0923 group are given twice-a-week subcutaneous doses of EC1669 at a dosage of 375 nmol/kg in conjunction to EC0923 at a dosage of 187.5 μmol/kg. The study endpoints are shown in FIG. 8A, FIG. 8B, FIG. 9A, and FIG. 9B are: (a) arthritis score; (b) change in body weight; and (c) paw swelling, assessed by percent increase in paw weight (collected 4 days after the last dose), and (d) bone radiography. EC1669 is found to be highly effective in alleviating paw swelling (by ~80% compared to control) and bone damage (by ~80% compared to control). The anti-arthritic activity of EC1669 is compatable (blocked) with the folate competitor (EC0923).

Example

In a subsequent dosing study, various EC1669 dosing regiments were evaluated including once-a-week at 1000 nmol/kg, twice-a-week at 250 nmol/kg, and twice-a-week at 500 nmol/kg. Surprisingly, twice-a-week dosing at 250 nmol/kg was superior to once-a-week dosing at 1000 nmol/kg, a two-fold decrease in total dose. EC1669 was found more efficacious when dosed biweekly than once weekly in reducing paw swelling at 81% reduction at 500 nmol/kg, biw, and 64% reduction at 250 nmol/kg, biw, compared to a 44% reduction at 1000 nmol/kg, siw.

Example

Figure 10:
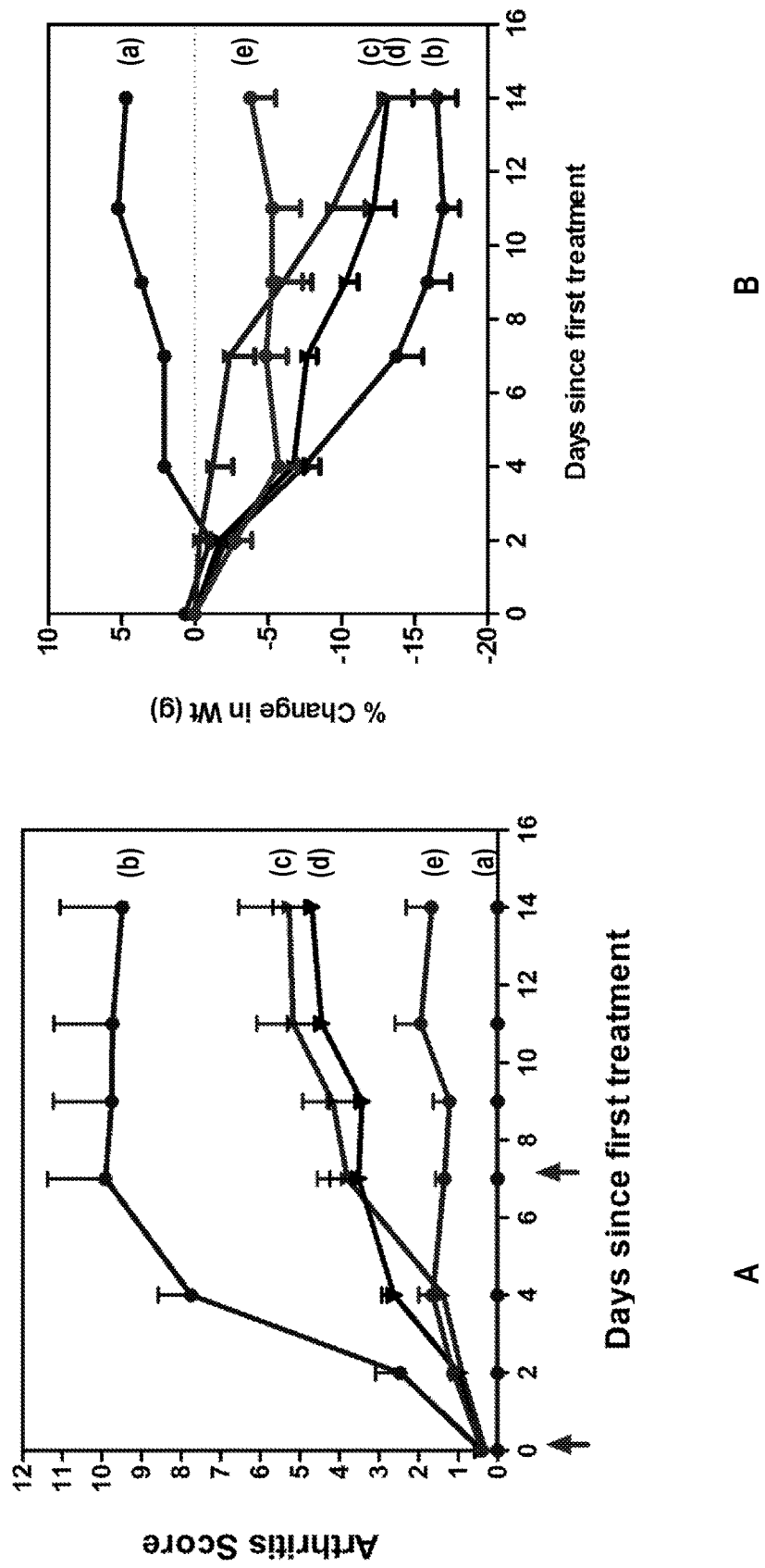
FIG. 10A shows the in vivo efficacy of EC1669 alone, and EC1669 plus CellCept combination co-therapy in AIA rats, where day 0 is 9 days post induction, and the arrows indicate treatment days, (a) healthy control, (b) untreated control, (c) EC1669 (1000 nmol/kg, siw, sc), (d) CellCept™ (30 mg/kg, po, qdx5), (e) EC1669+CellCept™.
FIG. 10B shows the whole animal toxicity compared to control for each of the administration protocols.
Figure 11:
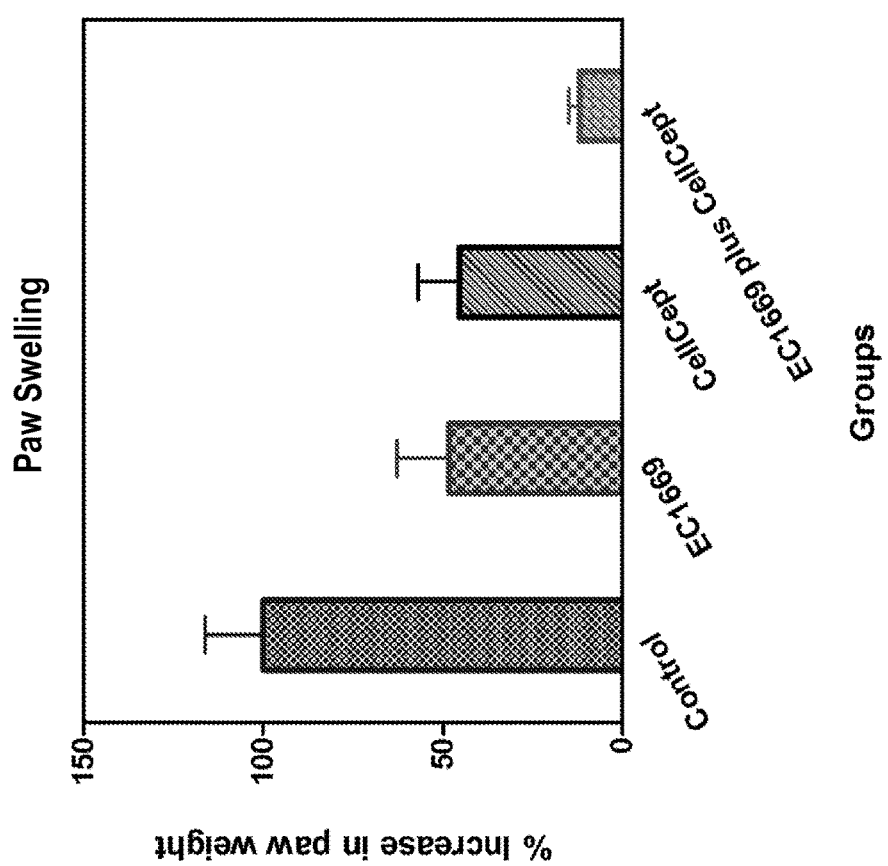
FIG. 11 shows the in vivo efficacy of EC1669 alone, and EC1669 plus CellCept combination co-therapy in AIA rats, as determined by paw swelling.

EC1669 plus CellCept is more effective than either agent alone against adjuvant-induced arthritis. CellCept is a prodrug of mycophenolic acid, an immunosuppressant drug used to prevent organ rejection in transplantation. CellCept is activated in vivo and releases its active product that can inhibit T cell proliferation and interfere with leukocyte adhesion to endothelial cells. To test the combination effect of EC1669 and CellCept, rats with developing AIA are distributed according to arthritis scores into four groups (n=5): (1) the untreated AIA control, (2) the EC1669 treated group, (3) the CellCept treated group, and (4) the EC1669 and CellCept combination group. All treatments start on day 9 after AIA induction and last 2 consecutive weeks. The animals in the AIA control group are untreated. The animals in the EC1669 treatment group are given weekly subcutaneous doses of EC1669 at a dosage of 1000 nmol/kg. The animals in the CellCept treatment group are given daily oral doses of CellCept at a dosage of 30 mg/kg, 5 days per week. The animals in the EC1669 and CellCept combination treatment group are given weekly subcutaneous doses of EC1669 at a dosage of 1000 nmol/kg and daily oral doses of CellCept at a dosage of 30 mg/kg, 5 days per week. As shown in FIG. 10A and FIG. 11, the EC1669 and CellCept combination therapy is more effective than either agent alone in reducing arthritis scores, paw swelling, and weight loss due to disease progression. FIG. 10B shows that the EC1669 and CellCept combination therapy causes lower toxicity than either drug given alone.

Method

Collagen-Induced Arthritis (CIA) Model. The collagen-induced arthritis (CIA) is induced in female Lewis rats on folate-deficient diet (Harlan Teklad, Indianapolis, Ind.). On Day 0, rats are immunized with 500 μg of bovine collagen Type II (Chondrex, Redmond, Wash.) formulated with Freund's complete adjuvant. A booster immunization is given on Day 7 with 250 μg of the bovine collagen formulated with Freund's incomplete adjuvant. Arthritis disease is assessed by a qualitative clinical score system described by the manufacturer (Chondrex, Redmond, Wash.): 0=normal, 1=Mild, but definite redness and swelling of the ankle or wrist, or apparent redness and swelling limited to individual digits, regardless of the number of affected digits, 2=Moderate redness and swelling of ankle of wrist, 3=Severe redness and swelling of the entire paw including digits, and 4=Maximally inflamed limb with involvement of multiple joints. On Day 10 post first immunization, rats are distributed evenly (according to the arthritis score) across the control and treatment groups. The CIA rats are given ten consecutive subcutaneous doses of test compound on days 10-19. For each drug, an induction dose (for example, 500 nmol/kg) is given on days 10 and 15 and a maintenance dose (for example, 100 nmol/kg) is given on days 11-14 and 16-19. The animals in the arthritis control group are left untreated. The arthritis score and animal body weight are recorded five times a week.

Method

Animal Experimental Autoimmune Uveitis Model. Experimental autoimmune uveitis (EAU) is induced in female Lewis rats maintained on a folate-deficient diet (Harlan Teklad, Indianapolis, Ind.). On Day 0, the animals are immunized subcutaneously with 25 µg of bovine S—Ag PDSAg peptide formulated with Freund's incomplete adjuvant containing 0.5 mg of grounded *M. Tuberculosis* H37Ra. Purified pertussis toxin (PT) is given at a dosage of 1 µg per animal on the same day via intraperitoneal injection. The severity of uveitis in each eye is assessed by a qualitative visual score system: 0=No disease, eye is translucent and reflects light (red reflex); 0.5 (trace)=Dilated blood vessels in the iris, 1=Engorged blood vessels in iris, abnormal pupil contraction; 2=Hazy anterior chamber, decreased red reflex; 3=Moderately opaque anterior chamber, but pupil still visible, dull red reflex; and 4=Opaque anterior chamber and obscured pupil, red reflex absent, proptosis. This assessment yields a maximum uveitis score of 8 per animal.

Example

Figure 12:
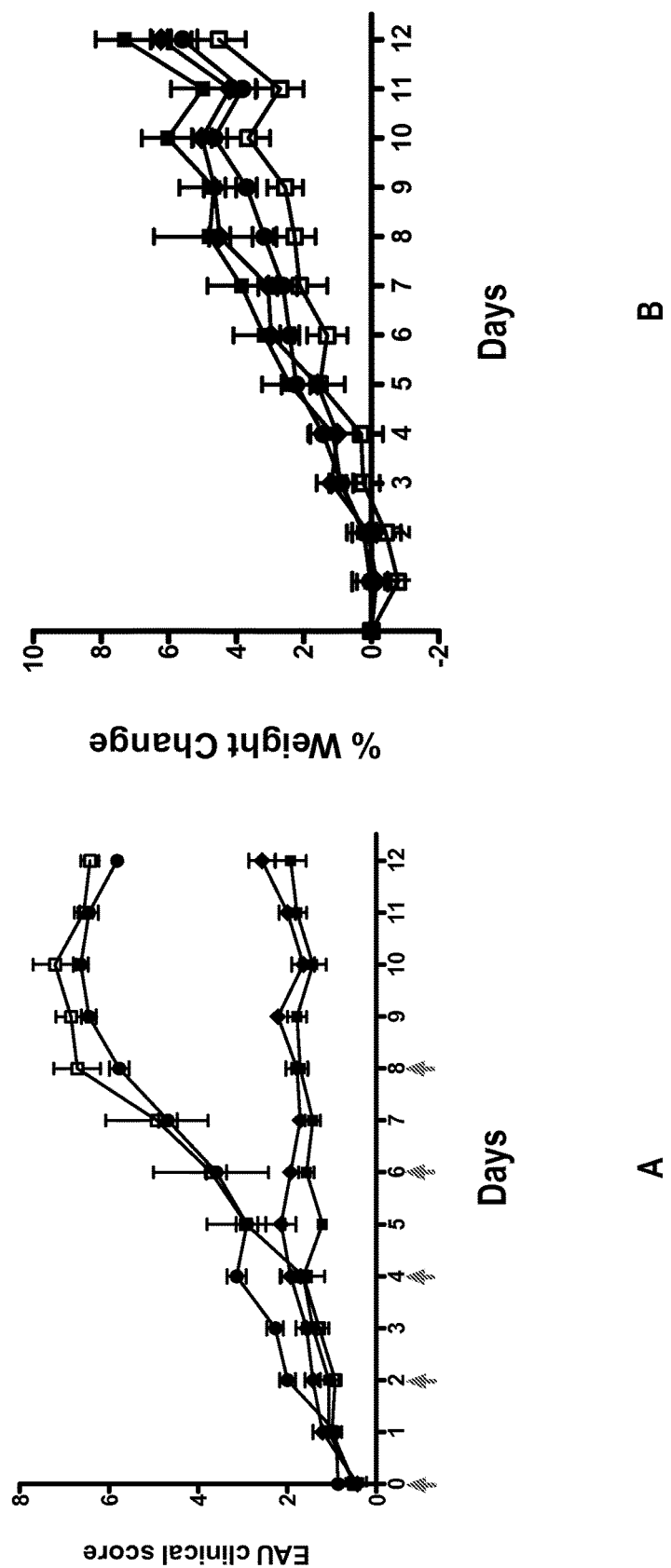
FIG. 12A shows the in vivo efficacy of EC1669 against EAU (total uveitis scores for both eyes). Animals are treated with EC1669 (■), EC1669 plus EC0923 (□), and MTX (♦) every other day starting on day 8 after EAU induction or from untreated animals (●). Day 0 is 8 days post induction, and the arrows indicate treatment days.
FIG. 12B shows that EC1669 does not cause whole animal toxicity.

Compounds described herein are potent in treating autoimmune uveitis. EC1669 displays folate receptor-specific activity against autoimmune uveitis. Animals presenting EAU are randomized and distributed into three groups: (1) the untreated EAU control (n=11), (2) the test compound treated group (n=7), such as EC1669, (3) the test compound and competitor compound treated group (n=7), such as EC1669 plus EC0923, and (4) the positive control treated group (n=7), such as methotrexate (MTX). All treatments start on day 8 after EAU induction. The animals in the EAU control group are untreated. The animals in the EC1669 treatment group are given five subcutaneous doses of EC1669 at a dosage of 250 nmol/kg every other day (q2d). The animals in the EC1669 plus EC0923 treatment group are given five subcutaneous doses of EC1669 at a dosage of 250 nmol/kg every other day plus a 500-fold excess of EC0923 at a dosage of 125 µmol/kg as the folate competitor. The animals in the MTX treatment group are given five subcutaneous doses of MTX at a dosage of 250 nmol/kg every other day. The uveitis score and animal body weight are recorded for each animal at predetermined frequencies. The clinical severity of EAU is monitored on a daily basis using an ophthalmoscope and graded on a scale of 0 to 4 per eye with a maximum possible score of 8 per animal. On day 16, the animals are euthanized and rat eye balls are fixed in formalin for histology. As shown in FIG. 12A, EC1669 treatment at disease on-set effectively reduces the symptoms of EAU in a FR-dependent manner and its activity is competitive with subcutaneous MTX. Treatment-related weight loss was not observed with the conjugate compounds described herein that include a linker comprising at least one unnatural amino acid, as shown in FIG. 12B.

Example

Figure 13:
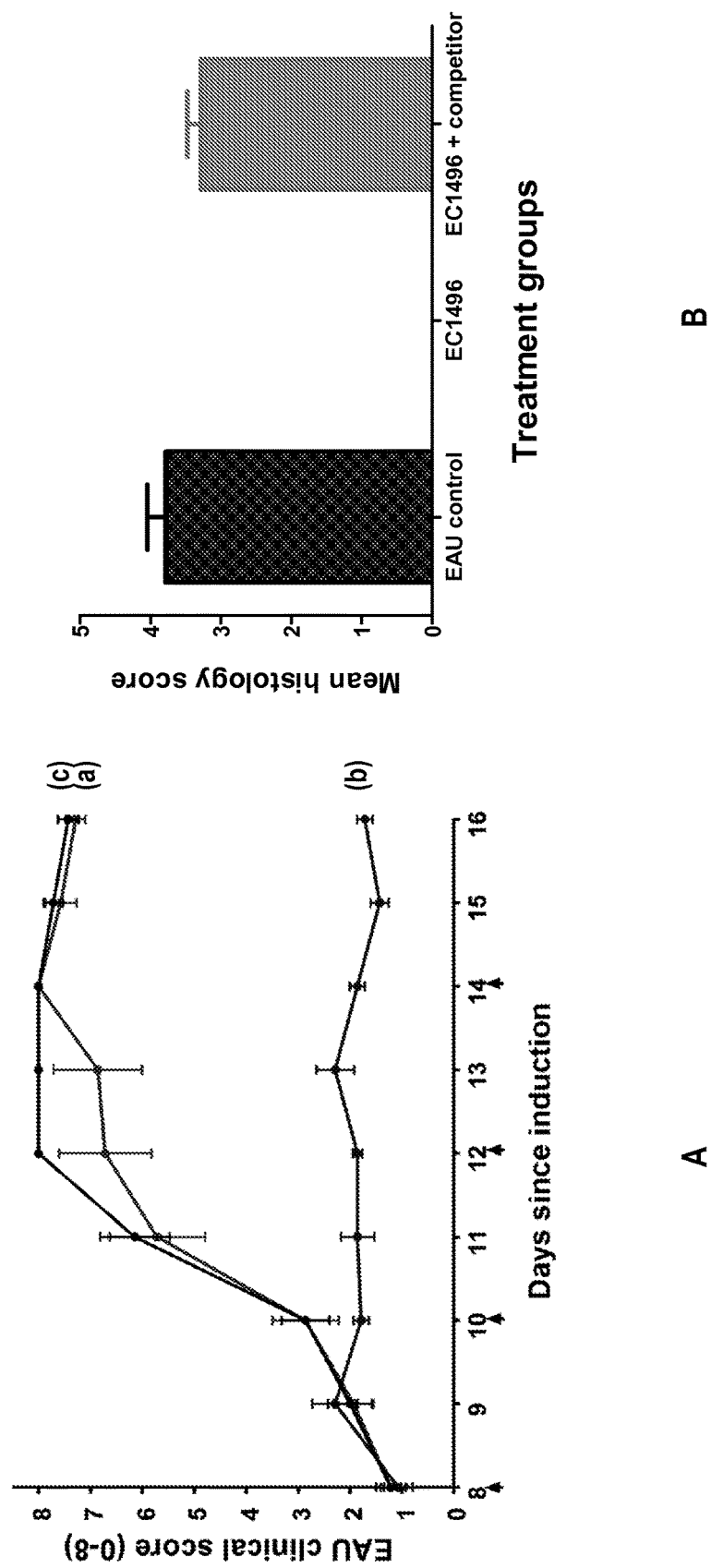
FIG. 13A shows the in vivo efficacy of EC1496 against EAU (total uveitis scores for both eyes), (a) uveitis untreated control, (b) EC1496 (375 nmol/kg), (c) EC1496+excess EC0923.
FIG. 13B shows the in vivo efficacy of EC1496 against EAU, as determined by histology.

EC1496 is potent and efficacious against folate receptor specific autoimmune uveitis, as shown in FIG. 13A. Tissues are evaluated by histology as shown in FIG. 13B.

Method

Autoimmune Encephalomyelitis (EAE) Model. EAE is induced in rats by immunization against 25 µg of guinea pig myelin basic protein (MBP) formulated with CFA containing 1 mg of grounded *Mycobacterium tuberculosis* H37Ra. Pertussis toxin is given intraperitoneally (1 µg/rat) to enhance the organ-specific autoimmunity. Starting 8 days after induction, rats are divided into 4 groups: (1) untreated control (n=8), (2) test compound (n=7), and (3) test compound plus competitor compound (n=7), such as EC0923 competition. All treatments start on day 8 after EAE induction. The animals in the EAE control group are left untreated. The animals in the test compound treatment group are given four subcutaneous doses of test compound at a dosage of 250 nmol/kg every other day (q2d). The animals in the test compound plus competitor compound treatment group are given four subcutaneous doses of test compound at a dosage of 250 nmol/kg every other day plus a 500-fold excess of competitor compound, such as EC0923 at a dosage of 125 µmol/kg as an illustrative folate receptor competitor. The clinical severity of EAE is monitored on a daily basis and graded on a scale of 0 to 5 per animal. The clinical signs of ascending paralysis of EAE rats are divided into a 0-5 scale: 0=No disease, 0.5=distal limp tail, 1=limp tail, 2=mild paraparesis; ataxia-weakened hind limbs, 3=moderate paraparesis; hind limbs paresis, 4=complete hind limb paralysis, 5=complete hind limb paralysis and incontinence (euthanasia). On day 16, the animals are euthanized and brain and spinal cords are fixed in formalin for histology.

Example

Figure 14:
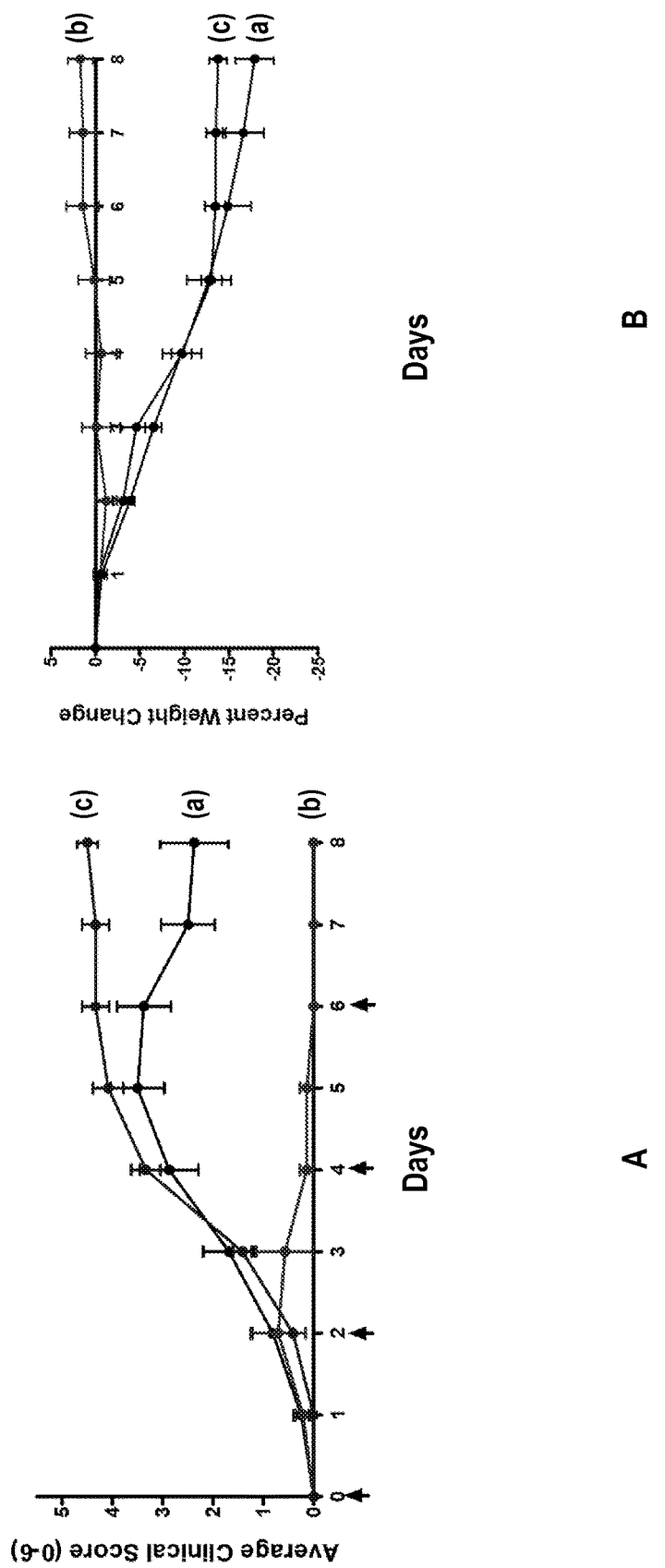
FIG. 14A shows the in vivo efficacy of EC1669 against EAE, (a) untreated EAE control, (b) EC1669 (250 nmol/kg), (c) EC1669+excess EC0923. Animals are treated every other day (as indicated by arrows) starting on day 8 after EAE induction, and compared to untreated control.
FIG. 14B shows the percent changes in body weight (B), averaged for each group.

Compounds described herein are potent in treating experimental autoimmune encephalomyelitis (EAE). EC1669 displays folate receptor-specific activity against EAE. As shown in FIG. 14A, EC1669 treatment at disease on-set effectively suppresses the neurological symptoms during the acute phase of EAE. Treatment-related weight loss was not observed with EC1669 when dose alone, as shown in FIG. 14B. The therapeutic effect of EC1669 is blocked by the folate receptor competitor EC0923.

Example

Figure 15:
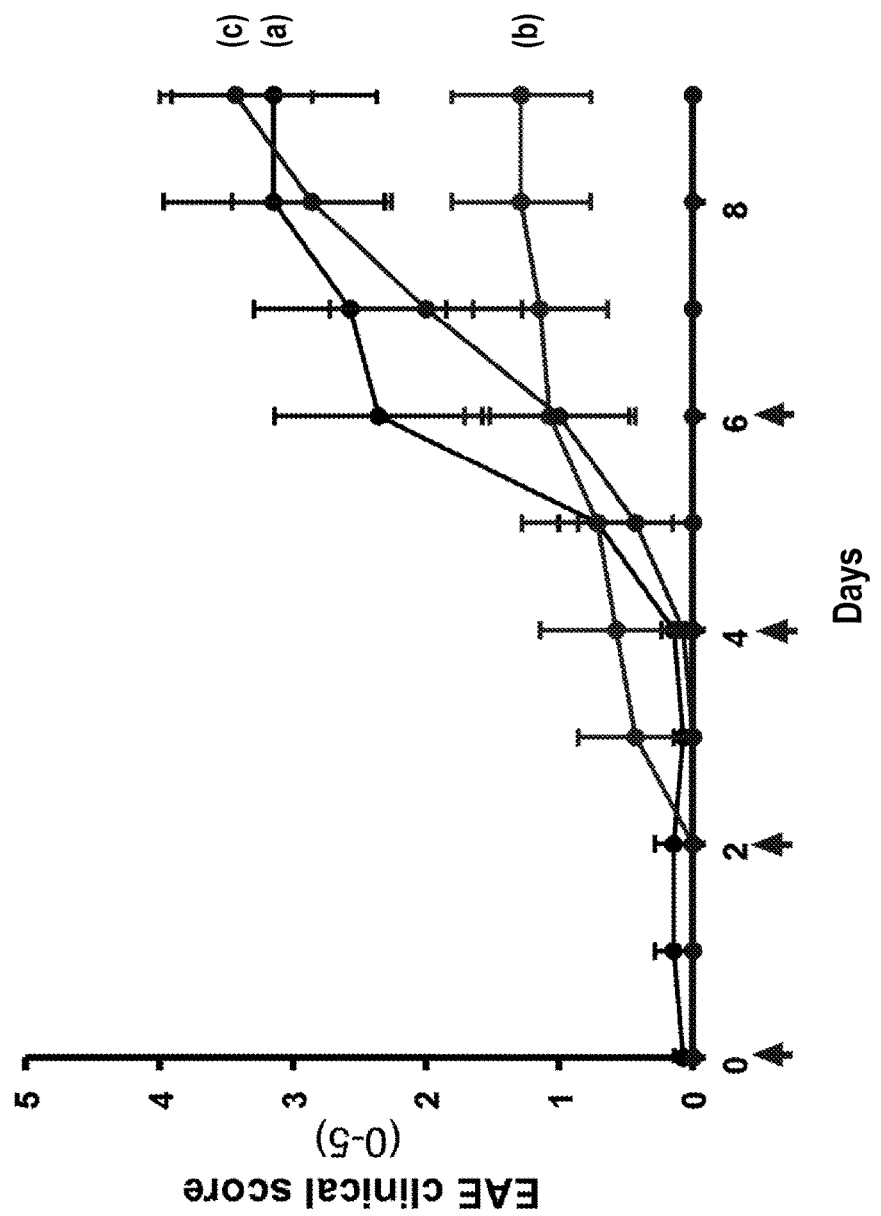
FIG. 15 shows the in vivo efficacy of EC1496 against EAE. Individual EAE scores from untreated animals and animals treated with EC1496 and EC1496 plus EC0923 every other day starting on day 8 after EAE induction are shown, and compared to untreated control.

EC1496 is potent and efficacious against EAE, as shown in FIG. 15. Treatment-related weight loss was not observed with EC1496 when dosed alone.

Method

Human serum stability. Compounds described herein are tested in human serum for stability using conventional protocols and methods. Briefly, test compound is administered to the test animal, such as by subcutaneous injection. The plasma concentration of the conjugate, and optionally one or more metabolites, is monitored over time. The results are graphed to determine Cmax, Tmax, half-life, and AUC for the test compound and metabolites.

Example

Figure 16:
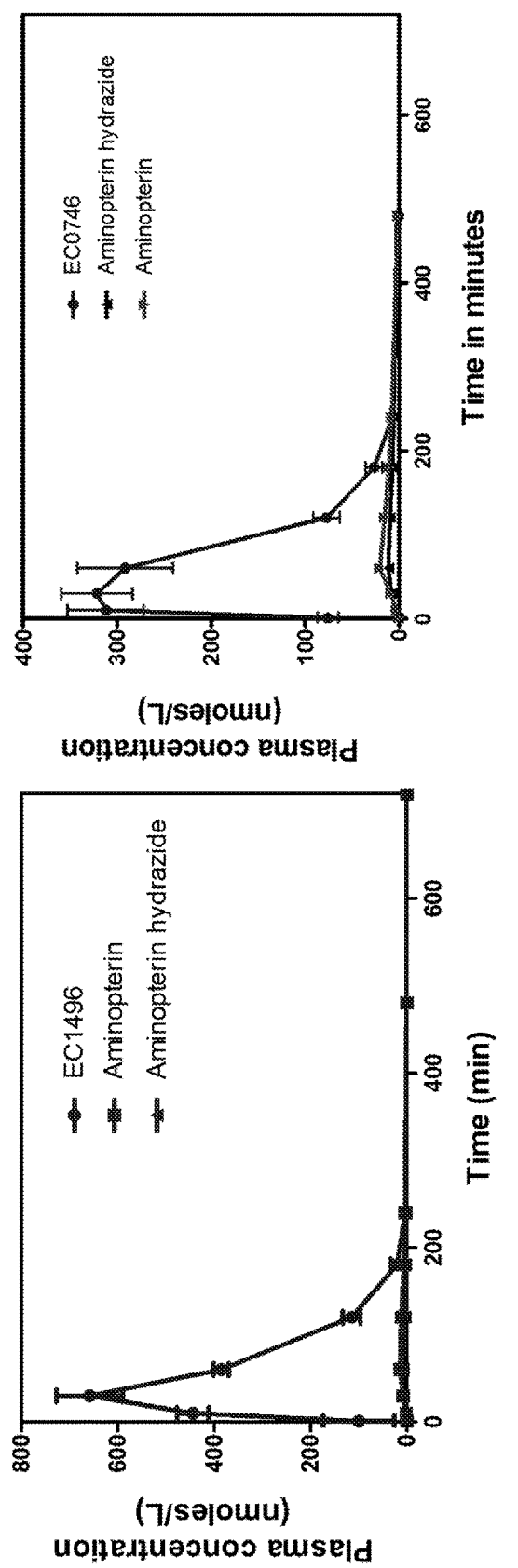
FIG. 16A shows the pharmacokinetics of EC1496 (500 nmol/kg, s.c.), and in vivo production of aminopterin and aminopterin hydrazide.
FIG. 16B shows the pharmacokinetics of EC0746 (comparator compound, 500 nmol/kg, s.c.), and in vivo production of aminopterin and aminopterin hydrazide.

Conjugate compounds described herein that include a linker comprising at least one unnatural amino acid are more stable in plasma than comparator conjugate compounds that do not have a linker comprising at least one unnatural amino acid. EC1495 and EC0746 (comparator compound) are each administered at 500 nmol/kg by subcutaneous injection. The plasma concentration of the conjugate and the metabolites (aminopterin and aminopterin hydrazide) are monitored over time. EC1496 shows a higher Cmax than EC0746, as shown in FIG. 16A and FIG. 16B, respectively. In addition, FIG. 16A and FIG. 16B show that EC1496 releases substantially less drug in plasma than does EC0746. As also shown in the following table, free drug is released as the parent aminopterin and the hydrazide derivative (EC0470).

| Free drug released (%) | From EC0746 | From EC1496 |
|---|---|---|
| AMT | 11.0 | 5.13 |
| AMT-hydrazide (EC0470) | 7.4 | 3.15 |
| Total | 18.4 | 8.28 |

Without being bound by theory, it is believed herein that the data indicate that the compounds described herein that include a linker comprising at least one unnatural amino acid, such as EC1496, exhibit greater plasma stability. In addition, the comparative example EC0746, which does not include a linker comprising at least one unnatural amino acid, releases more than 2-fold more drug than the EC1496 after a subcutaneous dose in rats. EC1496 also shows a higher Cmax than EC0746 leading to a higher effective therapeutic dose. Finally, EC1496 shows a shorter half-life. Without being bound by theory, it is believed herein that rapid clearance may further lead to lower toxicity because the duration of exposure to prematurely released drug from the conjugates described herein, compared to compounds that do not include a linker comprising at least one unnatural amino acid, will also be decreased.

Method

Plasma clearance. In vivo studies include a minimum of 3 test animals, such as rats, per time point. Illustratively, female Lewis rats with jugular vein catheters (Harlan, regular rodent diet) are given a single subcutaneous injection of test compound, such as EC1669 at 500 nmol/kg. Whole blood samples (300 µL) are collected at the following time points: 1 min, 10 min, 30 min, 1 h, 2 h, 3 h, 4 h, 8 h, and 12 h after injection. The blood samples are placed into anticoagulant tubes containing 1.7 mg/mL of $K_3$-EDTA and 0.35 mg/mL of N-maleoyl-beta-alanine (0.35 mg/mL) in a 0.15% acetic acid solution. Plasma samples are obtained by centrifugation for 3 min at ~2,000 g and stored at −80° C. The amounts of test compound in the plasma and any metabolites, such as EC1669 and its two active metabolites aminopterin (AMT) and AMT hydrazide (EC0470), respectively, are quantified by LC-MS/MS.

Example

EC1669 shows fast plasma clearance after subcutaneous administration in rats. EC1669 is detectable in the blood stream within minutes, with a Cmax of ~472 nM occurring at ~30 min post dose, and it maintained a plateau until 60 min after the injection. The EC1669-derived AMT and EC0470 are detected at similar Cmax values of 27 nM and 21 nM, respectively, but there is a 30-min delay in comparison to the EC1669 Cmax. While EC1669 itself is cleared rapidly from the blood with an elimination half-life of ~37 min, the elimination half-lives of the two metabolites are approximately 2-3 times longer at 66 min (AMT) and 112 min (EC0470), respectively. The corresponding area-under-the-curve (AUC) values for EC1669, AMT and EC0470 are 52, 5.9, and 3.9 nmol*min/mL, respectively. Based on their AUC responses, ~15.8% of active drug exposure/release (AMT plus EC0470) is estimated in the plasma over the 12 h collection period, a shown in the following table.

| Metabolites | % Released | AMT/EC0470 Ratio |
|---|---|---|
| Total | 15.8 | 1.51 |
| AMT | 9.5 | |
| EC0470 | 6.3 | |

Without being bound by theory, it is believed herein that the fast plasma clearance observed for the compounds described herein, such as EC1669, may result in lower host animal toxicity because the duration of exposure to prematurely released drug from the conjugates described herein, compared to compounds that do not include a linker comprising at least one unnatural amino acid, will also be decreased.

Method

Pharmacokinetic biodistribution. Studies in this section included a minimum of 3 test animals (mice) per time point. The pharmacokinetic biodistribution of test compound, such as $^3$H-EC1669 (label on the drug), compared to positive control, such as $^3$H-methotrexate ($^3$H-MTX), is observed in female Balb/c mice on folate-deficient diet. Compounds are administered as a single subcutaneous (SC) injection at 500 nmol/kg. Whole blood (>300 µL) along with ~100 mg each of various tissues of interests are collected at various time points (such as 10 min, 30 min, 1 h, 2 h, 4 h, 8 h, 12 h, 24 h, and 72 h). The blood samples are placed in BD microtainer tubes (heparin) and centrifuged (4,000 g×3 min, 4° C.) to separate plasma (>100 µL). The remaining red blood cell (RBC) mass is washed 2× with phosphate buffered saline (PBS, pH 7.4) to obtain RBCs. The collected tissues are weighed and processed to determine $^3$H-EC1669 and $^3$H-MTX distribution: plasma, RBC, heart, lung, liver (the smallest lobe), spleen, kidney (1), intestine (above cecum), fecal material (from colon), muscle, and brain.

Example

Figure 17:
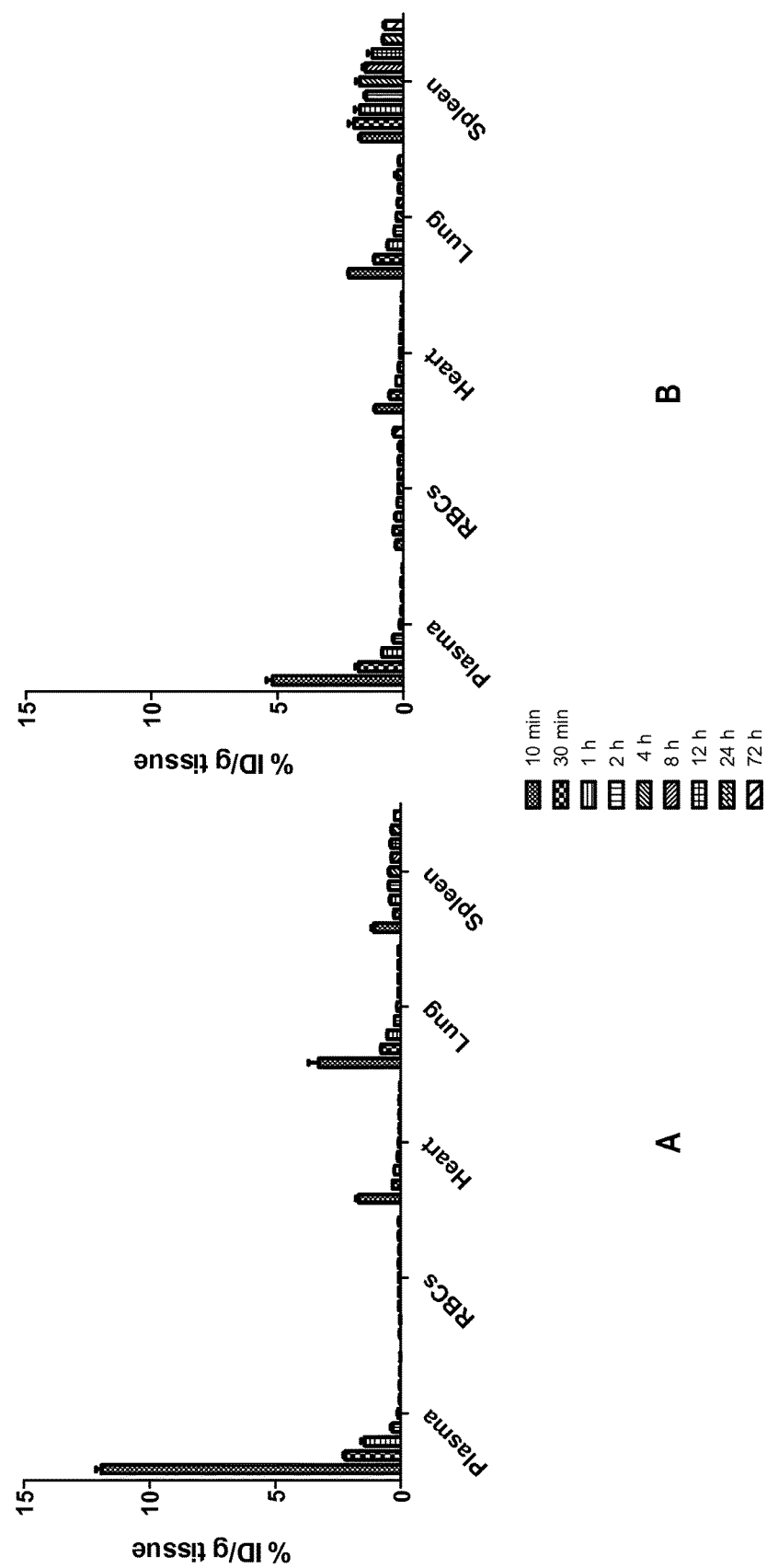
FIG. 17 shows the pharmacokinetic biodistribution of $^3$H-EC1669, panels (A), (C), and (E); and $^3$H-methotrexate in mice, panels (B), (D), and (F). Test compounds were administered to Balb/c mice at 500 nmol/kg, s.c.
Figure 17:
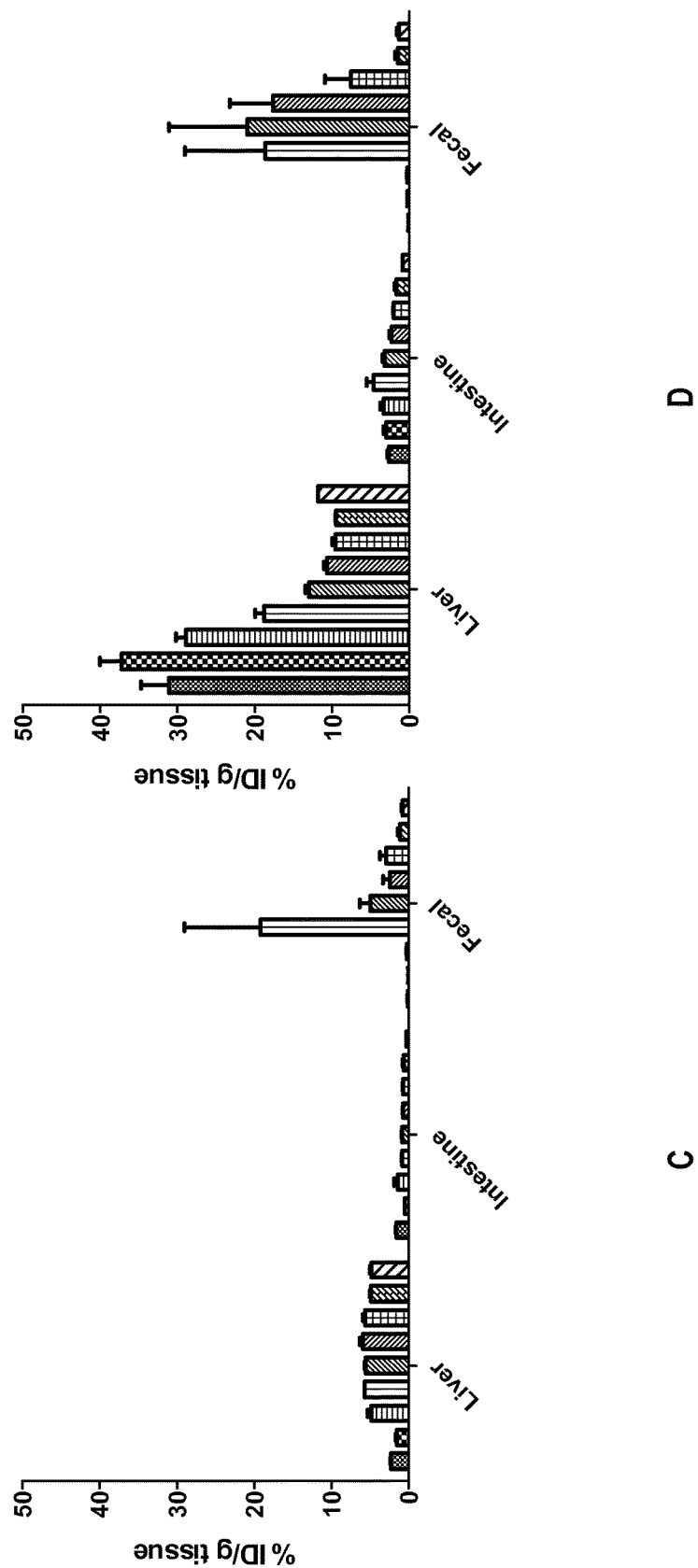
Figure 17:
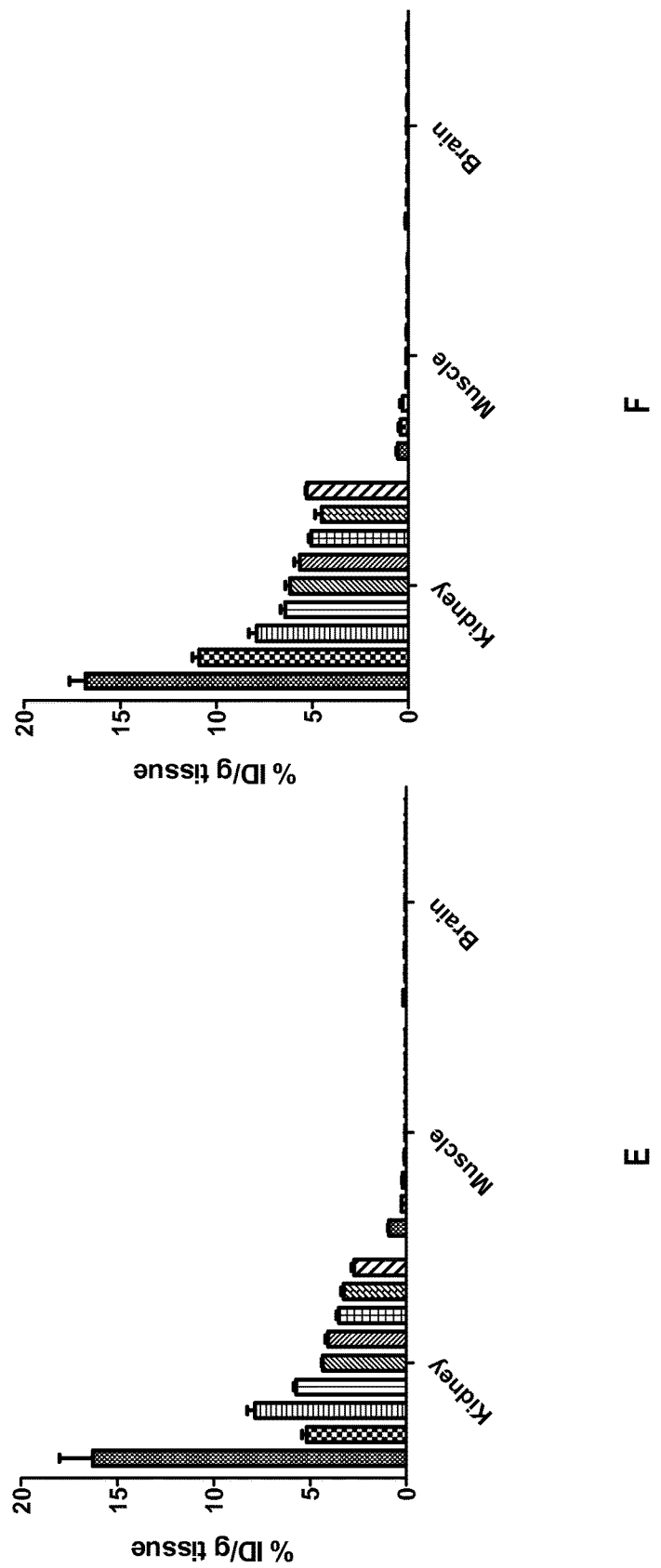
Figure 18:
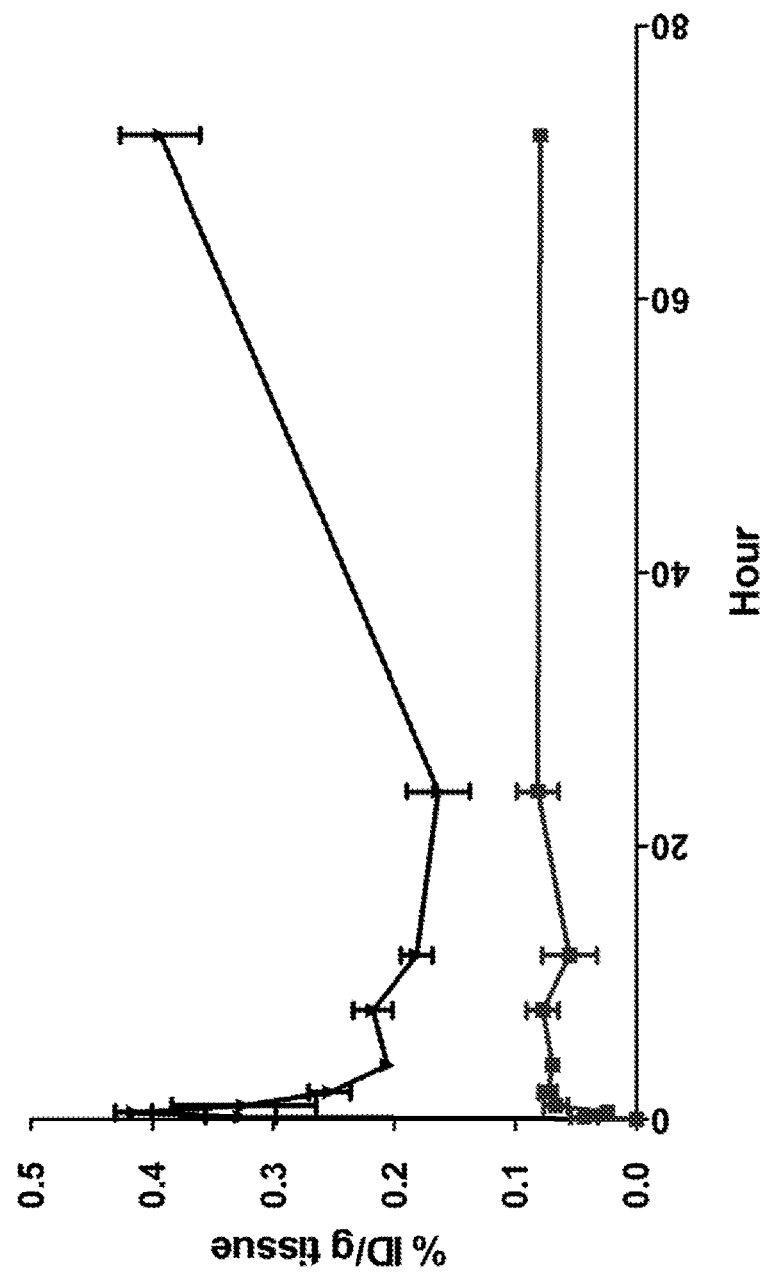
FIG. 18 shows the comparison of RBC uptake of $^3$H-EC1669 (■) and $^3$H-MTX (▼) in mice, as a measure of radioactivity over time.

Comparison of pharmacokinetic biodistribution of $^3$H-EC1669 and $^3$H-methotrexate after subcutaneous administration. The comparative pharmacokinetic biodistribution results are shown in FIG. 17 (as percent injected dose per gram (% ID/g)). At 10 min post-dose, 31% ID/g of $^3$H-MTX is captured by the liver. Twice as much $^3$H-EC1669 is found in the plasma than $^3$H-MTX (12% versus 5.2% ID/g). $^3$H-MTX retention in RBCs, spleen, liver, intestine, and feces are also consistently higher than that of $^3$H-EC1669 during the entire sampling period. The RBC data is also plotted in FIG. 18 showing that $^3$H-MTX retention is higher than EC1669. Without being bound by theory, it is believed herein these data suggest that EC1669 differs significantly from MTX in hepatic clearance, where MTX is preferentially cleared by the liver. Without being bound by theory, it is also believed herein these data suggest that EC1669 differs significantly from MTX in RBC uptake, suggesting different methods of cellular entry. MTX reportedly enters cells non-specifically, typically via the ubiquitously expressed reduced folate carrier (RFC). The compounds described herein are shown to enter cells specifically through the functional folate receptor. Without being bound by theory, it is believed herein that the RBC data further support the folate receptor mediated activity of the conjugates described herein.

In a subsequent renal/hepatic secretion study, mice are housed in metabolic cages with a 6-h fast before subcutaneous administration of $^3$H-EC1669 or $^3$H-MTX. At 24 h post-dose, ~14% more radioactivity is found in the pooled urine of $^3$H-EC1669 dosed animals than in $^3$H-MTX dosed animals. In contrast, twice as much radioactivity was found in the pooled feces of $^3$H-MTX dosed animals than in EC1669 dosed animals. Without being bound by theory, it is believed herein these data suggest that EC1669 differs significantly from MTX in renal to hepatic clearance ratio, where EC1669 is preferentially cleared by the kidneys, rather than the liver. MTX reportedly causes hepatotoxicity as a major side effect, especially after long-term use. Without being bound by theory, it is believed herein that the preferential renal clearance of the compounds described herein will lead to fewer side effects such as hepatotoxicity.

Example

Figure 19:
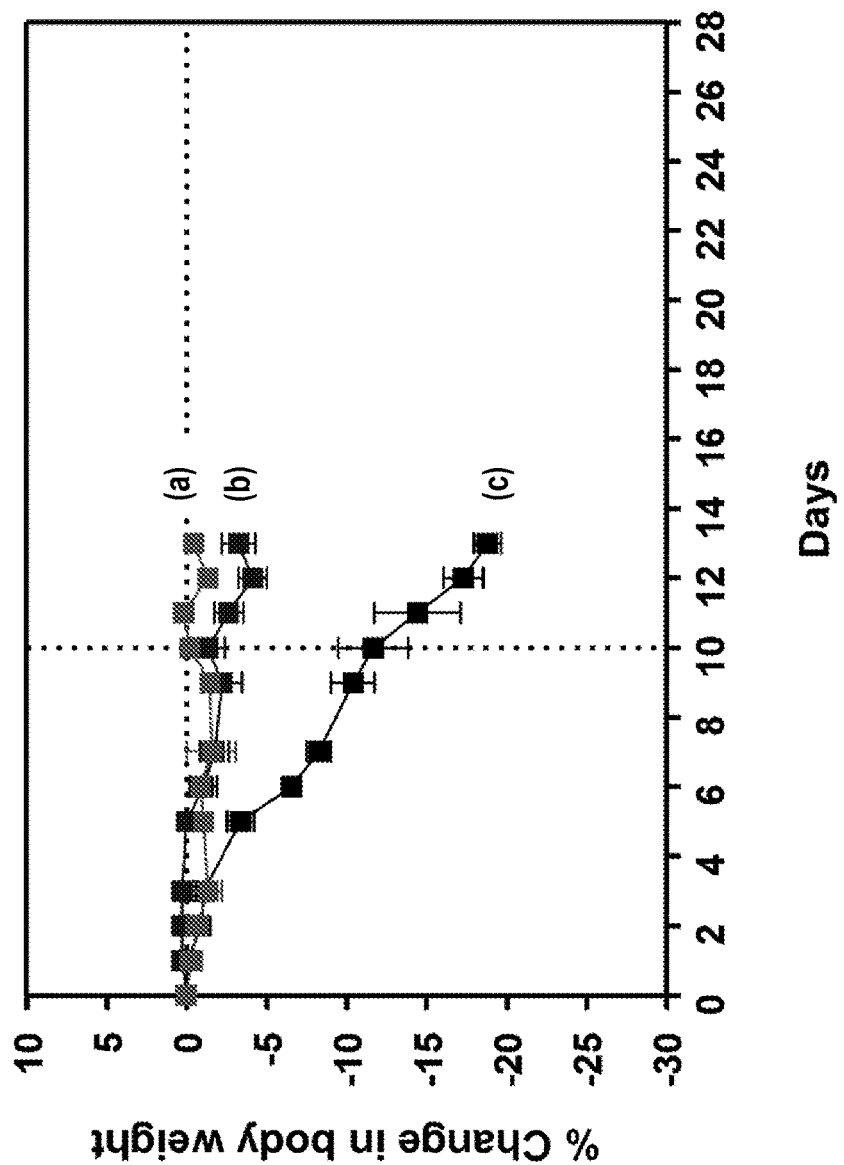
FIG. 19 shows the relative whole animal toxicity between (b) EC1496 (3 μmol/kg) and (c) EC0746 (comparator compound, 3 μmol/kg)), and compared to vehicle control (a) when dosed BIW for 2 weeks in folate deficient rats.

Compounds described herein are less toxic than compounds that do not have a linker comprising at least one unnatural amino acid. Test compounds are administered i.v. at equivalent doses to folate deficient rats. As shown in FIG. 19, conjugates described herein that include a linker comprising at least one unnatural amino acid, such as EC1496, are less toxic than the corresponding conjugate that does not, such as comparative example EC0746.

Example

Figure 20:
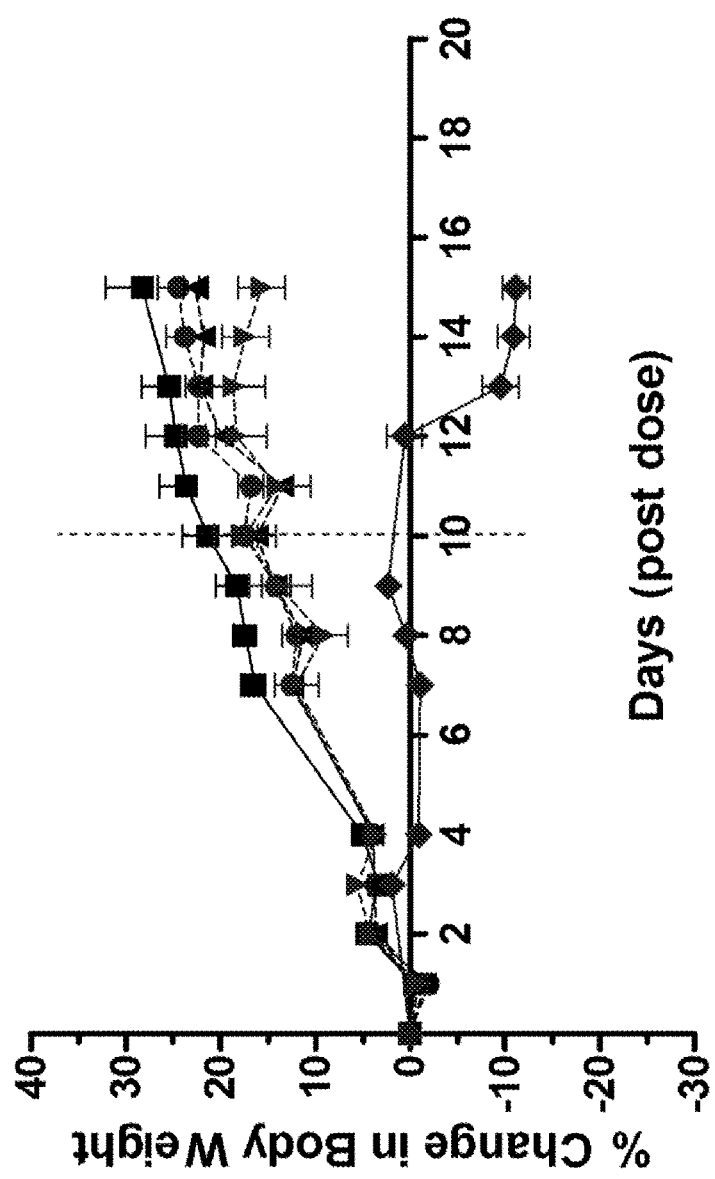
FIG. 20 shows the maximum tolerated dose (MTD) of EC1456 compared to vehicle controls. Vehicle control (●), EC1456 at 0.33 μmol/kg (■), EC1456 at 0.41 μmol/kg (▲), EC1456 at 0.51 μmol/kg (▼), and EC1456 at 0.67 μmol/kg (♦).

Maximum tolerated dose (MTD). Conjugate compounds described herein that include a linker comprising at least one unnatural amino acid show high MTDs, which are improved over compounds that do not have linkers comprising one or more unnatural amino acids. Test compounds are administered by i.v., BIW, 2 wks in female Sprague-Dawley rats. Comparator compound EC0531 has a MTD of 0.33 µmol/kg, while EC1456 has a MTD of at least 0.51 µmol/kg, a 65% improvement, as shown in FIG. 20. Histopathologic changes were not observed with doses of EC1456 at or below the MTD.

What is claimed is:
1. A compound of the formula

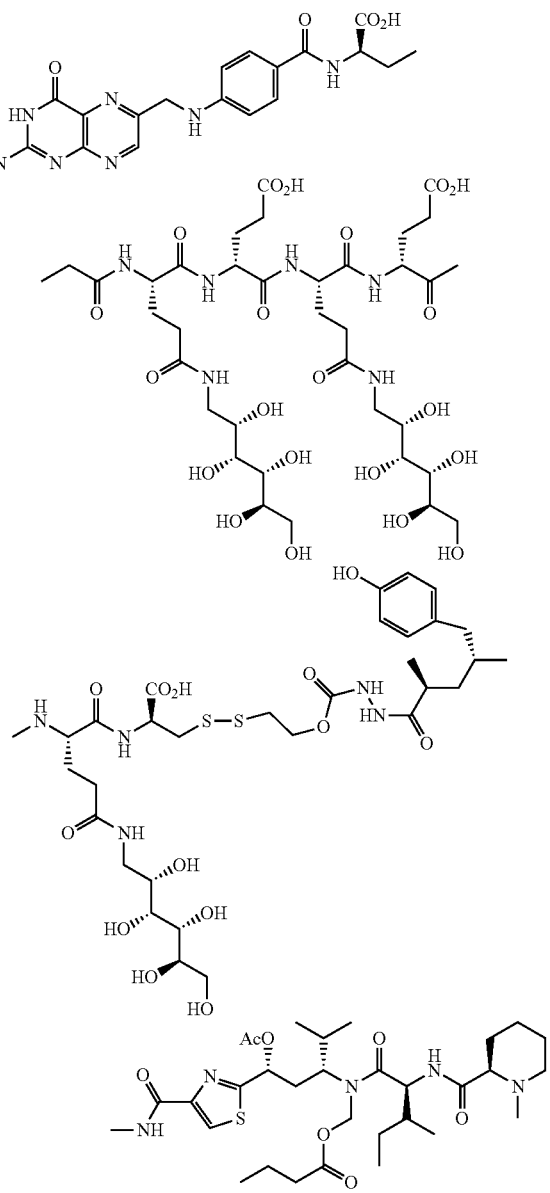

or a pharmaceutically acceptable salt thereof.
2. A pharmaceutical composition comprising the compound of claim 1, or a pharmaceutically acceptable salt thereof, in combination with one or more carriers, diluents, or excipients, or a combination thereof.

* * * * *